(12) United States Patent
Rodriguez-Saona et al.

(10) Patent No.: US 11,976,972 B2
(45) Date of Patent: May 7, 2024

(54) PORTABLE SPECTROMETER SYSTEM AND METHODS FOR DETERMINING NUTRITIONAL AND QUALITY TRAITS

(71) Applicant: Ohio State Innovation Foundation, Columbus, OH (US)

(72) Inventors: Luis Rodriguez-Saona, Dublin, OH (US); Christopher Ball, Westerville, OH (US); Xin Rong Sia, Columbus, OH (US); Sanjay Krishna, Plain City, OH (US); Theodore James Ronningen, Lewis Center, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 285 days.

(21) Appl. No.: 17/612,634

(22) PCT Filed: May 21, 2020

(86) PCT No.: PCT/US2020/034009
§ 371 (c)(1),
(2) Date: Nov. 19, 2021

(87) PCT Pub. No.: WO2020/237055
PCT Pub. Date: Nov. 26, 2020

(65) Prior Publication Data
US 2022/0221338 A1 Jul. 14, 2022

Related U.S. Application Data

(60) Provisional application No. 62/850,597, filed on May 21, 2019.

(51) Int. Cl.
*G01J 3/02* (2006.01)
*G01J 3/44* (2006.01)
(Continued)

(52) U.S. Cl.
CPC ........... *G01J 3/0272* (2013.01); *G01J 3/0256* (2013.01); *G01J 3/0264* (2013.01); *G01J 3/44* (2013.01);
(Continued)

(58) Field of Classification Search
CPC ...... G01J 3/0272; G01J 3/0256; G01J 3/0264; G01J 3/44; G01J 3/28; G01J 3/0291;
(Continued)

(56) References Cited

U.S. PATENT DOCUMENTS 6,646,264 B1 * 11/2003 Modiano ............ G01N 21/3563
356/326
6,675,030 B2  1/2004 Ciurczak et al.
(Continued)

FOREIGN PATENT DOCUMENTS

| CN | 202583066 U | 12/2012 |
| CN | 203798735 U | 8/2014 |
| JP | H11216131 A * | 8/1999 |

OTHER PUBLICATIONS

International Search Report and Written Opinion, issued by the International Searching Authority (ISA/US) in PCT Application No. PCT/US2020/034009 dated Oct. 8, 2020. 15 pages.
(Continued)

*Primary Examiner* — Kiho Kim
(74) *Attorney, Agent, or Firm* — Meunier Carlin & Curfman LLC

(57) ABSTRACT

Disclosed herein are systems and devices for use in determining a level of a trait in an agriculture or food product sample. Further disclosed is a portable spectrometer system coupled with chemometric analysis methods to determine a level of a trait in an agriculture or food product sample, the portable spectrometer system comprising: a spectrometer; a sample stage adjacent the spectrometer; a motor coupled to
(Continued)

the sample stage; and a system housing enclosing the motor and the spectrometer; wherein rotation of the motor rotates the sample stage, and wherein the motor is controllable in response to spectroscopy requirements.

18 Claims, 87 Drawing Sheets

(51) Int. Cl.
  *G01N 21/3563* (2014.01)
  *G01N 21/359* (2014.01)
  *G01N 33/02* (2006.01)
(52) U.S. Cl.
  CPC ....... *G01N 21/3563* (2013.01); *G01N 21/359* (2013.01); *G01N 33/02* (2013.01)
(58) Field of Classification Search
  CPC .. G01N 21/3563; G01N 21/359; G01N 33/02; G01N 21/552; G01N 21/65; G01N 2021/3595; G01N 2021/8466; G01N 2201/0221; G01N 2201/129
  See application file for complete search history.

(56) References Cited

U.S. PATENT DOCUMENTS

| | | | |
|---|---|---|---|
| 7,211,413 B2 | 5/2007 | Matsumoto et al. | |
| 7,787,924 B2 | 8/2010 | Acosta et al. | |
| 2002/0011567 A1 | 1/2002 | Ozanich | |
| 2003/0020011 A1 | 1/2003 | Anderson et al. | |
| 2004/0019462 A1 | 1/2004 | Gehrlein et al. | |
| 2006/0063992 A1* | 3/2006 | Yu ......................... | G01N 21/65 600/322 |
| 2016/0003746 A1* | 1/2016 | McCrary .................. | G01J 3/44 356/301 |
| 2018/0188111 A1 | 7/2018 | Day et al. | |

OTHER PUBLICATIONS

"GlucoWatch Automatic Glucose Biographer and AutoSensors", Cygnus Inc., Document #1992-00, Rev. Mar. 2001.
A. MacLeod, "Understanding Malting Barley Quality," https://www.canr.msu.edu/uploads/234/78941/Understanding_Malting_Barley_Quality_-_Aaron_MacLeod.pdf (accessed Sep. 29, 2019).
Adebiyi, A.P., Jin, D.H., Ogawa, T., Muramoto, K., Acid hydrolysis of protein in a microcapillary tube for the recovery of tryptophan. Biosci. Biotechnol. Biochem. 2005, 69, 255-7.
Barnes, R. J., Mewa Singh Dhanoa, and Susan J. Lister. "Standard normal variate transformation and de-trending of near-infrared diffuse reflectance spectra." Applied spectroscopy 43.5 (1989): 772-777.
Beer, W.H.; Murray, E.; Oh, S.H.; Pedersen, H.E.; Wolfe, R.R.; Young, V.R. A long-term metabolic study to assess the nutritional value of and immunological tolerance to two soy-protein concentrates in adult humans. Am. J. Clin. Nutr. 1989, 50, 997-1007.
C. Lin, X. Chen, L. Jian, C. Shi, X. Jin, G. Zhang, "Determination of grain protein content by near-infrared spectrometry and multivariate calibration in barley," Food Chemistry 162, 10-15 (2014).
Dobbin, K., Simon, R., Sample size determination in microarray experiments for class comparison and prognostic classification. Biostatistics 2005, 6, 27-38.
Example costs listings: https://www.conflabs.com/testing-packages-pricing/; https://www.alpha-cat.org/resources/how-much-cost-cannabis-testing/ (accessed Feb. 20, 2020).
Fontaine et al., "Near-Infrared reflectance spectroscopy enables the fast and accurate prediction of the essential amino acid contents in soy, rapeseed meal, sunflower meal, peas, fishmeal, meat meal products, and poultry meal," J. Agric. Food Chem. 2001, 49, 57-66.

Gatlin et al., "Expanding the utilization of sustainable plant products in aquafeeds: a review," Aquaculture Research 2007, 38, 551-579.
Geladi, P., D. McDougall and H. Martens. "Linearization and Scatter-Correction for Near-infrared Reflectance Spectra of Meat," Applied Spectroscopy, vol. 39, pp. 491-500, 1985.
Gracia, M-B, Armstrong, PR, Rongkui, H, Mark, S. 2017. Quantification of betaglucans, lipid and protein contents in whole oat groats (*Avena sativa* L.) using near infrared reflectance spectroscopy. JNIRS 25(3): 172-179.
Grieshop, C.M.; Kadzere, C.T.; Clapper, G.M.; Flickinger, E.A.; Bauer, L.L.; Frazier, R.L.; Fahey, G.C. Chemical and nutritional characteristics of United States soybeans and soybean meals. J. Agric. Food Chem. 2003, 51, 7684-7691.
Henchion, M; Hayes, M.; Mullen, AM; Fenelon, M; Tiwari, B. Future protein supply and demand: strategies and factors influencing a sustainable equilibrium. Foods 2017, 6, 53-74.
Hoffman, J.R.; Falvo, M.J. Protein—Which is Best? J. Sports Sci. Med. 2004, 3, 118-130.
Hemp, https://thehempmag.com/2019/06/the-trouble-with-lab-testing-in-the-hemp-cbd-oil-industry/ (accessed Feb. 20, 2020).
International Preliminary Report on Patentability dated Dec. 2, 2021.
Irish, G. G.; Fickler, J.; Fontaine, J. Practical application of near infrared reflectance spectroscopy to predict amino acids in feed ingredients. Proc. Aust. Poult. Sci. Symp. 2003, 15, 69.
Isaksson, Tomas, and Bruce Kowalski. "Piece-wise multiplicative scatter correction applied to near-infrared diffuse transmittance data from meat products." Applied spectroscopy 47.6 (1993): 702-709.
J. Fontaine, B. Schirmer, J. Horr, "Near-Infrared Reflectance Spectroscopy (NIRS) enables the fast and accurate prediction of essential amino acid contents. 2. Results for wheat, barley, corn, triticale, wheat bran/middlings, rice bran, and sorghum," J. Agric. Food Chem. 50, 3902-3911 (2002).
Khoo, Hock Eng, et al. "Anthocyanidins and anthocyanins: colored pigments as food, pharmaceutical ingredients, and the potential health benefits." Food & nutrition research 61.1 (2017): 1361779.
Kovalenko. I.V; Rippke, G.R; Hurburgh, C.R; Determination of Amino Acid Composition of Soybeans (*Glycine max*) by Near-Infrared Spectroscopy. J. Agri Food Chem. 2006, 54, 3485-3491.
Lavine, B.K., Chemometrics, Anal. Chem.2000, 72, 91-98.
Lavine, BK and Workman, J. (2008) Chemometrics. Anal. Chem. 80:4519-4531.
Liu, Y., et al., "Studies on spectra/structure correlations in near-infrared spectra of proteins and polypeptides. Part I: a marker band for hydrogen bonds," Applied Spectroscopy 48, 10, 1994, 1249-1254.
M. Reese, "Amber waves of barley grain becoming more common in Ohio," Ohio's Country Journal, Jun. 18, 2019, https://www.ocj.com/2019/06/amber-waves-of-barley-grain-becoming-more-common-in-ohio/ (accessed Sep. 27, 2019).
Martens, Harald, and Edward Stark. "Extended multiplicative signal correction and spectral interference subtraction: new preprocessing methods for near infrared spectroscopy." Journal of pharmaceutical and biomedical analysis 9.8 (1991): 625-635.
Marventano, S.; Izquierdo Pulido, M.; Sánchez-González, C.; Godos, J.; Speciani, A.; Galvano, F.; Grosso, G. Legume consumption and CVD risk: A systematic review and meta-analysis. Public Health Nutr. 2017, 20, 245-254.
Neospectra, NeoSpectra Micro Development Kit, http://www.neospectra.com/shop-products/ (accessed Oct. 19, 2018).
NeoSpectra, Si-Ware Systems, "NeoSpecta-Micro—SWS62231—Spectral Sensor," Spec Sheet, https://662292468.r.worldcdn.net/wp-content/uploads/2019/09/NeoSpectra-SWS62231-Datasheet.v2-2.5-22-19.pdf.
Oppenheim, Alan V. and R. W. Schafer, Digital Signal Processing, Englewood Cliffs, N.J.: Prentice Hall, 1975, pp. 195-271. https://azrael.digipen.edu/MAT321/DiscreteTimeSignalProcessing3.pdf.
Paudel, D, Caffe-Treml, M. and Krishnan P. 2018. A Single Analytical Platform for the Rapid and Simultaneous Measurement of Protein, Oil, and beta-Glucan Contents of Oats Using Near-Infrared Reflectance Spectroscopy. Cereal Foods World, 63(1):17-25.

(56) References Cited

OTHER PUBLICATIONS

Pazdernik, D.L; Killiam, A. S.; Orf, J. H. Analysis of amino and fatty acid composition in soybean seed using near infrared reflectance spectroscopy. Agron. J. 1997. 86, 679-685.

PRNewswire, "US retail sales of CBD to increase 133% in 2019, surpass $10 billion by 2024," Oct. 17, 2019. https://www.prnewswire.com/news-releases/us-retail-sales-of-cbd-to-increase-133-in-2019-surpass-10-billion-by-2024-300940056.html.

Richter, C.K.; Skulas-Ray, A.C.; Champagne, C.M.; Kris-Etherton, P.M. Plant Protein and Animal Proteins: Do They Differentially Affect Cardiovascular Disease Risk? Adv. Nutr. Int. Rev. J. 2015, 6, 712-728.

Rinnan, Å., Van Der Berg, WJ., Engelsen SB. (2009) Review of the most common pre-processing techniques for near-infrared spectra. TRAC Trends in Analytical Chemistry, 28 (10):1201-1222.

Rizzo, G and Baroni, L. Soy, Soy Foods and Their Role in Vegetarian Diets. Nutrients 2018, 10, 43-94.

S.A. Halsey, "Analysis of whole barley kernels using near infrared reflectance spectroscopy," J. Inst. Brew. 93, 461-464 (1987).

Savitzky, A. and M. J. E. Golay. "Smoothing and Differentiation of Data by Simplified Least Squares Procedures," Anal. Chem., vol. 36, No. 8, pp. 1627-1639, 1964.

Schaafsma G. Advantages and limitations of the protein digestibility-corrected amino acid score (PDCAAS) as a method for evaluating protein quality in human diets. J Nutr. 2012, 108.

Sterna, V., Zute, S., and Brunava, L. 2016. Oat Grain Composition and its Nutrition Benefice. J. Agric Food Chem. 8:252-256.

Sum, S. and S. D. Brown, "Standardization of Fiber-Optic Probes for Near-Infrared Multivariate Calibrations," Applied Spectroscopy, vol. 52, No. 6, pp. 869-877, 1998.

Sum, S. T., "Spectral Signal Correction for Multivariate Calibration," Doctoral Dissertation, University of Delaware, Summer 1998.

T. B. Blank, S. T. Sum, S. D. Brown and S. L. Monfre, "Transfer of near-infrared multivariate calibrations without standards," Analytical Chemistry, 68, pp. 2987-2995, 1996.

Tilman, D.; Clark, M. Global diets link environmental sustainability and human health. Nature 2014, 515, 518-522.

United States Soybean Export Council, "United States Soybean Quality Annual Report 2016," Nov. 2016, 18 pages.

USDA National Agricultural Statistics Service, National Statistics for Barley, https://www.nass.usda.gov/Statistics_by_Subject/result.php?1D276BD8-3324-3051-B34F-SED84AE56A38§or=CROPS&group=FIELD%20CROPS&comm=BARLEY (accessed Oct. 3, 2019).

USSEC 2018. United States Soybean Export Council, "Global Demand for Enhanced-Quality Soybeans Equals Premiums Paid to U..S. Farmers", USSEC 2018.

Van Kempen. T. A. T. G.: Simmins, P.H. Near-infrared reflectance spectroscopy in precision feed formulation. J. ApplPoult. Res. 1996, 6, 471-477.

Van Zanten, H.H.E.; Mollenhorst, H.; Klootwijk, C.W.; van Middelaar, C.E.; de Boer, I.J.M. Global food supply: Land use efficiency of livestock systems. Int. J. Life Cycle Assess. 2016, 21, 747-758.

Weiss, M., Manneberg, M., Juranville, J.F., Lahm, H.W., Fountoulakis, M., Effect of the hydrolysis method on the determination of the amino acid composition of proteins. J. Chromatogr. A. 1998, 6, 263-75.

Wold, S.; Sjöström, M; Eriksson, L. PLS-regression: a basic tool of chemometrics, Chemometrics and Intelligent Laboratory Systems, 2001, 58, 109-130.

World Health Organization; Food and Agriculture Organization of the United Nations; United Nations University. Joint WHO/FAO/UNU Expert Consultation. Protein and Amino Acid Requirements in Human Nutrition; World Health Organ: Geneva, Switzerland, 2007; pp. 1-265. https://apps.who.int/iris/bitstream/handle/10665/43411/WHO_TRS_935_eng.pdf?sequence=1&isAllowed=y.

Wu, J. G.; Shi, C.; Zhang, X. Estimating the amino acid composition in milled rice by near-infrared reflectance spectroscopy. Fields Crops Res.2002, 75, 1-7.

* cited by examiner

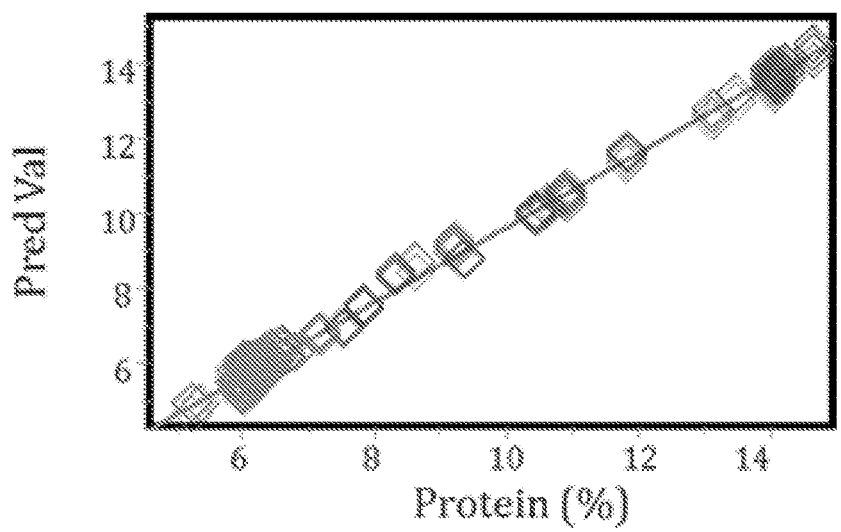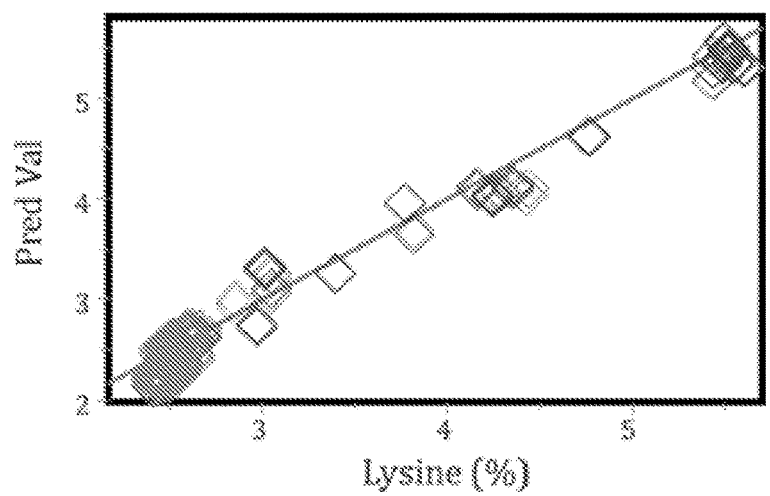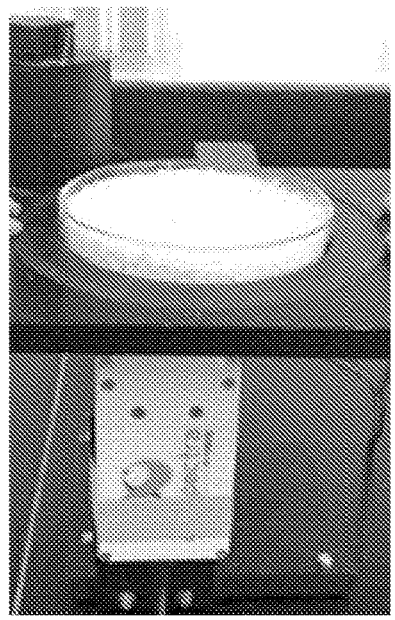
FIG. 16

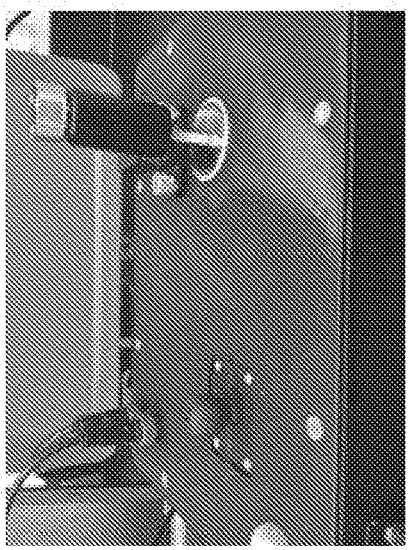
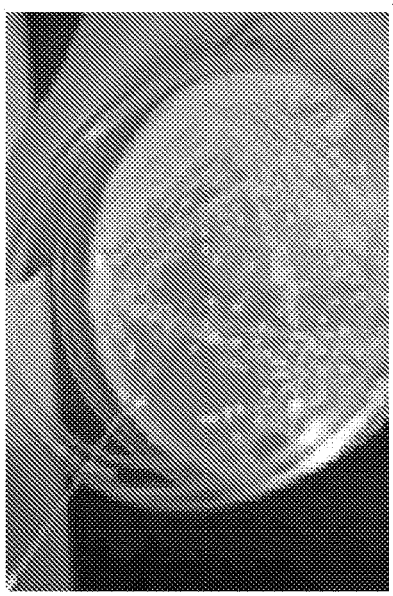
FIG. 22

|  | Conc (nmol/mL) | Average CV (%) |
|---|---|---|
| Low | 200 | 8.3 |
| Medium | 800 | 4.9 |
| High | 1600 | 5.1 |

Hydrolysis

| Amino acid | Leverage of Factors (p-value) | | | |
|---|---|---|---|---|
| | Hydrolysis Errors | Defatting | Mass | pH |
| Overall | <0.001 | 0.105 | <0.001 | 0.036 |

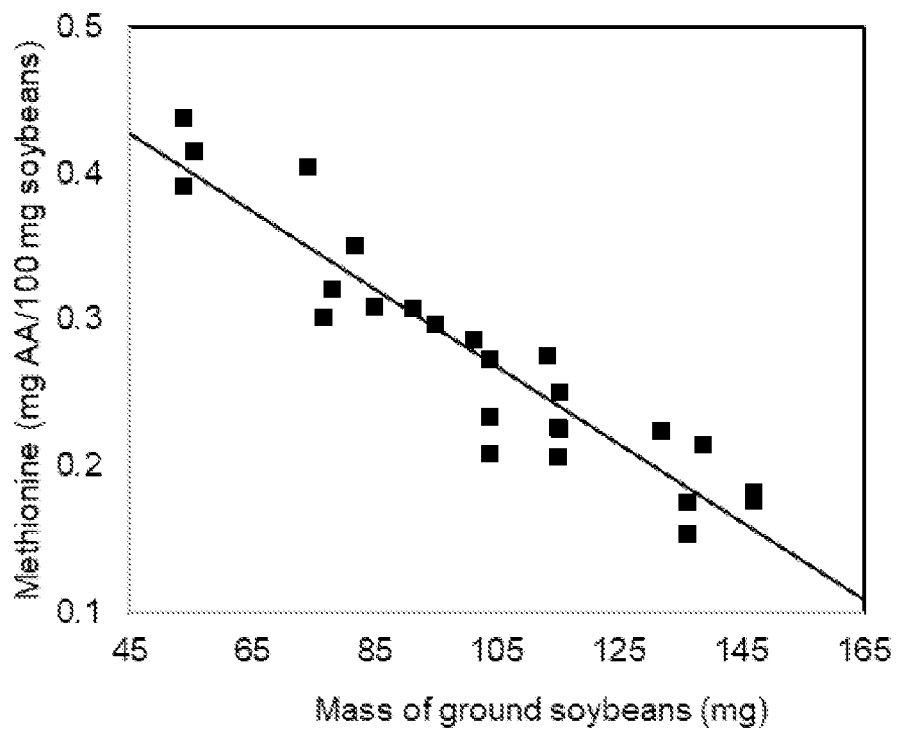
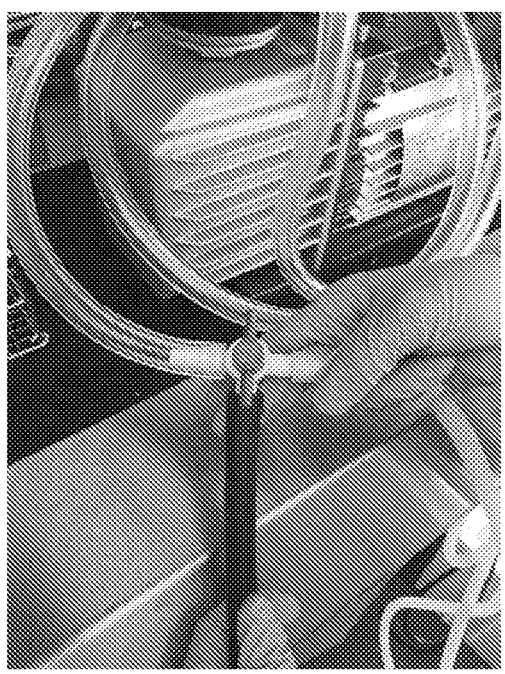
FIG. 36A

| | | Calibration Model | | | | Validation Model | | |
|---|---|---|---|---|---|---|---|---|
| | | Range | Factors | SECV | Rcal | Range | SEP | Rval |
| Powder | Threonine (%) | 1.34 - 3.23 | 4 | 0.051 | 0.998 | 1.40 - 3.16 | 0.062 | 0.995 |
| | Cysteine (%) | 0.45 - 1.06 | 4 | 0.041 | 0.981 | 0.54 - 1.00 | 0.043 | 0.978 |
| | Methionine (%) | 0.47 - 1.14 | 4 | 0.044 | 0.985 | 0.47 - 1.13 | 0.090 | 0.900 |
| | Lysine (%) | 2.34 - 5.54 | 5 | 0.246 | 0.983 | 2.43 - 5.37 | 0.238 | 0.981 |
| | Tryptophan (%) | 0.30 - 1.32 | 3 | 0.080 | 0.970 | 0.30 - 1.23 | 0.097 | 0.962 |
| | Crude protein (%) | 33.00 - 84.30 | | .630 | 0.997 | 33.35 - 79.25 | 2.801 | 0.985 |
| Intact Seeds | Threonine (%) | 1.36 - 1.53 | Carrera et al. 2011 0.87 - 2.19 | .012 | 0.971 | 1.40 - 1.45 | 0.011 | 0.902 |
| | Cysteine (%) | 0.51 - 0.62 | 0.14 - 0.68 | .014 | 0.944 | 0.56 - 0.60 | 0.068 | 0.796 |
| | Methionine (%) | 0.52 - 0.61 | 0.31 - 0.85 | .013 | 0.948 | 0.52 - 0.57 | 0.055 | 0.939 |
| | Lysine (%) | 2.37 - 2.57 | 0.88 - 3.92 | .014 | 0.981 | 2.38 - 2.54 | 0.035 | 0.878 |
| | Tryptophan (%) | 0.30 - 0.47 | 0.30 - 0.80 | .015 | 0.960 | 0.36 - 0.43 | 0.022 | 0.946 |
| | Total Protein (%) | 32.83 - 36.66 | 5 | 0.221 | 0.980 | 33.80 - 35.86 | 0.634 | 0.882 |

FIG. 41

| Value of R | Interpretation (Williams 1978) | Powder Models | Intact Seed Models |
|---|---|---|---|
| 0.71 – 0.80 | Suitable for rough screening | | Cysteine |
| 0.81 – 0.90 | OK for screening and approximate work | | Lysine, Crude Protein |
| 0.91 – 0.95 | Usable with caution for most applications | | Threonine, Methionine, Tryptophan |
| 0.96 – 0.98 | Usable in most applications | Cysteine, Lysine, Tryptophan, Crude Protein | |
| ≥ 0.99 | Excellent, usable in any application | Threonine | |

FIG. 42

|  | Brix | Titratable Acidity (%citric) | Glucose (g/100g) | Fructose (g/100g) | Ascorbic Acid (mg/100g) | Citric Acid (g/100g) | Malic Acid (g/100g) |
|---|---|---|---|---|---|---|---|
| Minimum | 2.98 | 0.15 | 0.39 | 0.59 | 4.39 | 0.17 | 0.01 |
| Maximum | 10.43 | 0.95 | 4.59 | 4.69 | 61.87 | 2.36 | 0.37 |
| Mean | 5.03 | 0.44 | 1.54 | 1.73 | 20.71 | 0.58 | 0.08 |
| Standard deviation | 1.06 | 0.13 | 0.52 | 0.52 | 9.57 | 0.23 | 0.06 |
FIG. 44
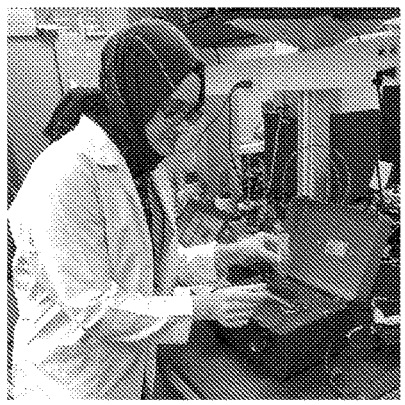 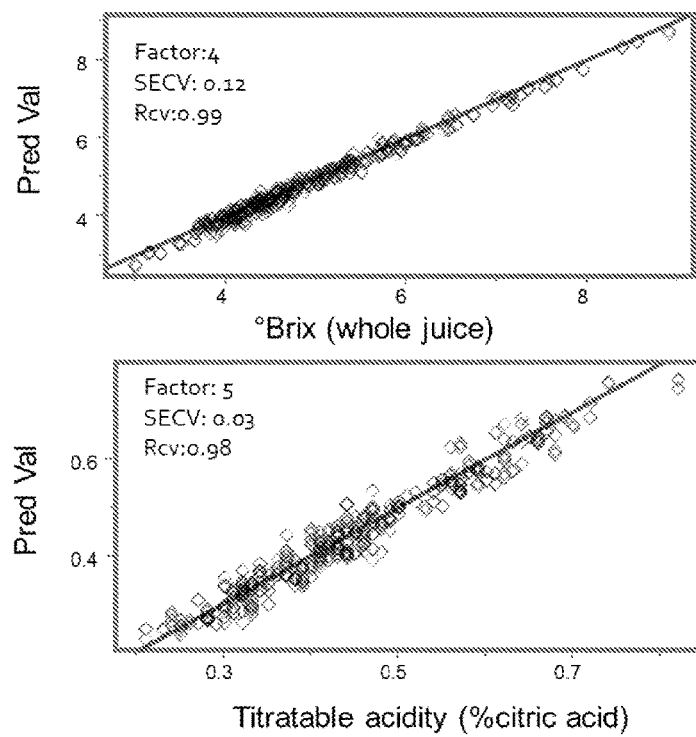
FIG. 45

| Parameter | Spectrometer | N | Range | Factors | SECV | Rcv |
|---|---|---|---|---|---|---|
| Brix | Cary 630: supernatant | 625 | 2.98-9.33 | 4 | 0.13 | 0.99 |
| | Cary 630: whole juice | 270 | 2.98-10.43 | 4 | 0.17 | 0.99 |
| | 4500: whole juice | 205 | 2.98-8.89 | 4 | 0.12 | 0.99 |
| Titratable acidity (%citric) | Cary 630: supernatant | 578 | 0.17-0.99 | 4 | 0.04 | 0.96 |
| | Cary 630: whole juice | 246 | 0.21-0.83 | 5 | 0.05 | 0.93 |
| | 4500: whole juice | 187 | 0.21-0.82 | 5 | 0.03 | 0.98 |
| Glucose (g/100g) | Cary 630: supernatant | 512 | 0.39-3.01 | 4 | 0.09 | 0.98 |
| | Cary 630: whole juice | 218 | 0.55-2.76 | 5 | 0.06 | 0.99 |
| | 4500: whole juice | 174 | 0.60-2.54 | 4 | 0.06 | 0.99 |
| Fructose (g/100g) | Cary 630: supernatant | 522 | 0.59-3.03 | 3 | 0.10 | 0.97 |
| | Cary 630: whole juice | 225 | 0.59-2.71 | 5 | 0.08 | 0.98 |
| | 4500: whole juice | 178 | 0.89-3.07 | 5 | 0.07 | 0.99 |
| Ascorbic Acid (mg/100g) | Cary 630: supernatant | 310 | 4.39-45.77 | 6 | 4.59 | 0.78 |
| | Cary 630: whole juice | 128 | 8.08-45.77 | 4 | 3.38 | 0.87 |
| | 4500: whole juice | 96 | 10.78-56.58 | 6 | 3.51 | 0.91 |
| Citric Acid (g/100g) | Cary 630: supernatant | 407 | 0.32-1.24 | 4 | 0.06 | 0.94 |
| | Cary 630: whole juice | 116 | 0.33-1.04 | 4 | 0.05 | 0.95 |
| | 4500: whole juice | 106 | 0.36-1.20 | 5 | 0.06 | 0.94 |

FIG. 46

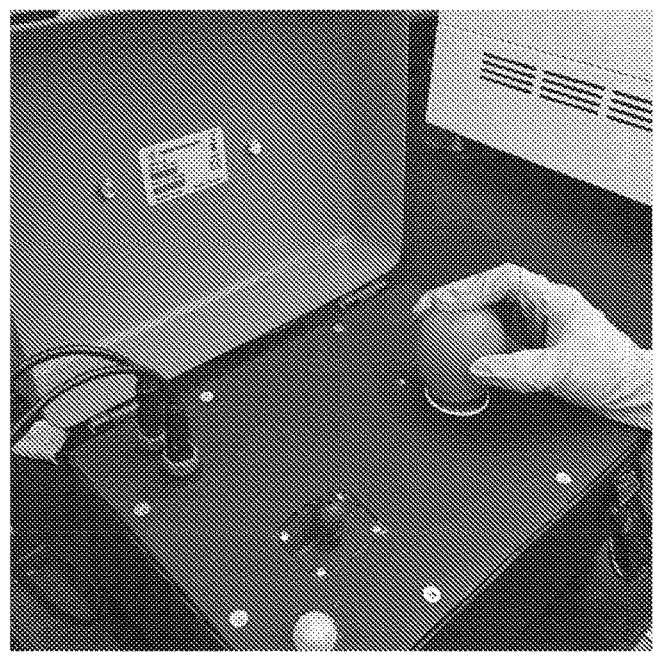
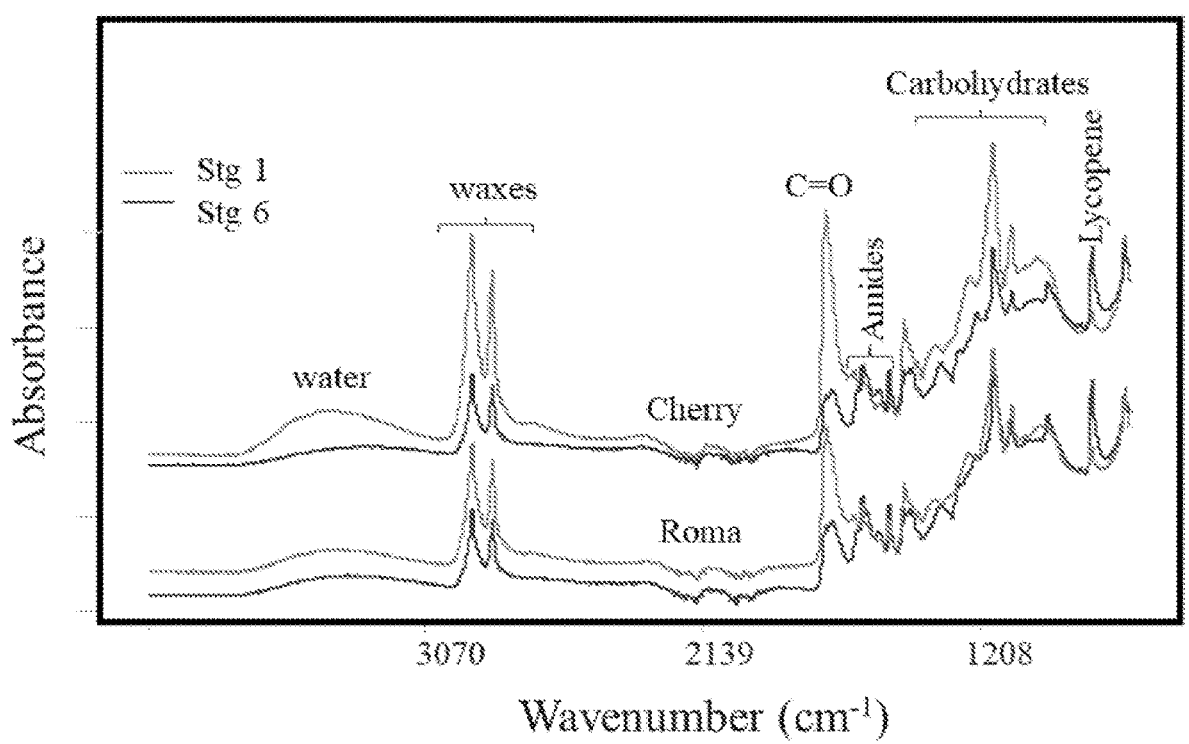
FIG. 47

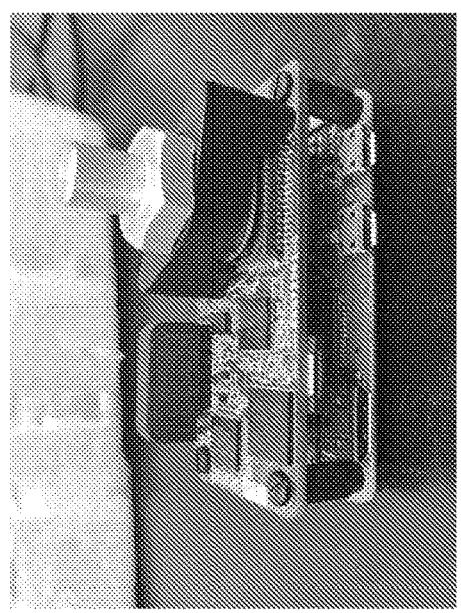
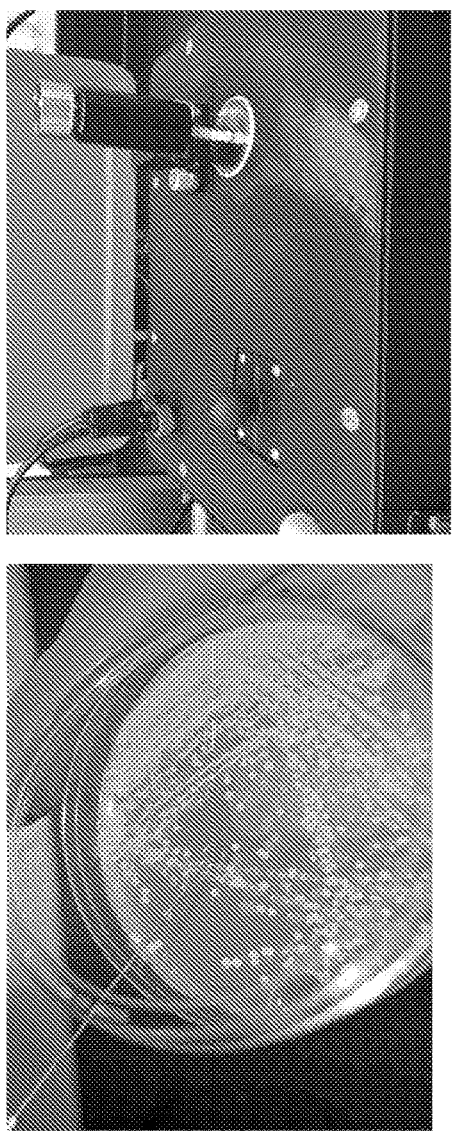
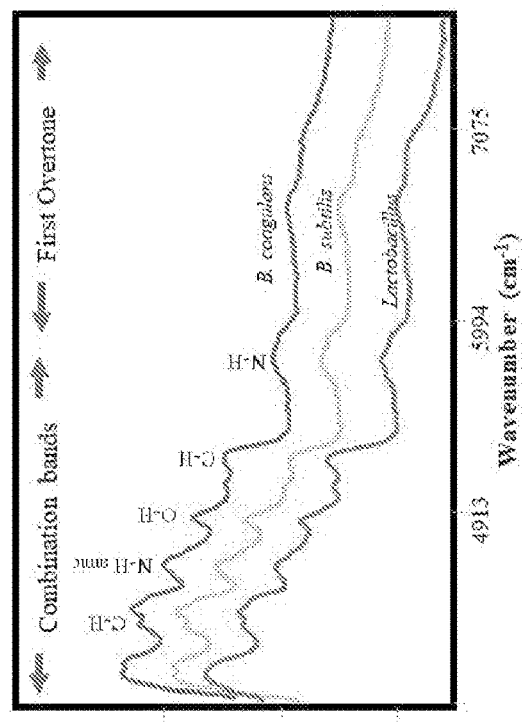
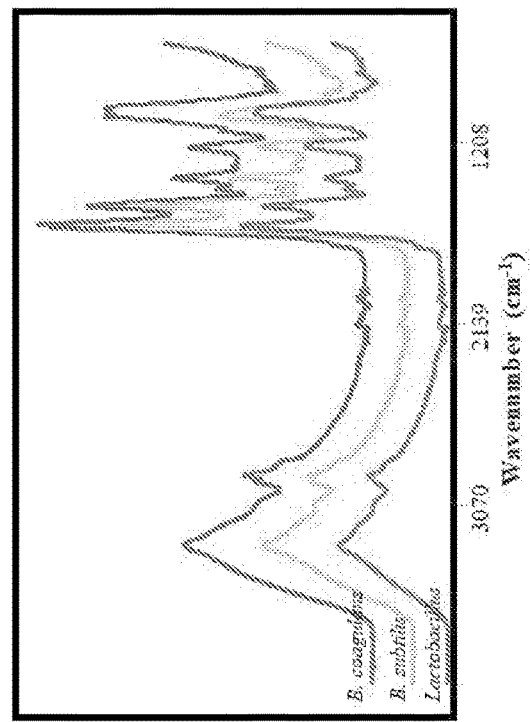
FIG. 50

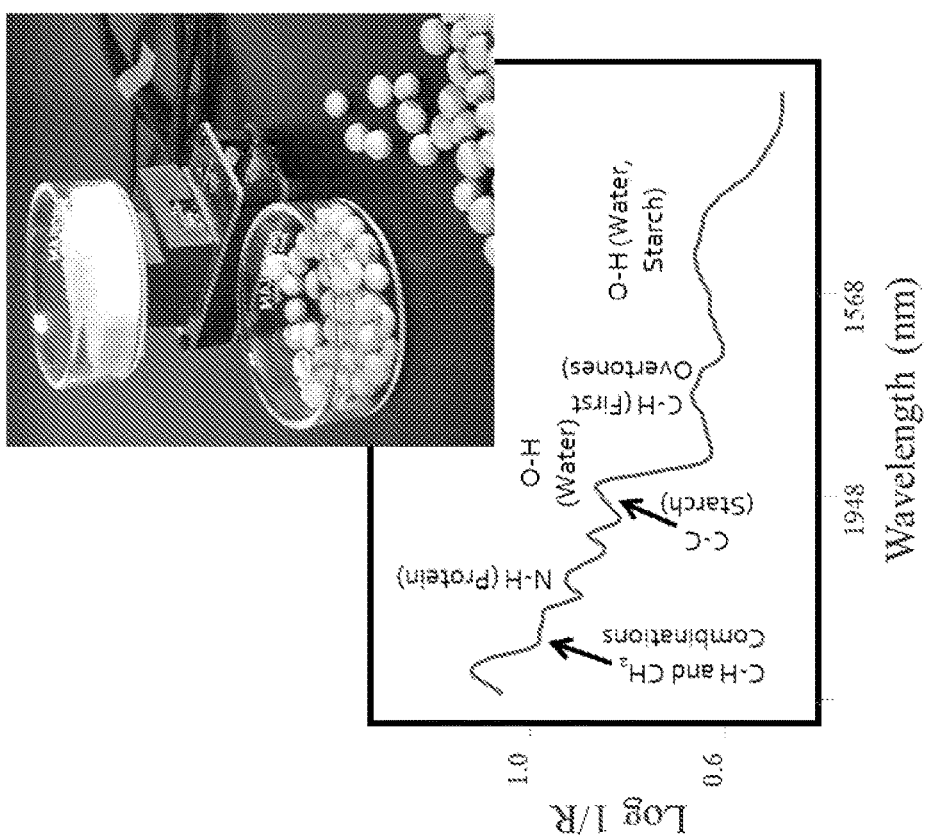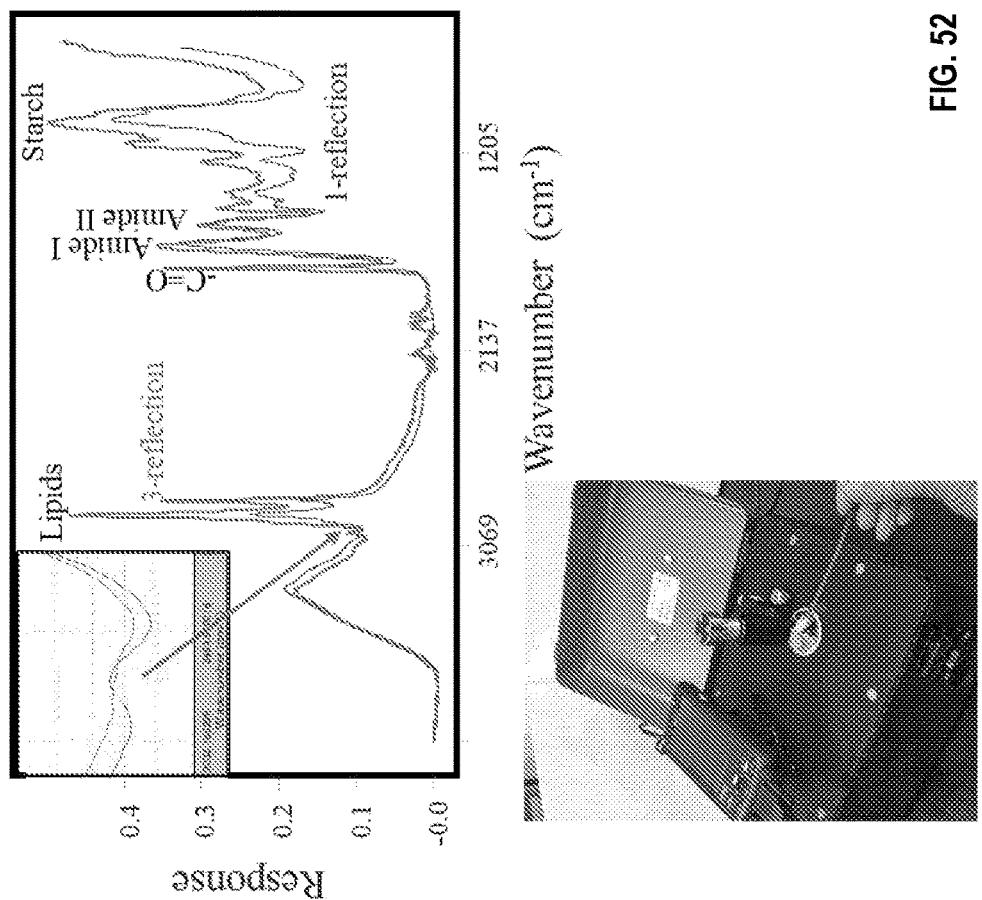
FIG. 52

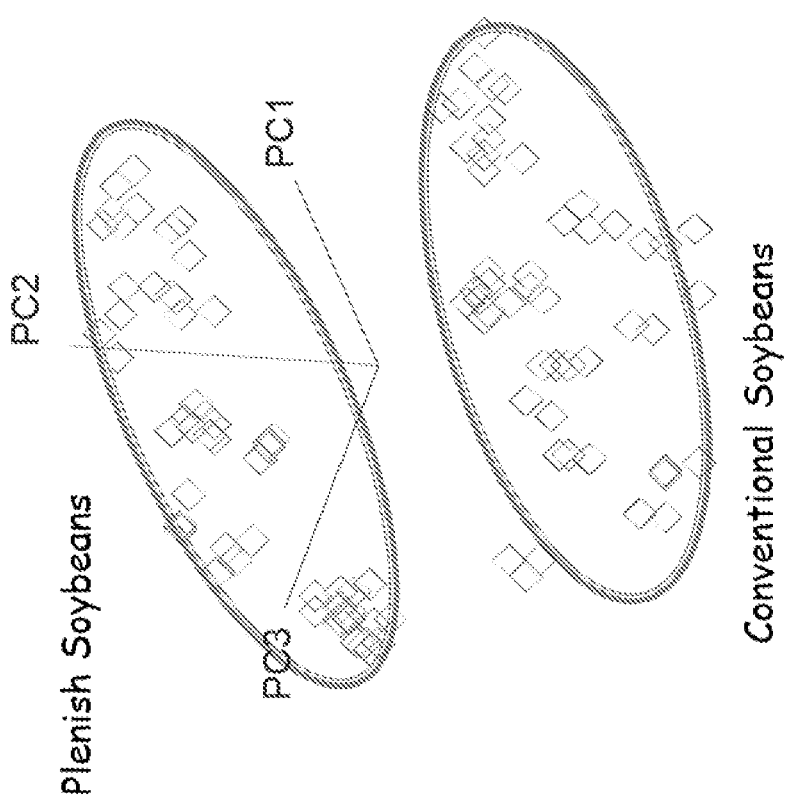
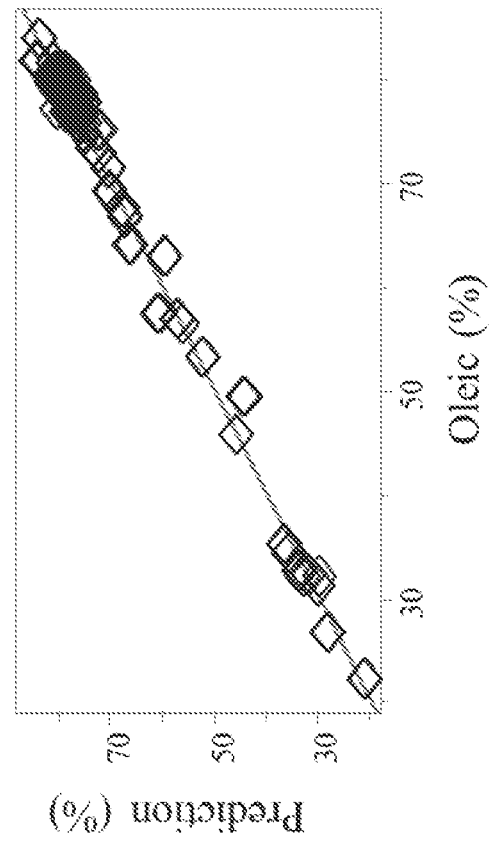
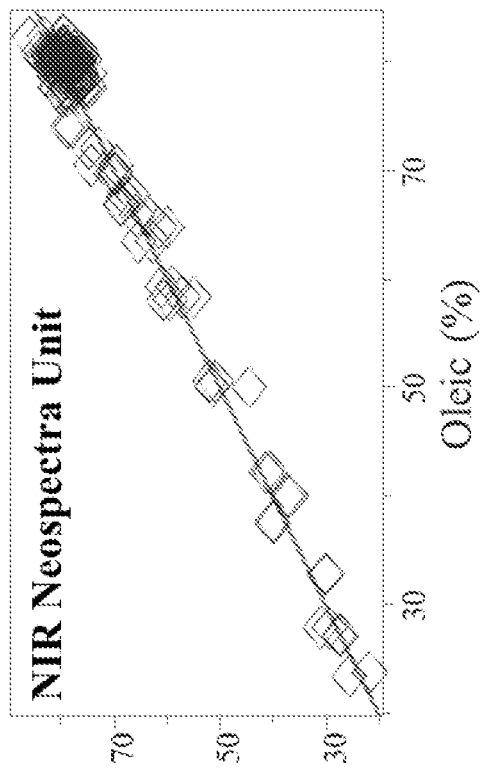
FIG. 53

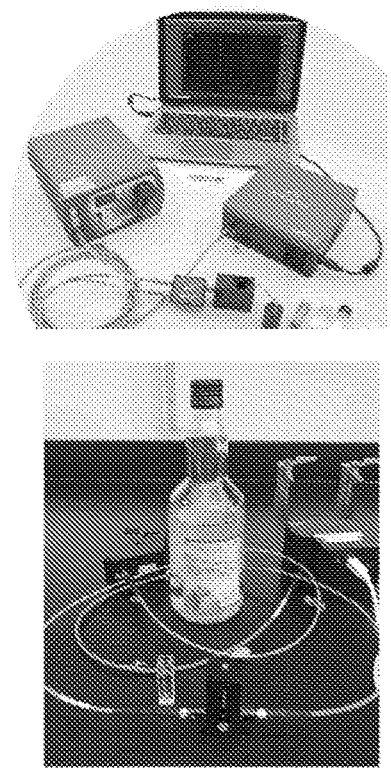
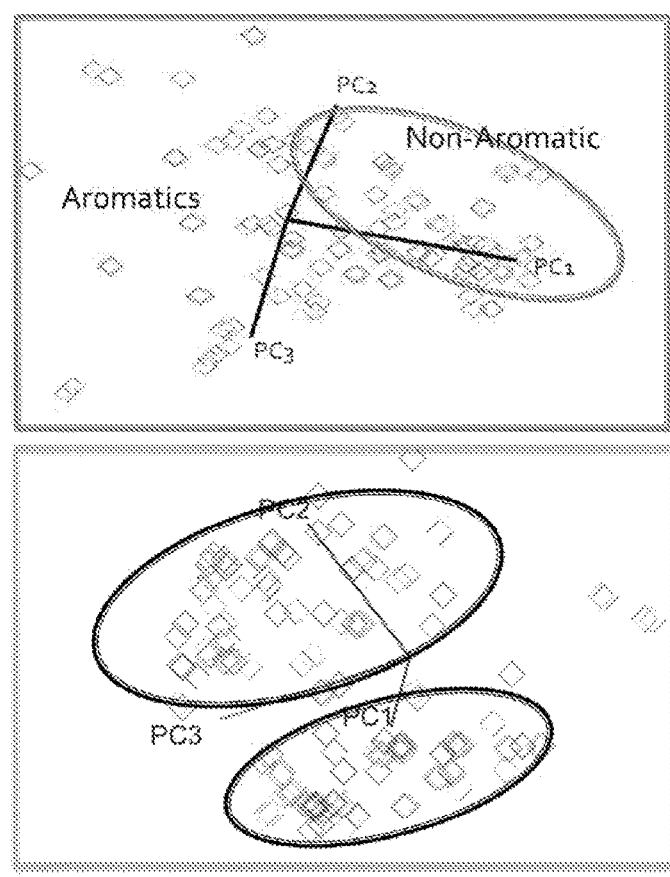
FIG. 54B

FIG. 55

| Model Type | Technology | Samples | Sensitivity (%) | Specificity (%) |
|---|---|---|---|---|
| Multiclass | FT-IR | VOO & Refined OO blends | 100 | 100 |
| | | EVOO with other vegetable oils | 100 | 100 |
| | Raman | VOO & Refined OO blends | 100 | 100 |
| | | EVOO with other vegetable oils | 100 | 100 |
| One-class | FT-IR | | 100 | 89 |
| | Raman | | 100 | 66 |

FIG. 60

|  |  | Calibration Model | | | | | Validation Model | | | |
|---|---|---|---|---|---|---|---|---|---|---|
|  |  | Range | N | Factor | SECV | Rcal | Range | n | SEP | Rval |
| FT-IR | Palmitic (%) | 5.3-18.9 | 120 | 6 | 0.44 | 0.98 | 6.5-18.1 | 30 | 0.53 | 0.98 |
|  | Stearic (%) | 2.7-3.6 | 120 | 4 | 0.03 | 0.98 | 2.7-3.5 | 30 | 0.02 | 0.99 |
|  | Oleic (%) | 11.0-78.2 | 120 | 4 | 1.13 | 0.99 | 29.9-78.0 | 30 | 1.41 | 0.99 |
|  | Linoleic (%) | 4.5-76.0 | 120 | 4 | 1 | 0.99 | 5.7-41.0 | 30 | 1.4 | 0.98 |
|  | Linolenic (%) | 0.5-1.8 | 117 | 4 | 0.02 | 0.99 | 0.6-1.0 | 29 | 0.02 | 0.97 |
| Raman | Palmitic (%) | 5.3-18.9 | 120 | 6 | 0.84 | 0.91 | 6.5-18.1 | 30 | 0.99 | 0.92 |
|  | Stearic (%) | 2.7-3.6 | 120 | 5 | 0.04 | 0.98 | 2.7-3.5 | 30 | 0.04 | 0.97 |
|  | Oleic (%) | 11.0-78.2 | 120 | 6 | 1.33 | 0.99 | 29.9-78.0 | 30 | 1.78 | 0.98 |
|  | Linoleic (%) | 4.5-76.0 | 120 | 4 | 1.09 | 0.99 | 5.7-41.0 | 30 | 1.63 | 0.99 |
|  | Linolenic (%) | 0.5-1.8 | 118 | 6 | 0.02 | 0.99 | 0.6-1.0 | 30 | 0.01 | 0.98 |

|  |  | Calibration Model | | | | | Validation Model | | | |
|---|---|---|---|---|---|---|---|---|---|---|
|  |  | Range | N | Factor | SECV | Rcal | Range | n | SEP | Rval |
| FT-IR | FFA (%) | 0.1-10.3 | 118 | 3 | 0.17 | 1 | 0.1-6.8 | 30 | 0.23 | 0.99 |
|  | PV (meqO₂/kg) | 2.5-32.7 | 120 | 5 | 0.65 | 0.98 | 4.9-19.1 | 30 | 0.79 | 0.96 |
|  | TPC (%) | 2.5-17.8 | 120 | 6 | 0.54 | 0.97 | 3.3-13.3 | 30 | 0.59 | 0.97 |
| Raman | FFA (%) | 0.1-10.3 | 118 | 6 | 0.55 | 0.94 | 0.1-6.8 | 30 | 0.52 | 0.93 |
|  | PV (meqO₂/kg) | 2.5-32.7 | 120 | 4 | 1.31 | 0.92 | 4.9-19.1 | 30 | 1.11 | 0.92 |
|  | TPC (%) | 2.5-17.8 | 119 | 6 | 0.76 | 0.94 | 3.3-13.3 | 30 | 0.83 | 0.93 |

FIG. 61

| Type | Sample | g trans/ 100g | g trans-fats/serving label | g trans-fats/ serving (GC-FAME) | g trans-fats/serving PLSR |
|---|---|---|---|---|---|
| Cookies | A | 1.0 | 0 | 0.06 | 0.01 |
| | B | 35.5 | 0 | 0.89 | 0.81 |
| | C | 0.7 | 0 | 0.08 | 0.08 |
| | D | 34.8 | 0 | 1.33 | 1.2 |
| Bakery Products | A | 2.0 | 0 | 0.11 | 0.12 |
| | B | 3.4 | 0 | 0.23 | 0.13 |
| | C | 49.6 | 5 | 3.58 | 3.57 |
| | D | 4.9 | 1 | 2.23 | 2.26 |
| Donuts | A | 37.5 | n.a. | 6.84 | 6.71 |
| | B | 26.4 | n.a. | 6.67 | 6.56 |
| | C | 45.6 | n.a. | 6.95 | 6.7 |
| Potatoes chips | A | 46.3 | 4 | 2.06 | 2.85 |
| | B | 1.6 | 0 | 0.36 | 0.33 |
| | C | 53.0 | 4 | 4.75 | 4.8 |
| Correlation with GC-FAME | | | | | 0.99 |

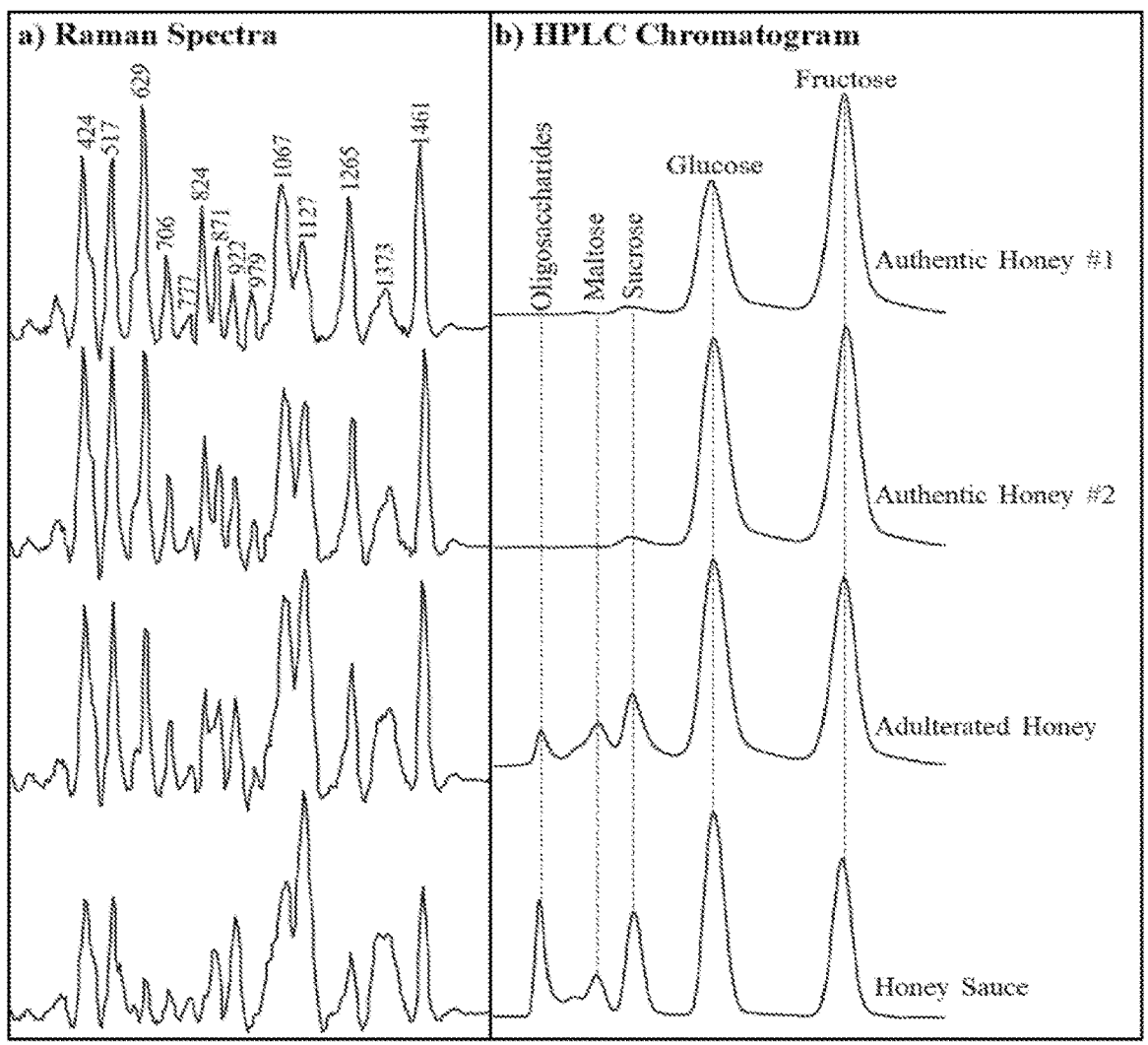
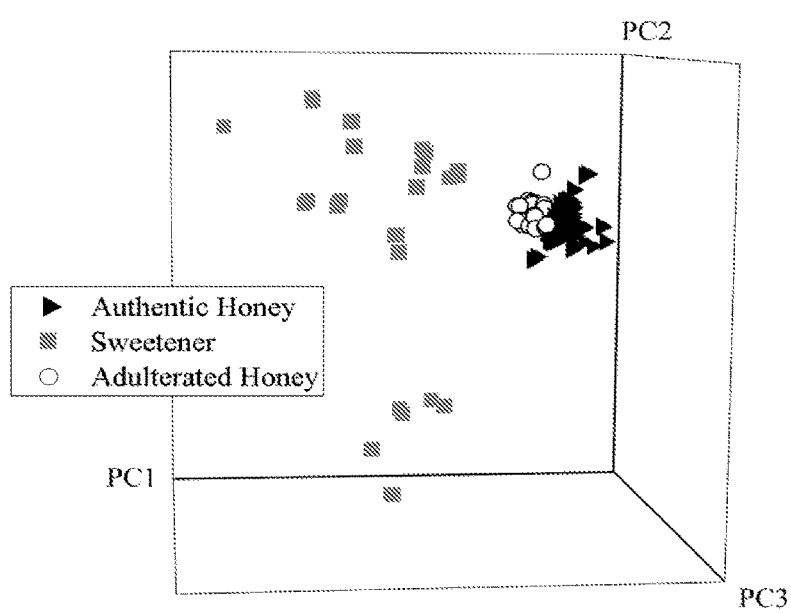
FIG. 65

| | Quality | Factors | SECV | Rcv |
|---|---|---|---|---|
| Powder | Moisture | 2 | 0.13 | 0.93 |
| | Starch | 4 | 1.21 | 0.93 |
| | Fat | 4 | 0.26 | 0.97 |
| | β-glucan | 6 | 0.20 | 0.92 |

FIG. 70

Table 3 Typical composition (as-fed basis) of fish meal and various plant feedstuffs

| Ingredient | International feed number | Dry matter (%) | Protein (%) | Lipid (%) | Ash (%) | Lysine (%) | Methionine (%) | Cystine (%) |
|---|---|---|---|---|---|---|---|---|
| Fish meal, herring* | 5-02-000 | 92.0 | 72.0 | 8.4 | 10.4 | 5.57 | 2.08 | 0.74 |
| Barley† | 4-00-552 | 88.0 | 14.9 | 2.1 | 2.9 | 0.53 | 0.18 | 0.23 |
| Canola* | 5-06-145 | 90.0 | 38.0 | 3.8 | 6.8 | 2.27 | 0.70 | 0.47 |
| Corn* | 4-02-935 | 88.0 | 8.5 | 3.6 | 1.3 | 0.25 | 0.17 | 0.22 |
| Corn gluten meal* | 5-28-242 | 91.0 | 60.4 | 1.9 | 2.1 | 1.11 | 1.63 | 1.20 |
| Cottonseed meal* | 5-01-619 | 92.0 | 41.7 | 1.9 | 6.4 | 1.89 | 0.50 | 0.45 |
| Lupin Lupinus angustifolius (whole) | 5-27-717 | 88.0 | 39.2 | 10.3 | 2.8 | 1.40 | 0.27 | 0.51 |
| Field peas (Vetch)† | 5-03-600 | 89.0 | 25.6 | 1.3 | 3.4 | 1.59 | 0.21 | 0.32 |
| Soybean meal, de-hulled* | 5-04-612 | 89.0 | 48.5 | 0.9 | 5.8 | 3.08 | 0.68 | 0.75 |
| Soy protein concentrate‡ | | 90.0 | 64.0 | 3.0 | 1.2 | 4.20 | 0.90 | 0.92 |
| Wheat* | 4-05-268 | 88.0 | 13.9 | 1.7 | 1.6 | 0.38 | 0.21 | 0.27 |

*Data from NRC (1993)
†Data from NRC (1998)
‡Data from Allan et al. (2000)

FIG. 71

| Wavelength [nm] | Wavenumber [cm⁻¹] | Assignment |
|---|---|---|
| 2500 | 4000 | combination S–H stretching |
| 2200–2460 | 4545–4065 | combination C–H stretching |
| 2000–2200 | 5000–4545 | combination N–H stretching; combination O–H stretching |
| 1620–1800 | 6173–5556 | first overtone C–H stretching |
| 1400–1600 | 7143–6250 | first overtone N–H stretching; first overtone O–H stretching |
| 1300–1420 | 7692–7042 | combination C–H stretching |
| 1100–1225 | 9091–8163 | second overtone C–H stretching |
| 1020–1060 | 9804–9434 | combination S=O stretching |
| 950–1100 | 10526–9091 | second overtone N–H stretching; second overtone O–H stretching |
| 850–950 | 11765–10526 | third overtone C–H stretching |
| 775–850 | 12903–11765 | third overtone N–H stretching |
| 600–700 | 16667–14286 | combination C–S stretching |
| 450–550 | 22222–18182 | combination S–S stretching | taken from B.H. Stuart, *Infrared Spectroscopy: Fundamentals and Applications* (2004)

FIG. 77

PORTABLE SPECTROMETER SYSTEM AND METHODS FOR DETERMINING NUTRITIONAL AND QUALITY TRAITS

CROSS-REFERENCE TO RELATED APPLICATIONS

This application is a national stage application filed under 35 U.S.C. § 371 of PCT/US2020/034009 filed May 21, 2020, which claims the benefit of U.S. Provisional Application No. 62/850,597, filed May 21, 2019, incorporated herein by reference in its entirety.

FIELD

The present disclosure relates a spectroscopic sensor and uses thereof for measuring traits in food products.

BACKGROUND

Improving quality in agricultural and food product is essential. Most phenotypic analyses are time-consuming, expensive and very labor-intensive for agriculture products improvement programs where many samples have to be screened. The community (farmers, nutritionists, food producers, researchers) need inexpensive tools to enable quick, accurate measurements of the quality of agricultural products. What is needed are improved devices and methods for quick and accurate measurement of traits in agricultural and food products and for grading the products. The devices and methods disclosed herein address these and other needs

SUMMARY

Disclosed herein are systems and devices for use in determining a level of a trait in an agriculture or food product sample. Further disclosed is a portable spectrometer system coupled with chemometric analysis methods to determine a level of a trait in an agriculture or food product sample.

In some aspect, disclosed herein disclosed herein is a portable spectrometer system comprising:
- a spectrometer;
- a sample stage adjacent the spectrometer;
- a motor coupled to the sample stage; and
- a system housing enclosing the motor and the spectrometer;
- wherein rotation of the motor rotates the sample stage, and
- wherein the motor is controllable in response to spectroscopy requirements.

In some embodiments, the system further comprises an interface device and an external processor, wherein the interface device and the external processor are each in electronic communication with the spectrometer and the motor.

In some embodiments, the external processor is configured to adjust the rotational position of the motor in response to spectroscopy measurement.

In some embodiments, the external processor is configured to adjust the rotational position of the motor to distribute near infrared (NIR) spectra about a specimen to minimize a spectroscopy scattering effect.

In some embodiments, the external processor is a mobile device.

In some aspects, disclosed herein is a method of determining a level of a trait in a sample using the system of any preceding aspects, comprising:
- placing the sample on the sample stage of the system;
- measuring a spectrum of the sample within a wavelength range using the spectrometer in the system; and
- determining the level of the trait based on the measured spectrum.

In some embodiments, the spectrometer is a NIR spectrometer. In some embodiments, the wavelength range is between about 700 nm to about 3000 nm. In some embodiments, the wavelength range is between about 1350 nm to about 2500 nm.

In some embodiments, the method of any preceding aspect further comprises commanding the system through the external processor to rotate the sample stage for rotating the sample.

In some embodiments, the method of any preceding aspect further comprises commanding the system through the external processor to process the data using algorithmic pre-processing. In some embodiments, the algorithmic pre-processing comprises: the collected spectrum is ratioed against a spectrum collected for a calibration standard In some embodiments, the method of any preceding aspect further comprises commanding the system through the external processor to apply a chemometric algorithm on the processed data to quantify the trait. In some embodiments, the chemometric algorithm comprises partial least squares regression, principal component analysis, or artificial neural networks.

In some embodiments, the method of any preceding aspect further comprises translating the quantitative results into a reporting format selected for a system operator. In some embodiments, the reporting format comprises a table of individual quantities, a graphical representation of the quantities, or an icon indicating the categorization or grade of the sample.

In some embodiments, the method of any preceding aspect further comprises displaying the level of the trait on the external processor.

In some embodiments, the sample comprises a sample of a field crop, a specialty crop, a raw ingredient, or a finished product.

In some aspects, disclosed herein is a method of determining a level of a trait in a field crop, comprising the following steps:
- obtaining a field crop sample;
- collecting spectroscopic data on the field crop sample;
- processing the data using algorithmic pre-processing;
- applying a chemometric algorithm on the processed data to quantify the trait; and
- translating the quantitative results into a reporting format selected for a system operator.

In some embodiments, wherein the reporting format comprises a table of individual quantities, a graphical representation of the quantities, or an icon indicating the categorization or grade of the sample.

In some embodiments, the field crop sample comprises a sample of soybean, oat, corn, barley, or potato.

In some embodiments, the trait measured in the soybean sample comprises an amino acid, a fatty acid, protein oil, fat, or water. In some embodiments, the amino acid comprises cysteine, lysine, methionine, threonine, or tryptophan. In some embodiments, the fatty acid comprises oleic, linoleic, or linolenic.

In some embodiments, the trait measured in the oat sample comprise β-glucan, protein, starch, or water.

In some embodiments, the trait measured in the corn sample comprises starch, sugar, water, protein, oil, or a toxin.

In some embodiments, the trait measured in the barley sample comprises valine, deoxynivalenol, protein, or water.

In some embodiments, the trait measured in the potato sample comprises acrylamide, starch, sugar, or water.

In some aspects, disclosed herein is a method of determining a level of a trait in a specialty crop, comprising the following steps:
  obtaining a specialty crop sample;
  collecting spectroscopic data on the specialty crop sample;
  processing the data using algorithmic pre-processing;
  applying a chemometric algorithm on the processed data to quantify the trait; and
  translating the quantitative results into a reporting format selected for a system operator.

In some embodiments, the specialty crop sample comprises a sample of cannabis, tomato, coffee, or fruit.

In some embodiments, the trait measured in the cannabis sample comprises tetrahydrocannabinol (THC), cannabidiol, or water.

In some embodiments, the trait measured in the tomato sample comprise comprises lycopene, sugar, moisture, or an acid.

In some embodiments, the trait measured in the coffee sample comprises acrylamide, caffeine, or water.

In some embodiments, the fruit sample comprises a sample of grape, blueberry, or apple.

In some embodiments, the trait measured in the fruit sample comprises anthocyanins, sugar, water, or an acid.

In some aspects, disclosed herein is a method of determining a level of a trait in a raw ingredient, comprising the following steps:
  obtaining a raw ingredient sample;
  collecting spectroscopic data on the raw ingredient sample;
  processing the data using algorithmic pre-processing;
  applying a chemometric algorithm on the processed data to quantify the trait; and
  translating the quantitative results into a reporting format selected for a system operator.

In some embodiments, the raw ingredient sample comprises a sample of meat or fish.

In some embodiments, the trait measured in the meat sample comprises an amino acid, protein, or fat.

In some embodiments, the trait measured in the fish sample comprises an amino acid, protein, or fat.

In some aspects, disclosed herein is a method of determining a level of a trait in a finished product, comprising the following steps:
  obtaining a finished product sample;
  collecting spectroscopic data on the finished product sample;
  processing the data using algorithmic pre-processing;
  applying a chemometric algorithm on the processed data to quantify the trait; and
  translating the quantitative results into a reporting format selected for a system operator In some embodiments, the finished product sample comprises a sample of pea protein or milk protein.

In some embodiments, the trait measured in the pea protein sample comprises an amino acid, protein, an adulterant, fungus, or bacteria.

In some embodiments, the trait measured in the milk powder sample comprises protein, lactose, an adulterant, fungus, or bacteria.

This analysis system is applicable to farmers growing food products, for example soybeans, for human or livestock consumption, crop distributors selecting the end use and determining the price of received crops, and food producers verifying the characteristics of crops they have purchased. This analysis system is advantageous over existing technology because of its speed, low cost, the relative simplicity and size of its hardware, the simplicity of the analysis approach (enable automation for less expert users), and the analysis for multiple quantitative characteristics simultaneously. Disclosed herein is a handheld, field deployable sensor that can measure and report accurate traits (for example, amino acid profiles) within seconds.

The accompanying figures, which are incorporated in and constitute a part of this specification, illustrate several aspects described below.

BRIEF DESCRIPTION OF THE DRAWINGS

The accompanying figures, which are incorporated in and constitute a part of this specification, illustrate several aspects described below.

FIG. 16 shows PLSR predictions of protein (top) and lysine (center) for ground soybean samples and enhanced soybean meals (bottom). Predictions show excellent linearity and strong predictive capability for both protein and essential amino acids based on data acquired from the handheld NIR NeoSpectra Micro.

FIG. 22 shows infrared devices (portable IR and handheld NIR) for fingerprinting bacteria biomass.

FIG. 23A shows infrared spectra of bacteria and their tentative band assignment. FIG. 23B shows PCA grouping of bacteria by genus.

FIGS. 36A-36B show key findings and important parameters to control. FIG. 36A shows factors including mass of samples and hydrolysis errors. Mass of Samples: higher mass correlated with lower recoveries of some amino acids, except for glycine, lysine, histidine, phenylalanine and cysteine ($p>0.05$). Hydrolysis Errors: Significant difference in yield for almost all amino acids. FIG. 36B shows factors including pH of hydrolysate (no significant effect on yield if pH is kept to between pH 1-pH 8, except for lysine, histidine, phenylalanine and cysteine ($p<0.05$)), defatting (only tyrosine recovery were significantly higher ($p=0.049$) if sample is defatted prior to hydrolysis), and oxidation inhibitor (yields of methionine, cysteine and lysine were significantly different depending on the inhibitor used. Zero cysteine recovery for 4% thioglycolic acid).

FIG. 41 shows PLSR performance statistics for calibration and validation models generated from handheld NIR spectra (NeoSpectra Micro) for the determination of major amino acids and protein content in soybeans. The insert shows the higher levels reported by Carrera et al. due to genotype and environmental differences.

FIG. 42 shows classification on how the data can be used for trait assessment based on the Rval. Suitability of PLSR models for quality monitoring based on guidelines developed by Williams (1978).

FIG. 44 shows compositional variability of tomato fruits employed for the development of predictive models using a portable mid-infrared spectrometer.

FIG. 45 illustrates data acquisition for tomato juice using a portable mid-infrared spectrometer and their corresponding PLSR correlation plots for Brix and titratable acidity.

FIG. 46 shows performance statistics of the PLSR models using spectra collected from tomato samples by portable mid-infrared spectrometers operating in the ATR and transmission modes.

FIG. 47 shows mid-infrared spectral differences of whole tomato fruits (green (stage 1) and ripe (stage 6)) collected by ATR.

FIG. 50 shows spectral (mid-infrared and NIR) differences of spoilage bacteria in tomato products.

FIG. 51A shows SIMCA pattern recognition based on mid-infrared spectra showing discrimination of spoilage bacteria at the (A) specie and strain levels for (B) *Bacillus* and (C) *Lactobacillus* strains. FIG. 51B shows SIMCA pattern recognition based on NIR spectra showing discrimination of spoilage bacteria at the (A) specie and strain levels for (B) *Bacillus* and (C) *Lactobacillus* strains.

FIG. 52 shows spectral differences of soybeans collected by a portable mid-infrared and a handheld NIR spectrometer.

FIG. 53 shows PLSR regression models for the determination of oleic acid in soybeans by using a portable mid-infrared and handheld NIR device. Classification of conventional and GMO soybeans based on their NIR spectra.

FIGS. 54A-54C show the classification approaches to authenticate the type of grape. FIG. 54B shows Raman and UV-Vis analysis of Pisco samples and their classification based on aromatic and non-aromatic grape varieties. FIG. 54C shows GC separation of major alcohols in Pisco spirits and their corresponding PLSR models for determination of ethanol and methanol levels.

Figure 55:
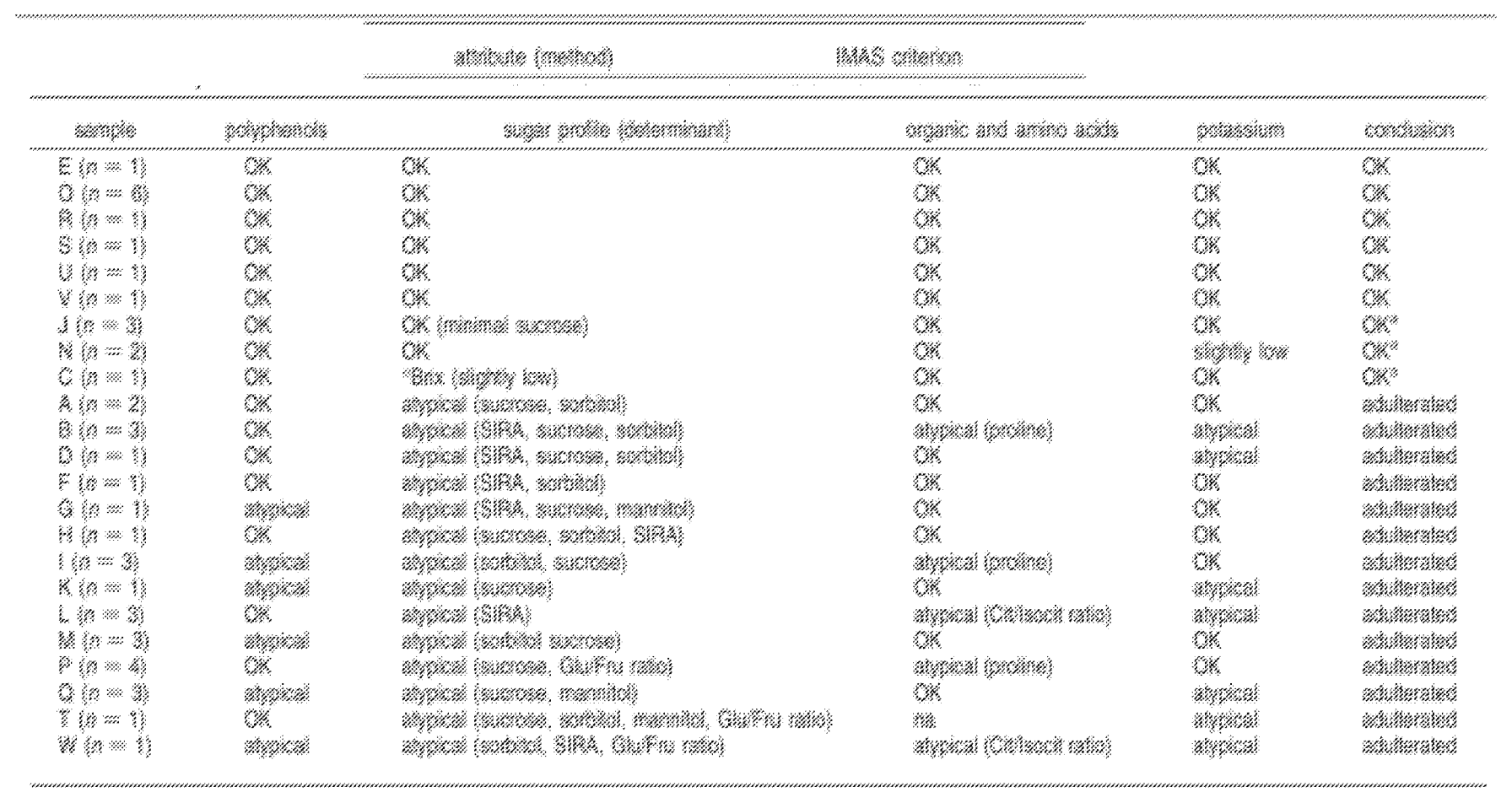

FIG. 55 shows Targeted LC approach for detection of adulteration.

FIG. 60 illustrates sensitivity and specificity of the detection of adulteration in extra virgin olive oils by mid-infrared and Raman technologies.

FIG. 61 shows Model Performance based on mid-infrared and Raman spectra for the determination of major fatty acids and quality parameters in olive oils.

FIG. 62A shows Mid-infrared spectra showing the unique marker band for detection of trans-fat at 966 $cm^{-1}$. FIG. 62B shows prediction of levels of trans-fat in bakery and snack products using the PLSR model developed by mid-infrared spectra.

FIG. 65 shows Raman spectra and LC analysis of sugars for honey samples and classification analysis for the detection of adulteration in commercial honey samples.

FIG. 66B shows classification of whey proteins by mid-infrared spectroscopy.

FIG. 70 shows performance of models of testing oats.

FIG. 71 shows amino acid compositions in fish meal and various plant-based alternatives. Samples with high quality means high levels of proteins and high levels of essential amino acids.

FIG. 77 shows near-infrared bands of organic compounds.

DETAILED DESCRIPTION

Figure 1:
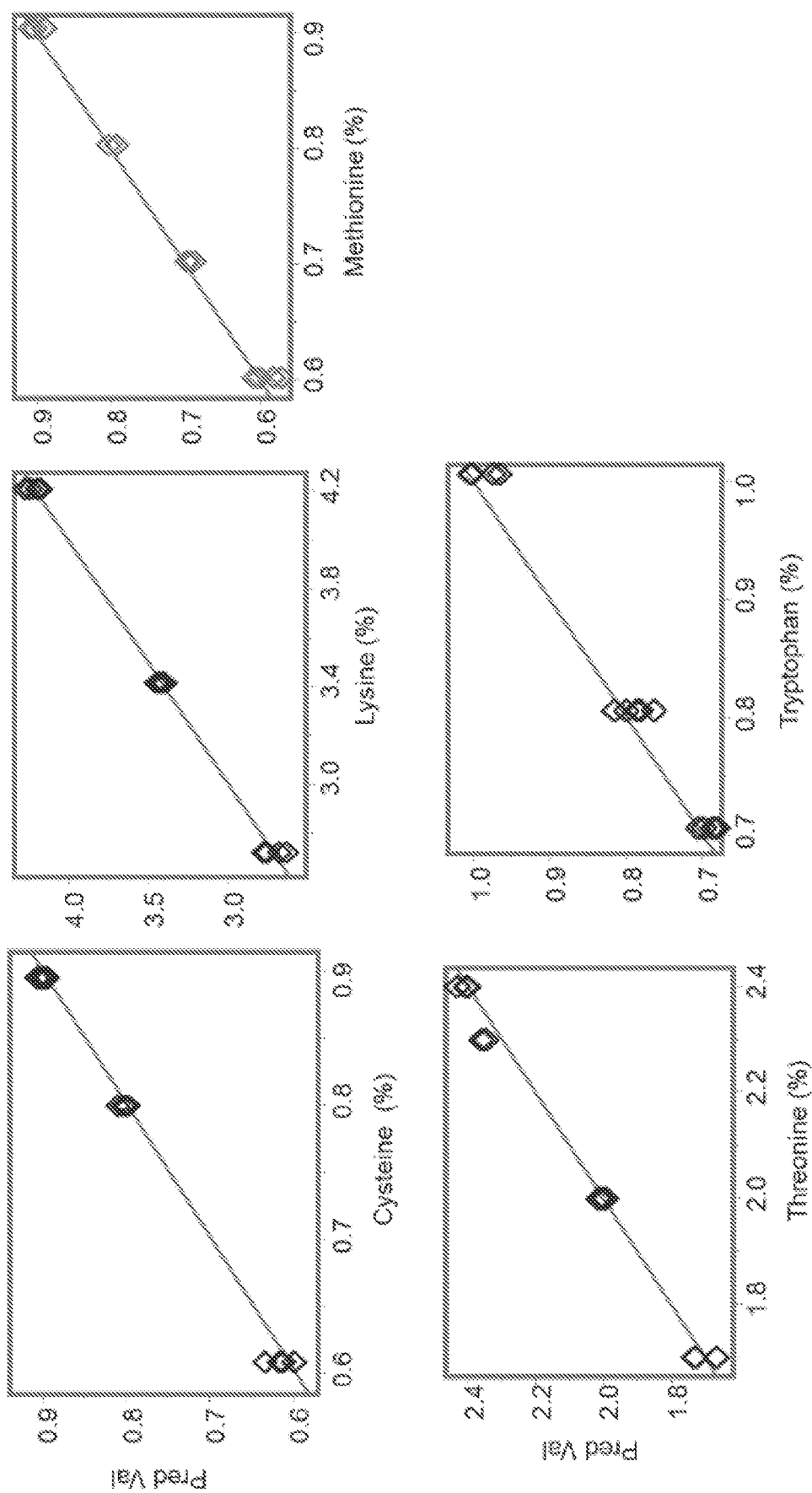
FIG. 1 shows correlation between amino acid concentrations measured by near infrared (NIR) spectroscopy (y-axis) and known concentration from gas chromatography methods (x-axis).

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs.

The following definitions are provided for the full understanding of terms used in this specification
Terminology The term "about" as used herein when referring to a measurable value such as an amount, a percentage, and the like, is meant to encompass variations of ±20%, ±10%, ±5%, or ±1% from the measurable value.

As used herein, the article "a," "an," and "the" means "at least one," unless the context in which the article is used clearly indicates otherwise.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed herein.
Devices and Systems In some aspects, disclosed herein is a portable spectrometer system comprising:
 a spectrometer;
 a sample stage adjacent the spectrometer;
 a motor coupled to the sample stage; and
 a system housing enclosing the motor and the spectrometer;
 wherein rotation of the motor rotates the sample stage, and
 wherein the motor is controllable in response to spectroscopy requirements.

In some embodiments, the portable spectrometer system disclosed herein further comprises an interface device and an external processor, wherein the interface device and the external processor are each in electronic communication with the spectrometer and the motor. In some embodiments, the external processor is configured to adjust the rotational position of the motor in response to spectroscopy measurement. In some embodiments, the external processor is configured to adjust the rotational position of the motor to distribute near infrared (NIR) spectra about a specimen to minimize a spectroscopy scattering effect. In some embodiments, the external processor is a mobile device (e.g., a cell phone, tablet, or laptop).

In some embodiments, the external processor is configured to acquire spectroscopic measurements to train a predictive algorithm.

In one example, disclosed herein is a sensor as illustrated in FIGS. 7A-7G. FIGS. 7A-7G show an implementation of a portable spectrometer system 100 that includes a spectrometer 102, a sample stage 104, a motor 106, and a system housing 108. In some implementations, the spectrometer is a Near Infrared (NIR) spectrometer such as NeoSpectra-Micro kit. In some implementations, the spectrometer is Raman Spectrometer. In some implementations, the spectrometer is NIRQuest Spectrometer. In some implementations the spectrometer 100 has an optical head which includes a light source and collection optics for photon collection during the spectroscopy process. The optical head is connected to application specific integrated circuits, and an interferometer such as a MEMS-based Michaelson interferometer, and detector. In some implementations, the detector is an uncooled InGaAs photodetector, but the detector can be any detector capable of reading spectroscopy measurements. The spectrometer is adjacent to the sample stage 104 such that spectroscopy measurements of a specimen 122 placed on the sample stage 104 can be taken by the spectrometer 102. In some implementations, the sample stage 104 is a transparent window. In some implementations, an inner surface of the sample stage 104 is spaced apart from the spectrometer 102, and in some implementations, the inner surface of the sample stage 104 is coupled to the spectrometer 102. In some implementations, the sample stage 104 is formed from a transparent material such as IR fused silica. In the implementation shown in FIGS. 7A-7G, the sample stage 104 is a circular shape and can receive and support a container having a spectroscopy specimen. In other implementations, the sample stage can be square or any other shape suitable for supporting a spectroscopy specimen or container.

Figure 7A:
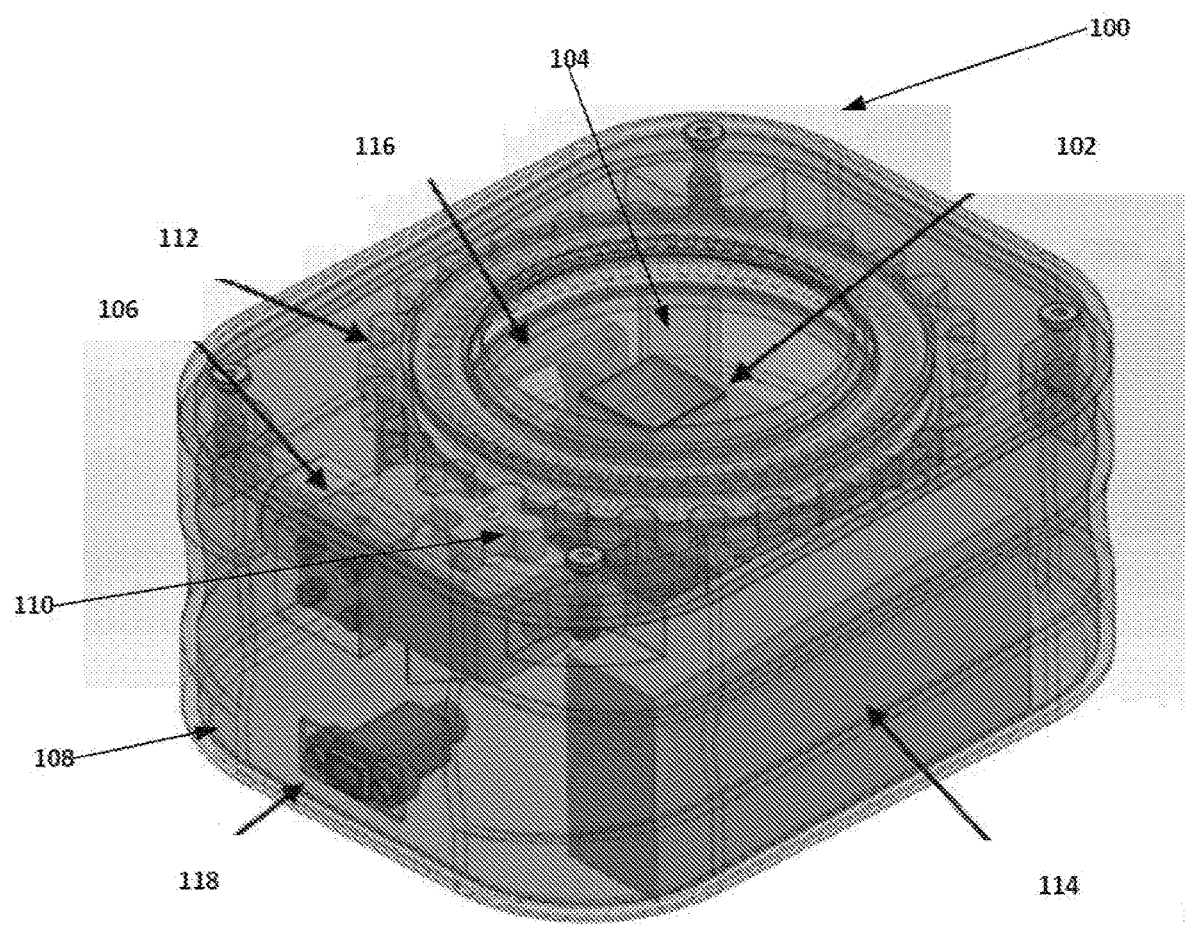
FIGS. 7A-7G show schematic drawings and photographs of the sensor device.
Figure 7B:
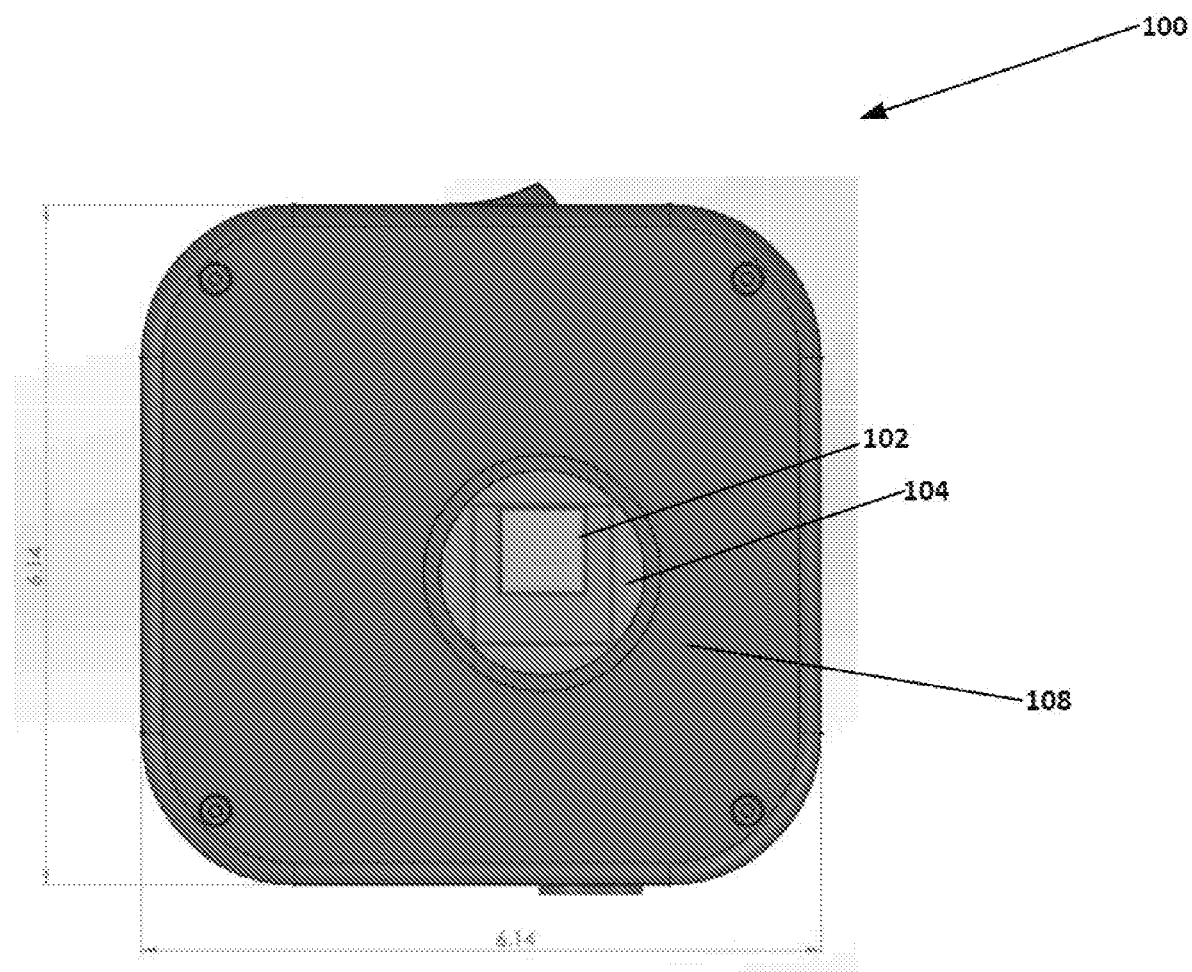
Figure 7C:
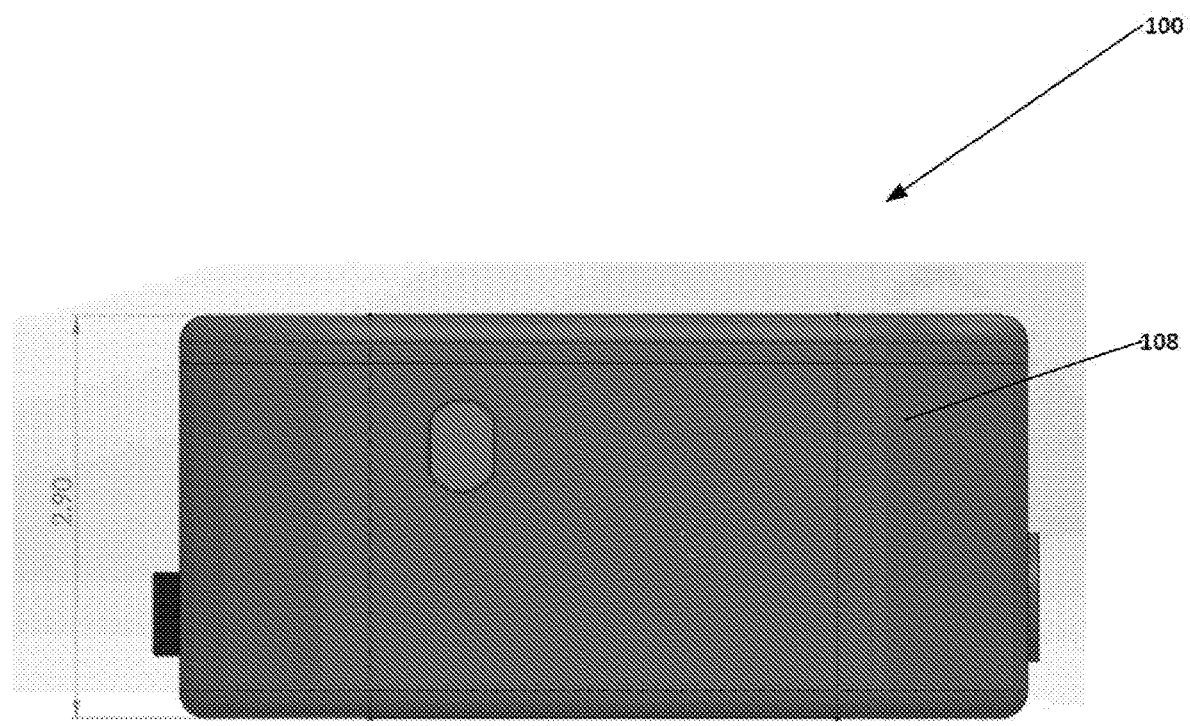
Figure 7D:
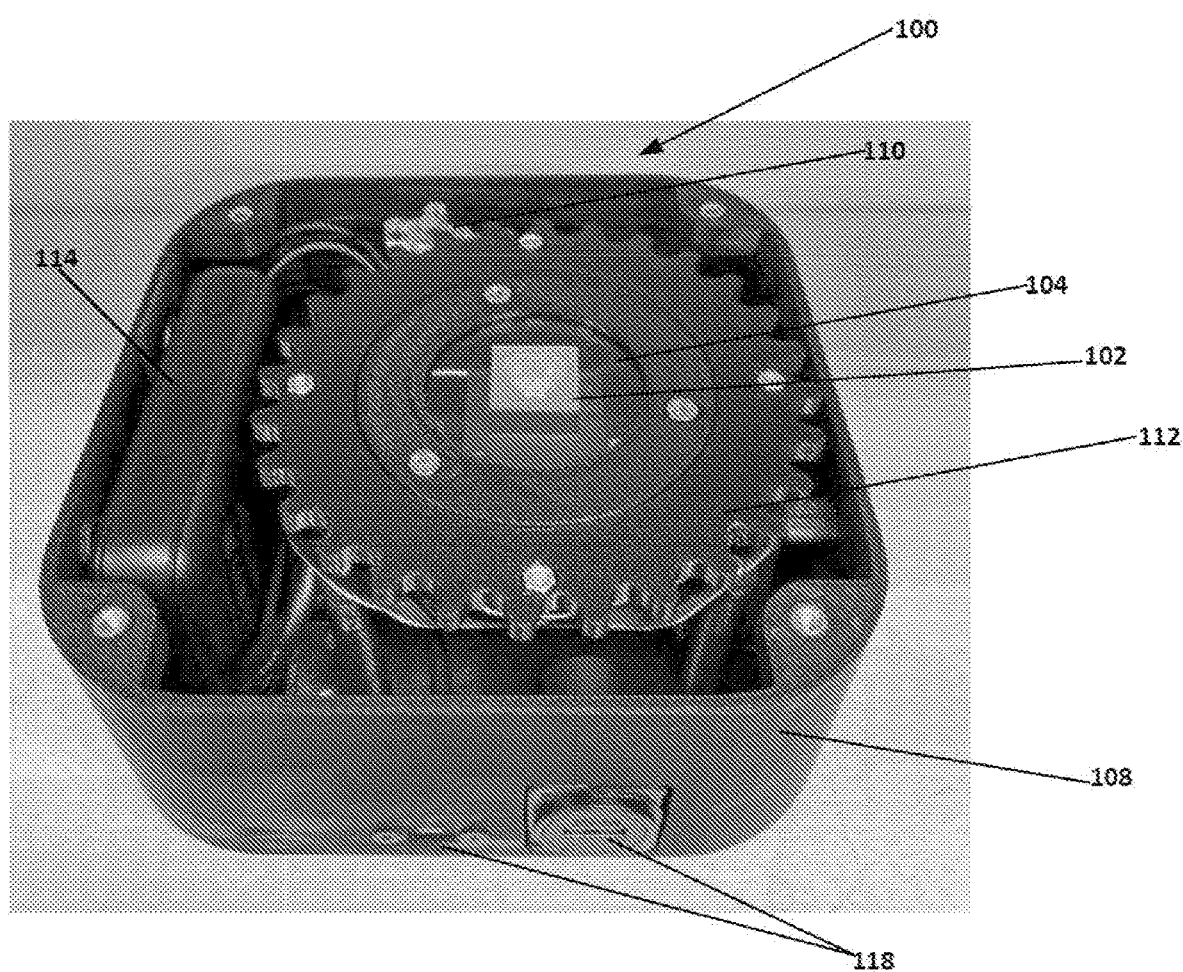
Figure 7E:
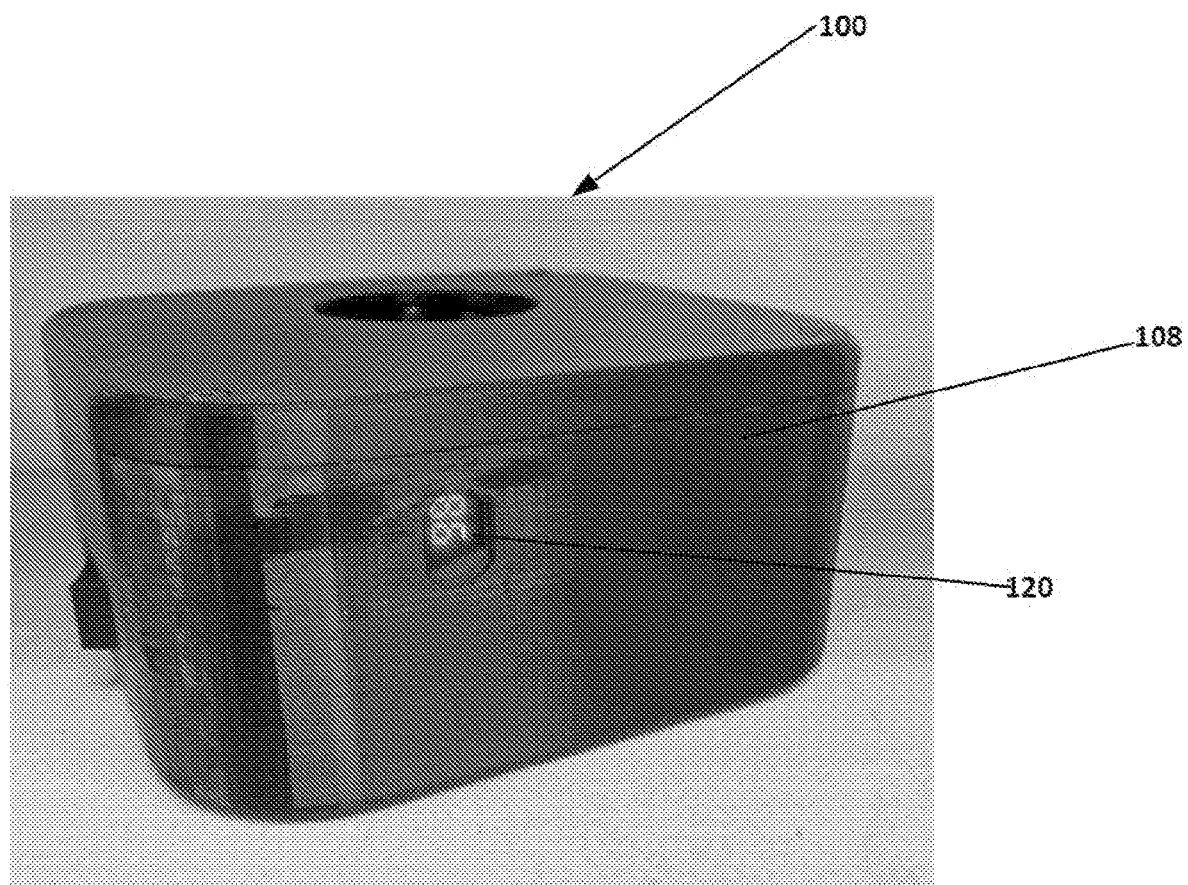
Figure 7F:
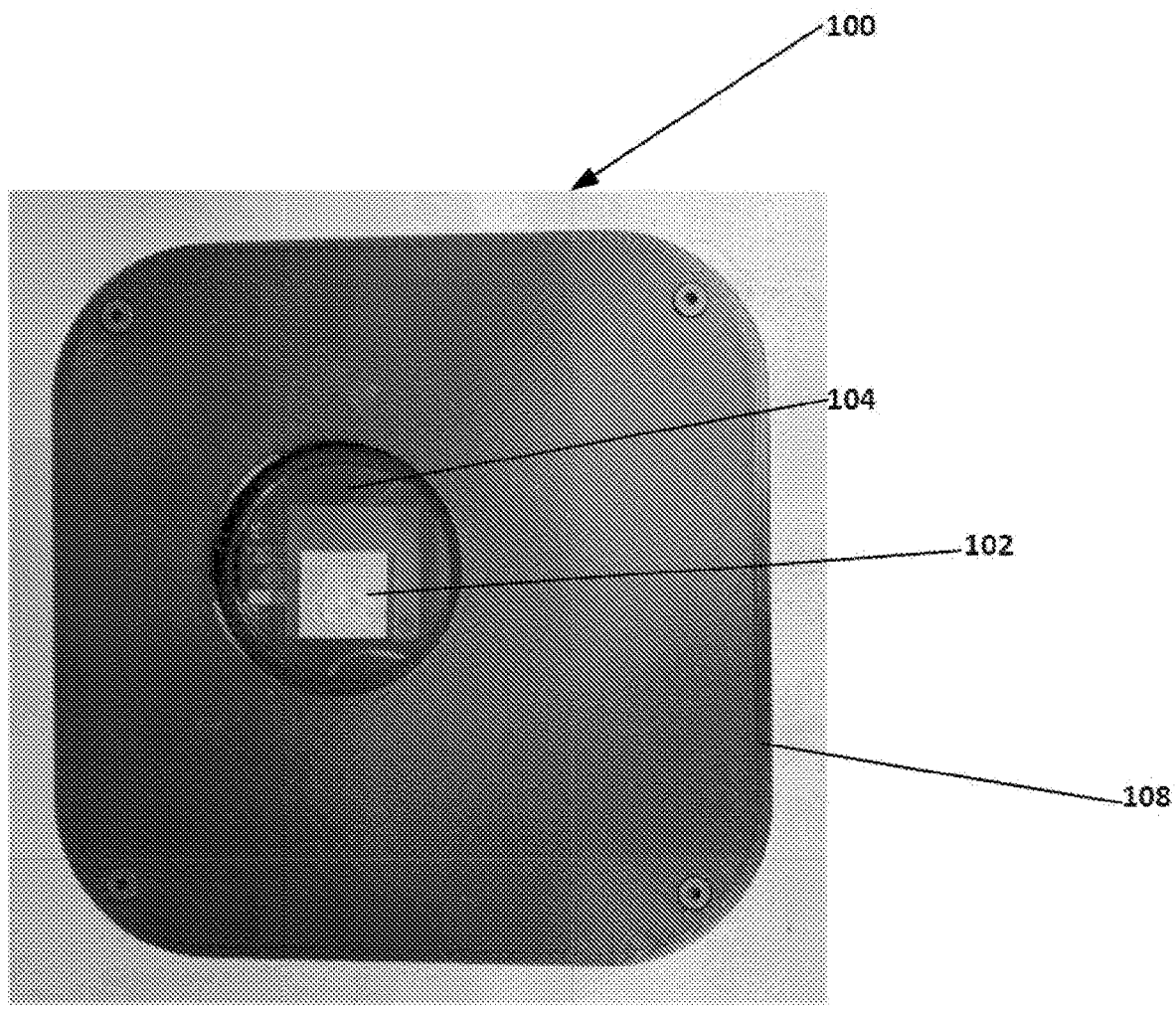
Figure 7G:
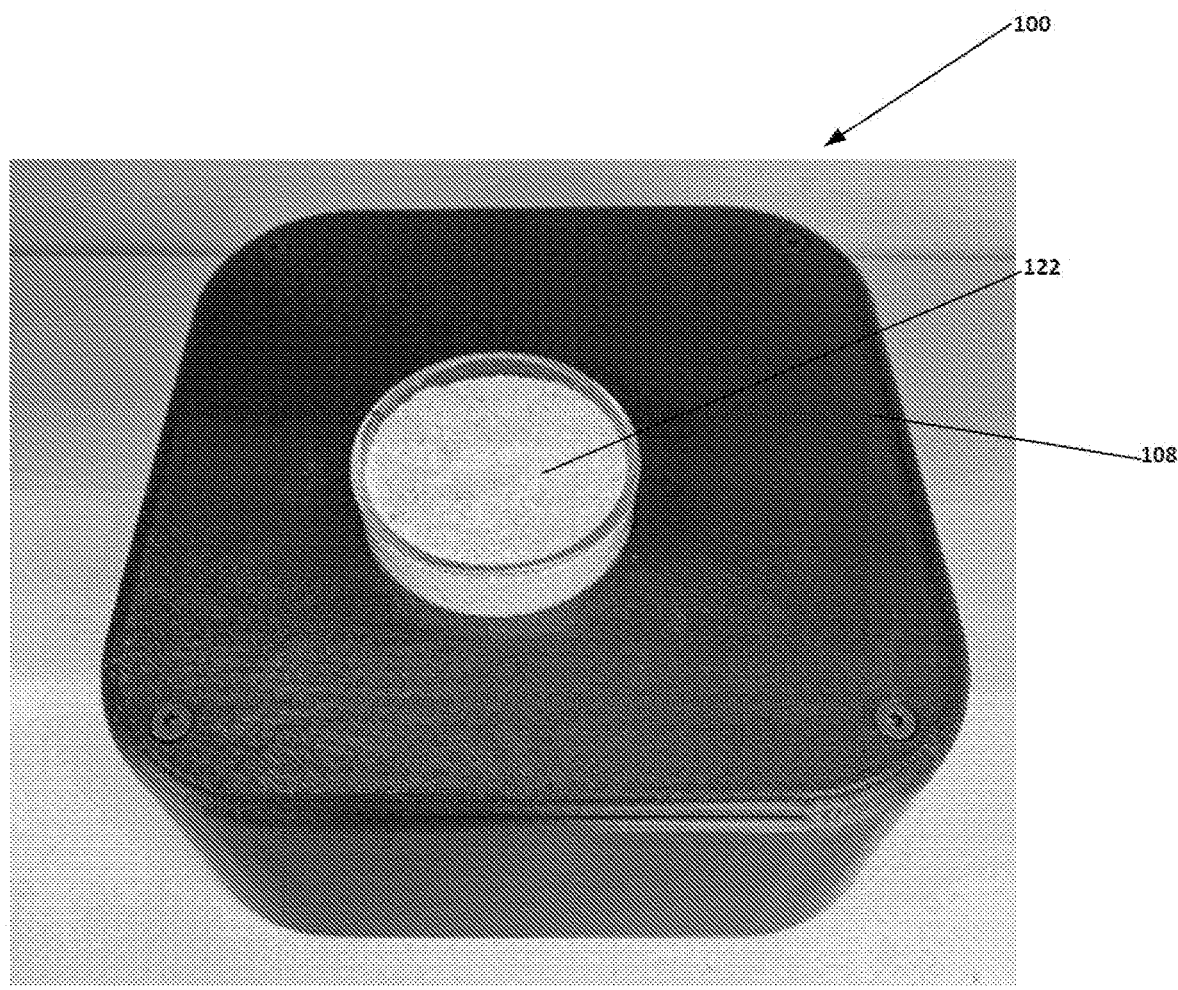

The sample stage 104 is coupled to the motor 106, such that rotation of the motor 106 rotates the sample stage 104. In some implementations, the motor 106 has a driving gear 110 connected to a shaft of the motor 106. In some implementations, the sample stage 104 is rigidly connected to a platform gear 112 which surrounds the sample stage 104 such that the sample stage 104 rotates uniformly with rotation of the platform gear 112. In some implementations, teeth of the driving gear 110 interconnect with teeth of the platform gear 112 such that rotation of the driving gear 110 by the motor 106 causes the platform gear 112 to rotate. As such, the rotation of the platform gear 112 rotates the sample stage 104 causing the specimen 122 placed on the sample stage 104 to rotate. In some implementations the motor 106 is also coupled to a battery pack 114, which provides the motor 106 with electricity. The battery pack 114 provides a portable power source, which is contained within the portable spectrometer 100. In some implementations, the portable spectrometer 100 also includes a cooling fan 116, which can be used to cool heated components such as the motor 106 and the battery pack 114. The cooling fan 116 is electrically coupled to the battery pack 114 which powers the cooling fan 116. In some implementations, the portable spectrometer 100 also includes an external system connector 118, such as a USB port as shown in FIGS. 7A and 7D. Although the system connector 118 shown in FIGS. 7A and 7D is a USB port, the external system interface can be any electronic connection capable of sending and receiving electronic signals such as a ZigBee interface or a Bluetooth interface.

In some implementations the portable spectrometer 100 includes the system housing 108. The system housing 108 encloses and supports each of the components described above. The system housing 108 is a rigid housing formed from a rigid or semi rigid material such that the system housing provides support and containment for each of the components of the portable spectrometer 100 during field use. In some implementations, the system housing 108 has an opening which outlines outer edges of the spectroscopy sample stage 104 and exposes the spectroscopy sample stage 104, such that a specimen can be placed directly on the sample stage 104. In some implementations, where the external system interface 118 is a connector, such as a USB port, which requires a physical connectivity, the system housing also has an opening that exposes the external system interface 118. In some implementations, such as the implementation shown in FIG. 7E, the system also includes a visual display 120 such as an LCD monitor. In implementations having the visual display 120, the system housing 108 also has an opening which exposes the visual display 120 such that a user can see the visual display 120 during operation.

Figure 5:
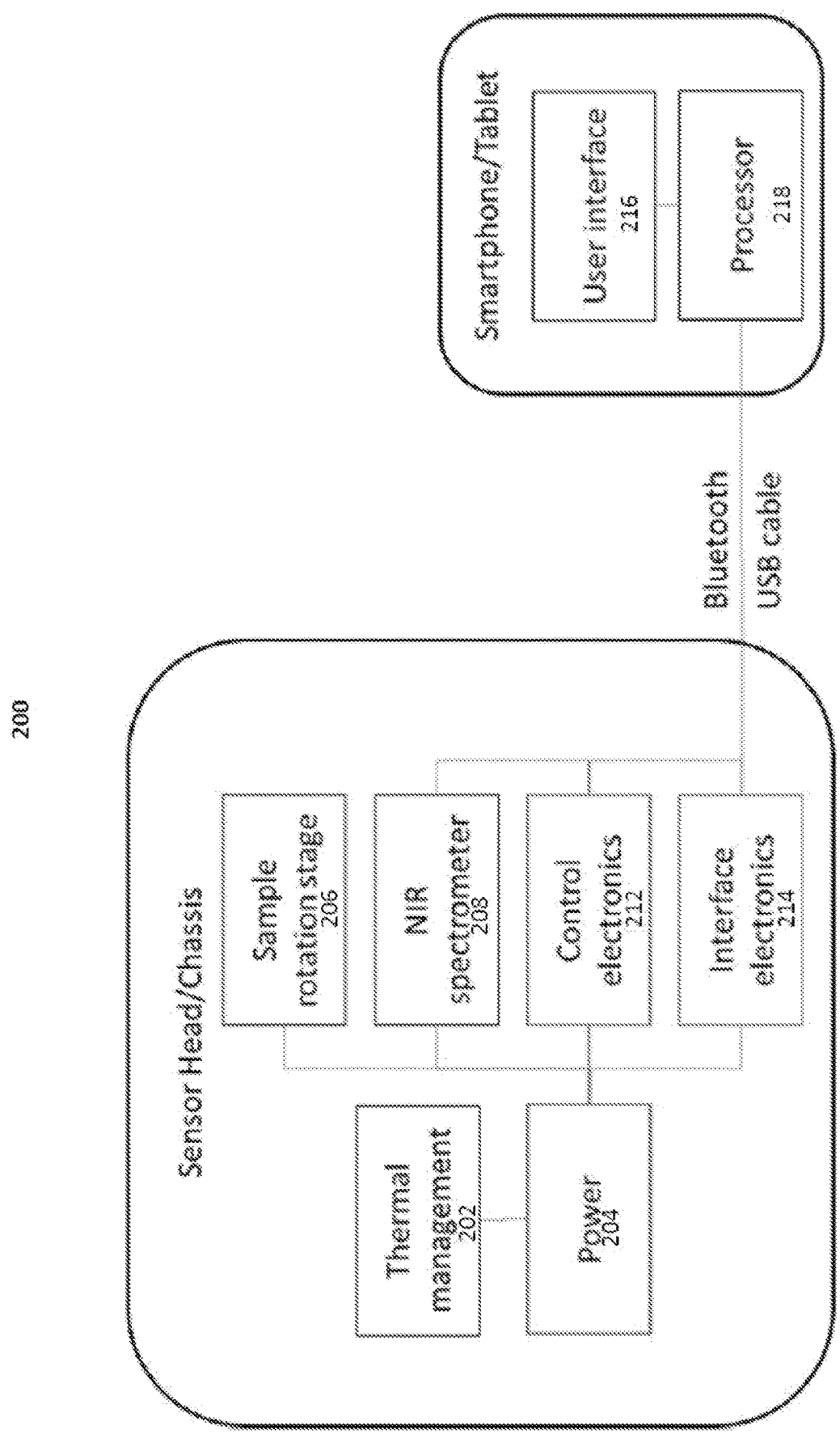
FIG. 5 shows a schematic of a spectroscopy system 200 which includes the portable spectrometer system 100, an interface 216, and an external processor 218. This shows high level, block diagram of the sensor design, including various subsystems within the sensor head and smartphone/tablet components. Red lines indicate power interfaces within the sensor head chassis, and blue lines indicate data/communications interfaces within and between the sensor head and smartphone/tablet.

FIG. 5 shows a schematic of a spectroscopy system 200 which includes the portable spectrometer system 100, an interface 216, and an external processor 218. As shown in FIG. 5, the portable spectrometer system 100 includes thermal management 202, such as the fan 116 shown in FIGS. 7A and 7D. The portable spectrometer 100 also includes a power source 204, such as the battery 114 shown in FIG. 7A. The portable spectrometer further includes a rotation stage 206, such as the motor 106 shown in FIG. 7A, and an NIR spectrometer 208, such as the spectrometer 102 in FIGS. 7A and 7D. The system also includes control electronics 212 which connect to external systems and allow external systems to exercise control functions for the rotation stage 206 and the thermal management 202. In some implementations, the control electronics 202 include electrical circuits, such as those in a raspberry-pi circuit board, which allow components of the spectrometer 208 to be integrated with other electronic elements such as controllers.

In some implementations, the user interface 206 is electrically coupled to the processor. The processor 208 is electrically coupled to the spectrometer 102, the control electronics 202, and the interface electronics 204. Further the power source 114 is electrically coupled to the rotation stage 106, the spectrometer 102, the control electronics 202, the interface electronics 204 and the thermal management 116. In some implementations, the user interface 206 and the external processor 208 are each components of a smart phone or a tablet. The processor 208 is capable of processing spectroscopy measurements to determine dimensions and material characteristics of a spectroscopy specimen. In some implementations, the processor is also capable of facilitating predictive algorithm training. In some implementations, the processor controls the supply of electricity from the power source 114 to the rotation stage 106, to facilitate the rotation of the rotation stage 106. The processor 208 is capable of controlling the spectroscopy sensor system 100 and analyzing resultant spectroscopic data.

Methods

In some aspects, disclosed herein is a method of determining a level of a trait in a sample using the system or sensor of any preceding aspect, comprising:
placing the sample on the sample stage of the system;
measuring a spectrum of the sample within a wavelength range using the spectrometer in the system;
determining the level of the trait based on the measured spectrum.

In some embodiments, the spectrometer is a NIR spectrometer.

In some aspects, disclosed herein is a method of determining a level of a trait in a field crop, a specialty crop, a raw ingredient, or a finished product, comprising:
placing the sample on a sample stage of a portable spectrometer system, wherein the portable spectrometer system comprises:
a spectrometer;
a sample stage adjacent the spectrometer;
a motor coupled to the sample stage; and
a system housing enclosing the motor and the spectrometer,
wherein rotation of the motor rotates the sample stage, and
wherein the motor is controllable in response to spectroscopy requirements;
measuring a spectrum of the sample within a spectral range using the spectrometer;
determining the level of the trait based on the measured spectrum.

In some embodiments, the sample stage may rotate. In some embodiments, the sample may rotate.

In some embodiments, the wavelength range is between about 400 nm to about 14000 nm, between about 600 nm to about 12000 nm, between about 700 nm to about 10000 nm, between about 700 nm to about 8000 nm, between about 700 nm to about 6000 nm, between about 650 nm to about 4300 nm, between about 650 nm to about 4000 nm, between about 650 nm to about 3800 nm, between about 650 nm to about 3600 nm, between about 650 nm to about 3400 nm, between about 650 nm to about 3200 nm, between about 650 nm to about 3000 nm, between about 650 nm to about 2800 nm, between about 650 nm to about 2600 nm, between about 650 nm to about 2500 nm, between about 650 nm to about 2400 nm, between about 650 nm to about 2200 nm, between about 650 nm to about 2000 nm, between about 700 nm to about 4300 nm, between about 700 nm to about 4000 nm, between about 700 nm to about 3800 nm, between about 700 nm to about 3600 nm, between about 700 nm to about 3400 nm, between about 700 nm to about 3700 nm, between about 700 nm to about 3000 nm, between about 700 nm to about 2800 nm, between about 700 nm to about 2600 nm, between about 700 nm to about 2400 nm, between about 700 nm to about 2200 nm, between about 700 nm to about 2000 nm, between about 750 nm to about 4300 nm, between about 750 nm to about 4000 nm, between about 750 nm to about 3800 nm, between about 750 nm to about 3600 nm, between about 750 nm to about 3400 nm, between about 750 nm to about 3200 nm, between about 750 nm to about 3000 nm, between about 750 nm to about 2800 nm, between about 750 nm to about 2600 nm, between about 750 nm to about 2400 nm, between about 750 nm to about 2200 nm, between about 750 nm to about 2000 nm, between about 800 nm to about 4300 nm, between about 800 nm to about 4000 nm, between about 800 nm to about 3800 nm, between about 800 nm to about 3600 nm, between about 800 nm to about 3400 nm, between about 800 nm to about 3200 nm, between about 800 nm to about 3000 nm, between about 800 nm to about 2800 nm, between about 800 nm to about 2600 nm, between about 800 nm to about 2400 nm, between about 800 nm to about 2200 nm, between about 800 nm to about 2000 nm, between about 800 nm to about 4300 nm, between about 800 nm to about 4000 nm, between about 800 nm to about 3800 nm, between about 800 nm to about 3600 nm, between about 800 nm to about 3400 nm, between about 800 nm to about 3200 nm, between about 800 nm to about 3000 nm, between about 800 nm to about 2800 nm, between about 800 nm to about 2600 nm, between about 800 nm to about 2400 nm, between about 800 nm to about 2200 nm, between about 800 nm to about 2000 nm, between about 900 nm to about 4300 nm, between about 900 nm to about 4000 nm, between about 900 nm to about 3800 nm, between about 900 nm to about 3600 nm, between about 900 nm to about 3400 nm, between about 900 nm to about 3200 nm, between about 900 nm to about 3000 nm, between about 900 nm to about 2800 nm, between about 900 nm to about 2600 nm, between about 900 nm to about 2400 nm, between about 900 nm to about 2200 nm, between about 900 nm to about 2000 nm, between about 1000 nm to about 4300 nm, between about 1000 nm to about 4000 nm, between about 1000 nm to about 3800 nm, between about 1000 nm to about 3600 nm, between about 1000 nm to about 3400 nm, between about 1000 nm to about 3200 nm, between about 1000 nm to about 3000 nm, between about 1000 nm to about 2800 nm, between about 1000 nm to about 2600 nm, between about 1000 nm to about 2500 nm, between about 1000 nm to about 2400 nm, between about 1100 nm to about 4300 nm, between about 1100 nm to about 4000 nm, between about 1100 nm to about 3800 nm, between about 1100 nm to about 3600 nm, between about 1100 nm to about 3400 nm, between about 1100 nm to about 3200 nm, between about 1100 nm to about 3000 nm, between about 1100 nm to about 2800 nm, between about 1100 nm to about 2600 nm, between about 1100 nm to about 2500 nm, between about 1100 nm to about 2400 nm, between about 1200 nm to about 4300 nm, between about 1200 nm to about 4000 nm, between about 1200 nm to about 3800 nm, between about 1200 nm to about 3600 nm, between about 1200 nm to about 3400 nm, between about 1200 nm to about 3200 nm, between about 1200 nm to about 3000 nm, between about 1200 nm to about 2800 nm, between about 1200 nm to about 2600 nm, between about 1200 nm to about 2500 nm, between about 1200 nm to about 2400 nm, between about 1300 nm to about 4300 nm, between about 1300 nm to about 4000 nm, between about 1300 nm to about 3800 nm, between about 1300 nm to about 3600 nm, between about 1300 nm to about 3400 nm, between about 1300 nm to about 3200 nm, between about 1300 nm to about 3000 nm, between about 1300 nm to about 2800 nm, between about 1300 nm to about 2600 nm, between about 1300 nm to about 2500 nm, between about 1300 nm to about 2400 nm, between about 1350 nm to about 4300 nm, between about 1350 nm to about 4000 nm, between about 1350 nm to about 3800 nm, between about 1350 nm to about 3600 nm, between about 1350 nm to about 3400 nm, between about 1350 nm to about 3200 nm, between about 1350 nm to about 3000 nm, between about 1350 nm to about 2800 nm, between about 1350 nm to about 2600 nm, between about 1350 nm to about 2500 nm, between about 1350 nm to about 2400 nm, between about 1400 nm to about 4300 nm, between about 1400 nm to about 4000 nm, between about 1400 nm to about 3800 nm, between about 1400 nm to about 3600 nm, between about 1400 nm to about 3400 nm, between about 1400 nm to about 3200 nm, between about 1400 nm to about 3000 nm, between about 1400 nm to about 2800 nm, between about 1400 nm to about 2600 nm, between about 1400 nm to about 2500 nm, or between about 1400 nm to about 2400 nm. In some embodiments, the wavelength is between about 700 nm to about 3000 nm. In some embodiments, the wavelength is between about 1350 nm to about 2500 nm.

In some embodiments, the method of any preceding aspect further comprises commanding the system through the external processor to rotate the sample stage for rotating the sample. In some embodiments, the sample stage always rotates during a measurement (without the system specifically commanding the system through the external processor to rotate the sample stage for rotating the sample).

In some embodiments, the method of any preceding aspect further comprises commanding the system through the external processor to process the data using algorithmic pre-processing. In some embodiments, the algorithmic pre-processing comprises: the collected spectrum is ratioed against a spectrum collected for a calibration standard.

Several approaches exist that employ diverse preprocessing methods to remove spectral variation related to the sample and instrumental variation including normalization, smoothing, derivatives, multiplicative signal correction (Geladi, P., D. McDougall and H. Martens. "Linearization and Scatter-Correction for Near-infrared Reflectance Spectra of Meat," *Applied Spectroscopy*, vol. 39, pp. 491-500, 1985), standard normal variate transformation (R. J. Barnes, M. S. Dhanoa, and S. Lister, *Applied Spectroscopy*, 43, pp. 772-777, 1989), piecewise multiplicative scatter correction (T. Isaksson and B. R. Kowalski, *Applied Spectroscopy*, 47, pp. 702-709, 1993), extended multiplicative signal correction (H. Martens and E. Stark, *J. Pharm Biomed Anal*, 9, pp. 625-635, 1991), pathlength correction with chemical modeling and optimized scaling ("GlucoWatch Automatic Glucose Biographer and AutoSensors", Cygnus Inc., Document #1992-00, Rev. March 2001), and FIR filtering (Sum, S. T., "Spectral Signal Correction for Multivariate Calibration," Doctoral Dissertation, University of Delaware, Summer 1998; Sum, S. and S. D. Brown, "Standardization of Fiber-Optic Probes for Near-Infrared Multivariate Calibrations," *Applied Spectroscopy*, Vol. 52, No. 6, pp. 869-877, 1998; and T. B. Blank, S. T. Sum, S. D. Brown and S. L. Monfre, "Transfer of near-infrared multivariate calibrations without standards," *Analytical Chemistry*, 68, pp. 2987-2995, 1996). In addition, a diversity of signal, data or pre-processing techniques are commonly reported with the fundamental goal of enhancing accessibility of the net analyte signal (Massart, D. L., B. G. M. Vandeginste, S. N. Deming, Y. Michotte and L. Kaufman, *Chemometrics: a textbook*, New York: Elsevier Science Publishing Company, Inc., 215-252, 1990; Oppenheim, Alan V. and R. W. Schafer, *Digital Signal Processing*, Englewood Cliffs, N.J.: Prentice Hall, 1975, pp. 195-271; Otto, M., *Chemometrics*, Weinheim: Wiley-VCH, 51-78, 1999; Beebe, K. R., R. J. Pell and M. B. Seasholtz, *Chemometrics A Practical Guide*, New York: John Wiley & Sons, Inc., 26-55, 1998; M. A. Sharaf, D. L. Illman and B. R. Kowalski, *Chemometrics*, New York: John Wiley & Sons, Inc., 86-112, 1996; and Savitzky, A. and M. J. E. Golay. "Smoothing and Differentiation of Data by Simplified Least Squares Procedures," *Anal. Chem.*, vol. 36, no. 8, pp. 1627-1639, 1964). The goal of all of these techniques is to attenuate the noise and instrumental variation without affecting the signal of interest. Methods for algorithmic pre-processing and NIR spectrometer calibration are known in the art. See, e.g., U.S. Pat. Nos. 6,675,030 and 7,787,924, incorporated by reference herein in their entireties.

In some embodiments, the method of any preceding aspect further comprises commanding the system through the external processor to apply a chemometric algorithm on the processed data to quantify the trait. In some embodiments, the chemometric algorithm comprises partial least squares regression, principal component analysis, or artificial neural networks. In some embodiments, the chemometric algorithm comprises partial least squares regression.

In some embodiments, the method of any preceding aspect further comprises translating the quantitative results into a reporting format selected for a system operator. In some embodiments, the reporting format comprises a table of individual quantities, a graphical representation of the quantities, or an icon indicating the categorization or grade of the sample.

In some embodiments, the method of any preceding aspect further comprises displaying the level of the trait on the external processor.

In some embodiments, the sample measured by the method disclosed herein comprises a sample of a field crop, a specialty crop, a raw ingredient, or a finished product.

In some embodiment, the sample comprises intact seeds or a non-processed sample of the field crop, the specialty crop, the raw ingredient, or the finished product. In some embodiments, the sample comprises a ground seeds or a powder sample of the field crop, the specialty crop, the raw ingredient, or the finished product.

The term "trait" used herein refers to a distinguishing quality or characteristic of a food product (e.g., a field crop, a specialty crop, a raw ingredient, or a finished product). The trait may be a compound or composition (e.g. an essential amino acid) or a category of nutrient (e.g., fat, protein, or starch).

In some aspects, disclosed herein is a method of determining a level of a trait in a field crop, comprising the following steps:
  obtaining a field crop sample;
  collecting spectroscopic data on the field crop sample;
  processing the data using algorithmic pre-processing;
  applying a chemometric algorithm on the processed data to quantify the trait; and
  translating the quantitative results into a reporting format selected for a system operator In some embodiments, the field crop sample comprises a sample of soybean, oat, corn, barley, or potato.

In some embodiments, the field crop sample is a soybean sample. In some embodiments, the trait measured in the soybean sample comprises an amino acid, a fatty acid, protein oil, fat, and/or water. In some embodiments, the measured amino acid is an essential amino acid, including, for example, phenylalanine, valine, threonine, tryptophan, methionine, leucine, isoleucine, lysine, or histidine. In some embodiments, the measured amino acid comprises cysteine, lysine, methionine, threonine, and/or tryptophan.

In some embodiments, the trait measured in the soybean sample comprises a fatty acid (e.g., oleic acid, linoleic acid, or linolenic acid).

In some embodiments, the field crop sample is an oat sample. In some embodiments, the trait measured in the oat sample comprises β-glucan, protein, starch, or water. In some embodiments, the trait measured in the oat sample comprises β-glucan. In some embodiments, the trait measured in the oat sample comprises protein. In some embodiments, the trait measured in the oat sample comprises starch.

In some embodiments, the field crop sample is a corn sample. In some embodiments, the trait measured in the corn sample comprises starch, sugar, water, protein, oil, or a toxin. In some embodiments, the trait measured in the corn sample is starch. In some embodiments, the trait measured in the corn sample is sugar. In some embodiments, the trait measured in the corn sample is protein. In some embodiments, the trait measured in the corn sample is oil. In some embodiments, the trait measured in the corn sample is a toxin. A toxin refers to a poisonous substance produced within living cells or organisms.

In some embodiments, the field crop sample is a barley sample. In some embodiments, the trait measured in the barley sample comprises valine, deoxynivalenol, protein, or water. In some embodiments, the trait measured in the barley sample is valine. In some embodiments, the trait measured in the barley sample is deoxynivalenol. In some embodiments, the trait measured in the barley sample is protein. In some embodiments, the trait measured in the barley sample is water.

In some embodiments, the field crop sample is a potato sample. In some embodiments, the trait measured in the potato sample comprises acrylamide, starch, sugar, or water. In some embodiments, the trait measured in the potato sample is acrylamide. In some embodiments, the trait measured in the potato sample is starch. In some embodiments, the trait measured in the potato sample is sugar. In some embodiments, the trait measured in the potato sample is water.

In some aspects, disclosed herein is a method of determining a level of a trait in a specialty crop, comprising the following steps:
  obtaining a specialty crop sample;
  collecting spectroscopic data on the specialty crop sample;
  processing the data using algorithmic pre-processing;
  applying a chemometric algorithm on the processed data to quantify the trait; and
  translating the quantitative results into a reporting format selected for a system operator In some embodiments, the specialty crop sample comprises a sample of cannabis, tomato, coffee, or fruit.

In some embodiments, the specialty crop sample is a cannabis sample. In some embodiments, the trait measured in the cannabis sample comprises tetrahydrocannabinol (THC), cannabidiol, other cannabinoids, and/or water. In some embodiments, the measured trait in the cannabis sample is tetrahydrocannabinol (THC). In some embodiments, the measured trait in the cannabis sample is cannabidiol. In some embodiments, the measured trait in the cannabis sample is water.

In some embodiments, the specialty crop sample is a tomato sample. In some embodiments, the trait measured in the tomato sample comprises lycopene, sugar, moisture, and/or an acid. In some embodiments, the measured trait in the tomato sample is lycopene. In some embodiments, the measured trait in the tomato sample is sugar. In some embodiments, the measured trait in the tomato sample is an acid. In some embodiments, the measured trait in the tomato sample is water.

In some embodiments, the specialty crop sample is a coffee sample. In some embodiments, the trait measured in the coffee sample comprises acrylamide, caffeine, and/or water. In some embodiments, the measured trait in the coffee sample is acrylamide. In some embodiments, the measured trait in the coffee sample is caffeine. In some embodiments, the measured trait in the coffee sample is water.

In some embodiments, the specialty crop sample is a fruit sample. In some embodiments, the trait measured in the fruit sample comprises a sample of grape, blueberry, or apple. In some embodiments, the fruit sample is a grape sample. In some embodiments, the fruit sample is a blueberry sample. In some embodiments, the fruit sample is an apple sample. In some embodiments, the trait measured in the fruit sample comprises anthocyanins, sugar, water, and/or an acid. In some embodiments, the trait measured in the fruit sample is anthocyanins. In one example, the measured anthocyanins refer to those disclosed In some embodiments, the trait measured in the fruit sample is sugar. In some embodiments, the trait measured in the fruit sample is water. In some embodiments, the trait measured in the fruit sample is an acid.

Anthocyan is a generic term for anthocyanidin, is known in the art. See, e.g., U.S. Pat. No. 7,211,413 and Hock Eng Khoo et al., *Food Nutr Res.* 2017; 61(1): 1361779, incorporated by reference herein in their entireties.

In some aspects, disclosed herein is a method of determining a level of a trait in a raw ingredient, comprising the following steps:
- obtaining a raw ingredient sample;
- collecting spectroscopic data on the raw ingredient sample;
- processing the data using algorithmic pre-processing;
- applying a chemometric algorithm on the processed data to quantify the trait; and
- translating the quantitative results into a reporting format selected for a system operator In some embodiments, the raw ingredient sample comprises a sample of meat or fish. The trait measured in the meat sample comprises an amino acid, protein, or fat. The trait measured in the fish sample comprises an amino acid, protein, or fat.

In some aspects, disclosed herein is a method of determining a level of a trait in a finished product, comprising the following steps:
- obtaining a finished product sample;
- collecting spectroscopic data on the finished product sample;
- processing the data using algorithmic pre-processing;
- applying a chemometric algorithm on the processed data to quantify trait; and
- translating the quantitative results into a reporting format selected for a system operator.

In some embodiments, the finished product sample comprises a sample of pea protein or milk protein.

In some embodiments, the finished product is a pea protein sample. In some embodiments, the trait measured in the pea protein sample comprises an amino acid, protein, an adulterant, fungus, or bacteria. In some embodiments, the trait measured in the pea protein sample is an amino acid. In some embodiments, the trait measured in the pea protein sample is protein. In some embodiments, the trait measured in the pea protein sample is an adulterant. In some embodiments, the trait measured in the pea protein sample is fungus. In some embodiments, the trait measured in the pea protein sample is bacteria.

In some embodiments, the bacteria comprise *Mycobaterium tuberculosis*, *Mycobaterium bovis*, *Mycobaterium bovis* strain BCG, BCG substrains, *Mycobaterium avium*, *Mycobaterium intracellular*, *Mycobaterium africanum*, *Mycobaterium kansasii*, *Mycobaterium marinum*, *Mycobaterium ulcerans*, *Mycobaterium avium* subspecies *paratuberculosis*, *Nocardia asteroides*, other *Nocardia* species, *Legionella pneumophila*, other *Legionella* species, *Acetinobacter baumanii*, *Salmonella typhi*, *Salmonella enterica*, other *Salmonella* species, *Shigella boydii*, *Shigella dysenteriae*, *Shigella sonnei*, *Shigella flexneri*, other *Shigella* species, *Yersinia pestis*, *Pasteurella haemolytica*, *Pasteurella multocida*, other *Pasteurella* species, *Actinobacillus pleuropneumonias*, *Listeria monocytogenes*, *Listeria ivanovii*, *Brucella abortus*, other *Brucella* species, *Cowdria ruminantium*, *Borrelia burgdorferi*, *Bordetella avium*, *Bordetella pertussis*, *Bordetella bronchiseptica*, *Bordetella trematum*, *Bordetella hinzii*, *Bordetella pteri*, *Bordetella parapertussis*, *Bordetella ansorpii*, other *Bordetella* species, *Burkholderia mallei*, *Burkholderia psuedomallei*, *Burkholderia cepacian*, *Chlamydia pneumoniae*, *Chlamydia trachomatis*, *Chlamydia psittaci*, *Coxiella burnetii*, *Rickettsial* species, *Ehrlichia* species, *Staphylococcus aureus*, *Staphylococcus epidermidis*, *Streptococcus pneumoniae*, *Streptococcus pyogenes*, *Streptococcus agalactiae*, *Escherichia coli*, *Vibrio cholerae*, *Campylobacter* species, *Neiserria meningitidis*, *Neiserria gonorrhea*, *Pseudomonas aeruginosa*, other *Pseudomonas* species, *Haemophilus influenzae*, *Haemophilus ducreyi*, other *Hemophilus* species, *Clostridium tetani*, *Clostridium difficile*, other *Clostridium* species, *Yersinia enterolitica*, and other *Yersinia* species, and *Mycoplasma* species. In one example, the bacteria comprise *Lactobacillus* spp, or spore-forming bacteria (*Bacillus coagulans*, *Clostridium pasterianum*, *Alicyclobacillus* spp.)

In some embodiments, the fungus comprises *Candida albicans*, *Cryptococcus neoformans*, *Histoplama capsulatum*, *Aspergillus fumigatus*, *Coccidiodes immitis*, *Paracoccidiodes brasiliensis*, *Blastomyces dermitidis*, *Pneumocystis carinii*, *Penicillium marneffi*, or *Alternaria alternate*.

In some embodiments, the finished product is a milk powder sample. In some embodiments, the trait measured in the milk powder sample comprises protein, lactose, an adulterant, fungus, or bacteria. In some embodiments, the trait measured in the milk powder sample is an amino acid. In some embodiments, the trait measured in the milk powder sample is protein. In some embodiments, the trait measured in the milk powder sample is an adulterant. In some embodiments, the trait measured in the milk powder sample is lactose.

In some embodiment, the sample comprises intact seeds or a non-processed sample of the field crop, the specialty crop, the raw ingredient, or the finished product. In some embodiments, the sample comprises a ground seeds or a powder sample of the field crop, the specialty crop, the raw ingredient, or the finished product.

EXAMPLES

The following examples are set forth below to illustrate the devices, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Handheld Optical Spectrometer for Real Time Characterization of Digestible Protein in Soybeans Amino acid content in soybeans is important for high quality feed, aquaculture, and human food products. While protein is ostensibly a key marker for soybean quality, the presence of certain amino acids indicates how "digestible" the protein is for the purpose of its target application. These "essential amino acids" (EAAs), including cysteine, lysine, methionine, threonine, and tryptophan, are tracked by the US Soybean Export Council in the annual report on soybean quality (United States Soybean Export Council, 2016). In addition, selecting soybeans with an abundance of these EAAs is critical for identifying plant-based fish meal substitutes for aquaculture.

The current, state-of-the-art method for EAA quantification involves sending samples to a laboratory to obtain an amino acid profile, which is costly and can take several weeks to get results. Handheld sensor technologies commercialized recently, based on near-infrared optical techniques, only provide total protein levels and do not provide amino acid profiles. Therefore, the need exists for a handheld, real-time, affordable system that can measure EAAs in soybeans. This approach can be particularly beneficial at the point of sale, where farmers can demand higher prices for their higher quality soybeans, which are characterized by the presence of these EAAs.

Successful development of portable, real-time soybean sensor technology provides several benefits that address known issues in agriculture, food, and the environment.

A real time, field deployable technology enables a transition to value-pricing of soybean commodities. Farmers (sellers) and food producers (buyers) can assess the quality of the soybean product at the point of sale, without having to resort to costly and slow laboratory analyses. This shift in the economic paradigm of soybean sales can benefit farmers and society by rewarding growers who focus on high quality products for human consumption and other specialty feed products.

In the domain of aquaculture, the sensor can enable characterization of amino acid content for soybean meal, which can replace fish meal as a primary feed source. Using fish meal is environmentally unsustainable, as it requires excessive resources to raise small fish just to feed them to bigger fish eventually slated for human consumption. A plant-based soybean meal can provide many key nutrients, including the five EAAs, and is a more sustainable feed source option.

The sensor technology can be generalizable for other agriculture and food applications. For example, the same instrumentation can be used with minor changes to the backend algorithms and training data to monitor lycopene in tomatoes as well as other types of nutrients in a wide variety of food products. An easy to use, flexible, and effective sensor can have great value within the nutrition and food production markets.

Background

Projected demand for animal-derived protein will double by 2050, resulting in concerns for sustainability and food security. Animal-based foods produce higher levels of greenhouse gases (GHG) than plant-based foods and these are associated with climate change. This is compounded by the fact that increased demand for animal-based protein may intensify pressure on land due to the need to produce more animal feed. This in turn will increase the conversion of forests, wetlands and natural grasslands into agricultural lands, which in itself has negative consequences for GHG emissions, biodiversity and other important ecosystem services. Animal products (meat, fish, milk and eggs) are major dietary sources of protein and can be partly replaced by more sustainable sources. Increased production and use of protein crops (e.g. soy and legumes) are part of the solution. Soybean production has proven to be a more favorable and environmentally sustainable source of protein because of the high protein quality and nutritional value of soybeans and the efficient use of land, water, and energy of soybean.

Increasing interest in protein from plant sources also derives from evidence that individuals consuming foods high in vegetable proteins have lower risk of cardiovascular disease and other metabolic disorders. The protein quality of soybeans is one of the most attractive reasons for the interest in soy and soy foods. High protein content, together with lower carbohydrate content, characterizes soy as a unique vegetable protein source compared to other legumes.

On a global basis, plant-based protein is of immense importance and there is significant interest in its ability to meet growing demand for protein from non-meat sources. Protein quality data can provide a useful way to define optimal foods to meet protein requirements in low income countries, where food availability can be very limited, and the choice of adequate protein sources can be vital. Plant-based protein is preferred to animal-based protein from an environmental perspective as it is associated with a lower land use requirement, and it is generally accepted that plant-based foods produce lower levels of GHG, which are associated with climate change, than animal-based foods. Soy exhibits wide variation in protein content mainly due to genetic, environmental and agronomic factors.

The protein content of soybean varies between 36% and 46%, depending on cultivars and among plant proteins, soy has been shown to have higher quality proteins. The Protein Digestibility Corrected for Amino Acid Score (PDCAAS), currently the most accepted method, for soy has been reported to range from 0.91 to 1.00. Table 1 summarizes data on food protein quality through different methods. Among the EAAs, lysine, methionine, tryptophan, and threonine are the most widely used in the animal feed industry. Soybean meals have higher protein content and superior levels of tryptophan, threonine, isoleucine, and valine than corn (*Z. mays*), sorghum (*S. bicolor*), and other cereal grains but lower levels of methionine, and cysteine, often leading to additional supplements to the meal. However, recent development of soybean cultivars with enhanced protein and amino acid content have further increase the economic value of the crop and can help to enrich the entire value chain from farmers to processors to end users.

TABLE 1

Protein quality of various food products using different indicators.

| Source | PDCAAS | Digestibility (%) | Amino Acid Score | PER | BV |
|---|---|---|---|---|---|
| Soy | 0.92-1.00 | 95-98 | 0.94 | 2.2 | 74 |
| Wheat | 0.25 | 96-99 | 0.26 | 0.8 | 64 |
| Beef | 0.92 | 94-98 | 0.94 | 2.9 | 80 |
| Egg | 1 | 97-98 | 1.21 | 3.8-3.9 | 100 |
| Milk | 1 | 95 | 1.27 | 2.5-3.1 | 91 |

Protein Digestibility Corrected for Amino Acid Score (PDCAAS), Protein Efficiency Ratio (PER), Biological Value (BV).

As a basis for sensor technology that can detect these EAAs, vibrational spectroscopy offers an attractive alternative to conventional biological sensing strategies and is a preferred detection and identification system technology by the food industry. Optical technology is rapidly developing, and instruments are already available commercially as portable, hand-held, and micro-devices that can be used when it is not practical or economical to use the more sophisticated and costly instruments used in research laboratories. Advantages of approaches based on vibrational spectroscopy include low cost, small size, compactness, robustness, high-throughput and ease of operation for in-field routine analysis.

Rapid in-field analysis of EAAs in soybeans requires the development and validation of sensors for implementation as quality control programs by farmers and food industry. Near-infrared has shown success for comparison of protein, lysine, and total sulfur amino acid content in feed formulations by screening raw materials from different suppliers. Van Kempen and Simmins evaluated near infrared (NIR) technology for the estimation of digestible amino acid content in several feed ingredients of animal origin with calibration models for the prediction of lysine and methionine resulted in determination coefficient ($r^2$) ranging from 0.80 to 0.95. Wu et al. showed the applicability of NIR spectroscopy for the amino acid analysis of milled rice powder. The accuracy of NIR screening for amino and fatty acid concentrations in soybeans can be improved by grinding seed samples. NIR calibration models were developed for the estimation of amino acid composition in whole soybeans were developed using partial least squares regression (PLSR), artificial neural networks (ANN), and support vector machines (SVM) regression methods. Most models were usable for research purposes and sample screening and the performance of PLSR and SVM was significantly better than that of ANN.

The feasibility of using a handheld NIR spectroscopy to quantify EAAs in soybeans was evaluated. A commercial, off-the-shelf (COTS) NIR spectrometer reliably and accurately detected the five EAAs (cysteine, lysine, methionine, threonine, and tryptophan) in ground soybean meal. FIG. 1 shows an example data set for NIR measurements of four different soybean samples with varying levels of amino acids. FIG. 1 shows that the spectroscopy technique predicts each amino acid concentration (y-axis) with strong correlation to concentrations determined using standard analytical methods (x-axis).

Disclosed herein is a design of a sensor that is capable of meeting market needs for soybean quality sensing. The end result is a design that can then be assembled, integrated, and tested in a field environment.

Experimental

The first part of this section describes the spectroscopy and algorithm methods that are used to characterize chemical constituents of food and agricultural products. Methods are described for handling soybean samples and the impact on measurement simplicity and accuracy. Then the overall sensitivity and accuracy of these measurements are then discussed as they relate to sensor requirements.

Spectroscopy and Algorithm Approaches.

Near Infrared Spectroscopy. NIR spectra of the soybean samples are collected with a handheld NIR system (Neo-Spectra, Si-Ware, Ciaro, Eygpt) constructed with an optical structure for sample illumination (halogen-tungsten source) and collection of diffuse reflected light, monolithic microelectromechanical system (MEMS) Michelson interferometer chip and a single indium-gallium-arsenide (InGaAs) photodetector. Soybean meal or whole soybeans (~3 g) are placed in a glass dish, rotated (Pike Technologies, Madison, WI, USA) and the spectra collected through the glass in the range from 7718 to 3829 cm$^{-1}$. The background spectrum data is collected before each sample with a highly reflective gold-ceramic standard material. For each soybean sample, two spectra are collected.

Profiling and Quantitation of Amino Acids in Soybeans. The amino acid content of soybeans is analyzed via gas chromatography/mass spectrometry (GC/MS) after acid hydrolysis. Approximately 0.10 g of the sample is weighed and 8 mL of 6M HCl is then added to vacuum hydrolysis tubes (18 mL, 19 mm×100 mm). Samples are deaerated, closed under nitrogen, placed in heater and hydrolyzed at 110° C. for 24 hours. For each product the samples are prepared in triplicate. GC/MS Agilent 5977B MSD with Stainless Steel Source and 7820 GC equipped with a diffusion pump and 50 vial automatic liquid auto sampler. All acquired data is analyzed with HP Chemstation version A.06.03. The extraction and derivatization of EAAs in plasma is carried out as described in the Phenomenex EZ:Faast™ Free (Physiological) Amino Acid Analysis by GC/MS manual. An aliquot (2 µL) of the derivatized samples is injected into the GC at a split ratio of 1:25. Amino acid separation is achieved using a Phenomenex Zebron ZB-A amino acid analysis dedicated column (length=10 m, internal diameter=0.25 mm, film thickness=25 µm). Carrier gas is high purity helium at constant flow of 1.1 mL/min. The injector and transfer line temperatures are maintained at 250° C. and 340° C., respectively. Initial oven temperature is 110° C., increased to 320° C. at 30° C./min and held at 320° C. for 3 min. A selective ion monitoring GC/MS method is applied for the detection of amino acids, based on the retention time (Rt) and a qualifier ion. Quantification is carried out employing norvaline as internal standard and constructing reference curves for every amino acid (AA) by means of standard solutions.

Data Analysis. Soybean samples, including different varieties and geographical origins, have been provided by soybean growers affiliated with the Ohio Soybean Council (OSC). The PLSR algorithm is optimized through sample variability, and thus samples used herein encompassed different genotypes, growth conditions, locations, soil among others. Due to the large number of variables (high-dimensional predictor space) in vibrational spectroscopy data from a limited number of subjects, estimation methods provide a rational simulation following Dobbin and Simon's recommendations. PLSR provides optimal EAA quantification results from optical spectroscopy measurements. PLSR combines the features of Principal Component Analysis (PCA) and Multi Linear Regression to compress a large number of variables into a few latent variables. It is particularly useful when the size of independent variables (spectra) is much larger than that of dependent variables. Thus, using the spectra obtained and reference concentrations from GC/MS, quantitative models are generated with PLSR for each EAA. Calibration models are internally validated using full cross-validation (leave-one-out approach) and externally validated with an independent set. A very important advantage of PLSR is that it considers errors both in the concentration measured by GC/MS and the NIR spectra. It does not assume that the concentrations of amino acids used as reference numbers (obtained from GC/MS) are error free since there could be errors in sample preparations, dilutions, weighing and such. Using the NIR spectra and reference amino acid concentrations, quantitative models are generated with PLSR. Independent validation study is conducted using approximately 75% of sample set to generate calibration models and about 25% serve as an independent validation set.

Figure 2:
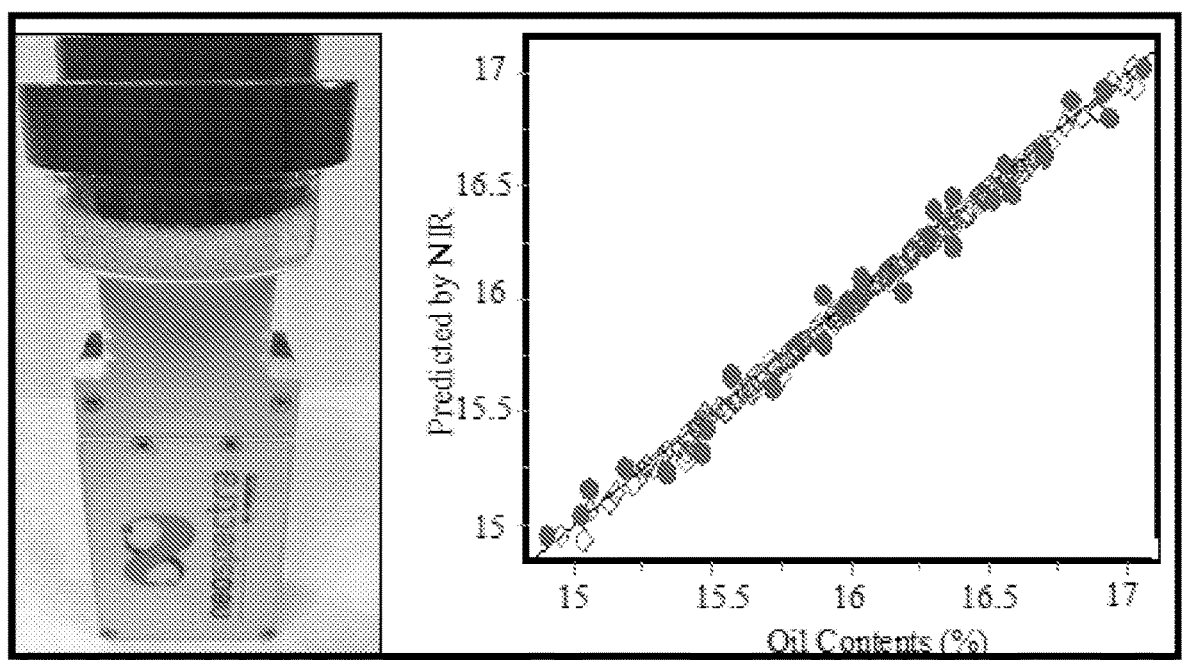
FIG. 2 shows a NIR NeoSpectra Module. A compact NeoSpectra NIR spectrometer (left) was used with Partial Least Squares Regression (PLSR) algorithm for accurate results.

Predictive Accuracy of the Models. Regression models are used to generate prediction models and the accuracy and ability of these models are examined with an independent test set representative of the classes modeled with the training set. Blind samples (the researcher does not have access to its identity before prediction) are included to test the ability of the models to predict the levels of essential amino acids. Results from the validation testing set are used to determine the sensitivity, specificity and positive predictive value of the patterns. PLSR models for determination of oil content have been developed based on the NIR spectra collected using a handheld unit (FIG. 2). The validated parsimonious PLSR model were strongly correlated with the reference values ($R_{pred}$>0.95) with standard error of prediction (SEP) for estimating levels of oil in soybean meal of 0.1%.

Investigation of Sample Preparation Methods. Research reported for measurement of crude protein and amino acid content in soybeans, as well as other oilseeds, has been limited to older benchtop equipment and have shown the challenges in developing predictive models for screening amino acids levels as their performance varied greatly depending on the amino acid, with tryptophan, cysteine and methionine models often showing lower performance (Table 2). However, these three amino acids have been shown to be the most critical for livestock diet and the ones that soybean breeders want to maximize.

TABLE 2

Summary of various studies that measured crude protein or amino acid composition using benchtop NIR spectroscopy

| Parameters | Instrument | Performance |
| --- | --- | --- |
| Crude protein, and selected amino acids (Fontaine et al. 2001) | Dispersive spectrometer with PbS detector (Benchtop) | Soybean meal and full-fat soybeans data were combined, n = 209 RSQ = 0.79 to 0.81 for sulfurous amino acids RSQ = 0.85 to 0.97 for Lys, Thr, Trp, Leu, Val |
| Crude protein and selected amino acids (Kovalenko et al. 2006) | Different spectrometers, including scanning monochromator, InGaAs, photodiode arrays and Fourier Transform-NIR (All are benchtop equipment) | Overall observations classified into RSQ ranges: <0.25: Trp 0.26-0.49: Cys 0.50-0.64: Met 0.65-0.81: Ala, Glu, Ile, Pro, Thr and Val 0.93-0.90: Arg, Asp, Gly, His, Leu, Lys, Phe and Tyr |

*Coefficient of Determination measures explained variation between modeled and reference values
**Standard Error of Cross-Validation (SECV)

The performance of the handheld NIR device was evaluated in a total of 41 soybean samples that included whole soybeans and powdered soy products including soy isolates (~90% protein), soy concentrates (~70% protein), soy flour, fish meal powder, as well as soy supplement drink powders. Although the soybean samples were sourced from various cultivars and growing regions across the Midwest, they exhibited a narrow range of amino acid levels which was extended by including the soybean meal products (Table 3).

TABLE 3

Protein and amino acid content of soybeans and meals

| | Parameters | Maximum value (%) | Minimum value (%) | Mean value (%) | Standard deviation |
| --- | --- | --- | --- | --- | --- |
| Soybeans (n = 22) | Threonine | 1.53 | 1.36 | 1.42 | 0.04 |
| | Cysteine | 0.64 | 0.49 | 0.57 | 0.04 |
| | Methionine | 0.61 | 0.47 | 0.54 | 0.04 |
| | Lysine | 2.57 | 2.35 | 2.45 | 0.06 |
| | Tryptophan | 0.52 | 0.30 | 0.41 | 0.06 |
| | Total Protein | 37.40 | 33.39 | 35.01 | 1.07 |
| Isolates, Concentrates, Soy powder products (n = 19) | Threonine | 3.23 | 1.34 | 2.49 | 0.70 |
| | Cysteine | 1.06 | 0.45 | 0.94 | 0.21 |
| | Methionine | 1.14 | 0.47 | 0.88 | 0.25 |
| | Lysine | 5.54 | 2.34 | 4.24 | 1.24 |
| | Tryptophan | 1.32 | 0.50 | 0.95 | 0.27 |
| | Total Protein | 84.30 | 33.00 | 62.67 | 18.46 |

It was shown that environmental variables during soybean growth impacted the amino acid composition, with the cysteine levels ranging from 0.14-0.68%, threonine ranging from 0.87-2.19%, methionine from 0.31-0.85%, tryptophan from 0.30-0.80, and lysine from 0.88-3.92%. All of these ranges are much wider than the soybean samples tested herein, so it is recommended to source soybeans with a diverse set of amino acid profiles by capturing soybeans grown in varied climatic conditions, not just varying cultivars.

Figures 3A, 3B:
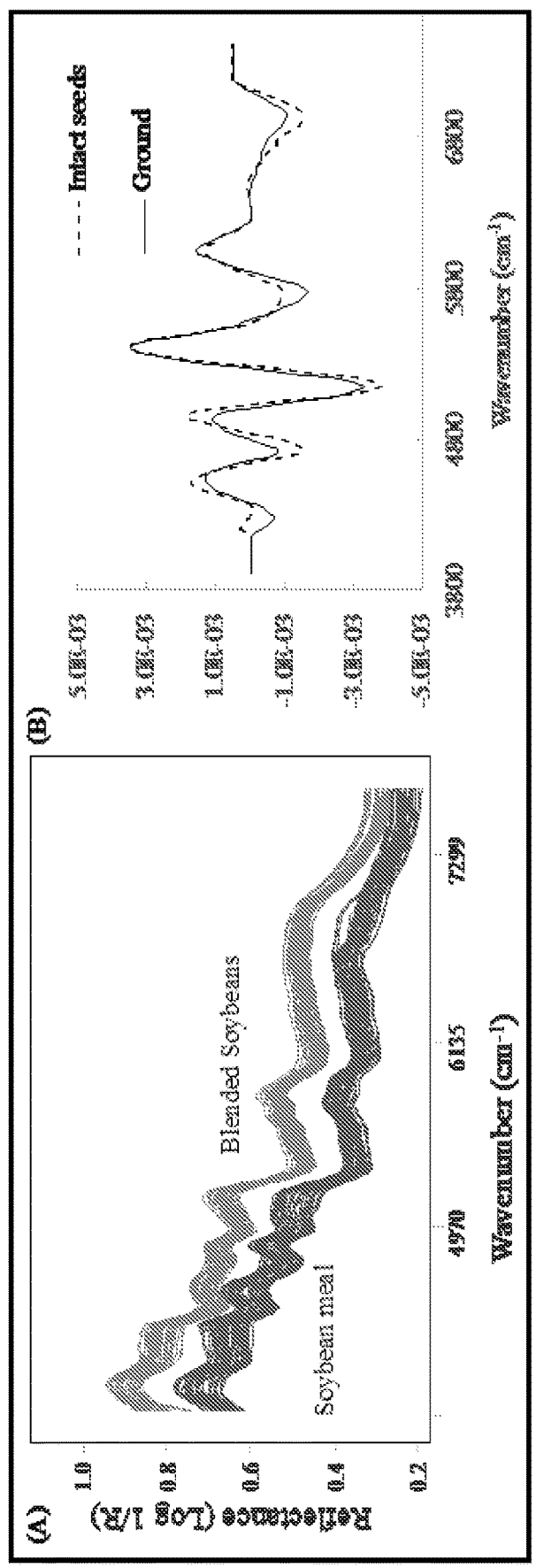
FIG. 3A shows comparison of NIR spectra for the whole intact seed of soybean and ground soybean, obtained without spectral pretreatment.
FIG. 3B shows the second derivative of the spectrum transformations for intact soybean seeds and ground soybean.

The NIR spectra and second derivative spectra of intact soybean seeds and ground soybeans can be seen in FIG. 3. The spectral patterns are similar between the intact seeds and ground soybean but appear different in the 5000-4500 cm$^{-1}$ region, showing two distinct peaks for ground samples but just one broader peak for intact seed samples. This variation becomes even more apparent when looking at the second derivative, showing that N—H and C═O stretching and combination vibrations (5000-4500 cm$^{-1}$) that corresponds to amide I and amide II bands. Additionally, the region between 5900-5600 cm$^{-1}$, associated with the second overtone of C—H groups of fatty acids, showed differences between the intact and ground soybeans.

Figure 4:
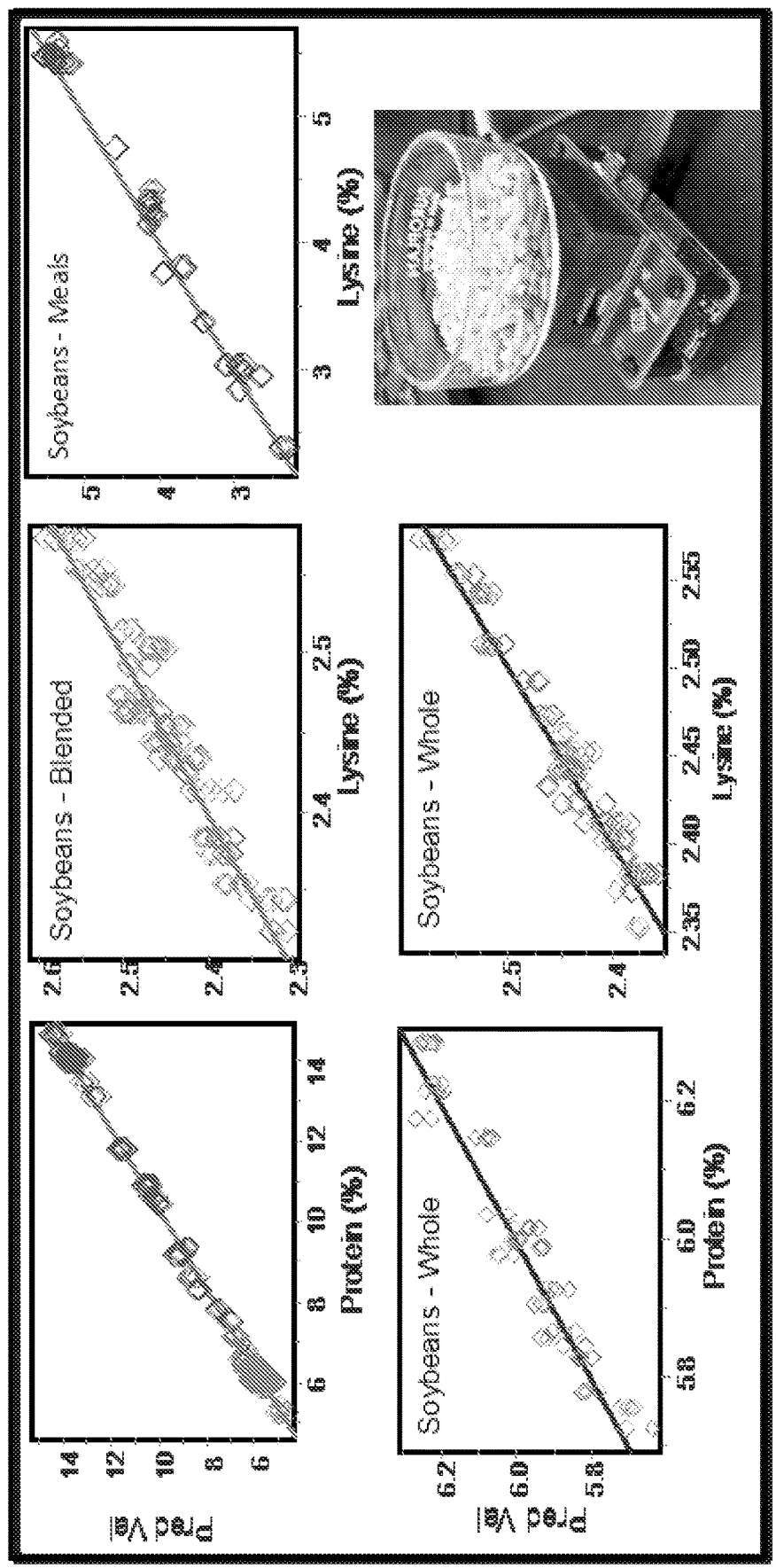
FIG. 4 shows PLSR calibration plots for crude protein and lysine levels in ground and whole soybean samples using a handheld NIR device, NeoSpectra.

Algorithm Optimization and Measurement Error Estimation. Regression models for powdered samples (including ground soybeans, isolates, concentrates and soy products) showed excellent fit as demonstrated in FIG. 4. All calibration models showed good performance statistics with low standard error and high correlation of determinations (Table 4). Models using NIR spectra collected from intact soybeans showed lower modeling performance as compared to the ground samples, similar results have been reported for models on soybean amino acid.

For the ground sample models, with the exception of methionine (R=0.90), all other amino acid and crude protein models gave performances usable for quality assurance applications (R>0.96) according to the guidelines for interpreting correlation of coefficients. Following the same guidelines for the intact seed models, the cysteine model was found to be suitable for rough screening (R=0.80), lysine and crude protein models were found to be suitable for trait screening (R=0.88-0.89), while models for threonine, methionine and tryptophan were found suitable for quality assurance applications (R=0.90-0.95). Amino acid prediction models generated from NIR spectroscopy measurement of whole intact soybean seeds gave lower coefficient of determinations ($R^2$=0.06-0.67) as compared to ground soybeans ($R^2$=0.40-0.85). A major challenge with developing a reliable predictive algorithm for intact seeds is the scattering effects that arise from uneven surfaces of whole seeds and kernels. This limitation was addressed with the employment of a rotating accessory that allows collection of NIR spectra at different positions of the sample and by using preprocessing algorithms to minimize the effect of scattering (ie. second derivatives, multiplicative scatter correction). The predictive algorithms based on intact seeds showed significant improvement in performance compared to those reported by using benchtop instruments. The performance of NIR spectroscopy for these constituents can be improved by increasing the sample size and introducing more samples with increased variability of trait levels into the calibration data sets. Since the commercial cultivars of soybeans used in this study exhibit a narrow range of amino acid levels, the confidence level needs to be increased by sourcing soybeans with much larger variability in total protein and amino acid levels. Amino acid composition of soybean is strongly affected by environmental factors during growth phases such as the seed filling and reproductive period, finding that environment was the most important source of variation for all traits, including levels of amino acids, followed by the genotype x environment interaction. Through collaboration with the OSC, soybean samples are sourced to capture environmental effects in soybeans besides genotypical differences.

TABLE 4

Performance of prediction models developed using a handheld NIR instrument for estimating total protein and select amino acids and in soy samples

| | | Calibration Model | | | | | Validation Model | | | |
|---|---|---|---|---|---|---|---|---|---|---|
| | | Range | n | Factor | SECV | Rcal | Range | n | SEP | Rval |
| Powder | Threonine (%) | 1.34-3.23 | 31 | 4 | 0.051 | 0.99 | 1.40-3.16 | 10 | 0.062 | 0.99 |
| | Cysteine (%) | 0.45-1.06 | 31 | 4 | 0.041 | 0.98 | 0.54-1.00 | 10 | 0.043 | 0.97 |
| | Methionine (%) | 0.47-1.14 | 30 | 4 | 0.044 | 0.98 | 0.47-1.13 | 11 | 0.090 | 0.90 |
| | Lysine (%) | 2.34-5.54 | 31 | 5 | 0.246 | 0.98 | 2.43-5.37 | 10 | 0.238 | 0.98 |
| | Tryptophan (%) | 0.30-1.32 | 31 | 3 | 0.080 | 0.97 | 0.30-1.23 | 10 | 0.097 | 0.96 |
| | Crude protein (%) | 33.00-84.30 | 31 | 6 | 1.630 | 0.99 | 33.35-79.25 | 10 | 2.801 | 0.98 |
| Intact Seed | Threonine (%) | 1.36-1.53 | 11 | 5 | 0.012 | 0.97 | 1.40-1.45 | 3 | 0.011 | 0.90 |
| | Cysteine (%) | 0.51-0.62 | 11 | 6 | 0.014 | 0.94 | 0.56-0.60 | 3 | 0.068 | 0.79 |
| | Methionine (%) | 0.52-0.61 | 11 | 6 | 0.013 | 0.94 | 0.52-0.57 | 3 | 0.055 | 0.93 |
| | Lysine (%) | 2.37-2.57 | 10 | 5 | 0.014 | 0.98 | 2.38-2.54 | 4 | 0.035 | 0.87 |
| | Tryptophan (%) | 0.30-0.47 | 11 | 2 | 0.015 | 0.96 | 0.36-0.43 | 3 | 0.022 | 0.94 |
| | Crude Protein (%) | 32.83-36.66 | 11 | 5 | 0.221 | 0.980 | 33.80-35.86 | 3 | 0.634 | 0.88 |

These results show the ability to parallel and/or outperform the quantitative techniques using benchtop systems from other research groups. The NIR technique is rapid, accurate and cost effective for analyzing the composition of protein, lipids, moisture, carbohydrates and fiber in soybeans, with $R^2=0.99\%$ and standard error of calibration<1.0%. Previous studies showed limited performance of the NIR technique for the quantitation of proteins in whole soybean grains with $R^2$ of 0.73% and SEP of 0.6, employing soybeans with a high protein range from 35 to 41.5%. Disclosed herein is a handheld NIR device that generated reliable PLSR models with good predictive abilities (R>0.9). The total time required for the preparation and analysis of samples was less than 5 min, compared to the 3-10 h required for the determination of the content of proteins and amino acid composition by reference methods. This technique can be effectively applied in the industry as an analytical tool for phenotyping soybeans and simultaneously measure several quality parameters.

Sensor Design. A list of "market needs" to address the demands of the potential user community for a handheld soybean quality sensor is shown below.

Based on these user needs, a set of engineering requirements have been derived for an ideal soybean quality sensor and listed in Table 5.

TABLE 5

Correlation of market needs with derived sensor design

| Market needs | Sensor design |
|---|---|
| Sensor shall measure quality of soybean samples | Measurement of % concentrations of 5 EAAs: cysteine, lysine, methionine, threonine, and tryptophan |
| | Measurement of % concentration of protein, moisture, fat, oleic and linoleic acids |
| | Measurement using ground or whole bean samples |
| Sensor measurements shall be accurate | Measurement absolute accuracy of 0.1% concentration (depending on the attribute concentration and accuracy of the reference method) |
| Sensor measurements shall be rapid | Complete measurement in 20 seconds or less |
| | Sensor and user interface application startup sequence less than 10 seconds |
| Sensor shall be of small, handheld size | Sensor head volume less than 110 cubic inches (<1800 cm$^3$) |
| | Sensor head weight less than 5 lbs (<2.3 kg) |
| Sensor shall be deployable at field locations (farm, grain elevator, etc.) | Sensor operation over temperature range from 23° F.-104° F. (−5° C.-40° C.) |
| | Sensor operation in presence of light precipitation |
| | Sensor withstand vibrations typically associated with tractor driving through a field |
| Sensor shall be easy to operate with minimal training | Sensor operation performed by user with high school diploma or equivalent |
| | User interface via display screen |
| | User interface can initiate measurement, halt measurement, adjust measurement parameters |
| | Measurement results provided to user interface display screen |
| | Measurement results (% concentration, measured spectrum) archived for subsequent processing |
| | User interface and data processing leverage commercial smartphone or tablet |
| | Smartphone or tablet connects to sensor head via Bluetooth and USB cable with equivalent functionality |
| Sensor shall require minimal maintenance | Sensor head operation of 8 hours on single battery charge |
| | Sensor lifetime > 10,000 hours |

To meet the design needs listed in Table 5, a high level, block diagram design is shown in FIG. 5, that illustrates major subsystems and components. This design comprises two major subsystems: the sensor head, which contains the NIR spectrometer and supporting electronics, and a smartphone or tablet, which contains the processor for analyzing spectral data as well as the UI. The decision to use a smartphone or tablet was predicated on discussions with the OSC and member farmers, who indicated that smartphone/tablet interface is preferable to an integrated processor and interface. Many other, high tech devices are currently being added to the farmers' "toolbox" that run off of smartphone/tablet devices, and generally the farmers were very comfortable with the simplicity that can be designed into an appropriate UI application (App).

Within the sensor head subsystem, the key component for measuring soybean traits is the NIR spectrometer. The spectrometer contains light sources, detectors, integrated optics, and integrated electronics that generate the spectroscopic data. Spectrometer operation is commanded via the Control Electronics component, which receives instructions from the UI through the Interface Electronics component. The Sample Rotation Stage component contains the soybean samples and allows for rotation of the samples to provide multiple view angles. Electrical power is provided to each of these components within the sensor head from the Power component, and the thermal management component is present to keep the spectrometer and sample rotation stage motors cool. The entire sensor head subsystem fits within a self-contained chassis structure for mechanical support.

The operation of the sensor head is commanded from the UI located in the Smartphone/Tablet subsystem. The UI is an application (app) that allows the user to command the spectrometer operation as well as to display measurement results. The processor mediates connectivity with the sensor head via Bluetooth (wireless) or USB (wired) connections. The processor also receives and analyzes the data from the spectrometer, provides measurement results to the UI, and archives measurement data on the local hard drive.

Sensor Head Subsystem. The design of this subsystem was driven by the selection of the NIR spectrometer (FIG. 6), which is the critical component the soybean sensor concept. The NeoSpectra-Micro Development Kit (Si-Ware Systems, $2500) was selected based on its excellent performance (wavelength range, signal-to-noise ratio) and small size. NeoSpectra products have been used for several years. The Micro spectrometer includes an optical head (light source, collection optics), electronics (Application Specific Integrated Circuits—ASICs), interferometer (MEMS-based Michaelson interferometer), and detector (uncooled InGaAs photodetector). The Development Kit includes the NeoSpectra-Micro spectrometer integrated with a Raspberry Pi board that facilitate easy interfacing with the sensor head. For example, the Raspberry Pi can allow the Development Kit to operate as a standalone device, interface with a personal computer, or interface to any other device with a Serial Peripheral Interface (SPI). The Raspberry Pi also contains software to operate the system as well as enable user-developed software to expand the system's functionality. Therefore, considering the block diagram in FIG. 5, the development kit provides capability for the NIR spectrometer, Control Electronics, and Interface Electronics boxes.

One of the most critical performance aspects is the wavelength range, which is 1350-2500 nm in this example. This range is enabled by the use of InGaAs detector technology and is distinguished from many other small NIR spectrometers that are based on Silicon detectors, which typically cover 400-1000 nm. Operating at the longer wavelengths provided by the NeoSpectra-Micro is advantageous for detecting chemical constituents, like amino acids, over the shorter wavelengths, because the overtone vibrational bands are stronger near 2000 nm than near 1000 nm. However, the detector technologies and optics are typically more expensive than silicon-based systems.

Therefore, using the NeoSpectra-Micro Development Kit as a starting point, a sensor head design was produced that leveraged a number of low-cost, COTS components. Key additional components include the following components:

Power: 10000 mAh external battery pack with LCD display, power switch, panel mount connector
Sample Rotation Stage: gear motor, motor bracket, turntable, IR fused quartz window
Thermal Management: 50 mm fan (5 VDC)
Chassis: custom 3D printed body and lid, acrylic window for LCD battery display, various fasteners.

A set of 3D drawings of the chassis and integrated components are shown in FIG. 7. Based on these drawings, CDME fabricated the Sensor Head, is shown.

Figure 8:
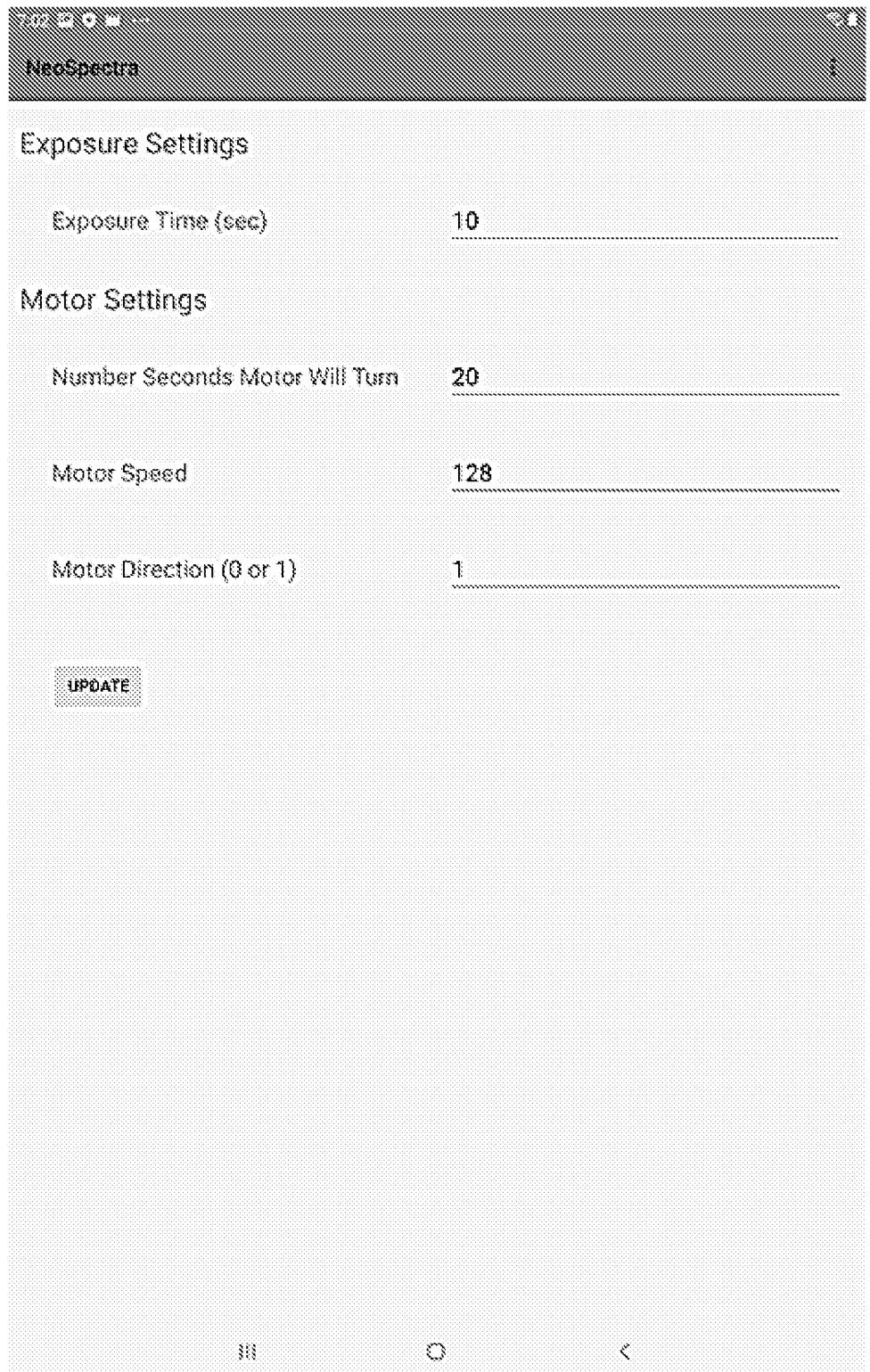
FIG. 8 shows an App screen shot showing user control of various operational parameters related to the Sensor Head, including measurement duration and sample rotation stage speed and direction.
Figure 9A:
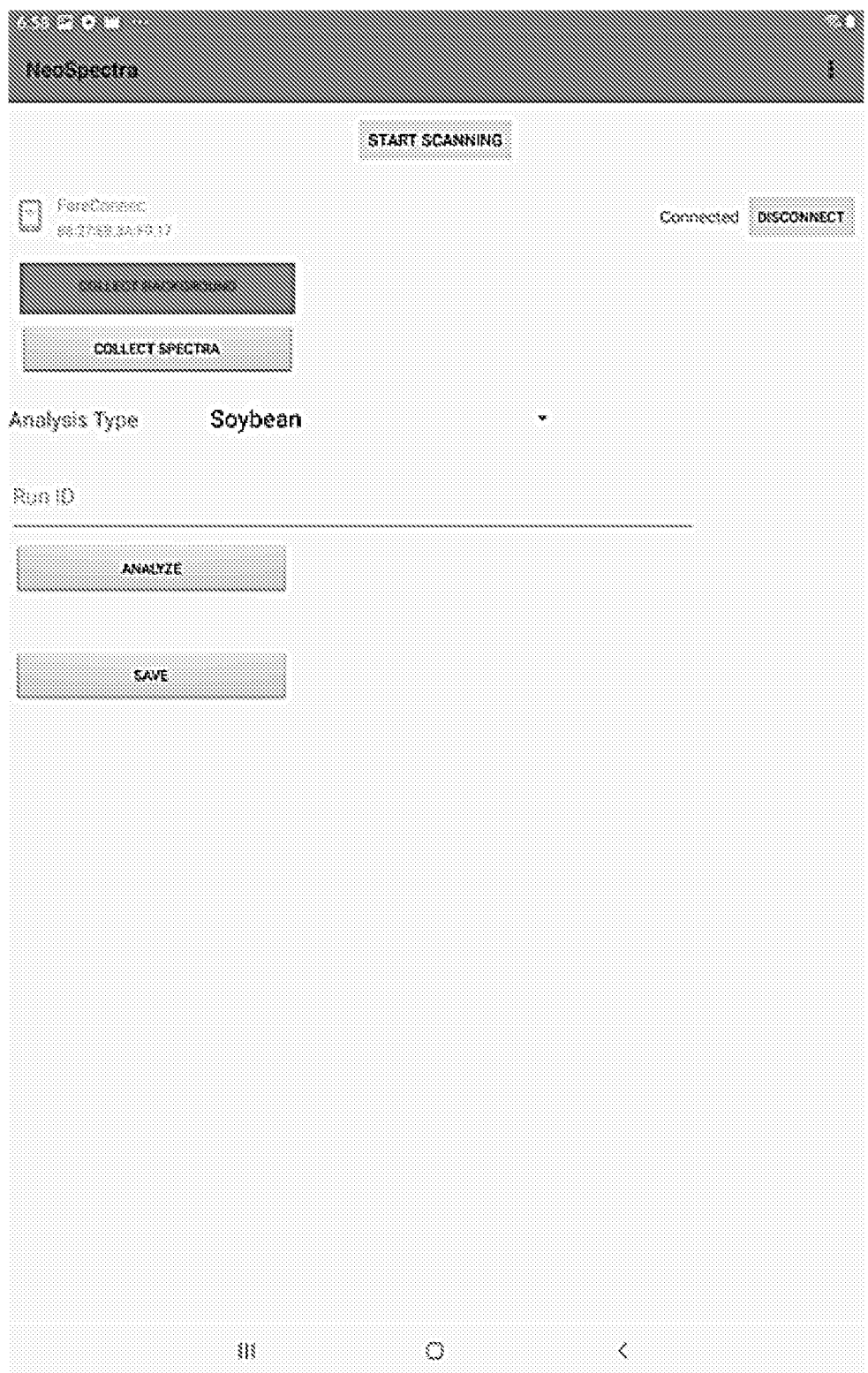
FIGS. 9A-9B show App screen shots showing that measurements are set for Soybean samples (Analysis Type) and indicating that background spectrum needs to be collected (FIG. 9A) and then has been collected (FIG. 9B).
Figure 9B:
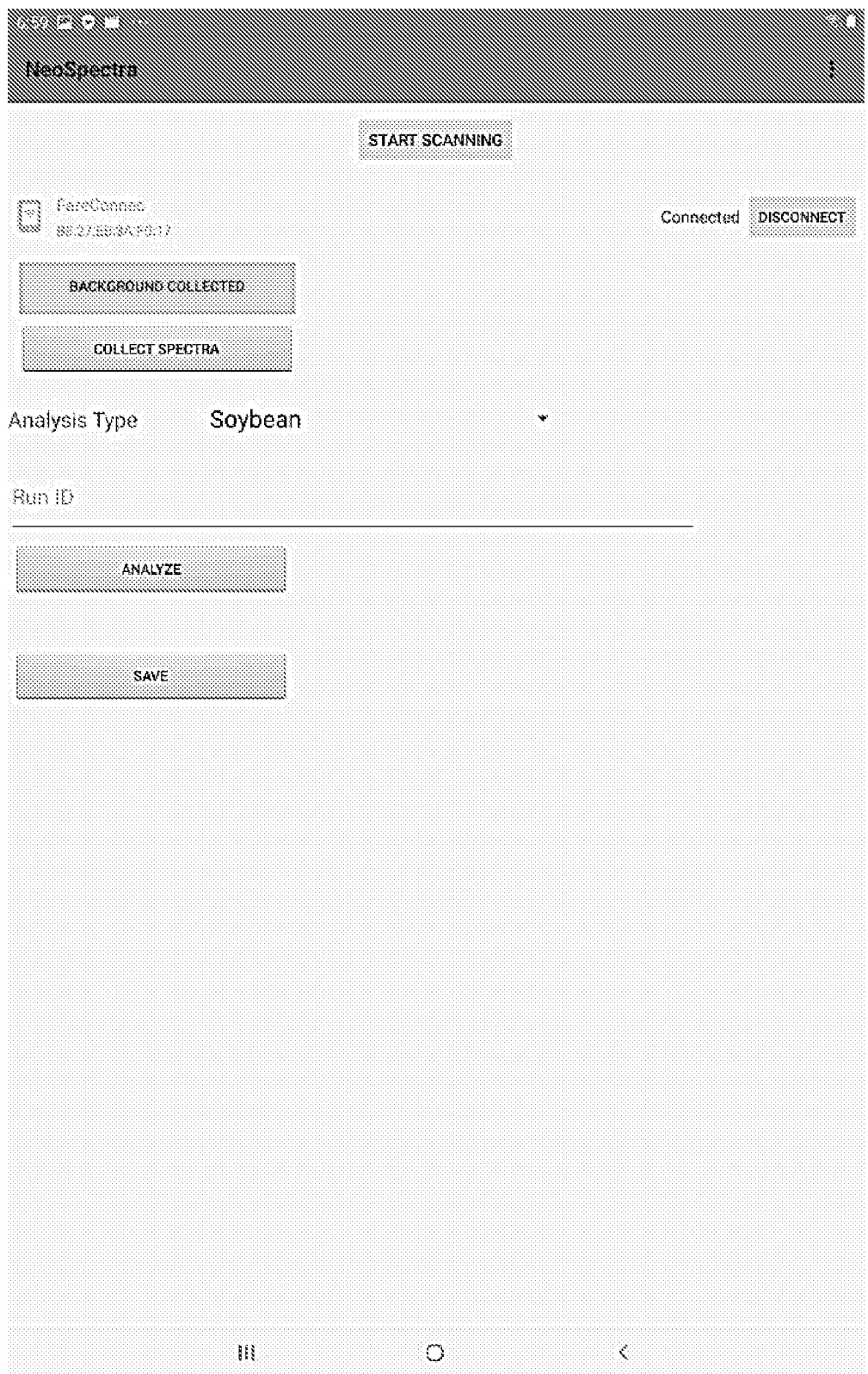
Figure 10A:
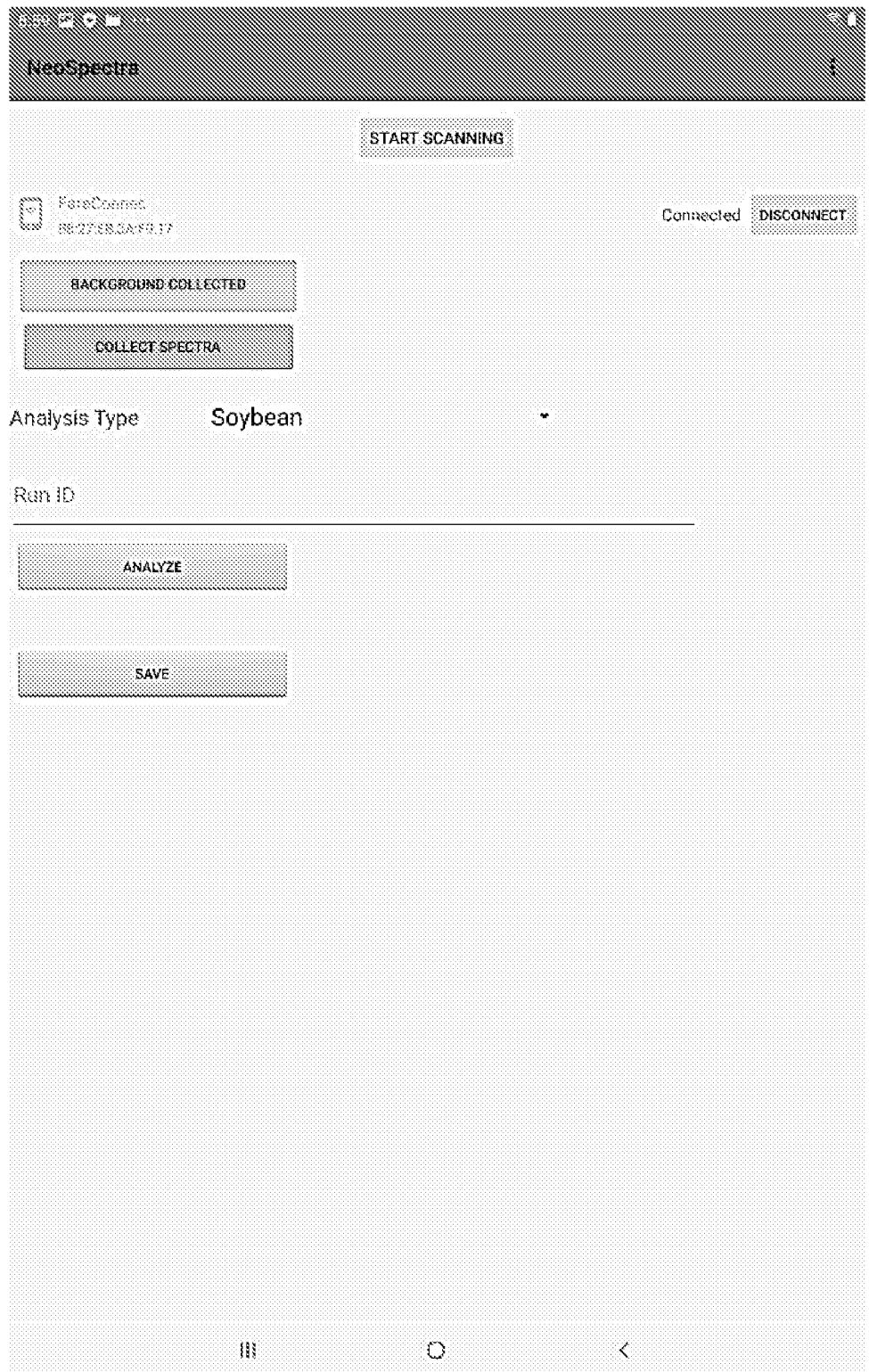
FIGS. 10A-10B show App screen shots showing indicating that soybean sample spectra are ready for collection (FIG. 10A) and the measurement results and user entry of file name for archiving (FIG. 10B).
Figure 10B:
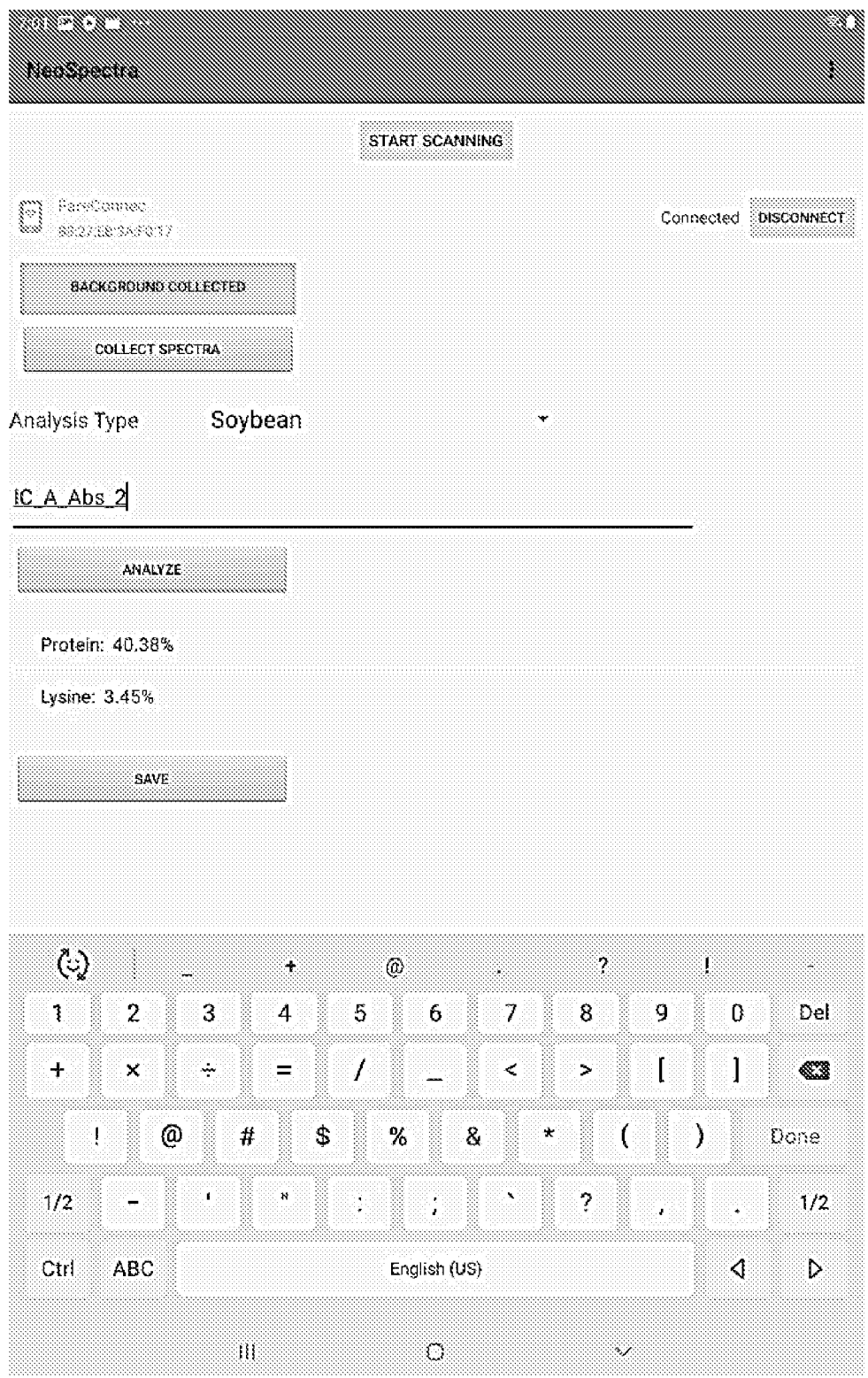

Smartphone/Tablet Subsystem. For the Smartphone/Tablet subsystem, an Android-based tablet was purchased, and a custom software application was developed for controlling the sensor head operation and to analyze the resultant spectroscopic data. This software development has two components. First, code was developed on the Raspberry Pi inside the Sensor Head to mediate connectivity via Bluetooth and/or USB cable to the Smartphone/Tablet subsystem. Second, the custom app was developed based on standard implementations of the NeoSpectra data acquisition routines as well as PLSR prediction algorithms based on laboratory-acquired regression vectors. FIGS. 8-10 show examples of the UI provided by the custom app.

Figure 11:
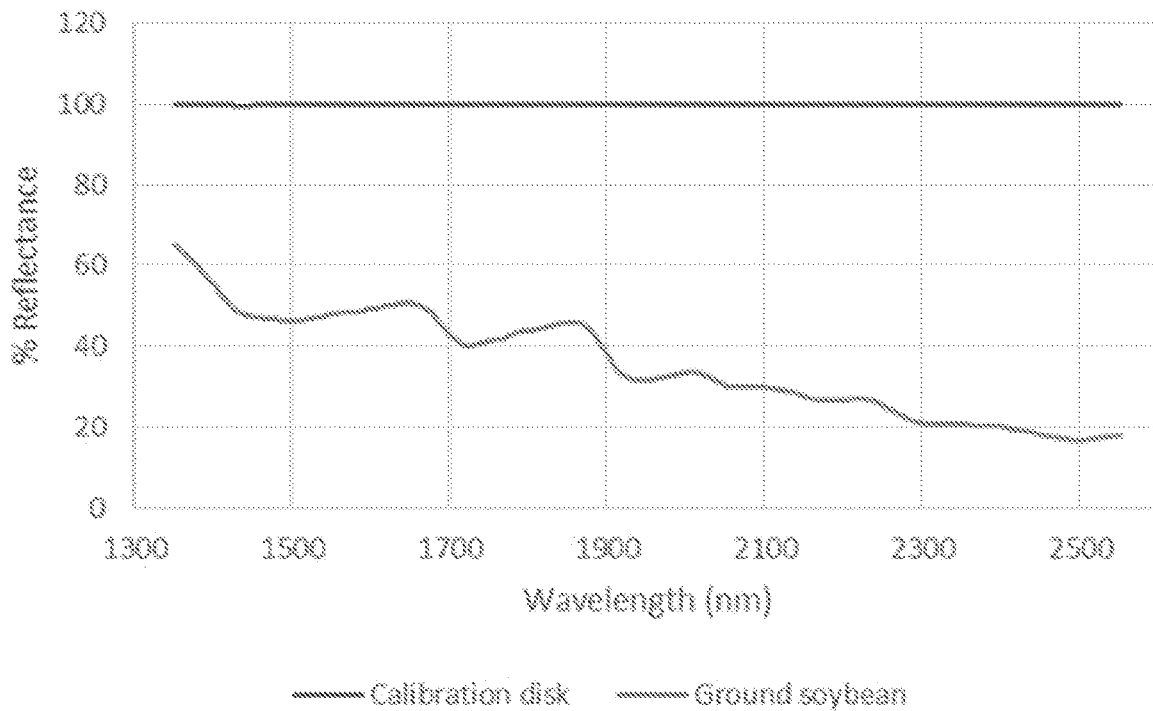
FIG. 11 shows comparison of spectrum of ground soybean sample to the calibration disk used to produce background spectra.

Diagnostic Test Data. Using the sensor, a variety of diagnostic test data were acquired to show that the system performed as designed. In general, the sensor measured soybean spectra as well as laboratory measurements, as shown in FIG. 11. This figure shows the reflectance spectrum of the calibration disk used for acquiring background spectra as well as the reflectance spectrum of a sample of ground soybeans. The soybean spectrum is very similar qualitatively (i.e., shape and location of spectral features) and quantitatively (i.e., magnitude of reflectance).

Figure 12:
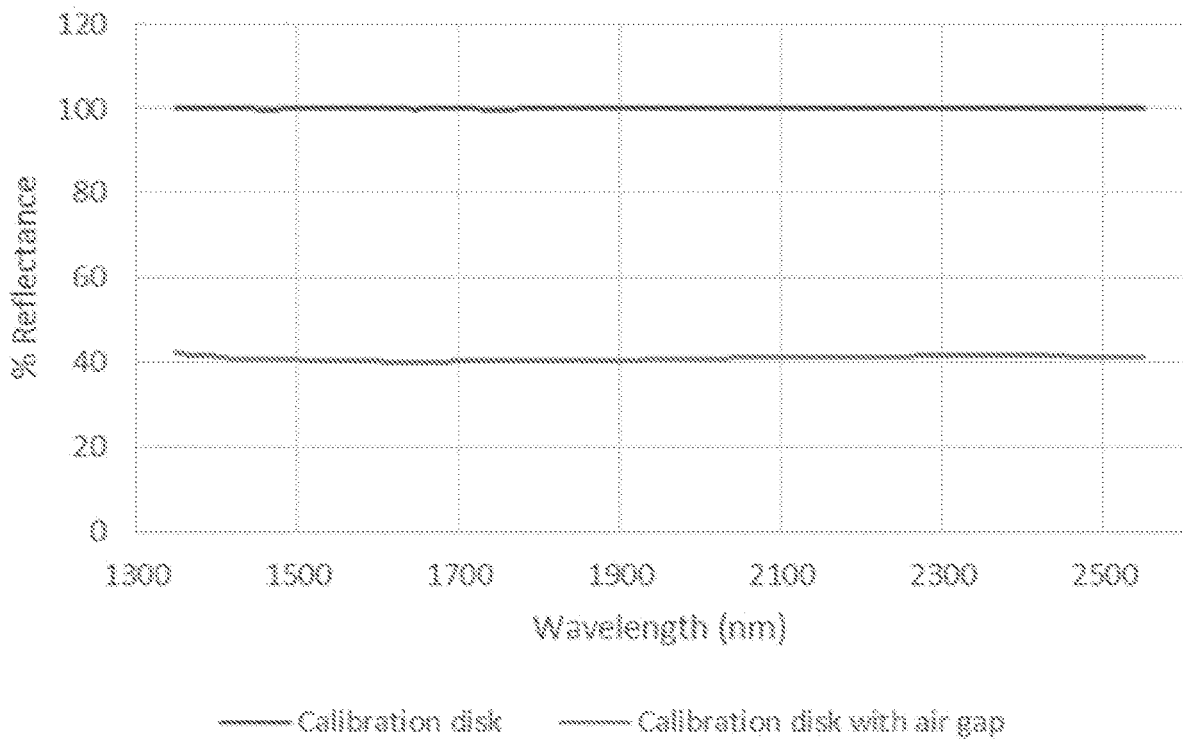
FIG. 12 shows comparison of spectrum of the calibration disk with and without a 0.057" air gap.

One aspect of the optical configuration is the air gap between the spectrometer and the sample under measurement. Air gaps introduce additional absorption, as shown in FIG. 12, which normally does not substantially impact the accuracy of a spectral measurement. This is because the air gap present in the background measurement is the same as for the sample measurement. The ratio of sample to background spectrum therefore removes the air gap contribution. However, if the air gap is too large, then it can negatively impact signal-to-noise ratio and therefore degrade measurement accuracy. Therefore, any Sensor Head design must be cognizant of the air gap effect and try whenever possible to minimize it.

The core spectrometer engine needs careful consideration to provide for hardware. There are some NIR spectrometers on the market, but most have a limited wavelength range up to 1700 nm and thus are not as advantageous in detecting chemical constituents. Examples include SCiO, MicroNIR by Viavi, DWARF-Star-NIR by StellarNet Inc, for example. Extended wavelength range spectrometers commercially available are much more expensive (priced at $8,000 and up) and not viable when compared to the starting cost of the NeoSpectra-Micro.

Example 2. Real-Time, In Situ Quantification of Cannabidiol (CBD) in Hemp

Figure 13:
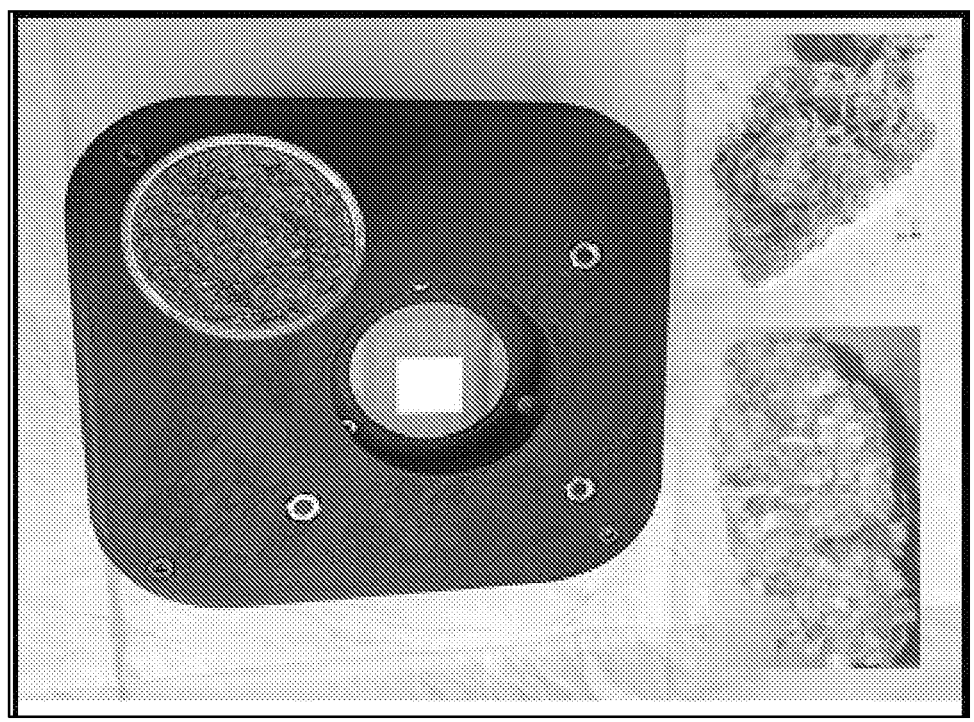
FIG. 13 shows NIR handheld sensor with a rotating accessory for hemp analysis.

This example investigates the burgeoning interests in hemp agriculture. The sensor technology solutions herein can support hemp production for the CBD market (FIG. 13). This sensor device can reduce costly and time-consuming laboratory analyses via real-time, in situ measurements of hemp samples.

Figure 14:
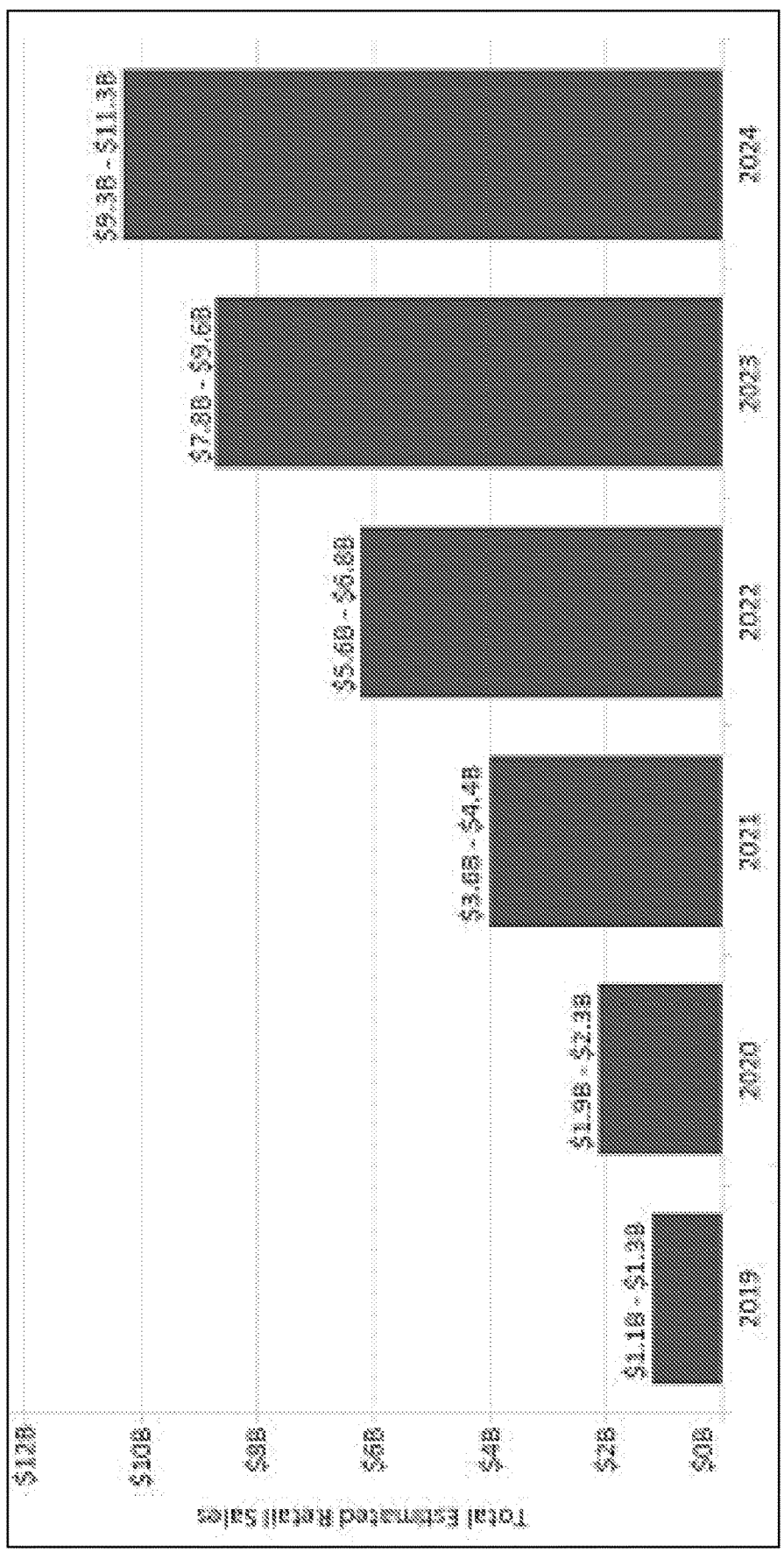
FIG. 14 shows annual US help-derived CBD retail sales estimates (2019-2024). Source: 2019 Hemp Business Factbook.

Hemp production (FIG. 14) supporting the CBD market is particularly attractive given prospects for order of magnitude growth over the next five years. In order to maximize profit, farmers need accurate assessment of the market value of their hemp product, which depends strongly on how much CBD can be extracted from the hemp biomass. Currently, hemp samples are sent to a laboratory to determine CBD levels, which is costly ($100-200/sample) and can take days to weeks to get results. Farmers can therefore benefit greatly from a low-cost, portable sensor technology that provides accurate, real-time, in situ CBD assays. This technology can save money and can increase efficiency of hemp transactions by rapid assessment of hemp quality. Similarly, hemp buyers, CBD product manufacturers, and researchers can benefit from this low-cost, real-time sensor.

Figure 15:
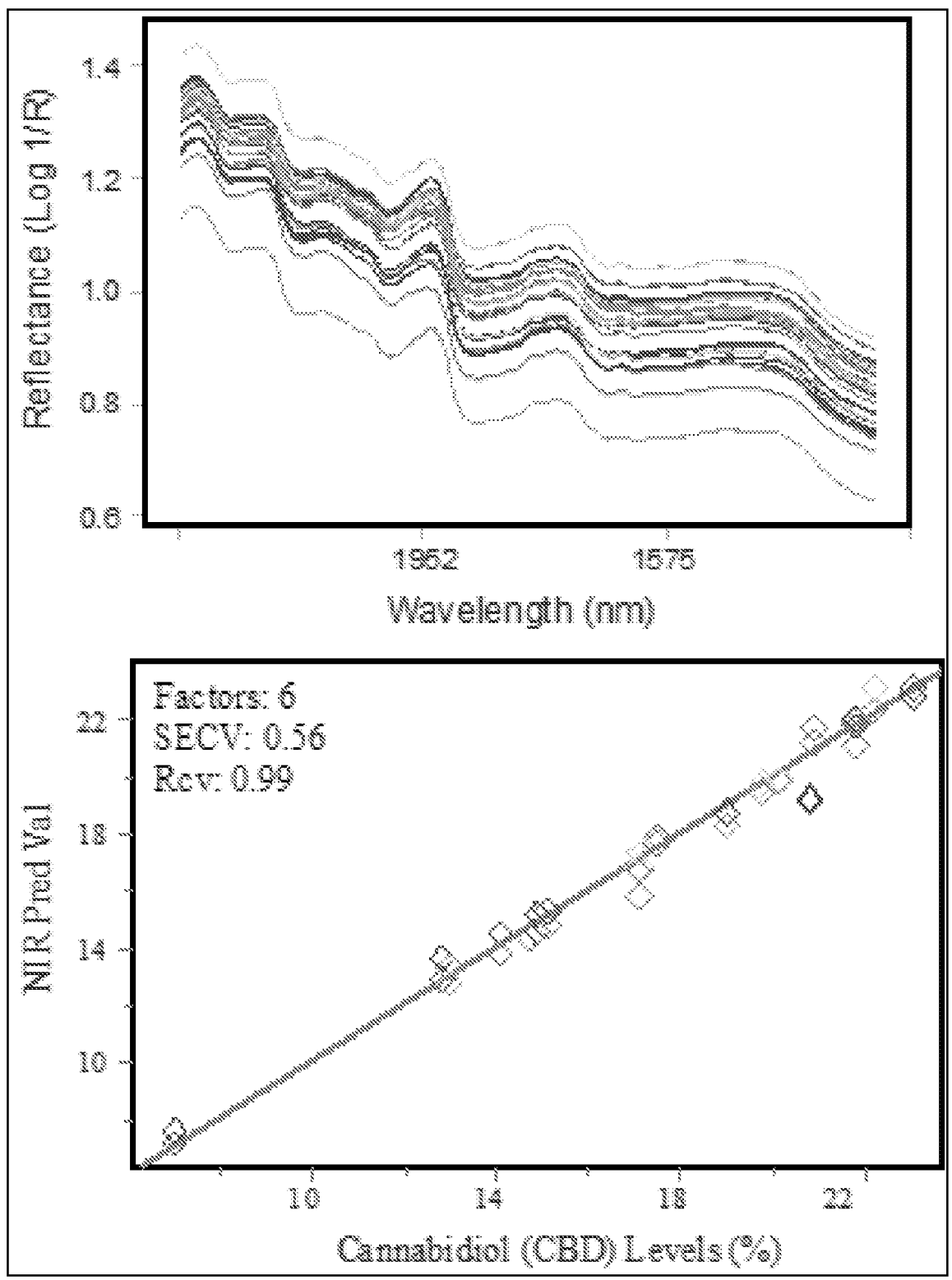
FIG. 15 shows NIR spectra collected with the handheld system, NIR NeoSpectra Micro, and regression model for determination of CBD in hemp in 20 sec analysis.

Developed herein is an optical sensor technology to address needs for real time, in situ measurements of crop quality indicators. This technology is based on a portable NIR spectrometer that uses light to non-destructively quantify chemical constituents in plants or food products. This easy-to-use system can be operated from an app on a smartphone and produces results in seconds. The data disclosed herein show methods for quantifying essential amino acids in soybeans, β-glucan in oats, and lycopene in tomatoes. This technology can also be used to measure CBD and other cannabinoids in cannabis plant samples. Recent measurements of several commercial hemp samples show that the spectrometer can quantify CBD based on short measurements (~20 sec) followed by application of PLSR techniques (FIG. 15). These results exhibit excellent signal-to-noise ratios and good linearity in predicted vs. reported CBD levels.

Example 3. Near Infrared Sensor Technology for Real-Time Assessment of Barley Quality Summary Disclosed herein is portable sensor that uses near infrared spectroscopy to assess barley quality in real-time, providing a low cost, in situ alternative to laboratory testing. This technology can support the production and malting of barley for the growing craft beer brewing industry.
Background Barley is an important small grain crop grown worldwide for both human and animal consumption and as a source of malt for the beer brewing industry. In 2017, US farmers harvested nearly two million acres of barley, resulting in a crop value of $614.3M. In recent years, there has been increasing interest in terms of growing barley to support the rapidly growing craft brewing industry. According to the Ohio Craft Brewers Association, the economic impact from Ohio's craft brewing was $967M in 2018, up nearly 38% from 2015, accounting for 8,341 jobs. Companies such as Ohio-based Origin Malt are contracting with a growing number of Ohio's farmers to produce barley that can be malted and provided directly to craft breweries. However, in order to produce a high-quality malt product, the barley provided to the maltster must meet very stringent quality requirements. Specifically, protein levels must be within a range of 9.5 to 12.5% (dry weight basis), moisture content below 13.5%, and deoxynivalenol (DON, aka vomitoxin) less than 1 ppm. Thus, it is important for farmers to grow and provide a quality product given the limited presence of secondary markets available for grain that fails to meet those standards.

To determine if barley meets requirements to produce high quality malt, samples are collected from the farm and analyzed in a laboratory using a variety of analytical methods. For example, Near Infrared (NIR) spectroscopy is used to determine protein, moisture, and amino acid content. Unlike conventional "wet chemistry" methods, NIR provides a quick, non-destructive method that requires minimal sample preparation for the acquisition of analytical measurements. Given the highly complex nature of the spectroscopic signatures of food matrices, multivariate calibration techniques, such as Partial Least Squares Regression (PLSR), are needed to quantify protein and other properties from the raw spectral data.

Although laboratory analysis of barley samples remains the "gold standard" for quality assessment, the associated cost and time required to collect and transport samples to the lab, followed by a lengthy process to measure and analyze the data greatly slows that assessment. The disclosed portable sensor herein incorporates a NIR spectrometer and on-board processor to perform PLSR and other multivariate calibrations, thus substantially reducing the costs of analytical measurements and providing barley quality assessment in real-time. Furthermore, this novel sensor can be used in the field when making harvest decisions. In field trials, grain quality was strongly influenced by plant stand (e.g., exhibiting a higher level of DON in the presence of uneven plant stand from a non-uniform head emergence). If farmers can easily assess the DON levels, as well as, they can choose to harvest a portion of their field separately. Similarly, farmers can monitor how grain protein varies throughout the field depending on environmental factors. Modern smartphones and tablets have the processing capability to control the operation of the spectrometer and perform PLSR or other multivariate techniques to analyze the spectroscopic data. The platform sensor technology is used for barley quality measurements, including protein, moisture, starch, amino acids, DON, and other properties.

Figure 6:
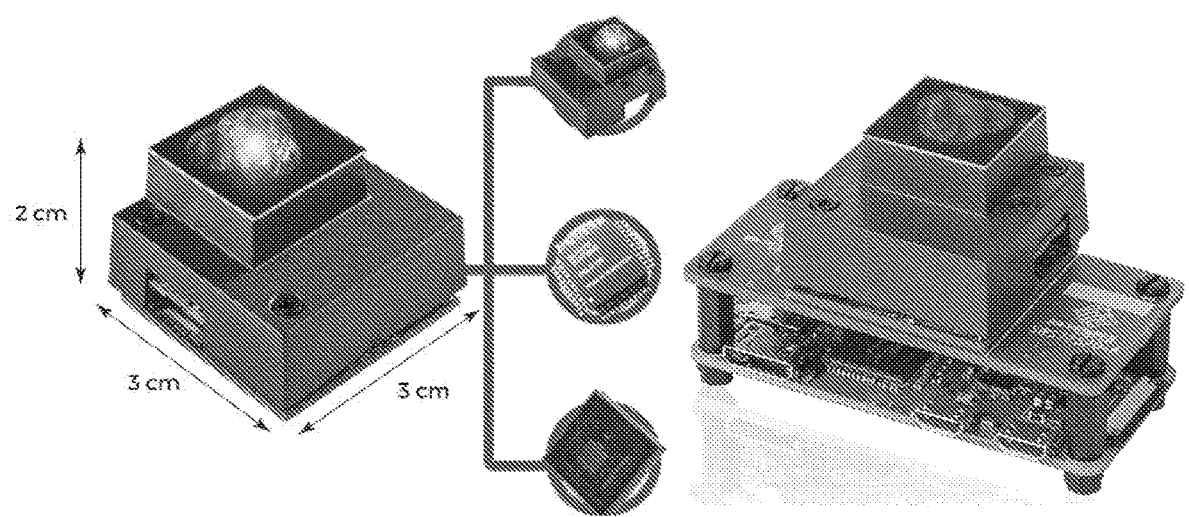
FIG. 6 shows the NeoSpectra-Micro (left) includes integrated optics, electronics, and spectrometer in a compact package that can be integrated easily within a sensor system. The NeoSpectra-Micro Development Kit (right) includes the Micro spectrometer connected to Raspberry Pi boards for electronic control and data interface.

NIR spectroscopy is an effective method for characterizing the chemical contents of food and agricultural products. While NIR measurements are primarily performed in a laboratory setting, the emerging commercialization of a new class of miniaturized spectrometers enables the development of handheld sensors for field measurements. In one example, NeoSpectra Micro spectrometer (SiWare Systems, Cairo, Egypt), shown in FIG. 6, is used to develop such a handheld sensor technology. This spectrometer provides excellent performance over a wavelength range of 1350-2500 nm, which includes signatures for all of the barley properties of interest (protein, starch, water, amino acids). It also provides a full band scan rate of 2 seconds, enabling real time spectroscopy measurements in the field.

Figure 17:
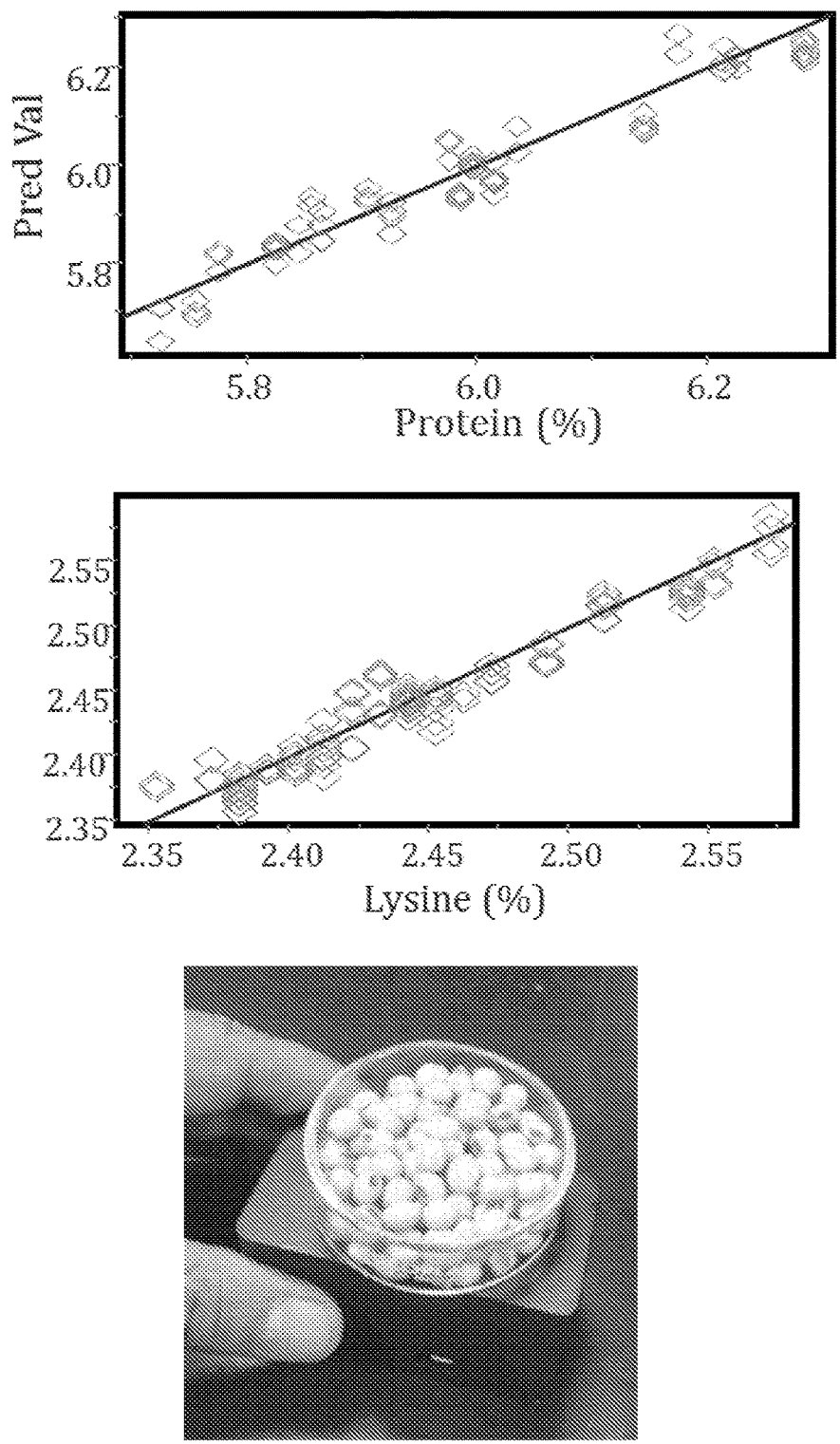
FIG. 17 shows PLSR predictions of protein (top) and lysine (center) for whole soybean samples (bottom) based on data acquired from the handheld NIR Neospectra Micro. Predictions show excellent linearity and accuracy of prediction when a rotating stage was used to average over spectral variations due to spatial heterogeneity of the whole bean structures.

It has been demonstrated that the NeoSpectra Micro, combined with the PLSR technique, is efficacious for quantifying protein and amino acid content in soybeans. The results of more than 20 distinct ground soybean and soybean meal samples are shown in FIG. 16. The predictions of both protein and lysine content (one of five amino acids studied in this example) were linear and highly accurate compared to the concentrations measured with conventional laboratory gas chromatography methods. Following the acquisition of these results, methods for measuring the same constituents in whole soybeans, rather than in ground samples, thus substantially simplifying the use-case in terms of field-deployment. Although the whole bean samples exhibit highly linear results with slightly less accuracy (as shown in FIG. 17), they are more than sufficient for characterizing the amino acid content at the 0.1-1% level. During these measurements, the whole bean samples were rotated to account for spatial heterogeneity effects in the reflectance spectra. These results indicate that while other products (e.g., barley or oats) can be characterized by NIR as whole grain samples, they require a rotating stage to present multiple viewing angles during field measurements.

A stand-alone sensor is controlled by a either a smartphone or tablet running a custom-built software application (app).

Spectroscopic and statistical methods. The chemometric algorithms are developed and validated to enable prediction of each target trait based on spectral signatures. These measurements are performed for samples that have been dried and ground as well as for whole seed samples using a rotating sample stage. By necessity, "truth" measurements using reference methods are performed for each barley sample, a necessary step for implementing the expanding training sets. Moisture content, starch content, and protein content are measured. And the Nitrogen result is multiplied by the conversion factor of 5.83. The amino acid profile is determined by GC-MS using the Phenomenex EZ:Faast™ kits after protein hydrolysis. DON levels are measured using an LC/MS/MS method package for mycotoxins (Shimadzu, Kyoto, Japan). The resultant algorithmic inputs (e.g., regression vectors for PLSR) are put into the cell phone app and tested against similar implementations on a conventional desktop or laptop computer to ensure consistency and accuracy.

Example 4. A Rapid Method for Screening High Oleic Acid Traits in Gene-Edited Soybean Genotypes Using Portable Vibrational Spectroscopy Sensors and Pattern Recognition Analysis Improving seed quality in soybeans continues to be a goal of soybean breeding programs. Most phenotypic analyses are time-consuming, expensive and very labor-intensive for soybean improvement programs where many samples have to be screened. For selection of soybean genotypes with altered fatty acid composition, wet chemistry, primarily gas chromatography, was used. Selection of genotypes using DNA markers is accurate and efficient, however, these systems can be cost prohibitive since they often require expensive chemicals and specialized equipment for genotyping.

Near infrared reflectance (NIR) is a very quick analysis method that has been used to accurately measure protein and oil content in soybeans. However, use of NIR to measure fatty acid profiles and other components of soybeans is not common. Easier and effective determination of soybean genotypes for fatty acid profiles, such as high oleic acid using NIR, greatly enhances progress toward improving soybean cultivars with high oleic acid. These sensor technologies are directed at improving efficiency, throughput and reliability of critical quality characteristics, such as screening for the phenotypic expression of the gene editing technology reflecting accumulation of oleic acid. Advantages of vibrational spectroscopy include portable and ruggedized instrumentation for field deployment, rapid testing (15 seconds), little or no sample preparation requirement, non-destructive capabilities and accurate results in complex matrices for routine analysis in foods involving minimal personnel training and laboratory supplies.

NIR systems can operate rapidly with minimal user interface and to provide high sensitivity and specificity for unique chemical signatures. The sensor technologies are directed at improving efficiency, throughput and reliability of critical quality characteristics, such as screening for the phenotypic expression of gene editing reflecting accumulation of oleic acid. The end-product is a simple, "near real-time" and automated system that provides for screening capabilities that save time and money while establishing a uniform quality. Field-deployable NIR sensors are evaluated for rapid screening of oleic acid and linolenic acids, fat, protein and moisture content expressed in gene-edited soybean material.

Materials and Methods:

Soybean material (n=136) included genotypes that were supplied by Calyxt (n=86) and other growers (n=50) encompassing a wide range of varieties and growing locations. The soybean samples were evaluated using a targeted screening method that analyzed the levels of major fatty acids (oleic, linoleic and linolenic), total fat, moisture and protein content.

Reference tests included fatty acid profiles (GC methyl esters, IOC COI/T.20/Doc No. 24-2001). Protein analysis was done using the Dumas combustion method and the Nitrogen result is multiplied with 5.83. Fat analysis was done by using a Soxhlet gravimetric method (AOAC #922.06). Finally, the moisture content is determined by using the Karl Fisher method (AOAC Official Method 2001.12).

Partial least squares regression (PLSR) analyses were used to develop the predictive models. PLSR combines the features of Principal Component Analysis (PCA) and Multi Linear Regression (MLR) to compress a large number of variables into a few latent variables (PLS-Factors). It is particularly useful when the size of independent variables (spectra) is much larger than that of dependent variables (oleic acid reference levels). Thus, using the spectra obtained and reference concentrations; quantitative models were generated with PLSR. Calibration models are internally validated using full cross-validation (CV) (leave-one-out approach). A very important advantage of PLSR is that it takes into account errors both in the concentration measured and the spectra collected by spectroscopy. It does not assume that the concentrations used as reference numbers are error free since there could be errors in sample preparations, dilutions, weighing and such.

Results and Discussion

A summary of the protein, oil and fatty acid composition of soybeans is given in Table 6. Oil and protein levels ranged from 15.5 to 16.2% and 33 to 38.5%, respectively, which are within the range reported by the USDA. Soybeans showed similar levels of protein (34%), moisture (5%) and oil (17%) levels, indicating that gene-edited soybean seeds that produced increased levels of oleic acid did not affect other traits which are considered as "identifying preserved" attributes that comprise a quality soybean. By including a diverse soybean material including gene-edited and conventional soybeans, a large variability in oleic, linoleic and linolenic acids were obtained (Table 6). The fatty acid composition showed an average increase in oleic acid from 24% (conventional) to 77% (gene edited) and a reduction in linoleic acid from 51% (gene edited) to 7% (conventional) while linolenic acid levels showed a reduction from 7% in gene-edited to 4% for their conventional counterpart, desirable traits to improve oil shelf life and avoid the need for hydrogenation that generates unwanted trans-fat which has been linked to many health problems in humans.

TABLE 6

Comparison of protein, moisture, total oil and fatty acid profile between high oleic and conventional soybeans.

| n = 136 | Fatty acid profile | | | | | Fat Content (%) | Protein (%) | Moisture (%) |
| --- | --- | --- | --- | --- | --- | --- | --- | --- |
| | Palmitic | Stearic | Oleic | Linoleic | Linolenic | | | |
| Mean | 8.8 | 4.0 | 63.9 | 17.8 | 4.8 | 16.9 | 33.9 | 4.9 |
| STDEV | 1.9 | 0.5 | 22.7 | 18.9 | 1.5 | 1.3 | 0.7 | 0.2 |
| Min | 6.4 | 3.2 | 17.6 | 3.0 | 1.9 | 14.0 | 32.5 | 4.2 |
| Max | 13.0 | 5.1 | 84.0 | 57.4 | 8.5 | 20.2 | 35.2 | 5.2 |

Figure 18:
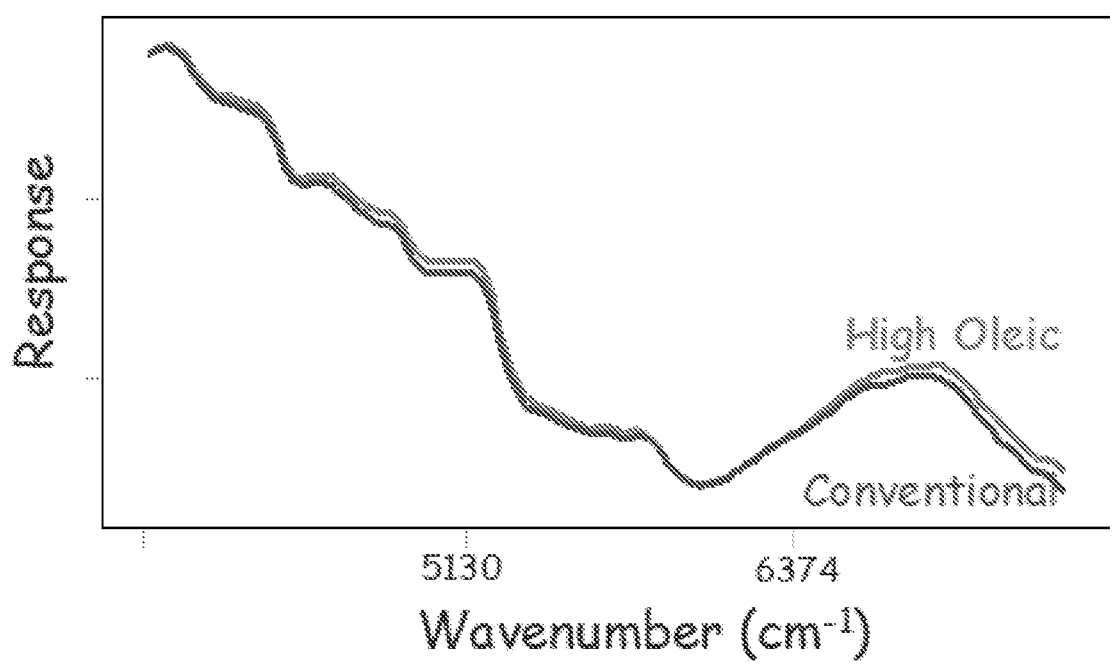
FIG. 18 shows collecting spectra of soybeans with the NeoSpectra Micro NIR device.

A palm-size handheld NIR spectrometer (FIG. 18) showed best results by using a data acquisition time of 15 seconds. FIG. 18 shows the NIR spectra of soybeans corresponding to the higher electromagnetic energy levels resulting in overtones and/or combination bands involving highly anharmonic X—H (mainly C—H, N—H, and O—H) stretching modes. Characteristic bands of the O—H stretching of water were centered 5170 cm$^{-1}$ (combination), C—H vibration modes of lipids at 5795 cm$^{-1}$ (first overtone) and 4260 cm$^{-1}$ (combination), and the N—H vibration band at 4747 cm$^{-1}$ (combination).

Figure 19:
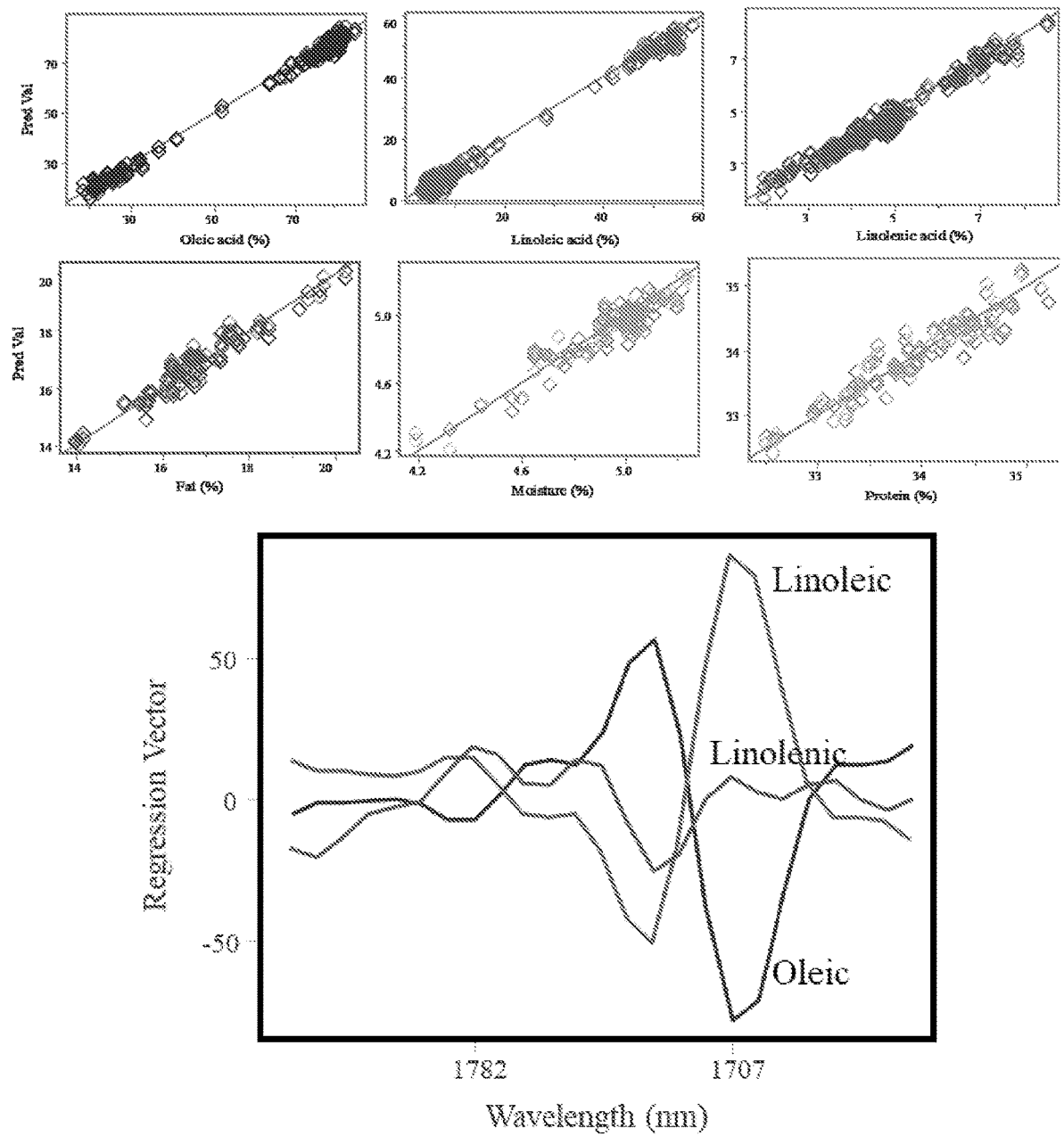
FIG. 19 shows Partial Least Squares Regression (PLSR) plots for oleic and linoleic acid content in soybeans by the handheld NIR NeoSpectra Micro.

PLS regression (FIG. 19) was the main algorithm used to generate the prediction models for the determination of quality traits in soybeans. The palm-size NIR NeoSpectra provided excellent prediction performance for all traits with correlation coefficients of >0.98 and low SECV (Table 7). The performance of the PLS models generated with the handheld NIR system outperform vibrational spectroscopic techniques reported in the literature using benchtop systems. PLS models were generated based on NIR reflectance of ground soybean meal with SECV of ~4% for estimating oleic acid from single soybean seeds; PLS models were reported with SEP of 4.27% and 3.39% for oleic and linoleic acids, respectively.

TABLE 7

Performance of cross-validation models developed by using NIR.

| | Factors | SECV | Rcv |
| --- | --- | --- | --- |
| Oleic | 3 | 1.74 | 0.997 |
| Linoleic | 3 | 1.62 | 0.996 |
| Linolenic | 5 | 0.28 | 0.981 |
| Fat | 4 | 0.34 | 0.964 |
| Moisture | 7 | 0.073 | 0.941 |
| Protein | 4 | 0.22 | 0.942 |

These results revealed that the models developed using NIR spectra from a handheld sensor device showed excellent prediction of key compositional traits and out-performed data reported in the literature. The NIR unit allowed rapid (~1 min) analysis with minimal sample preparation, and all that was needed was to blend the sample into a homogeneous material. The rapid measurements and ease of use of the technology allow screening of gene-edited soybeans and the advancement of optical technology can help save the industry both time and money for quality control applications.

Figure 20:
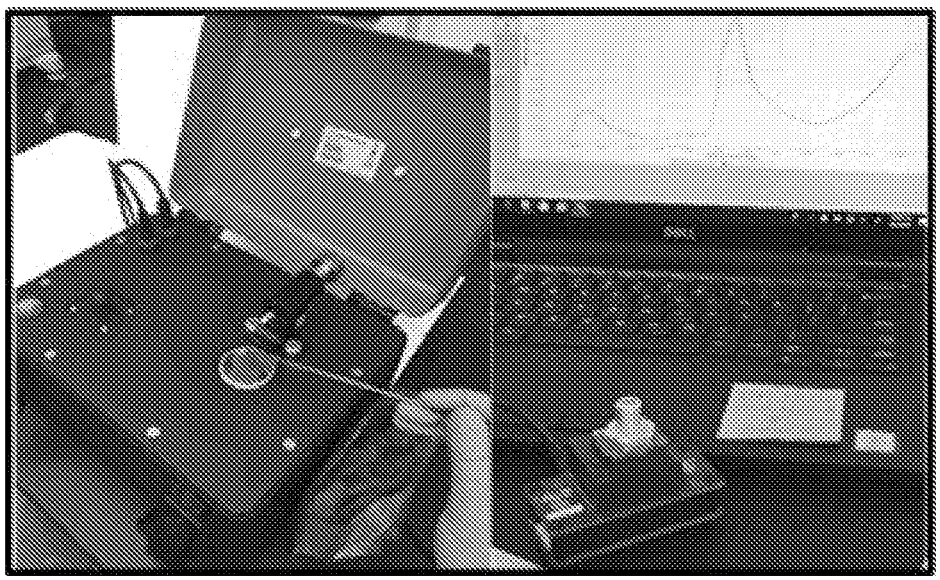
FIG. 20 shows portable and handheld infrared sensors for the tomato industry. Left panel is a portable mid-infrared system operating in an ATR mode. Right panel is the NIR Neospectra Micro collecting reflectance measurements of tomato paste.

Example 5. Rapid and Non-Invasive Approach for Real Time Quality Testing of Tomato Paste and Early Identification of Microbial Spoilage Current quality assurance analyses are often tedious, complicated, prone to error, and time-consuming. Vibrational spectroscopy has been the workhorses in analytical laboratories since its introduction in the 1960's, offering advantages over other fingerprinting technologies (ie. mass spectroscopy (MS), nuclear magnetic resonance (NMR)) by requiring minimal or no sample preparation, avoiding toxic chemicals, non-destructive, rapid data acquisition, and the ability to provide simultaneous information on different constituents in food products. Handheld spectrometers are highly optimized towards "point-and-shoot" capabilities with special attention to ruggedness (surviving drops and temperature fluctuations), power consumption, heat dissipation, and battery life, dust- and splash- and waterproof. One approach to significantly reduce the size and production cost of vibrational spectrometers is the integration of micro-electro-mechanical systems (MEMS) to miniaturize optical, mechanical and hardware components of large and stationary spectrometers. The MEMS optical technology enables rotation of miniature gratings, measure spectra at millisecond time resolution and co-add several scans to one spectrum, generating good signal-to-noise ratio. Using smart and powerful sensors (FIG. 20) allows manufacturers rapid, non-destructive, reliable and in/on-line quality control techniques to ensure the quality and safety of food products, reducing upfront and long-term costs and simplifying operator training. These cutting-edge systems provide a valuable window into in-process food manufacturing permitting optimization of production rate, quality and safety.

This example evaluates a novel miniature NIR sensor controlled wirelessly for predicting multiple quality traits (lycopene, Bostwick consistency, Serum Viscosity, NTSS, pH, total acidity) in tomato paste. Furthermore, the unique fingerprinting of the sensors (NIR and Mid-IR) allows for rapid identification of microbial contamination in tomato paste products. Infrared spectra of microcolonies (30 to 150 μm diameter) and pattern recognition analysis offers a reliable tool for screening and discriminating, at subspecies level, micro-organisms associated with product spoilage.

Tomato paste products provided by members of the California League of Food Processors were evaluated using a portable mid-infrared spectrometer. A validated algorithm was developed for accurately predicting NTSS, pH, Bostwick consistency (cm traveled in 30 sec), serum viscosity (centistoke), titratable acidity (% citric), acetic acid (g/100 g), lycopene, sugars (glucose, fructose) and acids (ascorbic and citric acid) by simply spreading the paste onto the sensing ATR crystal. The models included ~2000 tomato paste samples collected from 4 companies in CA. Accurate and robust algorithms allowed measuring all quality attributes with excellent correlation value, $R^2 > 0.85$, and prediction errors that would allow for quality control applications. Spectra from 250 paste samples were collected using the portable FTIR system and a novel palm-size NIR device. Their performances (Table 8) were able to predict major quality attributes with $R^2 > 0.95$ and prediction errors comparable with the portable FTIR system. The miniature NIR instrument showed similar performance than the FTIR unit, with the MR technology offering lower cost (~$5,000) compared to their mid-infrared (~$50,000) counterpart.

critical importance to prevent economic hardship on the manufacturer due to product spoilage.

Infrared spectra generated from bacteria can be used to examine cell components producing a global biochemical

TABLE 8

Comparison of the prediction models of tomato paste by using a portable FTIR and handheld NIR sensing devices

| Parameter | Concentration range | Portable Mid-IR (Agilent 4500) | | | Handheld NIR device | | |
|---|---|---|---|---|---|---|---|
| | | Factors | SECV | rPred | Factors | SECV | rPred |
| NTSS (%) | 25.5 to 39.4 | 7 | 0.46 | 0.99 | 5 | 0.71 | 0.98 |
| Bostwick Consistency (cm) | 0.5-9.5 | 6 | 0.41 | 0.98 | 4 | 0.50 | 0.95 |
| Serum Viscosity (cSt) (Log) | 48-775 (1.7-2.9) | 7 | 0.038 | 0.99 | 4 | 0.088 | 0.94 |
| Lycopene (mg/100 g) | 27-90 | 5 | 3.01 | 0.95 | 4 | 2.75 | 0.96 |

Figure 21:
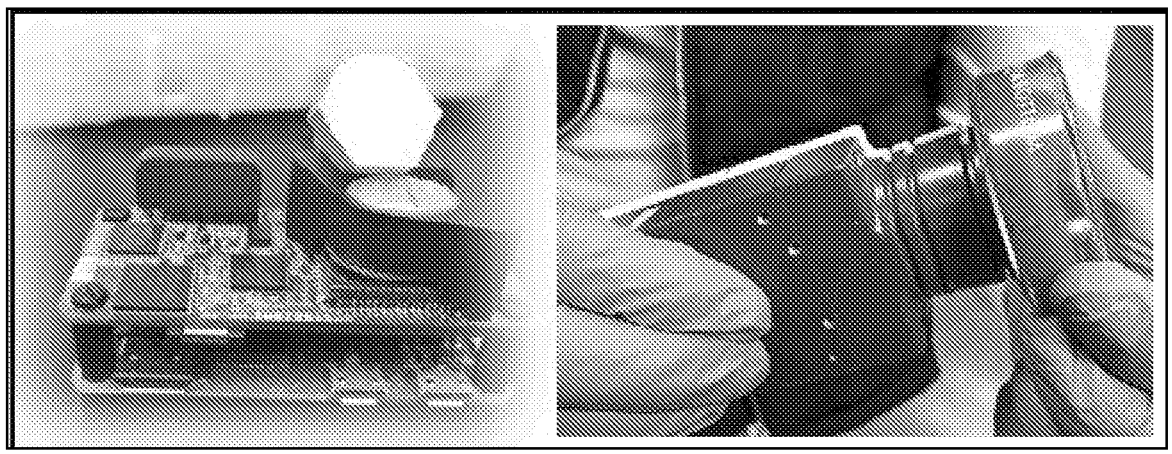
FIG. 21 shows a handheld NIR NeoSpectra Module for wireless data acquisition.

An FTIR unit is deployed to a tomato paste processing plant for "in-situ" validation of the predictive algorithms. The unit is equipped with a general (all companies data set) and individual company algorithms and be accessible for the use of CLFP program contributors; thus, companies can compare and test the performance characteristics of the unit. Additional tomato paste samples are collected and predictive algorithms are generated using a palm-size NIR unit (FIG. 21). Software is used to interface wirelessly with the low-cost palm-size NIR sensor with multimedia devices such as tablets or smart phones to implement the advanced chemometric algorithms to provide the tomato industry with a real-time, simple and accurate method for chemical profiling of tomato products providing the industry a valuable "out-of-the laboratory" analytical tool.

Furthermore, by using the same devices, chemically based screening algorithms are generated to detect spoilage in tomato paste by producing complex patterns or "fingerprints" that are reproducible and distinct for early identification of microbial contamination. This capability can provide a competitive edge to the industry by providing real-time information regarding the quality assurance of their products. Identification by genotypic characteristics are limited by requirements for dedicated equipment and personnel, time constraints for isolation and data processing, and results are sensitive to environmental conditions and food itself is a difficult matrix.

Figure 23A:
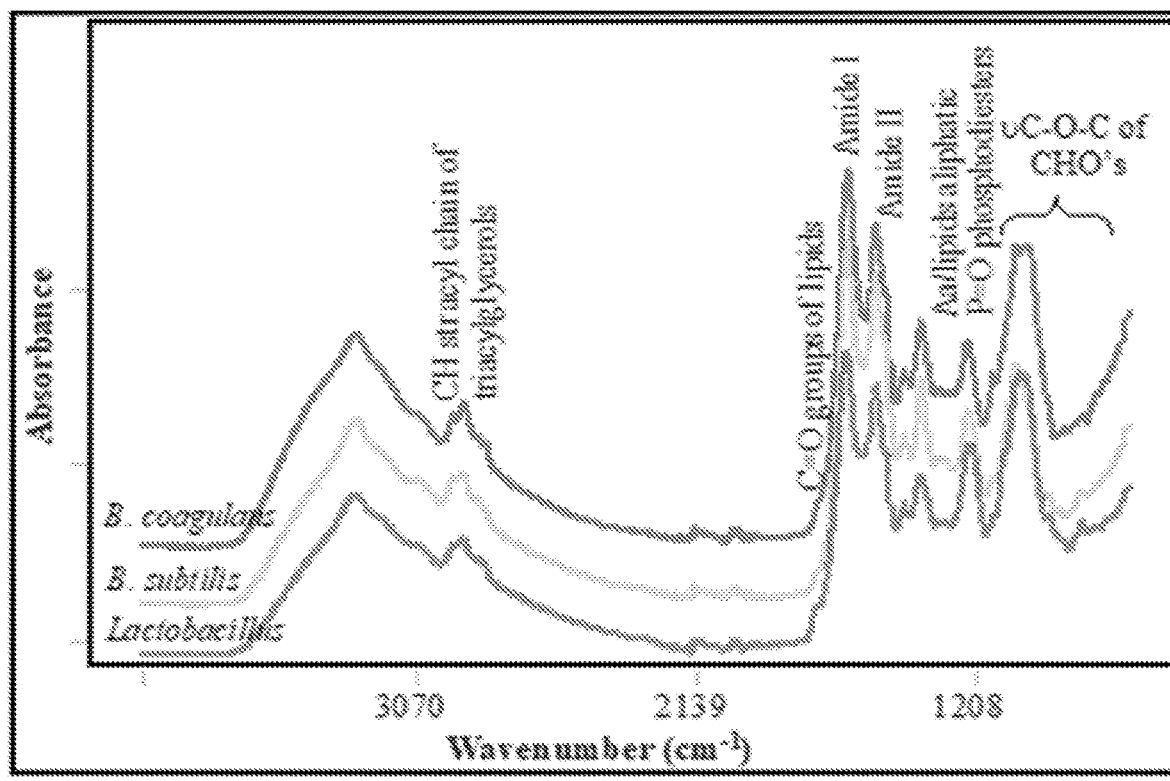
FIGS. 23A-23B show bacteria spectra in the mid-infrared spectral range of 4000 to 900 $cm^{-1}$ and its corresponding class projection using SIMCA pattern recognition showing discrimination of spoilage bacteria at the specie level.
Figure 23B:
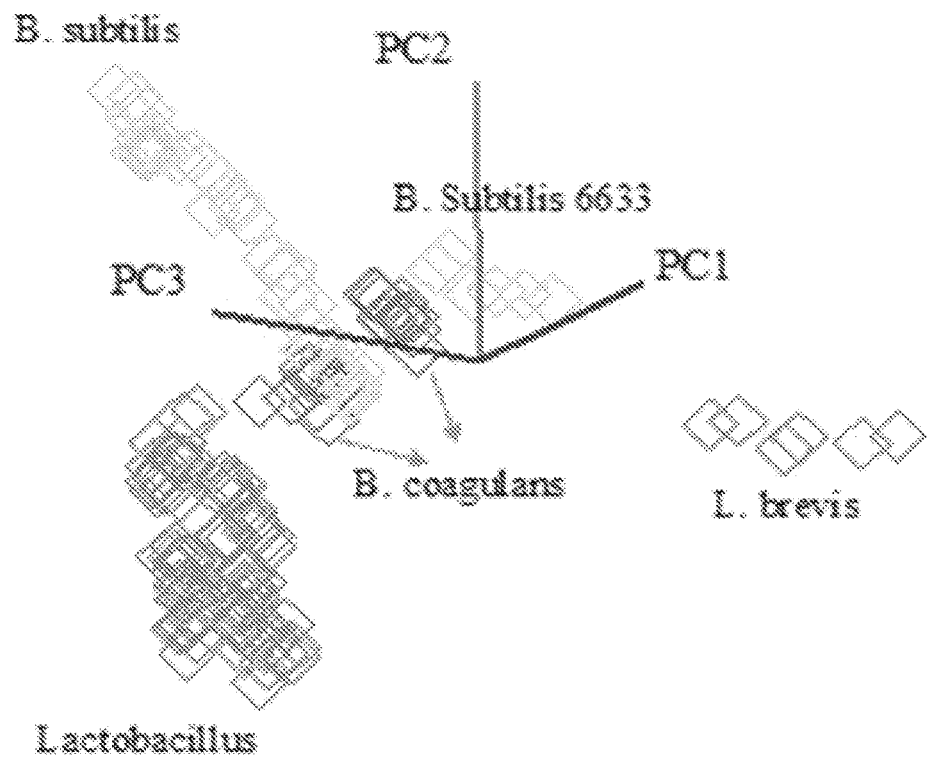
Figure 24A:
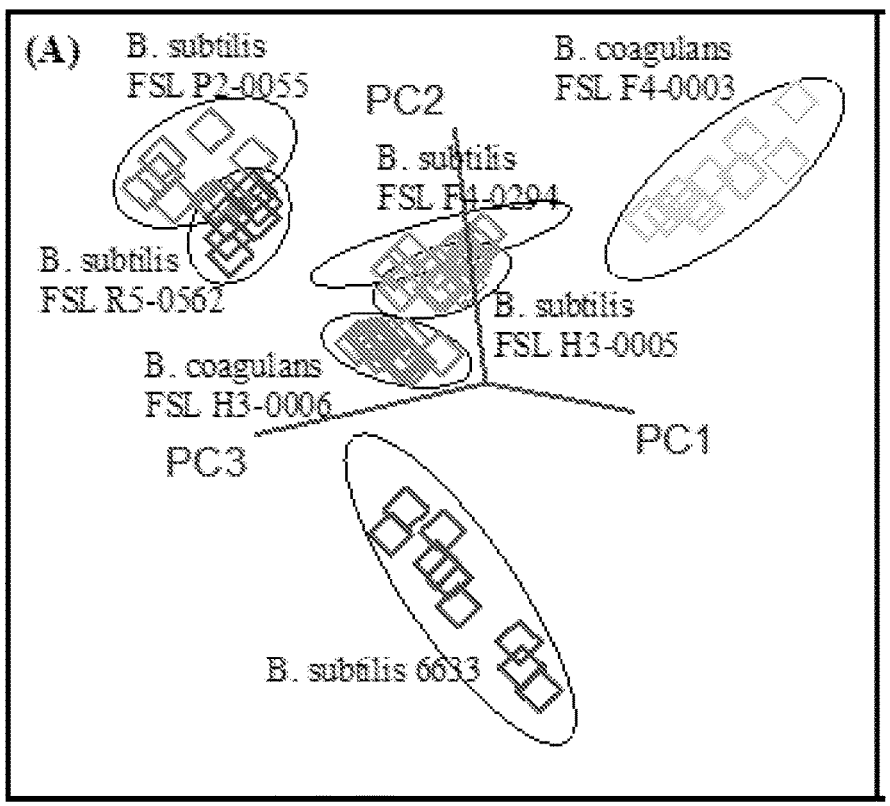
FIGS. 24A-24B show SIMCA pattern recognition based on mid-infrared spectra showing discrimination of spoilage bacteria at the strain level for (A) *Bacillus* and (B) *Lactobacillus* strains.
Figure 24B:
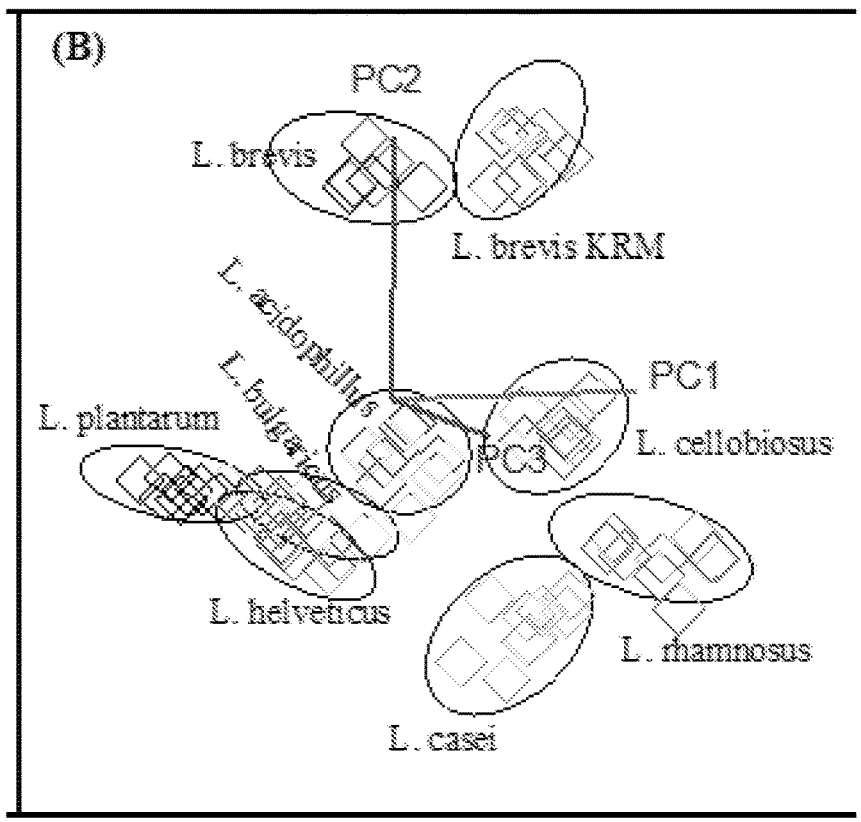

The presence and growth of microbial contaminants is a severe problem impacting the food chain due to organoleptic alterations of final products with resulting economic damages for manufacturers. Technologies that provide early identification of microbial contamination can provide a competitive edge to the industry by providing real-time information regarding the quality assurance of their products. Identification by genotypic characteristics, such as nucleic acid amplification methods (PCR), pulsed-field gel electrophoresis (PFGE), and whole genome sequencing (WGS) have become mainstream techniques however, limitations to broader application of these methods to address the needs in identification and subtyping commodity-specific spoilage organisms exist due to the requirement for dedicated equipment and personnel, time constraints for isolation, DNA extraction, and data processing, and the lack of existing database repositories for sequence comparison. In addition, the reactions are sensitive to environmental conditions and food itself is a difficult matrix. Development of simpler, quicker, sensitive, and cost-effective methods for effective microbial surveillance to ensure food quality is of fingerprint with the ability to differentiate bacteria at different taxonomic levels. The technique gives quick, user friendly and relatively inexpensive screening of microorganisms requiring no reagent and minimum consumables. An evaluation of a portable infrared and handheld NIR spectrometers for rapid identification of spoilage bacteria was conducted by direct analysis of the bacterial biomass (FIG. 22). The spectra displayed unique features for dentification at the genus and specie/strain level using pattern recognition analysis—SIMCA (FIG. 23).

Figure 25:
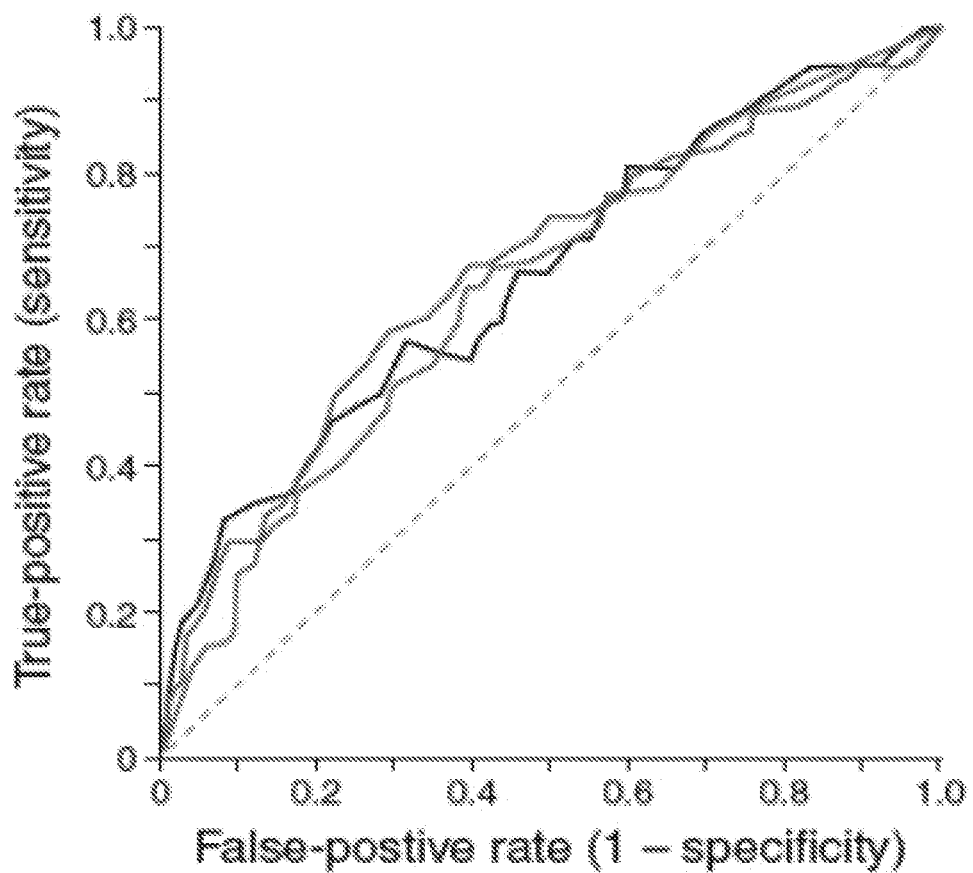
FIG. 25 shows area under the curve (AUC) of the receiver operating characteristic (ROC), graphical plot that illustrates the diagnostic (sensitivity and specificity) ability of a binary classifier system as its discrimination threshold is varied. ROC curves provide a comprehensive and visually attractive way to summarize the accuracy of predictions. Each point on the curve represents the true-positive rate and false-positive rate associated with a particular test value. The AUC provides a useful metric to compare different tests (indicator variables). Whereas an AUC value close to 1 indicates an excellent diagnostic test, a curve that lies close to the diagonal (AUC=0.5) has no information content and therefore no diagnostic utility.

IR proved to be quite reliable for bacteria typing purposes at different taxonomic levels (FIG. 25). Different strains belonging to the *Bacilli* and *Lactobacilli* spp were included for demonstrating the molecular biology and biochemical methods. Nevertheless, validated spectral databases are of utmost importance as they account for natural variability and allow Labs to resource references for results comparison. Also, applications require to be robust to growth media and environmental conditions (cultivation time and temperature). The ability of IR methods to be used in mixed cultures without resourcing to complex sampling methods are extremely important for high-throughput monitoring of bacteria strains associated with spoilage. Thus, in order to develop robust models for quality control applications, strains collected from spoiled tomato paste from CLFP members are incorporated to allow the development of predictive chemometric models for accurate typing of target microorganisms.

A breadboard optical sensor technology is used for accurately and precisely quantifying key quality parameters in tomato paste, including NTSS, lycopene, titratable acidity, pH, serum viscosity and consistency (Bostwick). The general process for performing such measurements includes the following key steps:

Sample handling (preparation and presentation of sample for spectroscopic measurement)

Spectroscopic measurement (acquisition of spectroscopic data for the prepared sample material)

Data analysis (use of chemometric algorithms to convert the raw spectroscopic data into content predictions)

Displayed results (interface that communicates results to user).

Spectroscopy measurements are performed in a broad set of tomato paste samples that encompass product manufactured by different companies from varied growing locations to capture the natural sample variations in the training sets and increase the accuracy and sensitivity of the quantification algorithm. Samples are collected in-situ at different facilities in California during different times of production. Tomato paste products (n=500) are obtained from the tomato processing industry associated with CLFP (CA). Reference analysis for total soluble solids, pH, TA, Juice Bostwick, and serum viscosity are obtained for all samples. In addition, lycopene content is measured based on the spectrophotometric method. Calibration models are internally validated using full cross-validation (CV) (leave-one-out approach) and externally validated with an independent set. A very important advantage of PLSR is that it considers errors both in the concentration measured by the reference methods and the NIR spectra. It does not assume that the concentrations used as reference numbers are error free since there could be errors in sample preparations, dilutions, weighing and such. Blind samples (the researcher will not have access to its identity before prediction) are included to test the ability of the models to predict the quality parameter levels. Results from the validation testing set are used to determine the sensitivity, specificity and positive predictive value of the patterns (FIG. 25).

Combination of infrared spectra of microcolonies (~100 μm diameter) and pattern recognition analysis can offer a rapid and reliable tool for screening and discriminating, at species and subspecies level, micro-organisms associated with tomato paste spoilage. This approach minimizes sample preparation and culture time by analyzing microcolonies and allows rapid prediction of the vulnerability of the tomato product to spoilage during storage.

CLFP members are requested to provide spoiled tomato paste to isolate the microorganisms, typing by genetic methods and collection of spectral information by NIR and FT-IR. A unique database of reference strains associated with tomato paste spoilage is developed, including *Lactobacillus* spp, spore-forming bacteria (*Bacillus coagulans, Clostridium pasterianum, Alicyclobacillus* spp.), and yeasts. The use of Fluorinert (3M Corp) to isolate microbial cells is evaluated. The immiscible and dense cushioning liquid (Fluorinert) collects the microbial cells upon centrifugation. Each microorganism is grown on agar under optimal temperature for aerobic or anaerobic conditions. Plates are evaluated for microcolonies after 6 hours of growth and cells are collected once ~5 μg biomass is produced. Infrared and NIR spectral measurements are collected by applying the biomass onto the ATR crystal (Agilent 4500 unit) or dispensing the biomass on a fiberglass support for NIR analysis.

Spectra are analyzed using multivariate classification software (SIMCA) for the identification of the spoilage microorganisms. SIMCA is a pattern recognition method based on principal component analysis (PCA) that reduces the dimensionality of multivariate data to permit investigation of any systematic variation present in the samples. The analysis generates a classification model that differentiates samples based on their group identification. The order of analysis of samples is randomized to avoid any possible systematic analytical bias. Blinded bacteria with random codes are provided to the analysts for testing. The predictive accuracy of the calibration models is validated with an independent test set of samples representative of the classes modeled with the training set. a select test database consisting of spectra of high-risk spoilage microorganisms, generating diagnostic data sets for method validation, and demonstrate the applicability and exportability of the methodology.

Receiver operating characteristics (ROC) curves (FIG. 25) are used to determine the ability of a classification model to discriminate negative from positive test results. Results from the validation testing set are used to determine the sensitivity, specificity and positive predictive value of the patterns. Sensitivity is defined as the true-positive test results expressed as a percentage of all tested samples (total of true positives and false negatives). Specificity describes the true-negative results expressed as a percentage of all tested authentic samples (the total of true negatives and false positives). The positive predictive value is the proportion of samples testing positive and adulterated.

This example shows a novel spectroscopic sensor technology, such as portable and handheld optical systems, allowing the industry to collect timely information concerning quality parameters and risk of spoilage by revealing the nature of the contamination. Decreasing turnaround time is critical in decision-making for processors.

Example 6. Report on Validation of Prediction Models for Tomato Paste Using Infrared Spectroscopy In 2016, 2017 and 2019, tomato paste products that were provided by members of the California League of Food Processors were used to generate models to predicted quality attributes that included NTSS (refractometer), pH, Bostwick consistency (cm traveled in 30 sec) viscosity, serum viscosity (centistoke), lycopene, and HPLC analysis for sugars and acids. The models gave excellent correlation values, R>0.87, and prediction errors that would allow for quality control applications. The robustness of the models benefited by partnering with the tomato industry and employing their QA (NTSS, pH, TA, Bostwick consistency and serum viscosity) data for each sample analyzed by the portable unit.

The validation of the algorithms was performed at processing facilities from 4 different companies using tomato paste samples manufactured in July to September 2019. The infrared spectra of paste samples were collected using a portable mi-infrared spectrometer (FIG. 20 and their corresponding reference data from the QA Lab was provided by the companies (Table 9).

The present example validates the models generated with portable spectroscopic sensor units to the specifications required by the industry for multiple quality traits of tomato products (paste, puree and sauce) with no sample preparation.

A validation set data that included 25 independent samples from each company and were used to test the predictive performance of the models. Models were developed using over 1400 tomato paste samples obtained from plants of member tomato processors of CLFP (CA). Improved performance statistics were obtained for models generated using the infrared region between 1800 and 900 $cm^{-1}$ depending on the trait parameter modeled by PLSR (Table 9).

TABLE 9

Model performance of PLS regression models collected on a portable spectrometer

| Parameter | Calibration Model | | | | | External Validation Model | | | |
|---|---|---|---|---|---|---|---|---|---|
| | Range | N[a] | Factor | SECV[b] | Rcal | Range | n[c] | SEP[d] | Rval |
| Oswald (log cSt) | 1.81-2.99 | 1304 | 6 | 0.08 | 0.96 | 1.85-2.99 | 326 | 0.08 | 0.96 |
| Bostwick Consistency (cm) | 0.8-7.9 | 1382 | 5 | 0.55 | 0.94 | 1.0-7.7 | 345 | 0.58 | 0.96 |
| Titratable Acidity (% Citric) | 0.99-2.40 | 1406 | 6 | 0.08 | 0.94 | 1.12-2.27 | 352 | 0.09 | 0.93 |
| NTSS (°Brix) | 24.1-38.0 | 1436 | 3 | 0.44 | 0.99 | 25.7-37.5 | 359 | 0.40 | 0.99 |
| pH | 4.14-4.49 | 1419 | 6 | 0.04 | 0.85 | 4.19-4.49 | 355 | 0.04 | 0.83 |
| Ascorbic Acid (mg/100 g) | 12.1-110.7 | 1040 | 6 | 6.99 | 0.94 | 16.7-105.6 | 260 | 7.32 | 0.93 |
| Citric Acid (g/100 g) | 5.9-11.2 | 1031 | 5 | 0.27 | 0.96 | 6.3-10.5 | 258 | 0.27 | 0.96 |
| Glucose (g/L) | 67.5-128.2 | 1043 | 5 | 3.16 | 0.96 | 68.9-122.6 | 261 | 3.39 | 0.97 |
| Fructose (g/L) | 74.7-128.8 | 1032 | 4 | 3.11 | 0.96 | 75.4-128.0 | 258 | 3.88 | 0.96 |
| Reducing Sugar (g/L) | 146.2-258.7 | 1043 | 3 | 5.59 | 0.97 | 148.2-250.5 | 261 | 6.98 | 0.96 |
| Lycopene | 400.6-903.7 | 46 | 6 | 42.35 | 0.92 | | NA | | |

[a]Number of samples used in calibration models.
[b]Standard error of cross validation.
[c]Number of samples used in external validation models.
[d]Standard error of prediction.

Figure 26:
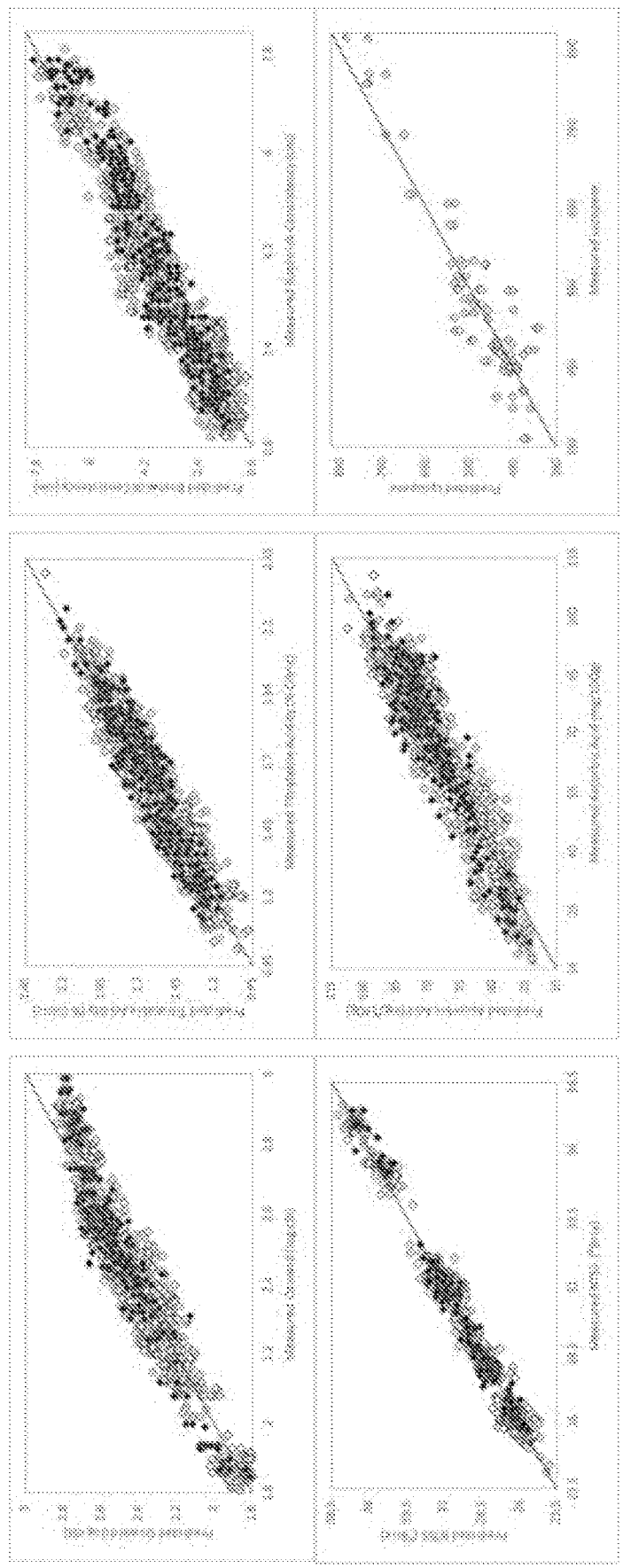
FIG. 26 shows PLSR correlation plots between quality traits and mid-infrared spectra for tomato paste samples.
Figure 27:
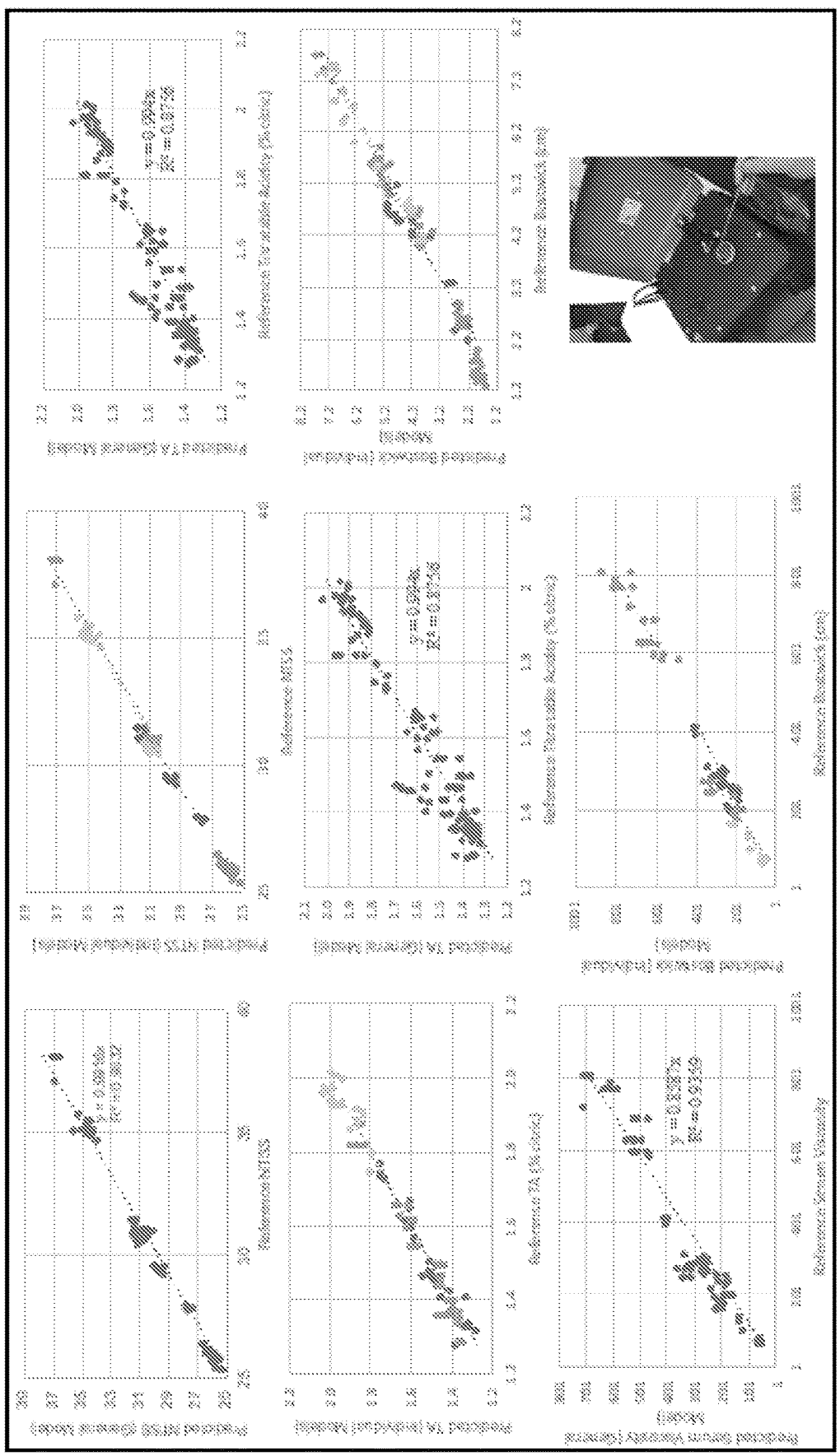
FIG. 27 shows correlation of a validation set of tomato paste samples using a portable mid-infrared device. Colors indicate different factories.
Figure 28:
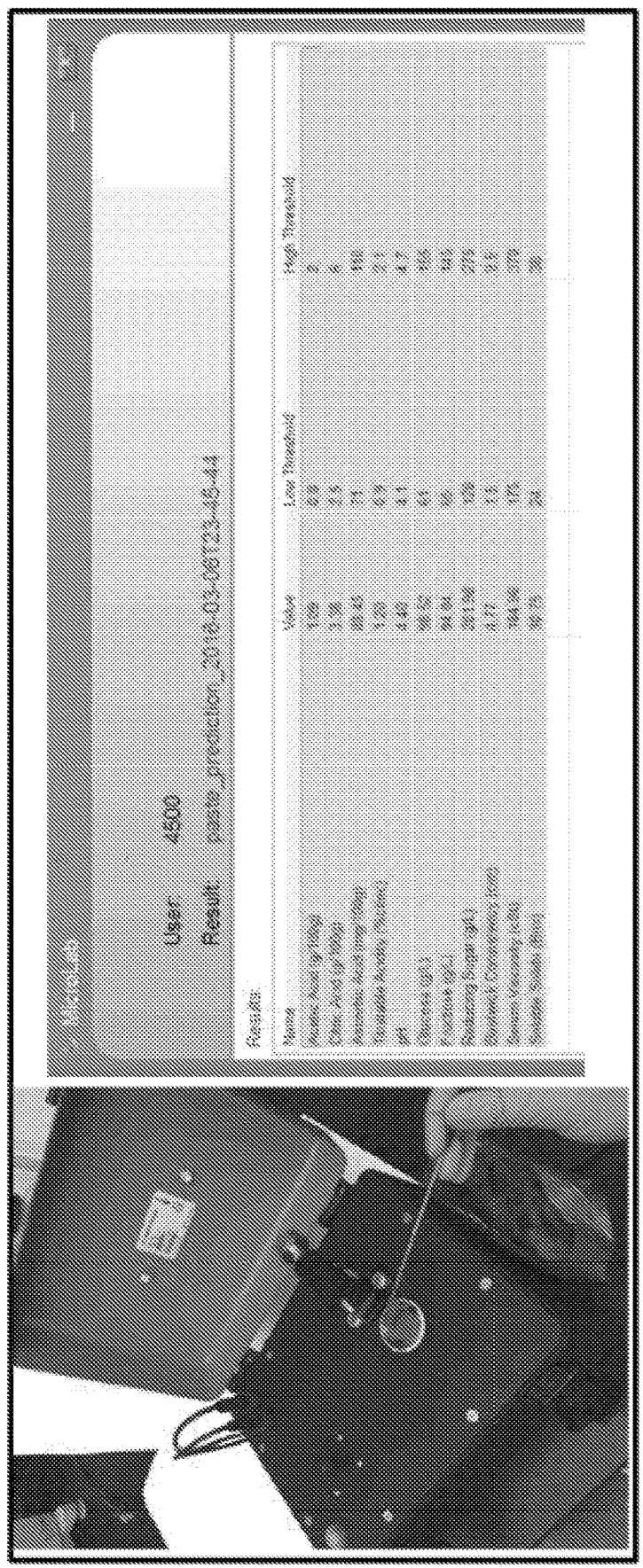
FIG. 28 shows results screen for predicting quality traits in tomatoes using a portable mid-infrared device.

Using the same spectral data, models were generated for the prediction of processing tomato chemical and textural characteristics, crucial parameters to guarantee the consumer acceptance of tomato products and to assist with the unit operations control to achieve better production yields. The correlation plots (FIG. 26) between reference values and predicted infrared levels of different quality parameters obtained from the paste spectra displayed excellent correlation (Rcv>0.9) for all chemical and textural parameters Results from the validation set showed strong prediction performance of the algorithm (FIG. 27). By using a small amount (1 g) of tomato paste applied onto the ATR crystal, models that can rapidly (<1 min) predict quality traits in tomato paste based on a unique spectral fingerprint were validated (FIG. 28). These findings support the use of a portable FTIR with a triple reflection ATR accessory for rapid assessment of quality parameters in tomato paste. These sensor systems provide the tomato processing industry with a rapid method to evaluate processing tomatoes with equivalent levels of reliability and sensitivity as benchtop systems but allow for more flexibility since the unit can be easily carried and transferred. Models have incorporated samples with vast characteristics allowing the chemometric model to filter random noise from the spectra in order to improve predictive ability with an end-product that is robust for quality control applications.

Example 7. Oat-β-Glucan and Protein Measurement

Cutting edge sensor technologies permit quality optimization and advances in vibrational (infrared (NIR and mid-IR) and Raman) spectroscopy instrumentation combined with multivariate data analysis have made this technology ideal for rapid analyte screening, providing sensitivity and resolution of unique chemical information that allows monitoring of subtle compositional changes for non-invasive analysis of seeds for plant breeding. Sensors disclosed herein are used for speeding-up identification and certification of materials, screening unique traits, and streaming quality control capabilities. These new generation of portable/handheld optical systems incorporate the analytical precision for chemical identification and quantitation with a spectral resolution equivalent to bench-top instruments. Advantages of vibrational spectroscopy include portable and ruggedized instrumentation for field deployment, rapid testing (<1 min), no sample preparation requirement, non-destructive capabilities and accurate results in complex matrices for routine analysis in foods involving minimal personnel training and Lab supplies. This capability allows breeders for rapid selection against unique traits, such as β-glucan (BG), because in oats have been associated with beneficial health effects including lowering of the serum cholesterol level, increased satiety, stabilization of the blood glucose and insulin rise after food consumption, having a positive influence against heart diseases and type-2 diabetes. Vibrational spectroscopy provides information about unique fingerprints, and that such information allows estimating levels of protein and BG in oats. Commercial varieties with high nutritional quality are an important objective in breeding programs and are important in the food industry since it can play an important role in providing potential value-added products for the food industry. It has been shown that unique spectral bands arising from functional group vibrations of target molecules can be reliably and accurately identified for routine analysis in foods involving minimal personnel training and consumable supplies. This sensing technology can be directed towards the non-invasive analysis of individual seeds for plant breeding.

A targeted screening approach was developed for determination of protein, starch and BG content by including a 128 oats different genotypes to develop a robust model to capture the natural variations from different sources. A subset of the samples was grounded using a Waring blender to obtain a homogenous powder. The grounded seeds were subsequently divided in two, so that half of the sample was used for BG, starch and protein determination and the other half was kept for spectral collection. Seed BG and starch content was measured with enzyme kits (Megazyme, Wicklow, Ireland). The seed protein analysis was done using the Dumas combustion method and the Nitrogen result was multiplied by the conversion factor of 5.83. Oat powder samples were placed in intimate contact with the spectrometer and spectra collected.

The hyper-spectral (mid-IR, NIR and Raman) data were evaluated for highly specific chemical signatures of oat samples.

Infrared spectral data was collected on portable 4500 Fourier Transform-infrared spectrometer (Agilent Technologies Inc., Santa Clara, CA) equipped with a triple-bounce attenuated total reflectance (ATR) diamond crystal interface and thermoelectrically-cooled dTGS. Oat powder was placed directly on the surface of the diamond ATR crystal and spectrum is collected in the 4,000-700 cm$^{-1}$ region at 4 cm$^{-1}$ resolution by pressing the sample onto the crystal using a pressure clamp. A background was taken prior to each sample run and the data was collected by co-adding 64 scans.

Near Infrared (NIR) spectra was collected with two palm-size systems (NeoSpectra, Si-Ware, Cairo, Eygpt). NeoSpectra's optical technology allows collecting spectra ranging from 7718 to 3829 cm$^{-1}$ using a permanently aligned Monolithic (MEMS) Michelson Interferometer chip and a single indium-gallium-arsenide (InGaAs) photodetector. Oat samples are placed directly onto the optical window of the NIR device and spectra were collected. The background spectrum data was collected before each sample with a highly reflective gold-ceramic standard material.

Raman spectra of oat samples was obtained using a Progeny Rigaku Handheld Raman spectrometer (Rigaku, Wilmington, MA, USA). Raman spectrometer was equipped with a 1064 nm (NIR) laser and TE Cooled Indium-Gallium Arsenide (InGaAs) array detector that eliminates the fluorescence limitation and improves the Raman signal intensity. A laser output power of 450 W was used; data was collected at 8 cm$^{-1}$ resolution with 15 co-scans and an exposure of 1200 ms. Spectra was obtained in the Raman shift range between 200 and 2500 cm$^{-1}$.

Partial least squares regression (PLSR) analysis was used to develop the predictive models. PLSR combines the features of Principal Component Analysis (PCA) and Multi Linear Regression (MLR) to compress a large number of variables into a few latent variables (PLS-Factors). It is particularly useful when the size of independent variables (spectra) is much larger than that of dependent variables (reference levels). Thus, using the spectra and reference concentrations, quantitative models were generated with PLSR. Calibration models were validated using full cross-validation (CV) (leave-one-out approach). Results from the validation testing set is used to determine the sensitivity, specificity and positive predictive value of the patterns. A very important advantage of PLSR is that it takes into account errors both in the concentration measured and the spectra collected by spectroscopy. It does not assume that the concentrations used as reference numbers are error free since there could be errors in sample preparations, dilutions, weighing and such.

Table 10 summarizes the information on reference analysis with regards to the levels of β-glucan, starch, protein and moisture levels based on reference methods. Variation in composition levels among samples can be related to differences in geographic origin, variety, latitude, climatic conditions, among others. Oats (*Avena sativa*) is a unique cereal crop that is rich in compounds associated with health benefits for humans that include β-glucan, a soluble dietary fiber found in the range of 2 to 6%, and protein containing legume-like globulins with high biological value.

TABLE 10

Reference concentration levels for the compounds measured in Oats samples.

| | β-glucan | starch | moisture | protein |
|---|---|---|---|---|
| MIN | 4.0 | 50.3 | 5.5 | 10.2 |
| MAX | 5.2 | 68.3 | 7.2 | 18.8 |
| Average | 4.6 | 60.2 | 6.2 | 15.1 |
| STDEV | 0.23 | 4.5 | 0.36 | 1.82 |

The values showed similar protein content (15.7%) and higher levels of starch (48.1%) and β-glucan (3.3%). However, these values were lower than those previously described with values of protein and β-glucan of 16.4% and 4.8%, respectively. Paudel and others (2018) reported several oat varieties with β-glucan levels above 5.5% and up to 7.5%. Gracia and others (2017) reported levels of β-glucan ranging from 2.8-6.7 (mean 4.3%) and protein ranging from 11.8-16.4 (mean 13.9%). The models used herein can be improved by including oat material with higher levels of β-glucan as the higher levels in the samples were 5.2%.

Figures 29A, 29B, 29C, 29D:
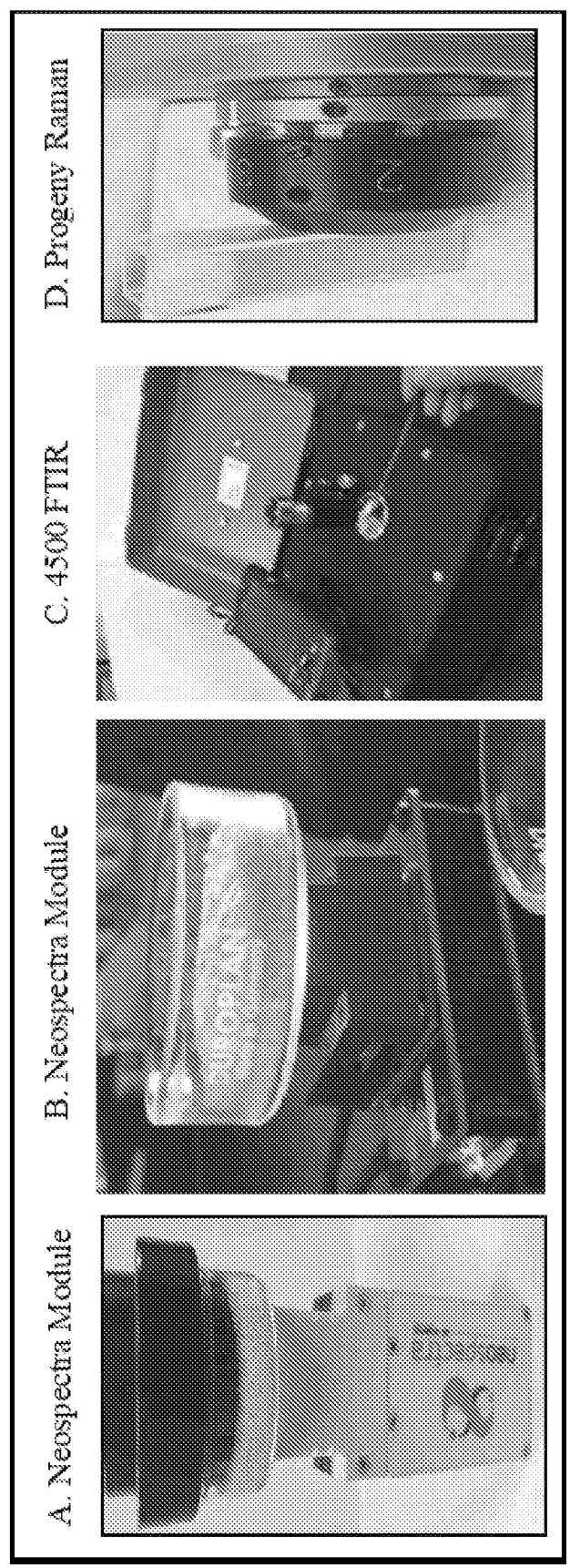
FIGS. 29A-29D show NeoSpectra (Module (FIG. 29A) and Micro (FIG. 29B)) NIR unit coupled with a moving plate, 4500 portable mid-infrared unit equipped with a triple reflection attenuated total reflectance (ATR) accessory (FIG. 29C), and portable Progeny Raman equipped with a 1064 nm laser excitation source (FIG. 29D).

The performance of new generation systems was evaluated, which included a portable mid-infrared, handheld Raman and palm-size NIR spectrometers (FIG. 29).

Figure 30A:
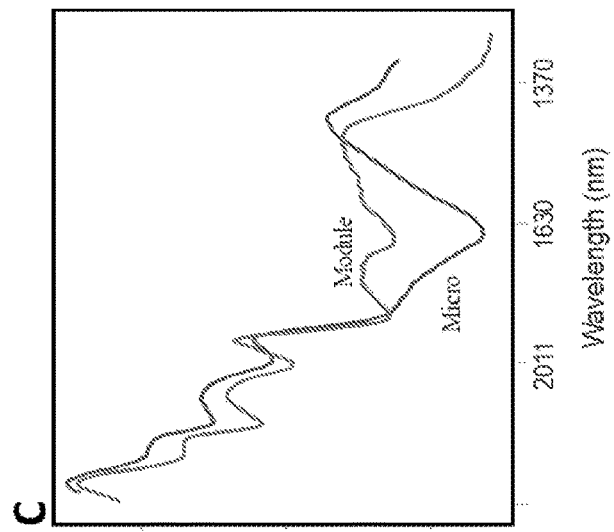
FIGS. 30A-30C show spectral differences of soybean powder collected using different vibrational spectroscopy systems that include (FIG. 30A) portable mid-infrared equipped with ATR accessory, (FIG. 30B) handheld Raman equipped with a 1064 nm excitation lase and (FIG. 30C) handheld NIR spectrometer.
Figure 30B:
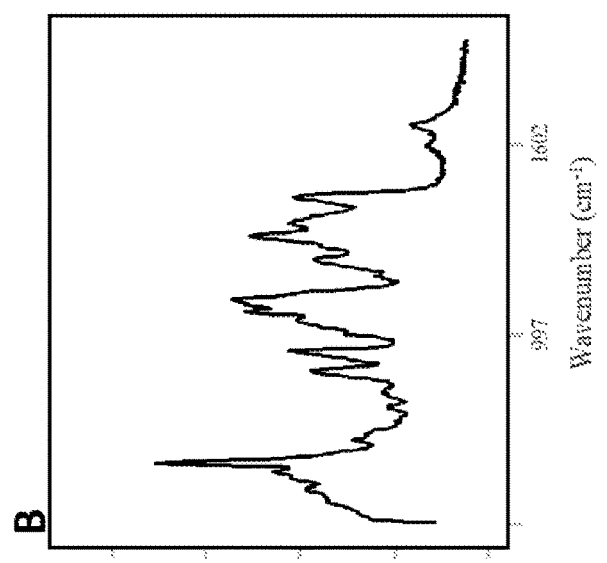
Figure 30C:
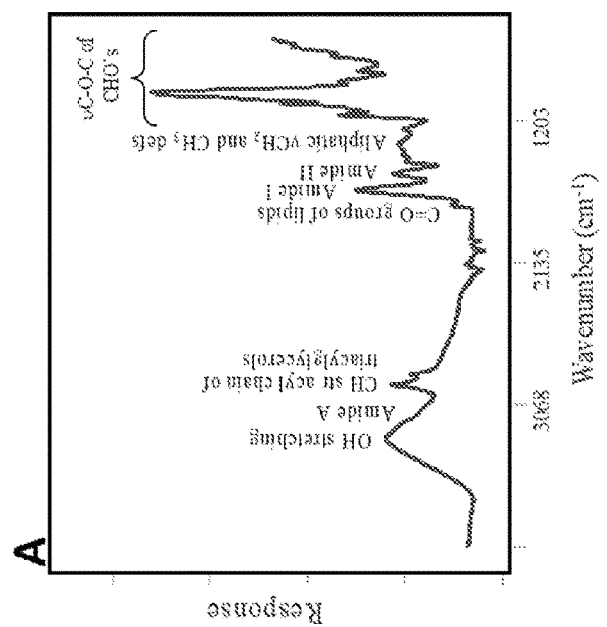

FIG. 30 shows the spectra collected using NIR, Mid-Infrared and Raman from the oats powder. The spectral data was used for targeted analysis of oats, providing a versatile analytical platform for screening unique breeding traits in plant materials. Mid-IR spectra (FIG. 30A) showed unique patterns (fingerprints) related to the vibrational modes of functional groups associated to moisture (3450 and 1640 cm$^{-1}$), proteins (amides at 1665 and 1550 cm$^{-1}$), acyl chain C—H (3000-2800 cm$^{-1}$) and C=O (1750 cm$^{-1}$) of the triacylglycerols ester bond of lipids and carbohydrates groups (1250-900 cm$^{-1}$) of oats. The signal from the handheld Raman device (FIG. 30B) shows the inelastic scattered radiation from the 1064 nm incident laser through its interaction with vibrating molecules. The Raman spectra was dominated by the complex vibrational contributions from the skeleton bending involving CCC, COC, OCC, and OCO mainly associated to structures of polysaccharides, especially those with β-1,4-glycosidic bonds due to the inter- and intra-chain hydrogen bonds making the structure highly ordered favoring Raman vibrations. FIG. 30C shows the NIR spectra of soybeans corresponding to the higher electromagnetic energy levels resulting in overtones and/or combination bands involving highly anharmonic X—H (mainly C—H, N—H, and O—H) stretching modes. Characteristic bands of the O—H stretching of water were centered 5170 cm$^{-1}$ (combination), C—H vibration modes of lipids centered at 5795 cm$^{-1}$ (first overtone) and 4260 cm$^{-1}$ (combination), and the N—H vibration band at 4747 cm$^{-1}$ (combination).

Figure 31:
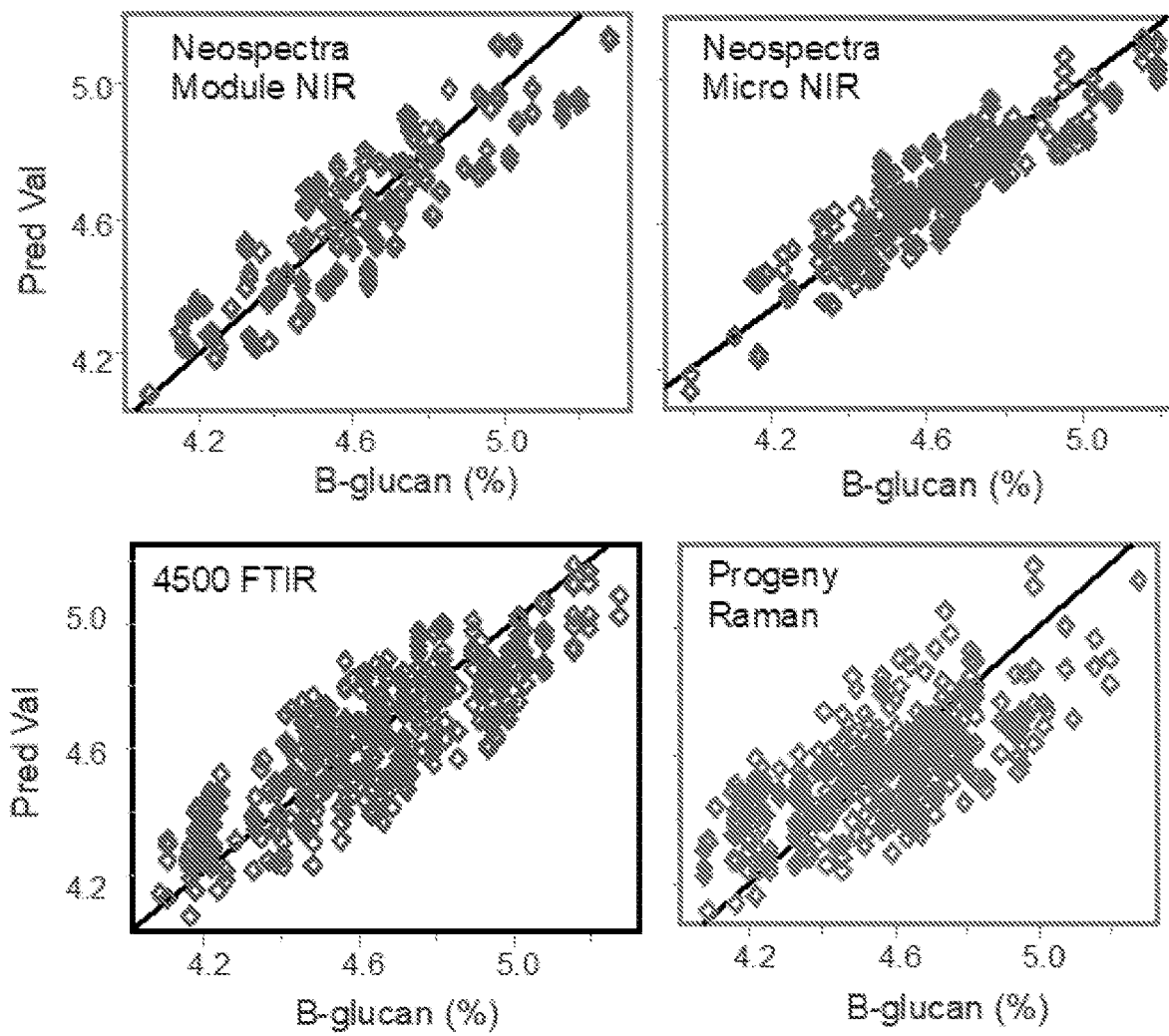
FIG. 31 shows PLSR correlation plots for predicting β-glucan in oats based on spectral patterns collected by handheld NIR (NeoSpectra Module & Micro), portable mid-infrared and handheld Raman systems.
Figure 32:
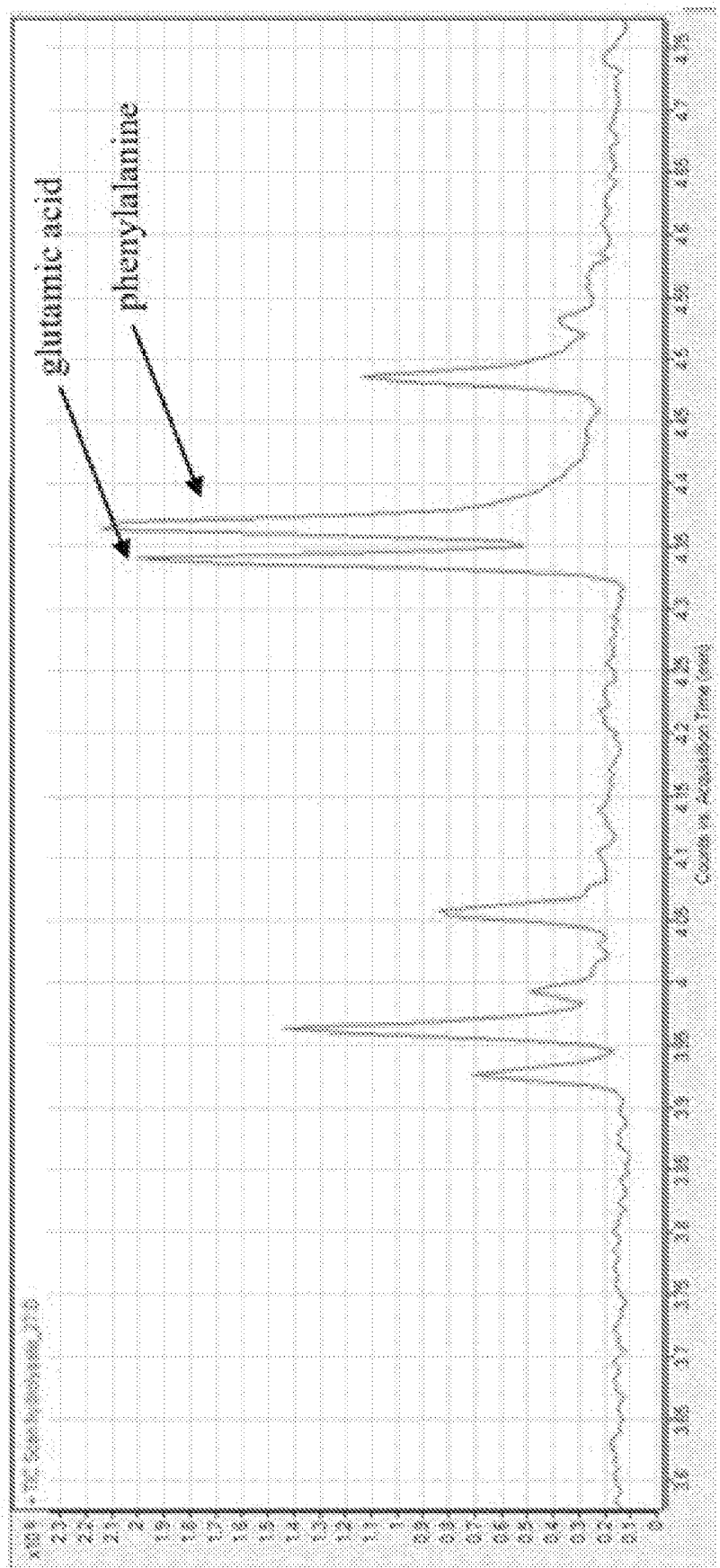
FIG. 32 shows GC-MS chromatogram of major amino acids separated from a soybean hydrolysate.
Figures 33, 34, 35:
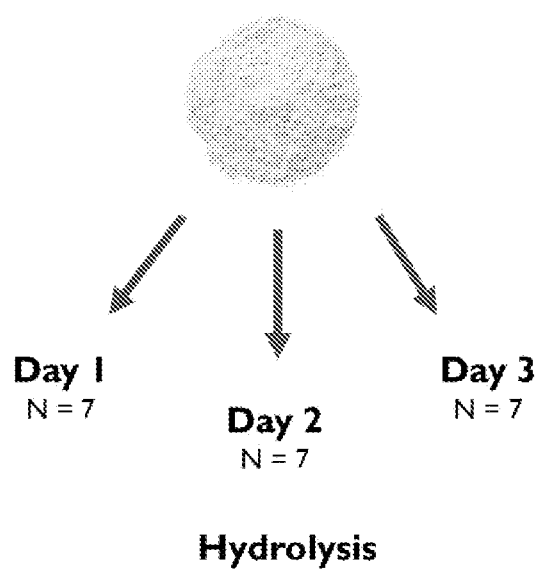
FIG. 33 shows intra-day precision (% CV). The compounds of high CV include hydroxyproline, glutamic acid, lysine, histidine, cysteine.
FIG. 34 shows that hydrolysis error is a factor that can affect amino acid yields. Other factors include defatting, mass, pH, and analysis methods (e.g., multiple linear regression may cause many independent variables and continuous dependent variable).
FIG. 35 shows leverage of factors. Null hypothesis=no relation between independent variable and dependent variable. Then investigate each factor.
Figure 36B:
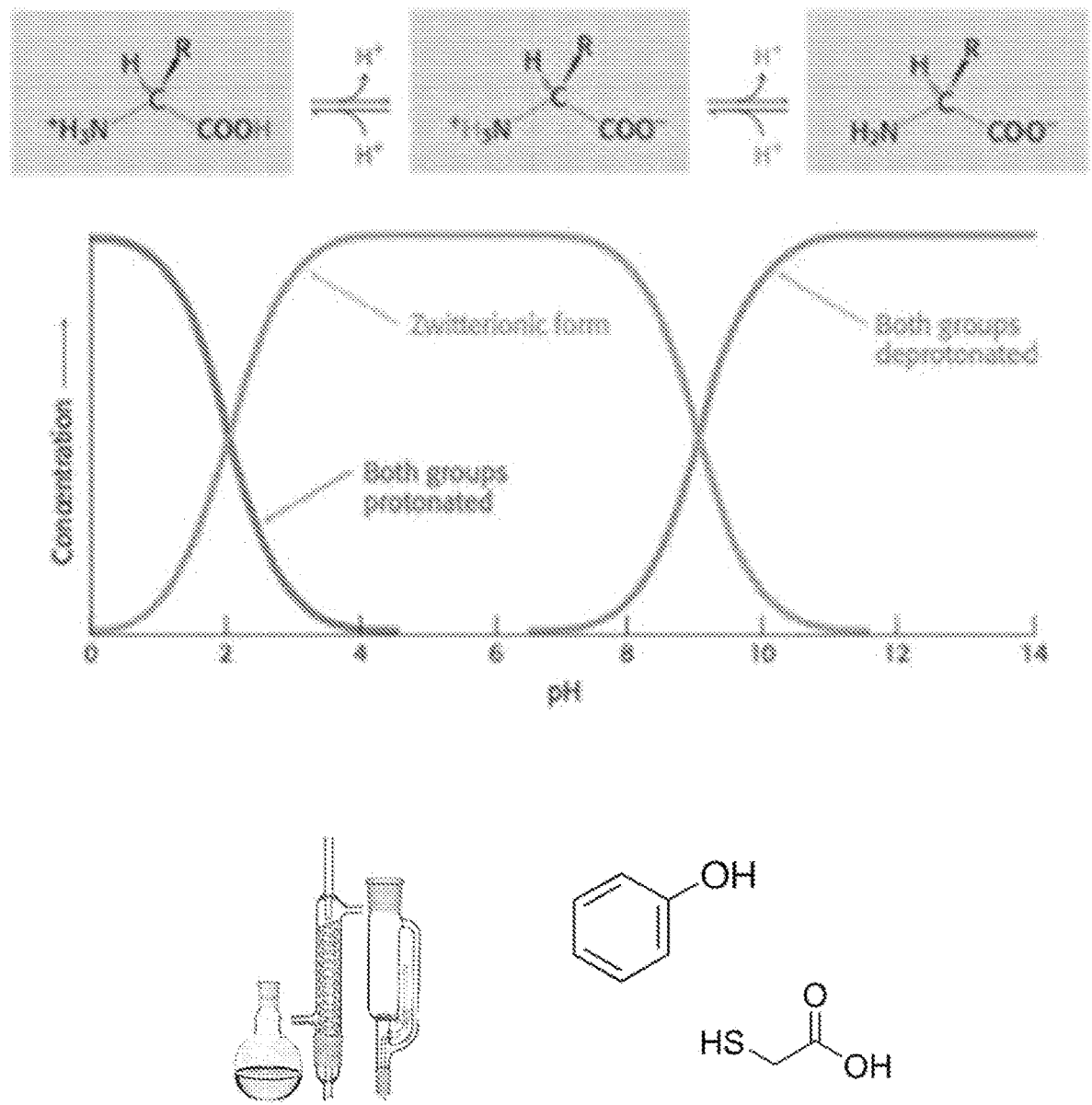
Figure 37:
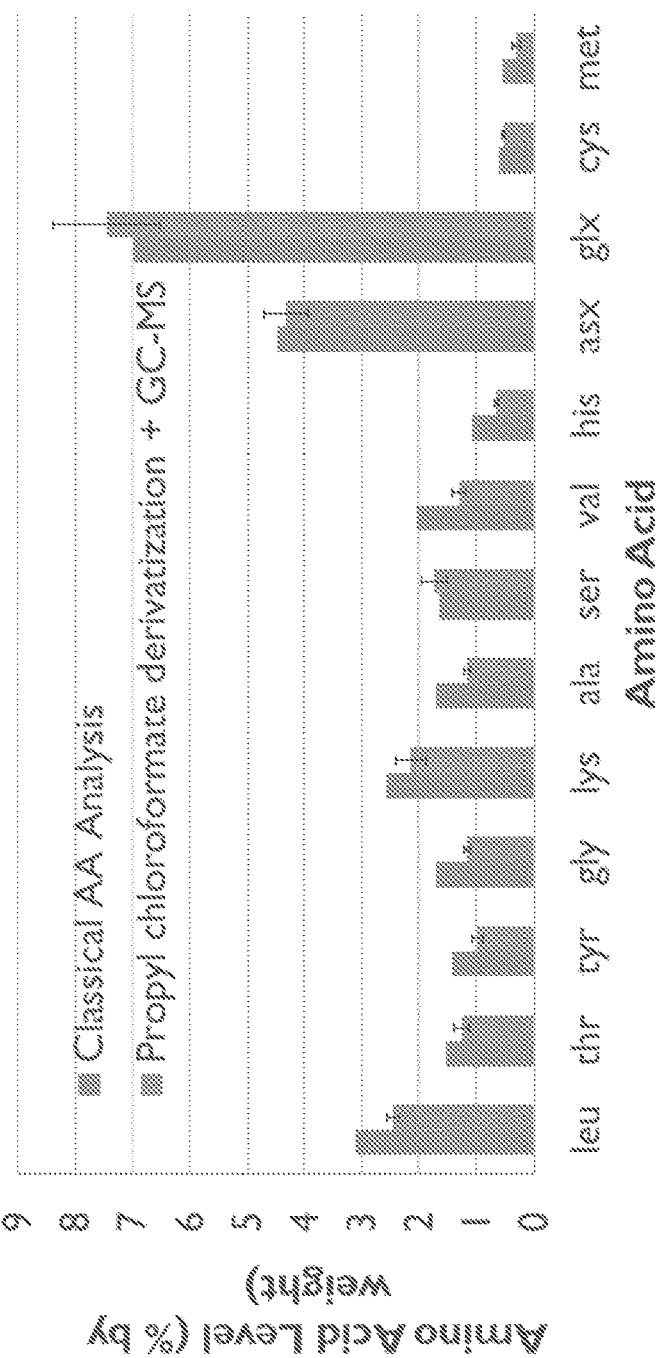
FIG. 37 shows results using non-optical spectroscopy methods for characterizing amino acids.
Figure 38:
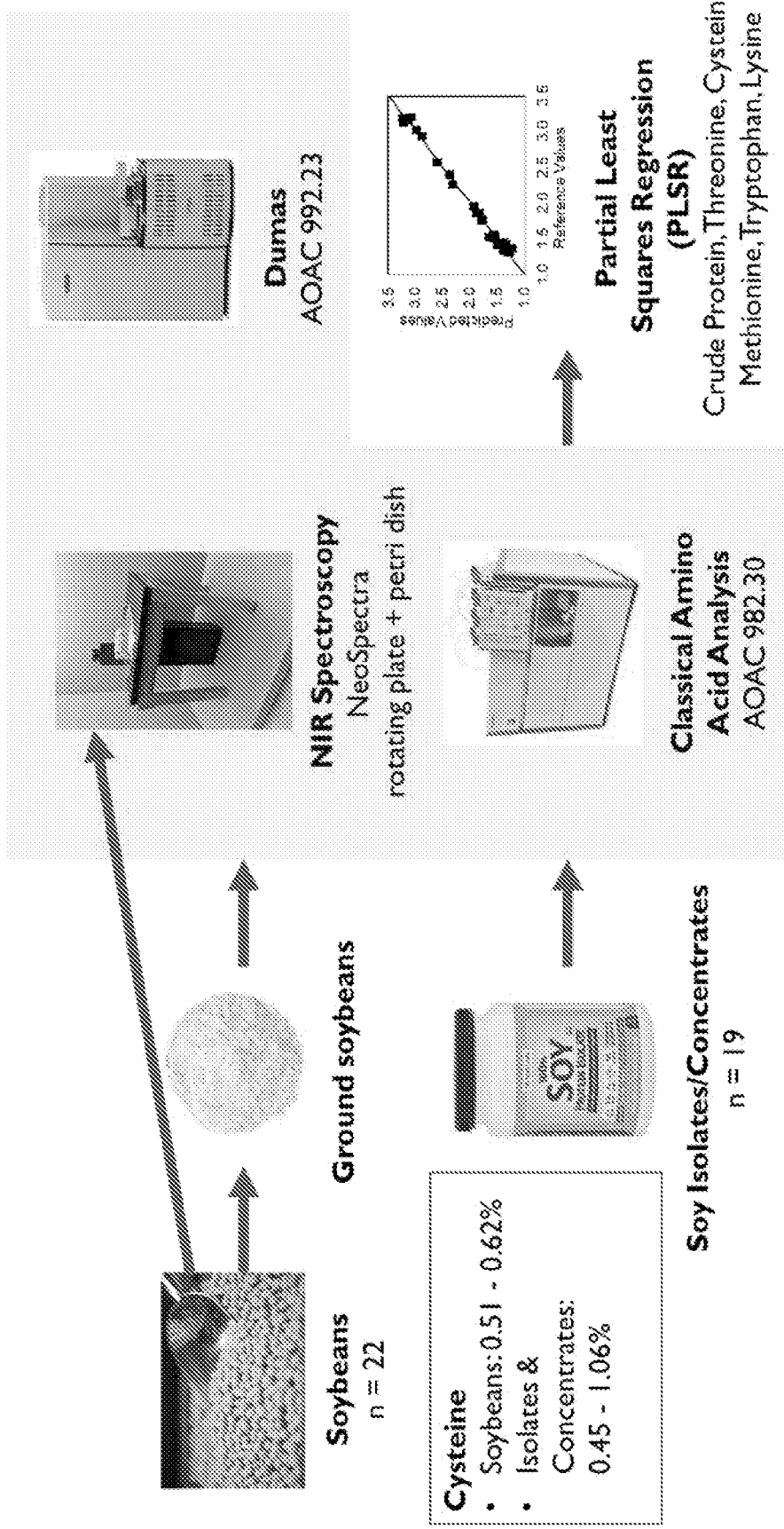
FIG. 38 shows the method of NIR prediction model.
Figure 39:
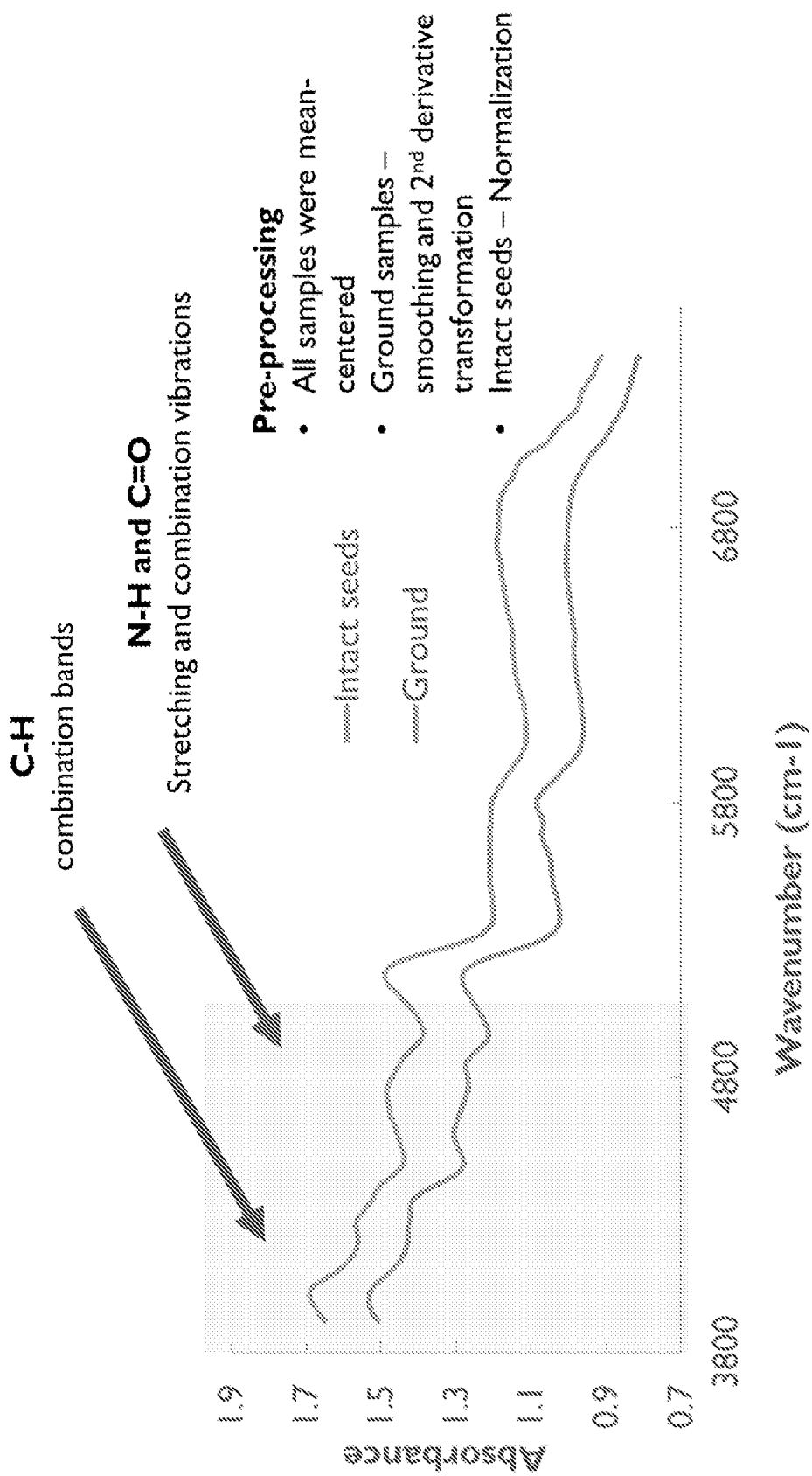
FIG. 39 illustrates NIR spectral differences between grounded and intact soybean samples. The 5000-4500 $cm^{-1}$ shows the stretching and combination vibrations of N—H and C=O bonds that corresponds to proteins and is assignable to a combination of amide I and amide II bands. The 4400-4033 $cm^{-1}$ region shows the C—H combination bands that could be related to fatty acids. Both regions are heavily utilized for model building. Mean-centering calculates average spectrum and subtracting that from spectrum of each sample. Smoothing can help reduce baseline noise while 2nd derivative transformation can resolve overlapping peaks by enhancing subtle peak shoulders that can highlight sample-to-sample differences. Normalization was applied where each data value was divided by the sample's maximum value.
Figure 40:
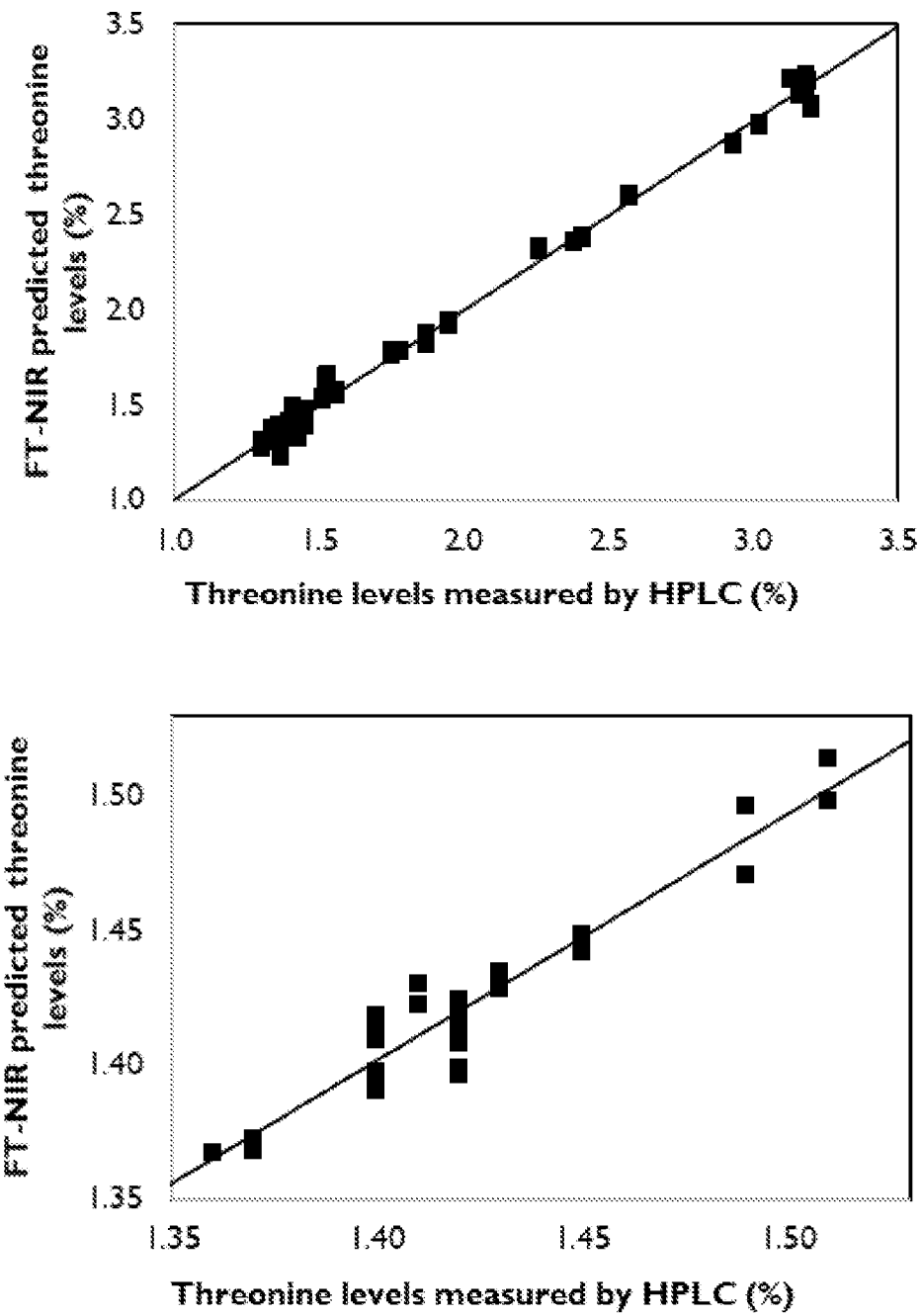
FIG. 40 illustrates Partial Least Squares Regression (PLSR). The upper panel shows the result of powder sample (Factors=4, Rcal=0.998, SECV=0.051, Rval=0.995, SEP=0.062), and the lower panel shows the result of intact seed sample (Factors=5, Rcal=0.971, SECV=0.012, Rval=0.902, SEP=0.011).
Figure 43:
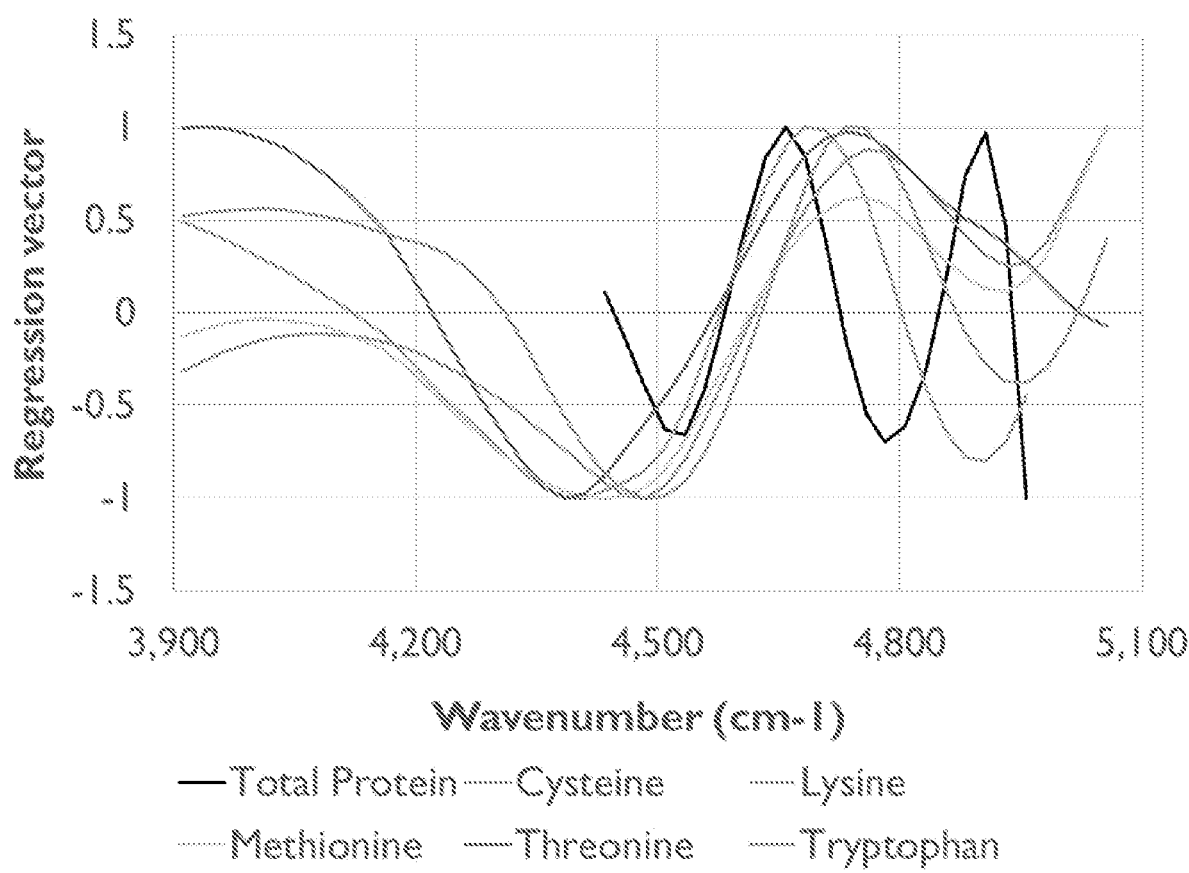
FIG. 43 shows bivariate correlation analysis of protein vs amino acids in soybeans and the regression loading vectors for the different traits analyzed showing the unique fingerprint NIR signals used for developing the regression models. There is a strong positive correlation between total protein and lysine levels (R=0.88), a moderate positive correlation between protein and threonine (R=0.61), cysteine (R=0.54), and methionine (R=0.43), and no correlation between total protein and tryptophan (R=0.09).
Figure 48:
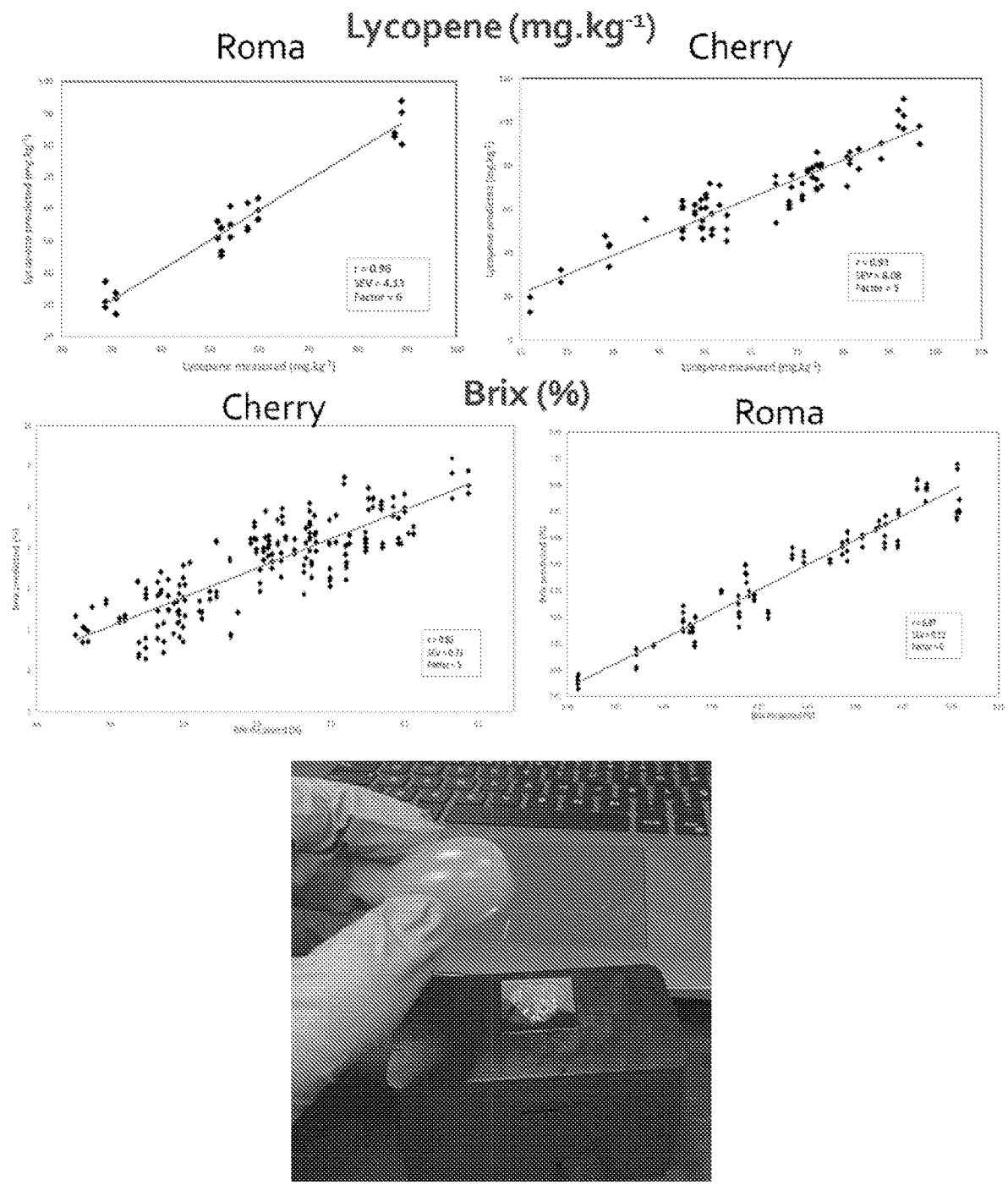
FIG. 48 shows PLSR regression for two tomato traits based on NIR sensor data. PLSR correlation plots for the determination of lycopene and Brix in tomato fruits by a handheld NIR device
Figure 49:
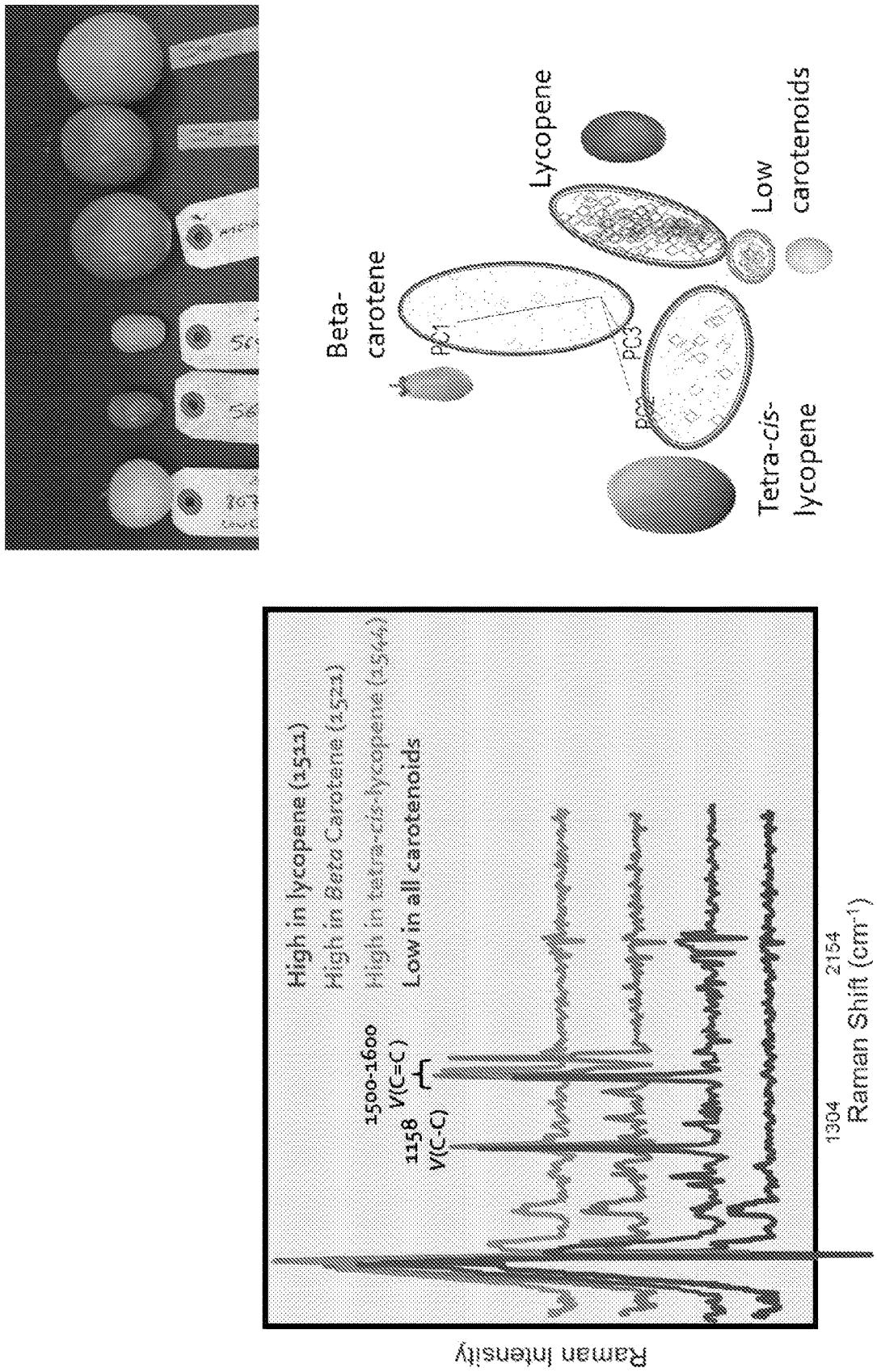
FIG. 49 shows Raman spectra of tomato fruits bred for accumulation of different carotenoids and the classification plot based on pattern recognition analysis.
Figure 51A:
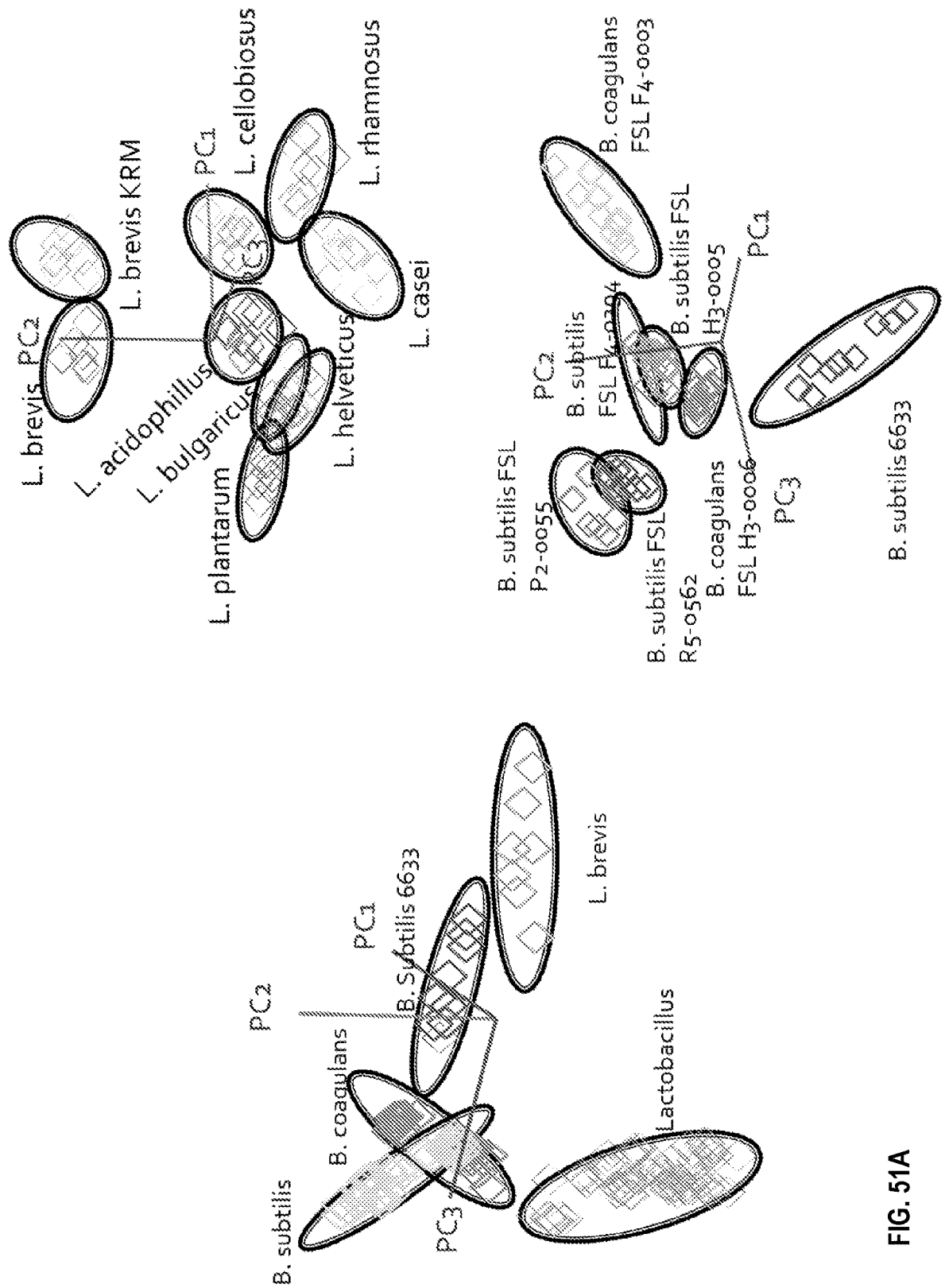
FIGS. 51A-51B show classification analysis.
Figure 51B:
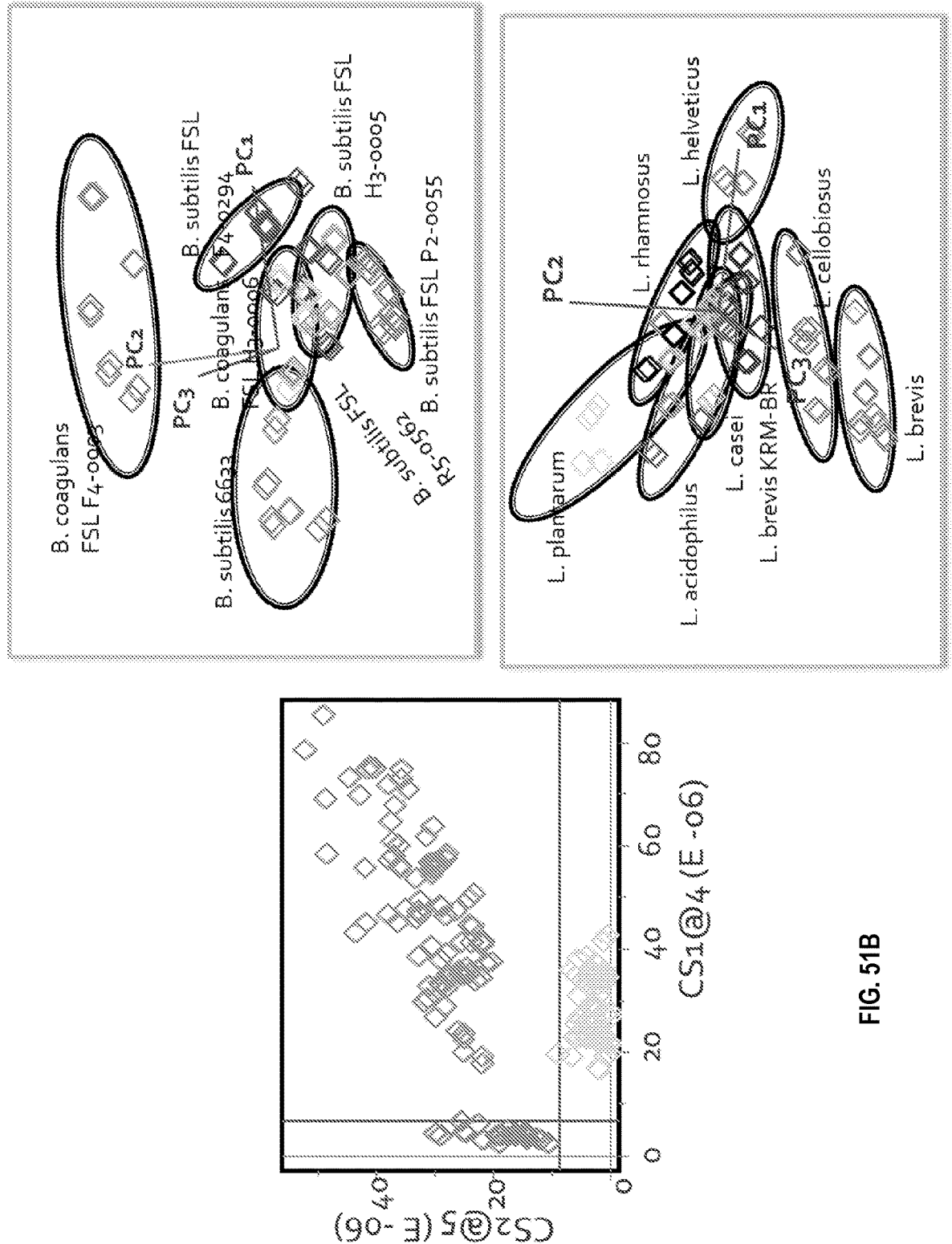
Figure 54A:
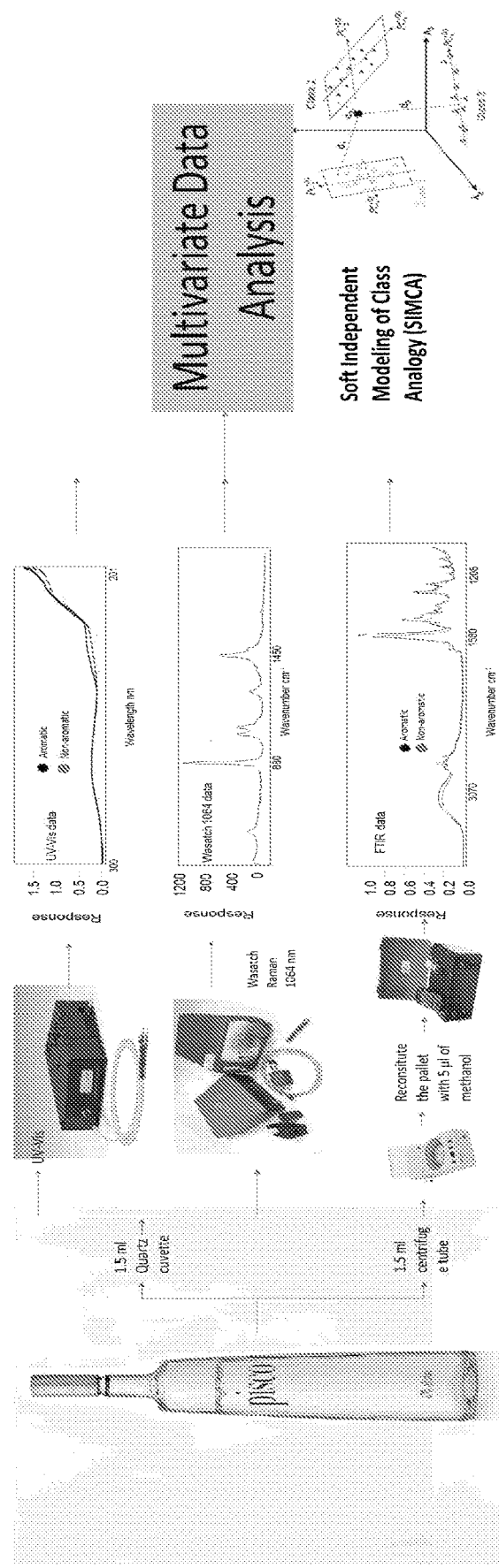
Figure 54C:
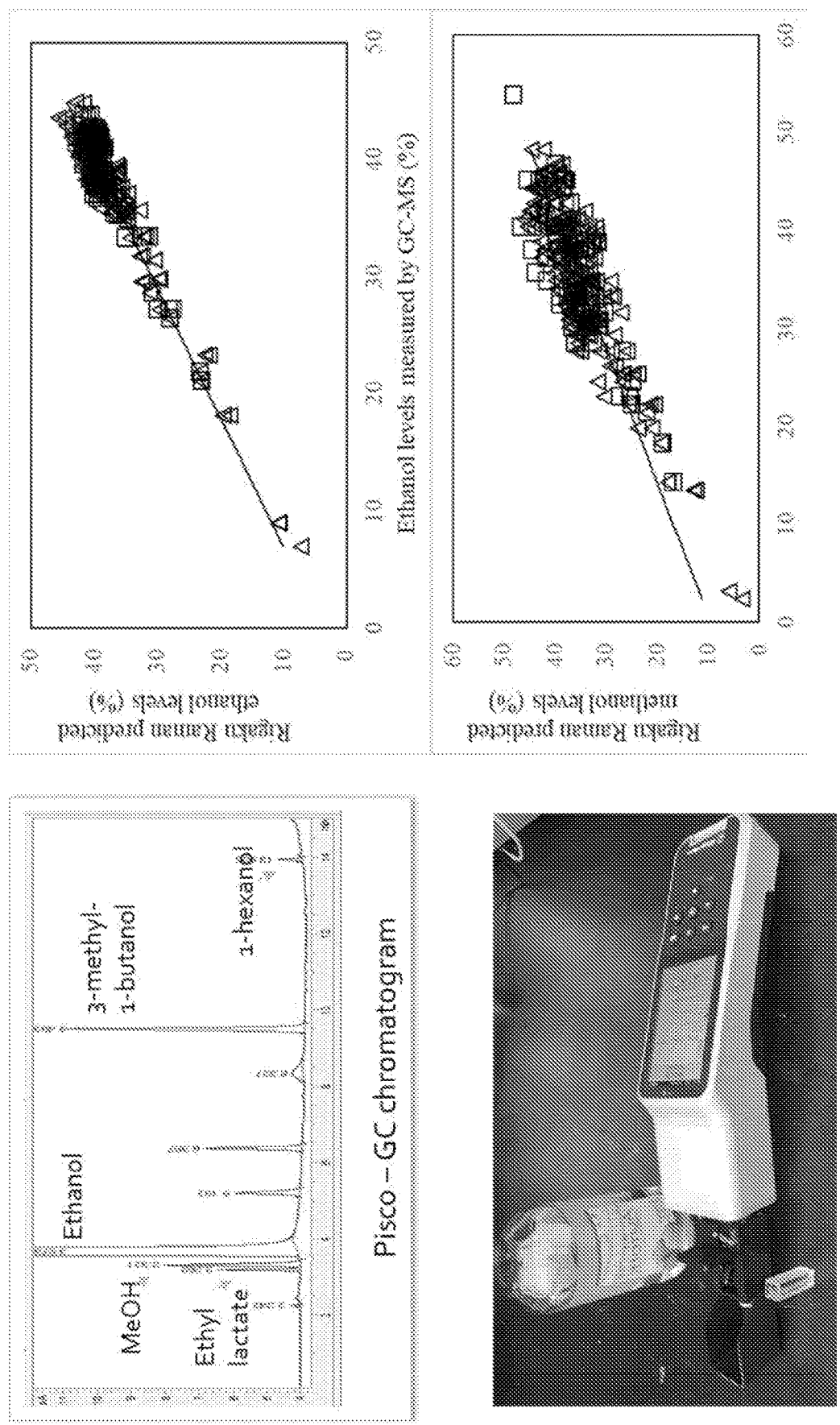
Figure 56A:
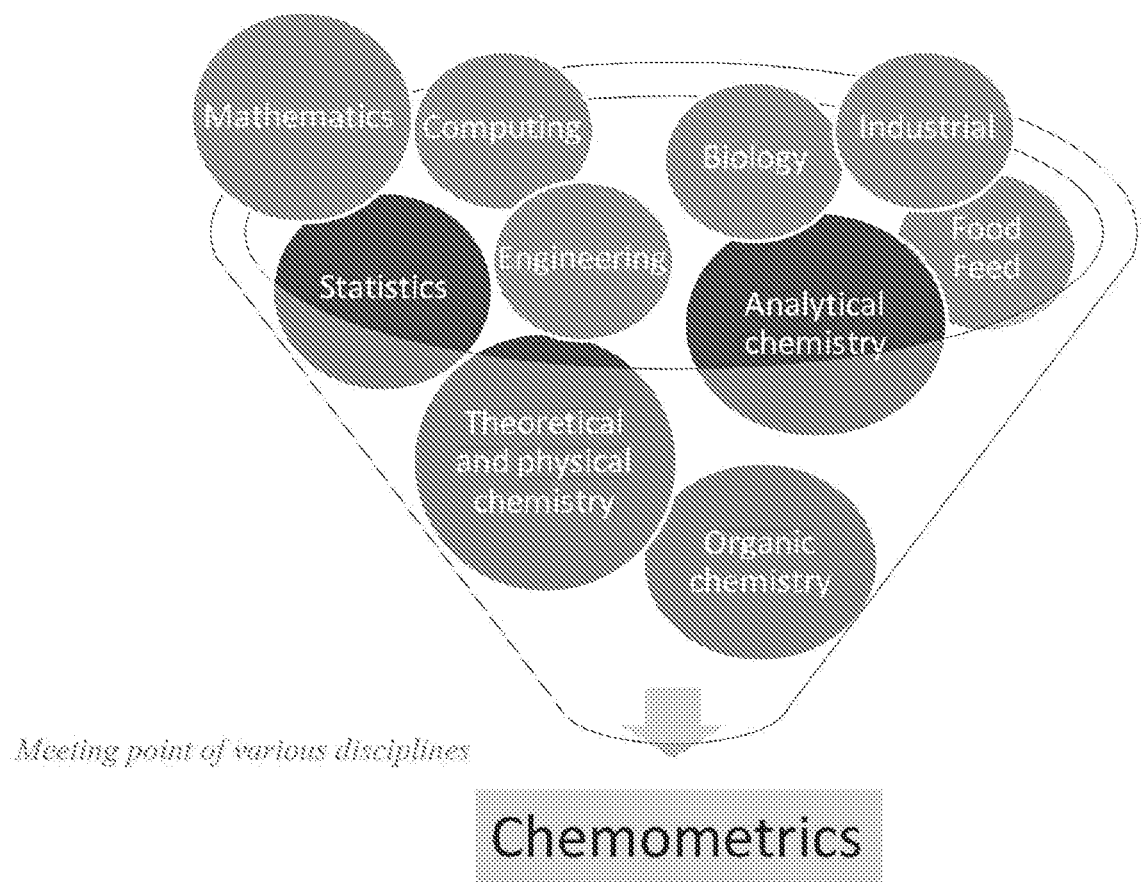
FIGS. 56A-56B show multivariate analysis. Multivariate analysis (MVA) techniques allow multiple variables to be analyzed at once.
Figure 56B:
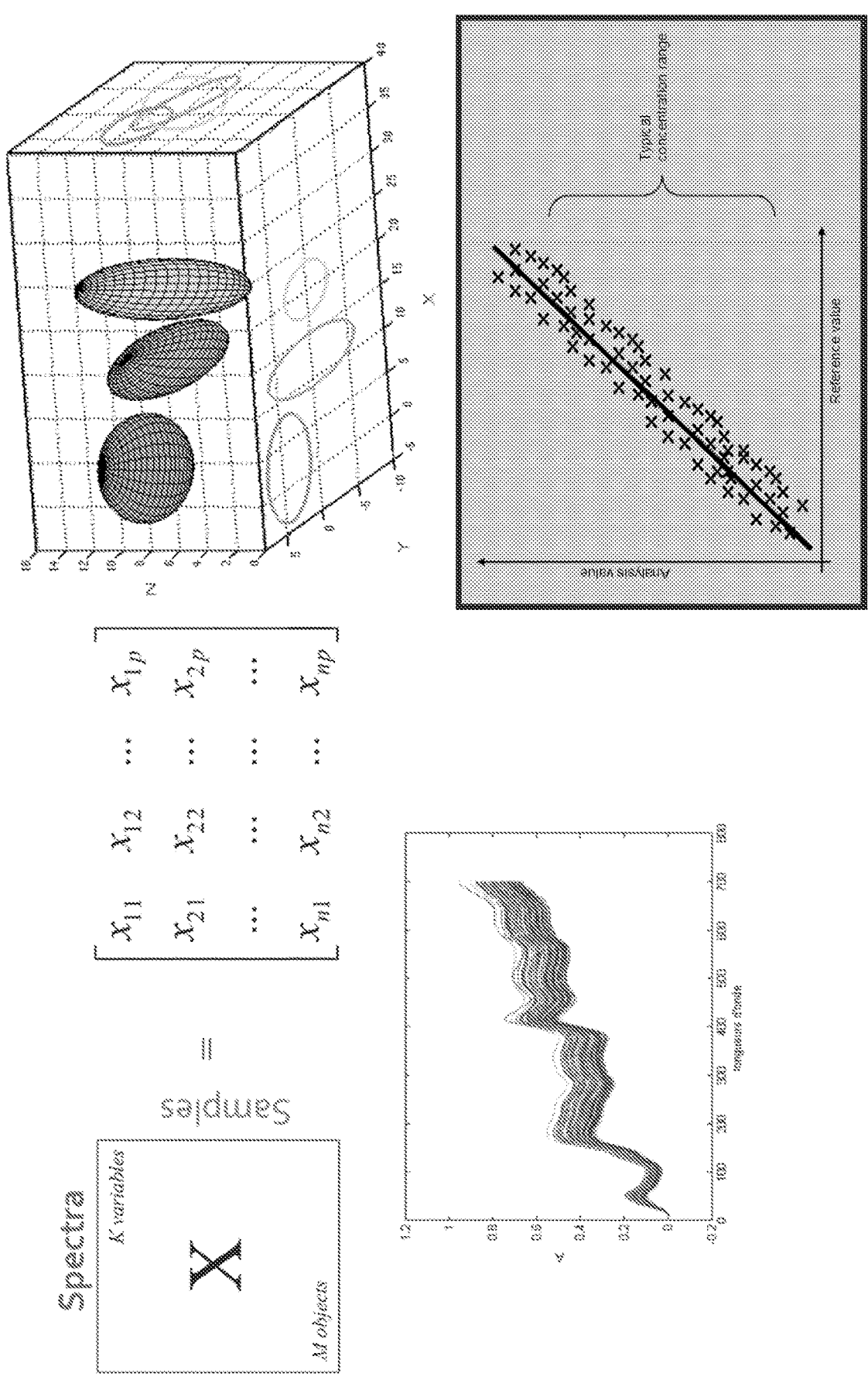
Figure 57:
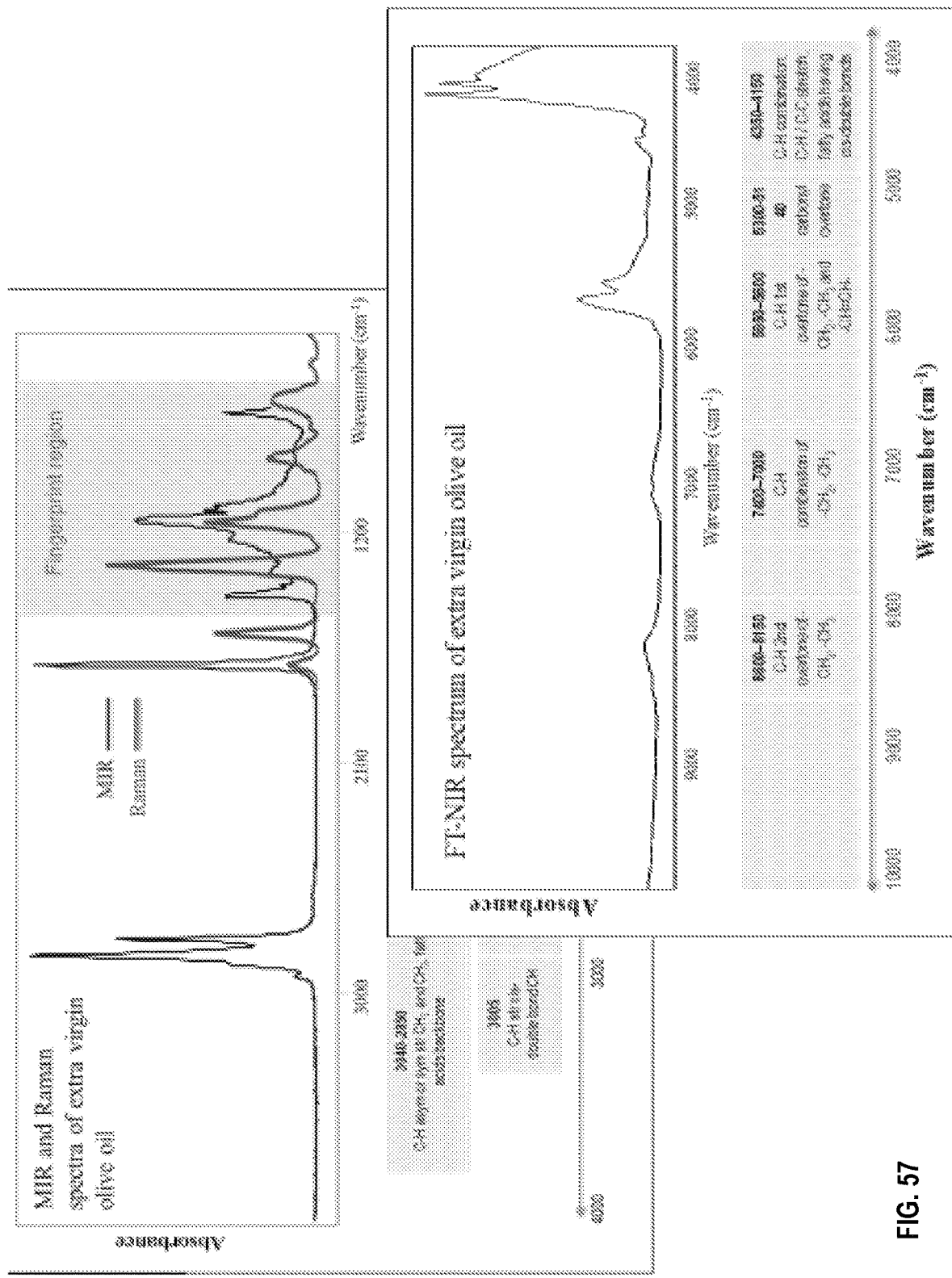
FIG. 57 shows spectral signatures of extra virgin olive oil as acquired by NIR, MIR, and Raman spectrometers.
Figure 58:
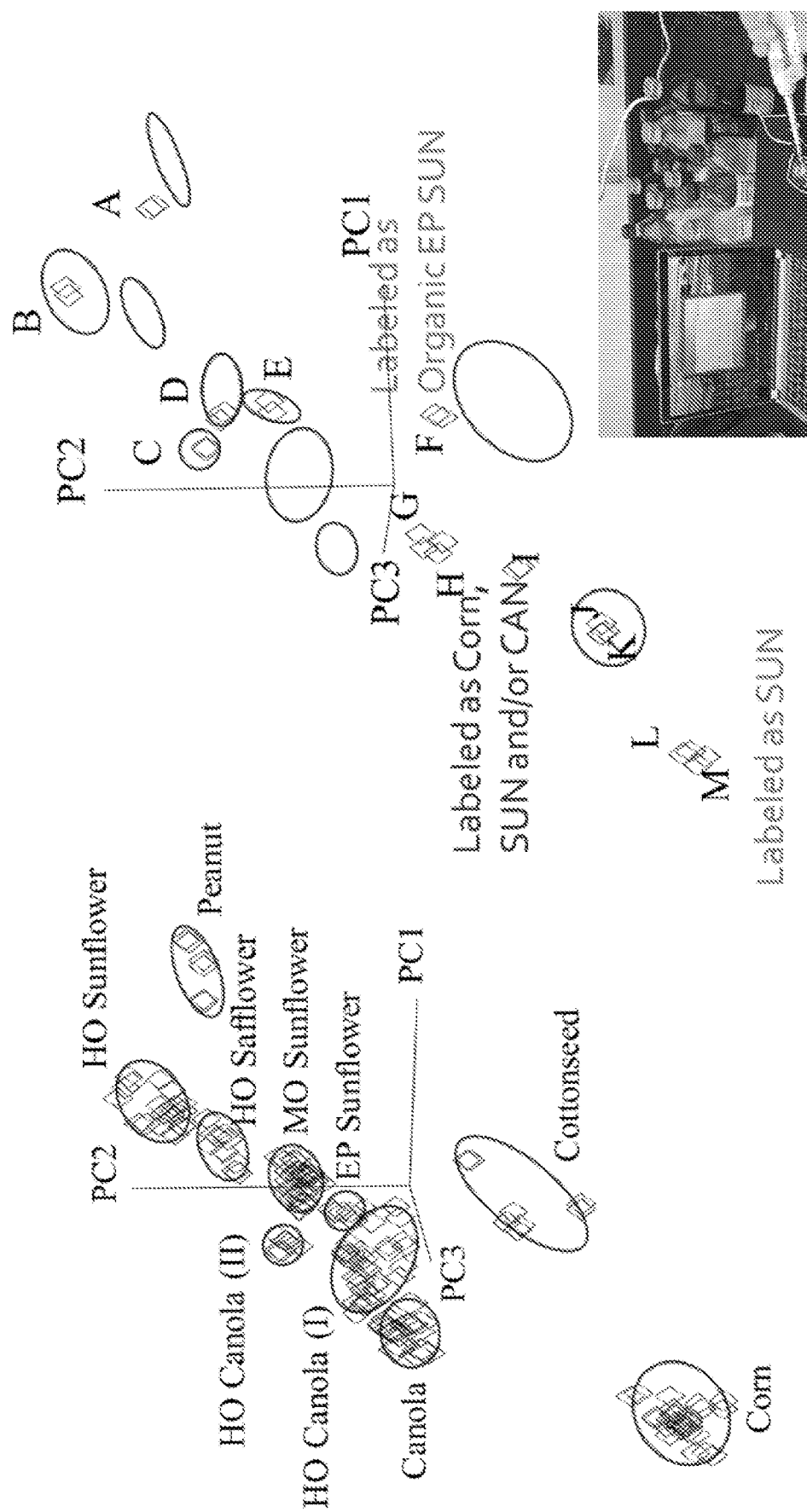
FIG. 58 shows Mid-Infrared Classification of vegetable oils used for manufacturing potato chips.
Figure 59:
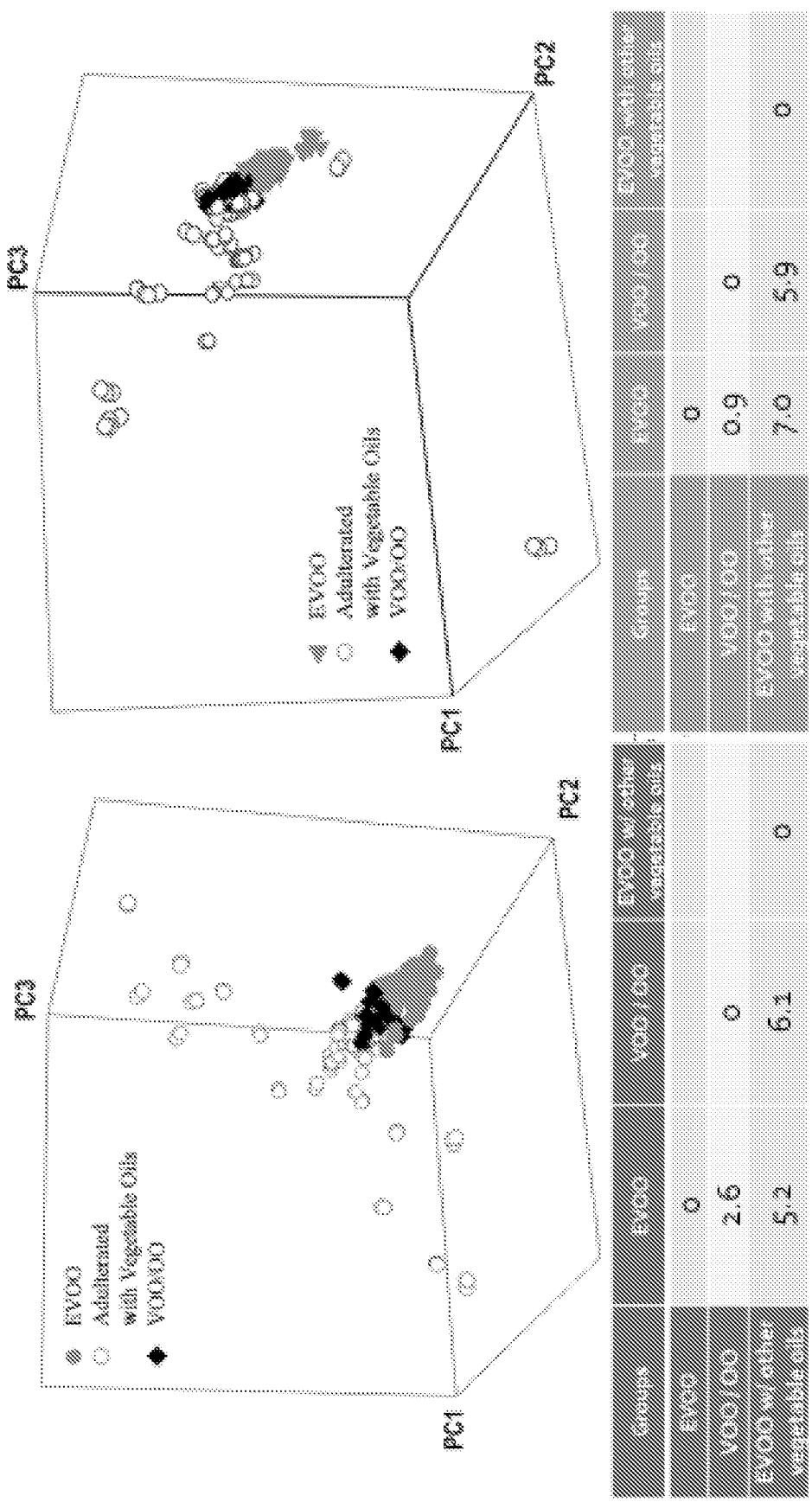
FIG. 59 shows Mid-Infrared Classification of Extra Virgin Olive Oils for detection of adulteration.
Figures 62A, 62B:
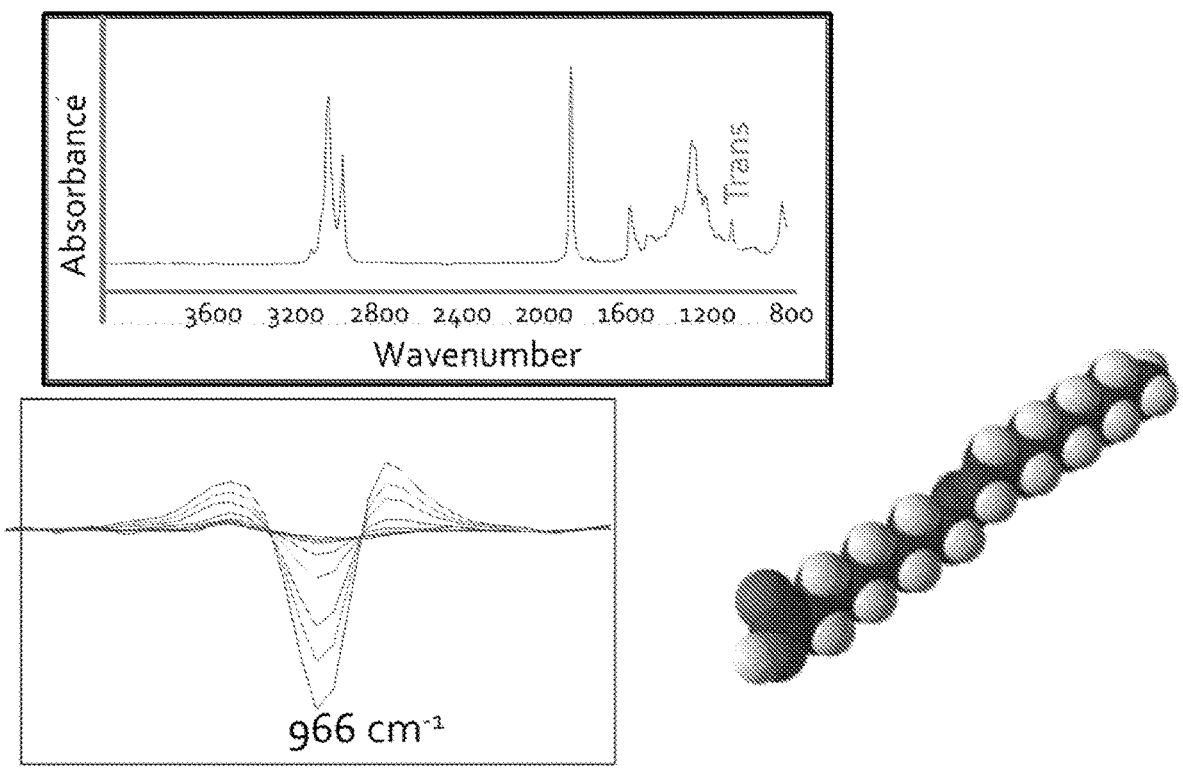
FIGS. 62A-62B show trans fat analysis in various food products.
Figures 63, 64:
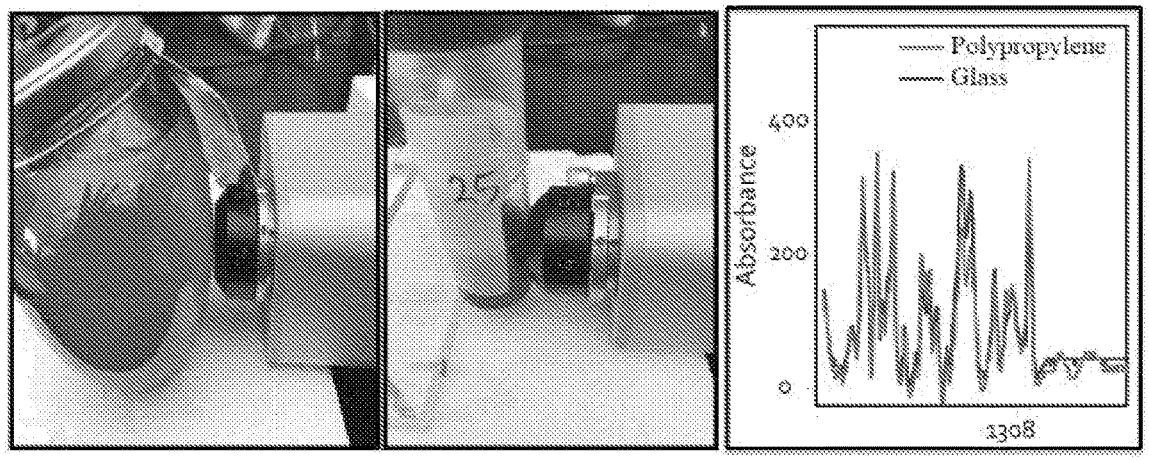
FIG. 63 shows Raman spectra collection of honey samples.
FIG. 64 shows geographical origin of honey samples.
Figure 66A:
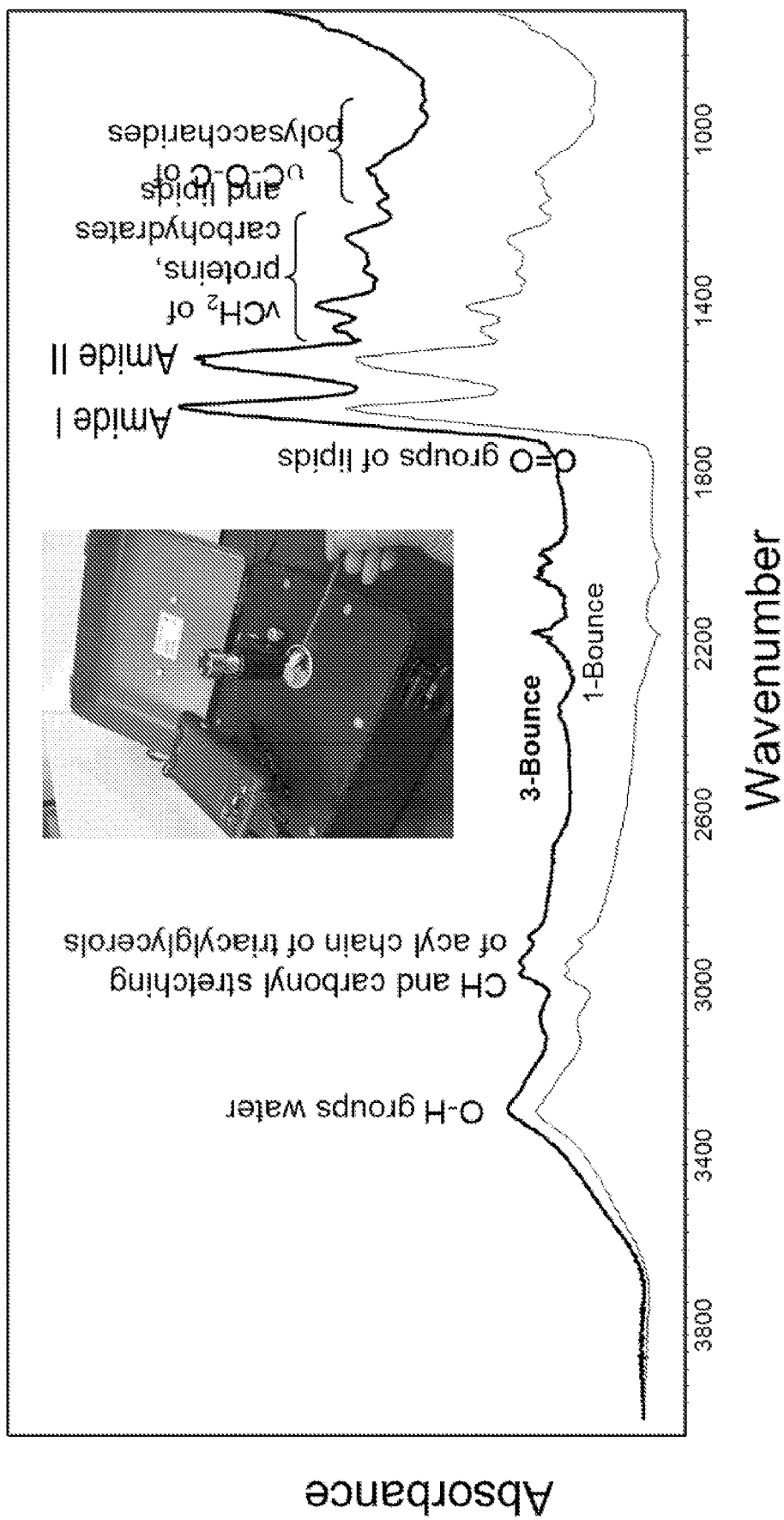
FIGS. 66A-66B show the analysis of whey protein.
Figure 66B:
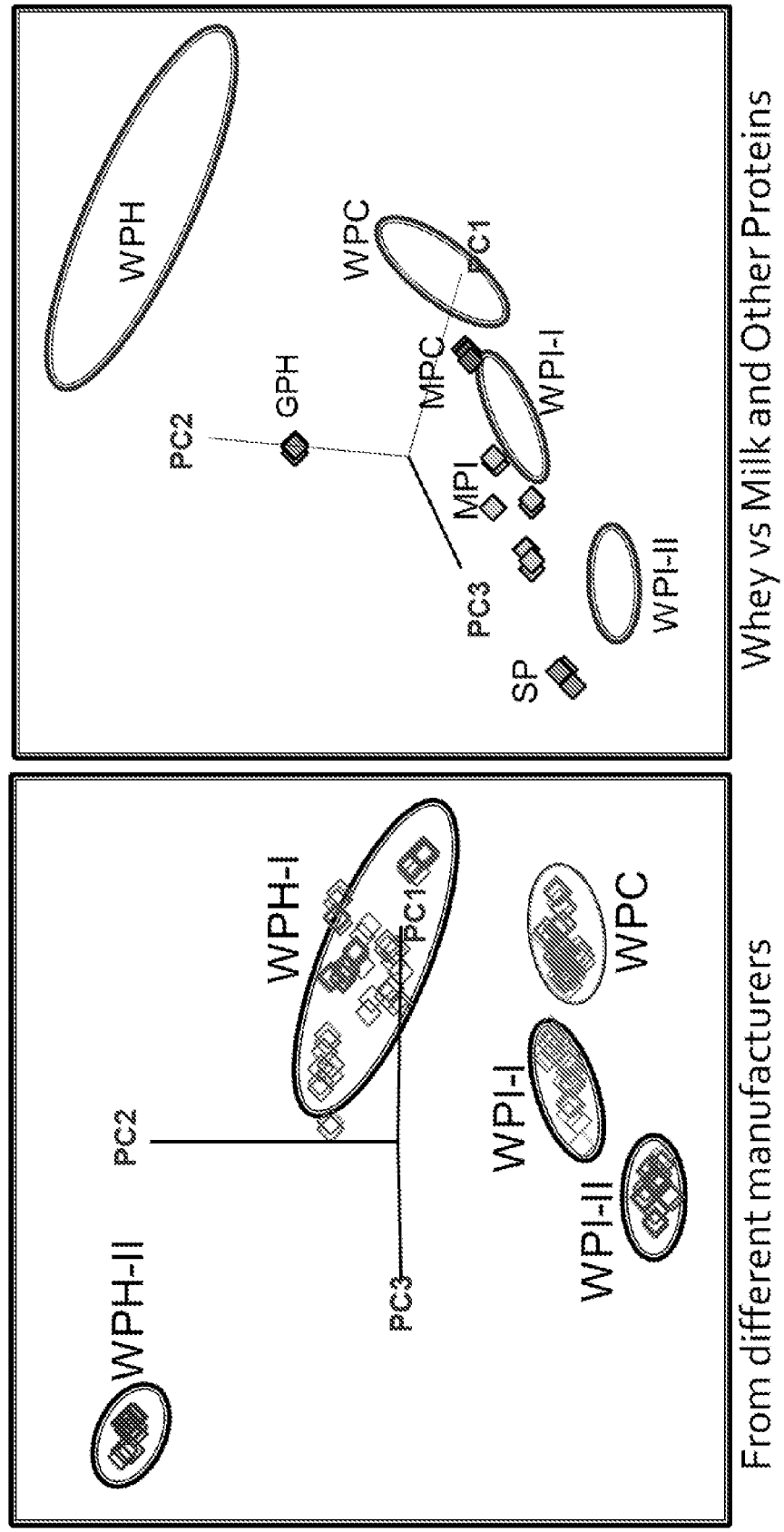
Figure 67:
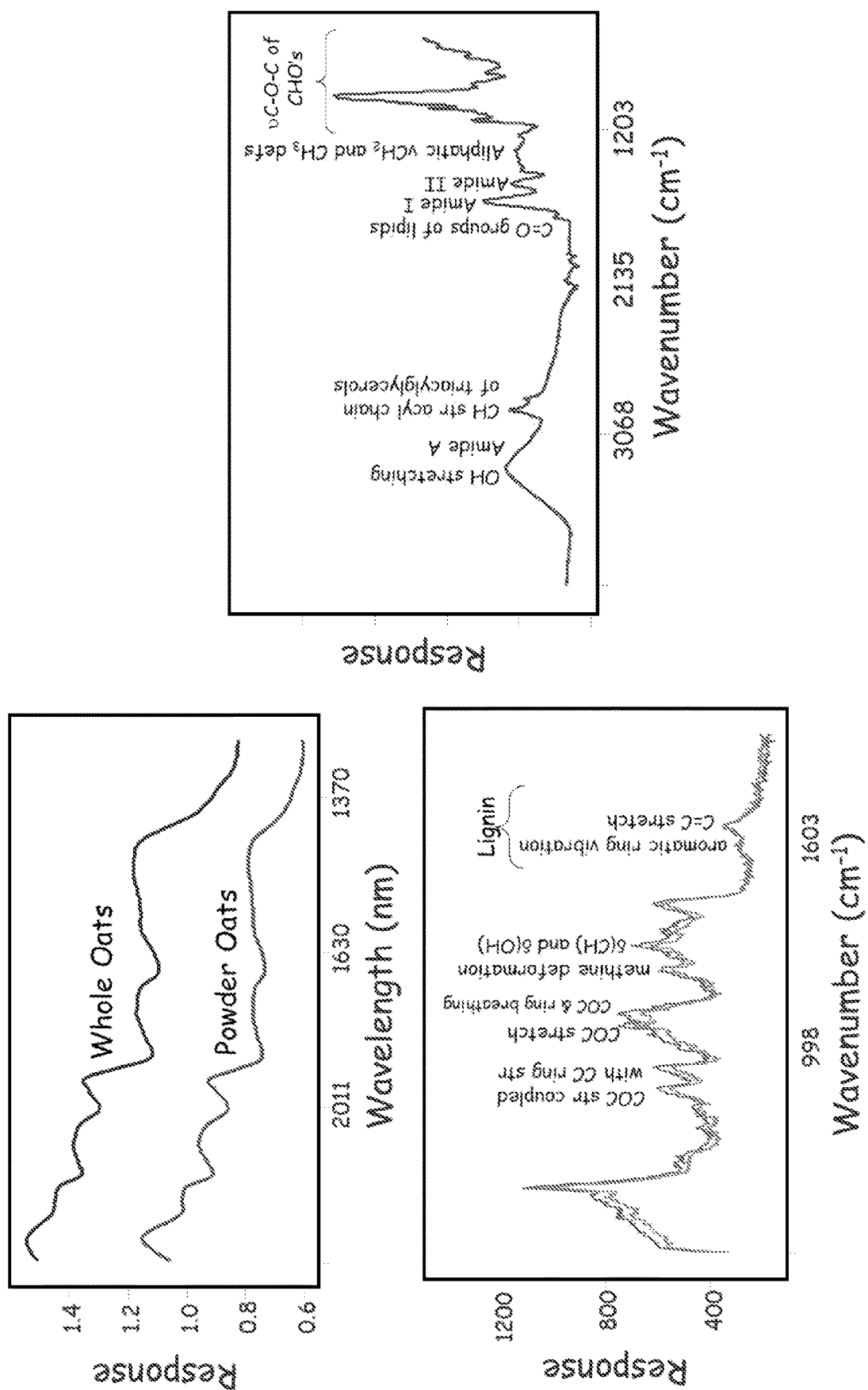
FIG. 67 shows data acquisition of oats with handheld technology.
Figure 68:
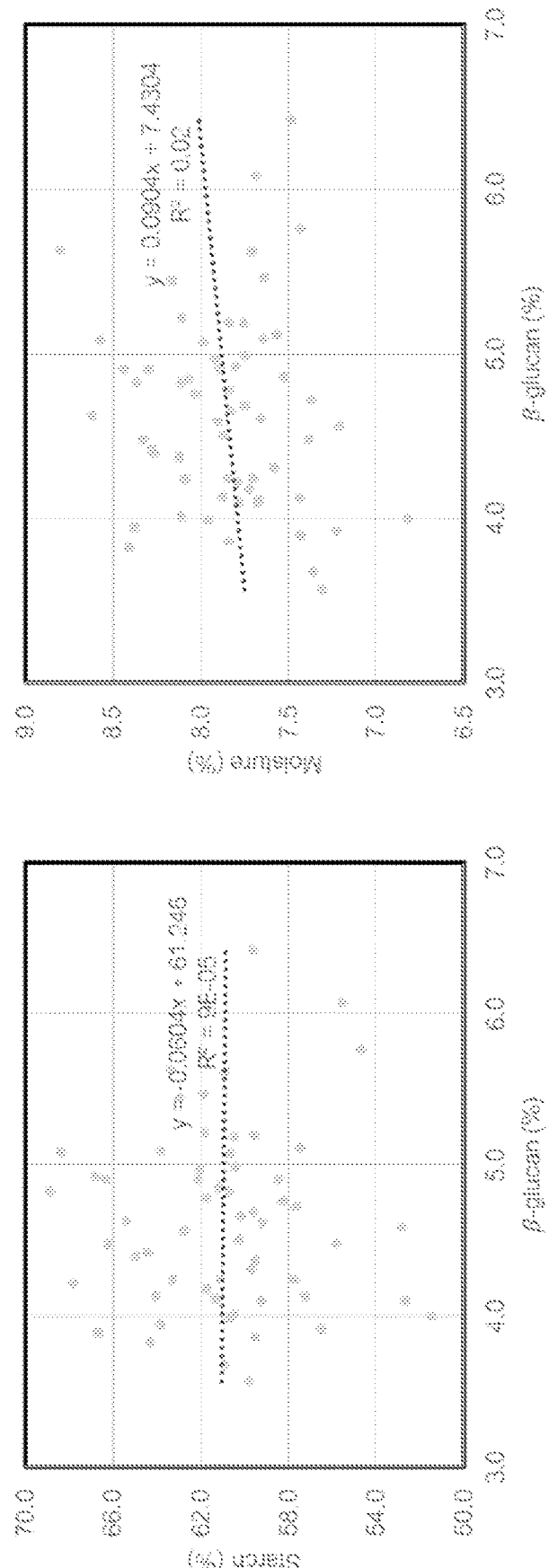
FIG. 68 shows the composition of oat samples and correlation of starch and moisture with β-glucan content.
Figure 69:
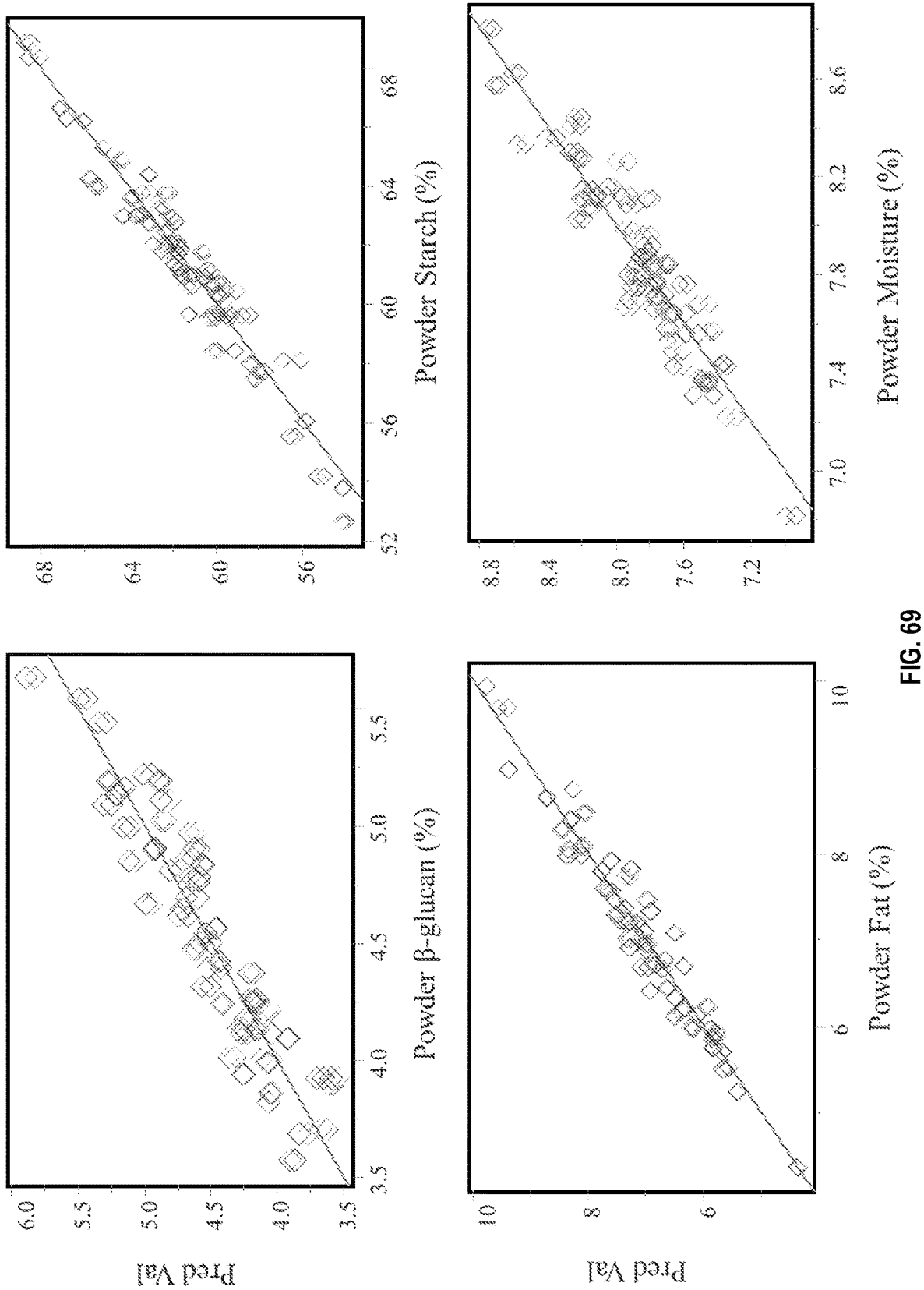
FIG. 69 shows PLSR analysis using regression models for various traits in oat samples.
Figure 72:
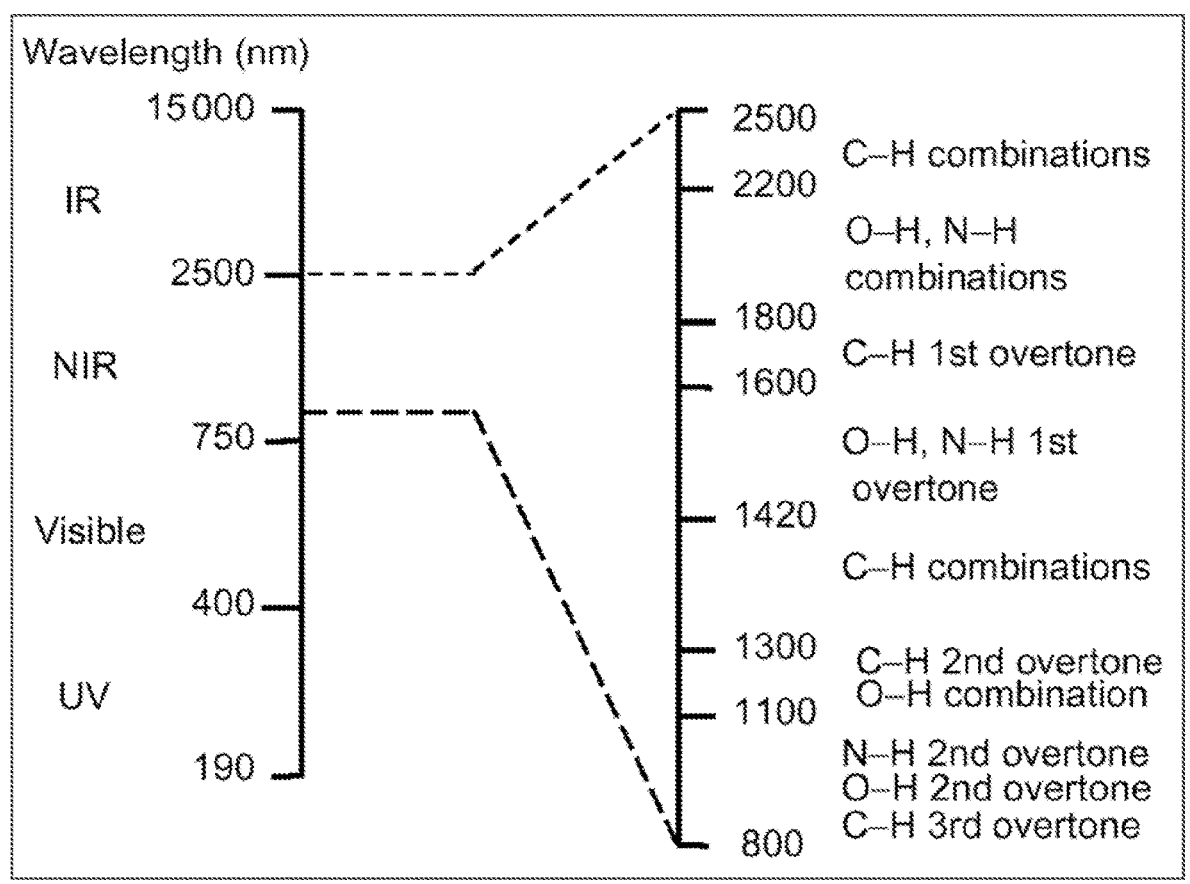
FIG. 72 shows NIR spectroscopy provides information of chemical constituents.
Figure 73:
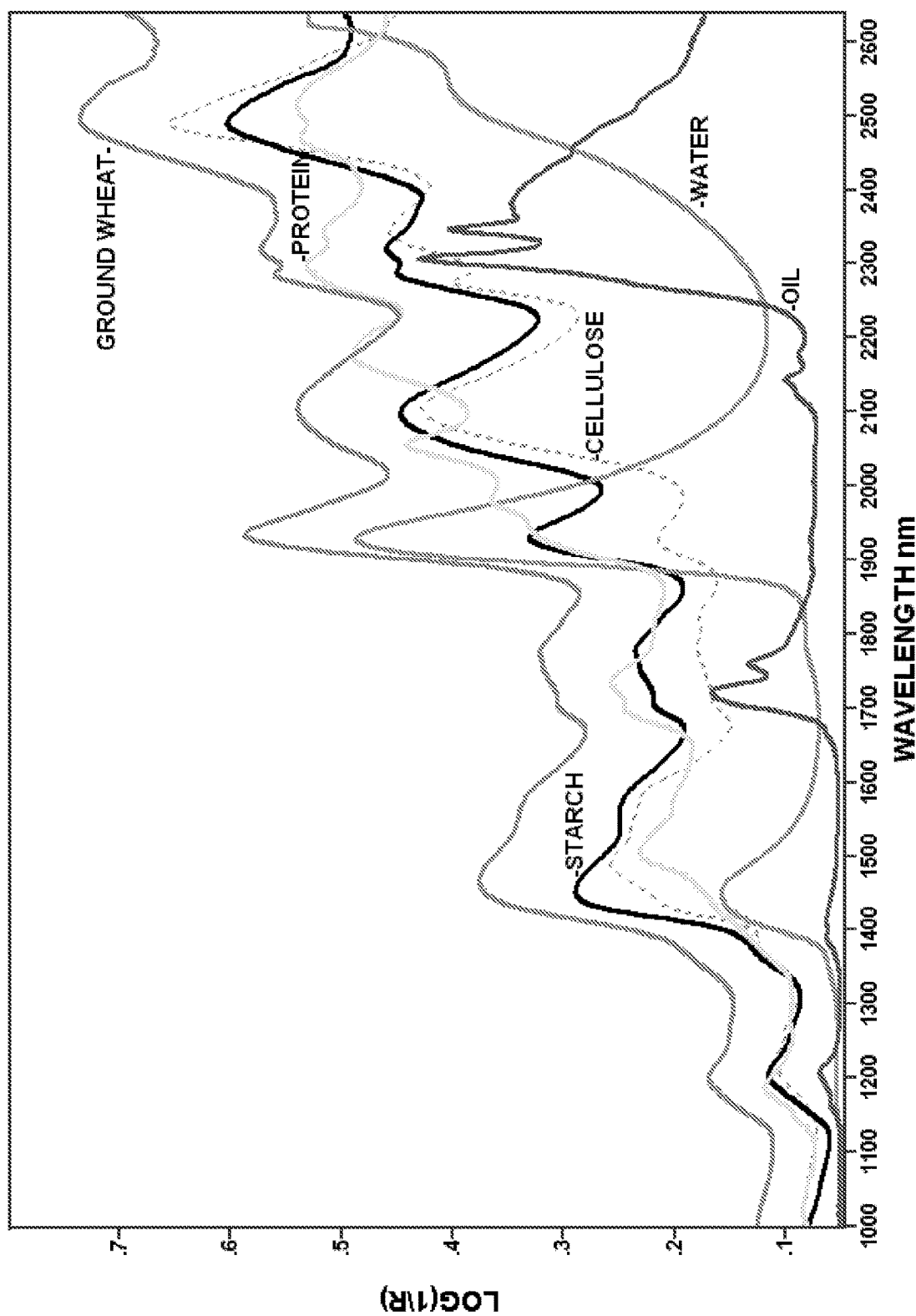
FIG. 73 shows that NIR spectroscopy enables decomposing food samples into major constituents.
Figure 74A:
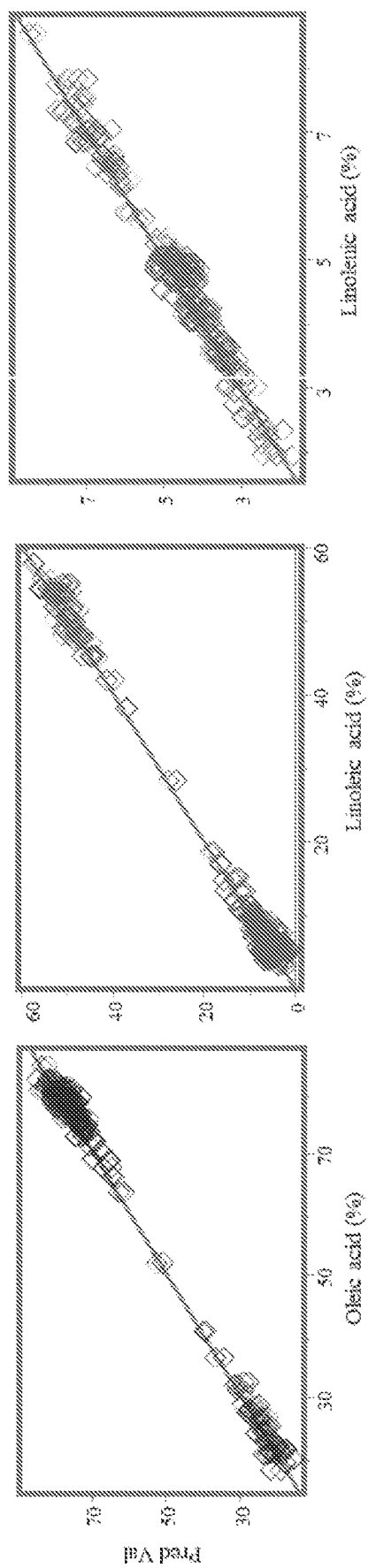
FIGS. 74A-74E show the analysis of compositions in soybeans (FIG. 74A), oats (FIG. 74B), barley (FIG. 74C), tomatoes (FIG. 74D), and hemp (FIG. 74E) using the portable sensor. Traits in soybeans include oleic acid, linoleic acid, and linolenic acid. Traits in oats include β-glucan, protein, starch, moisture, and fat Traits in barley include protein, valine, moisture, and deoxynivalenol (vomitoxin). Traits in tomatoes include lycopene and sugar. Traits in cannabis include THC (tetrahydrocannabinol) and CBD (cannabidiol). These data demonstrated a portable, real-time sensor to measure quality traits in food.
Figure 74B:
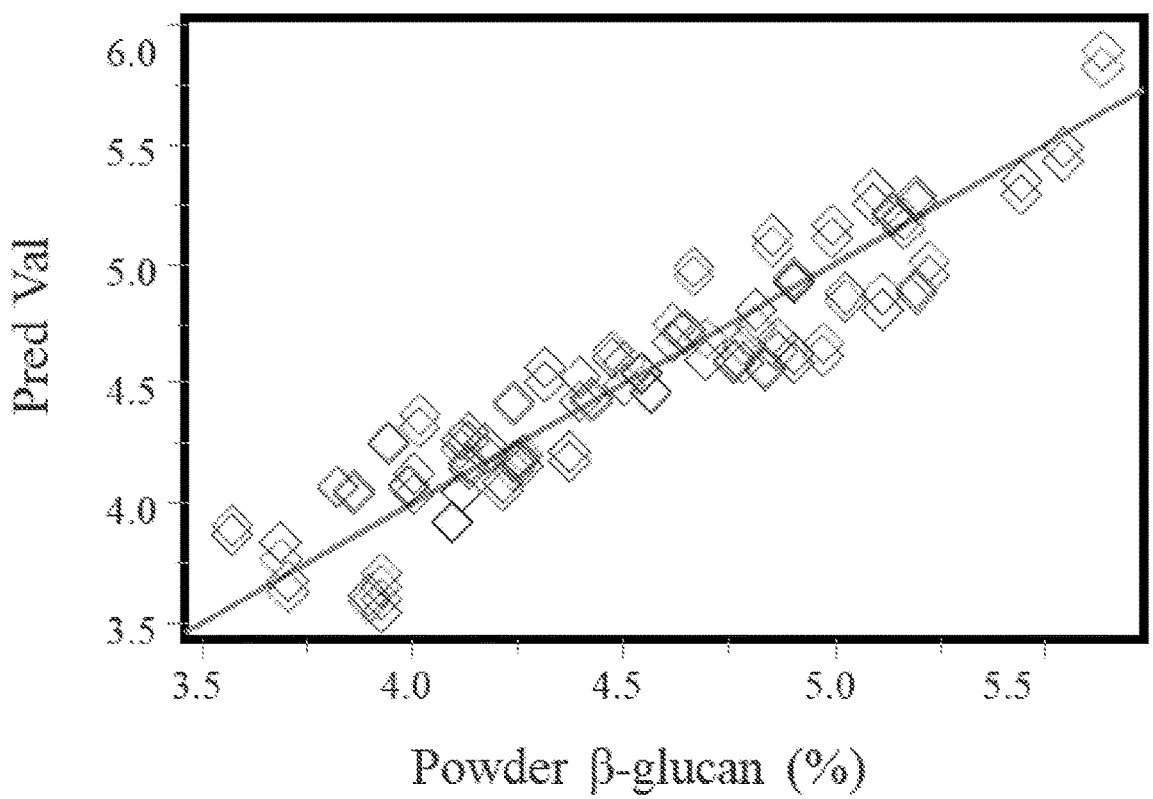
Figure 74C:
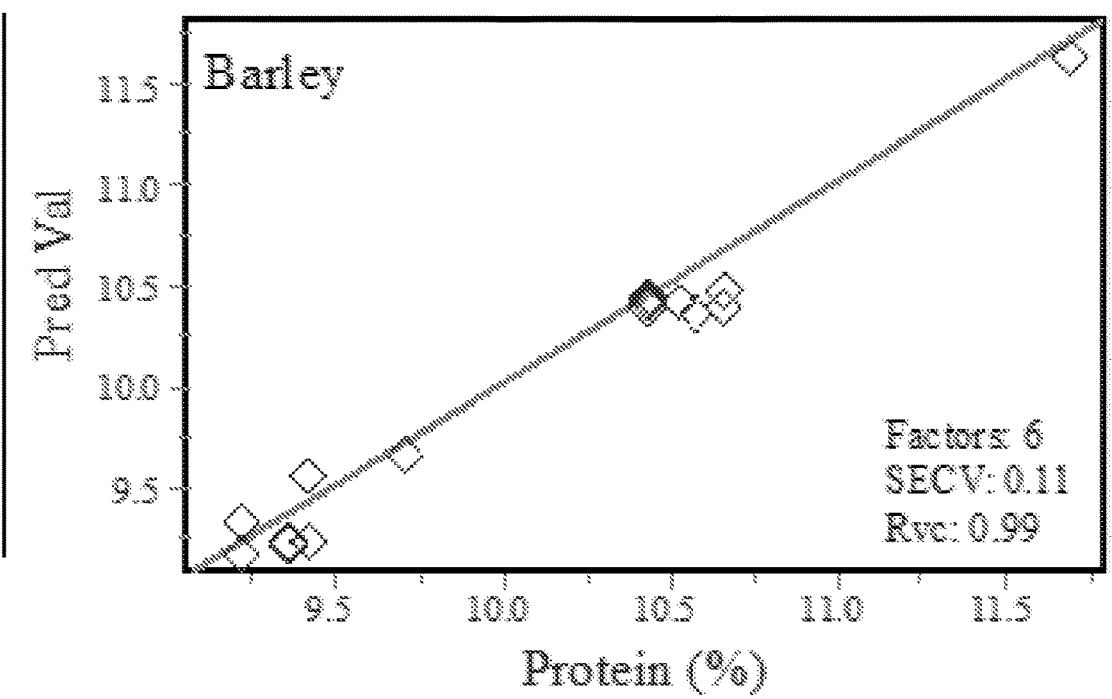
Figure 74D:
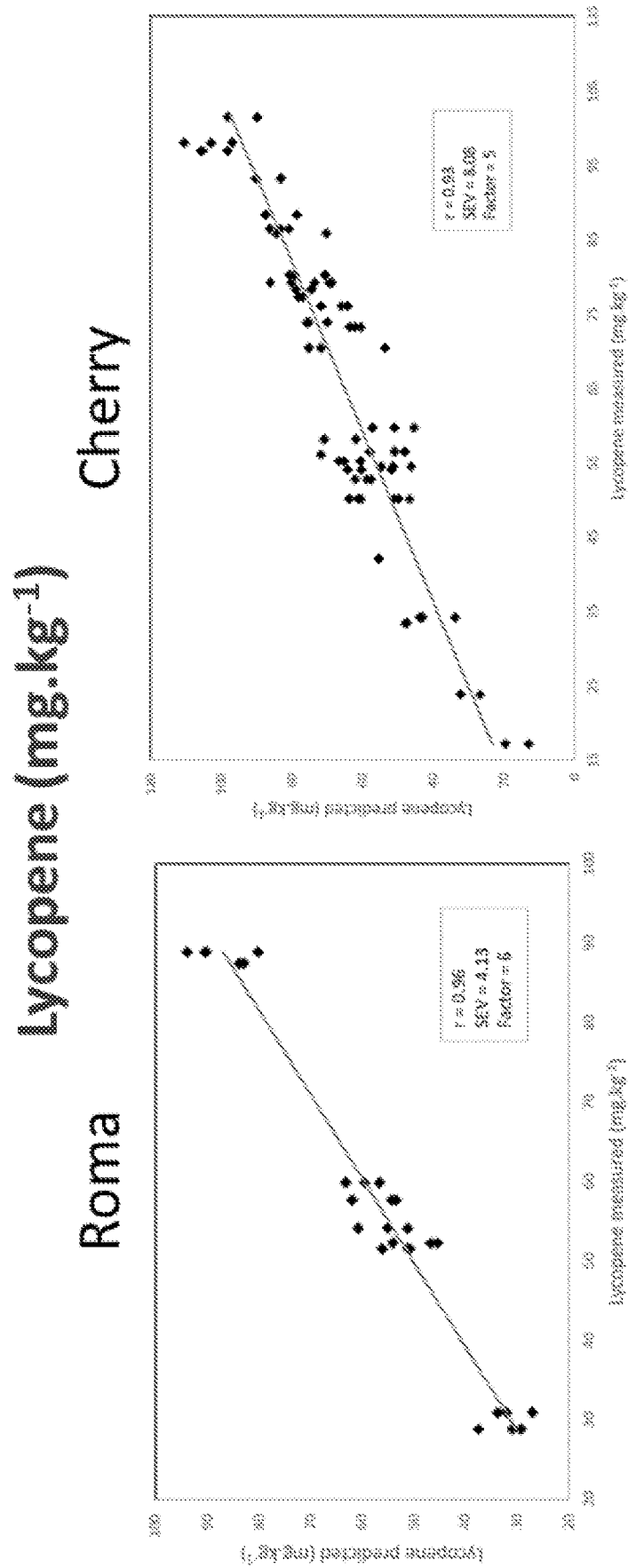
Figure 74E:
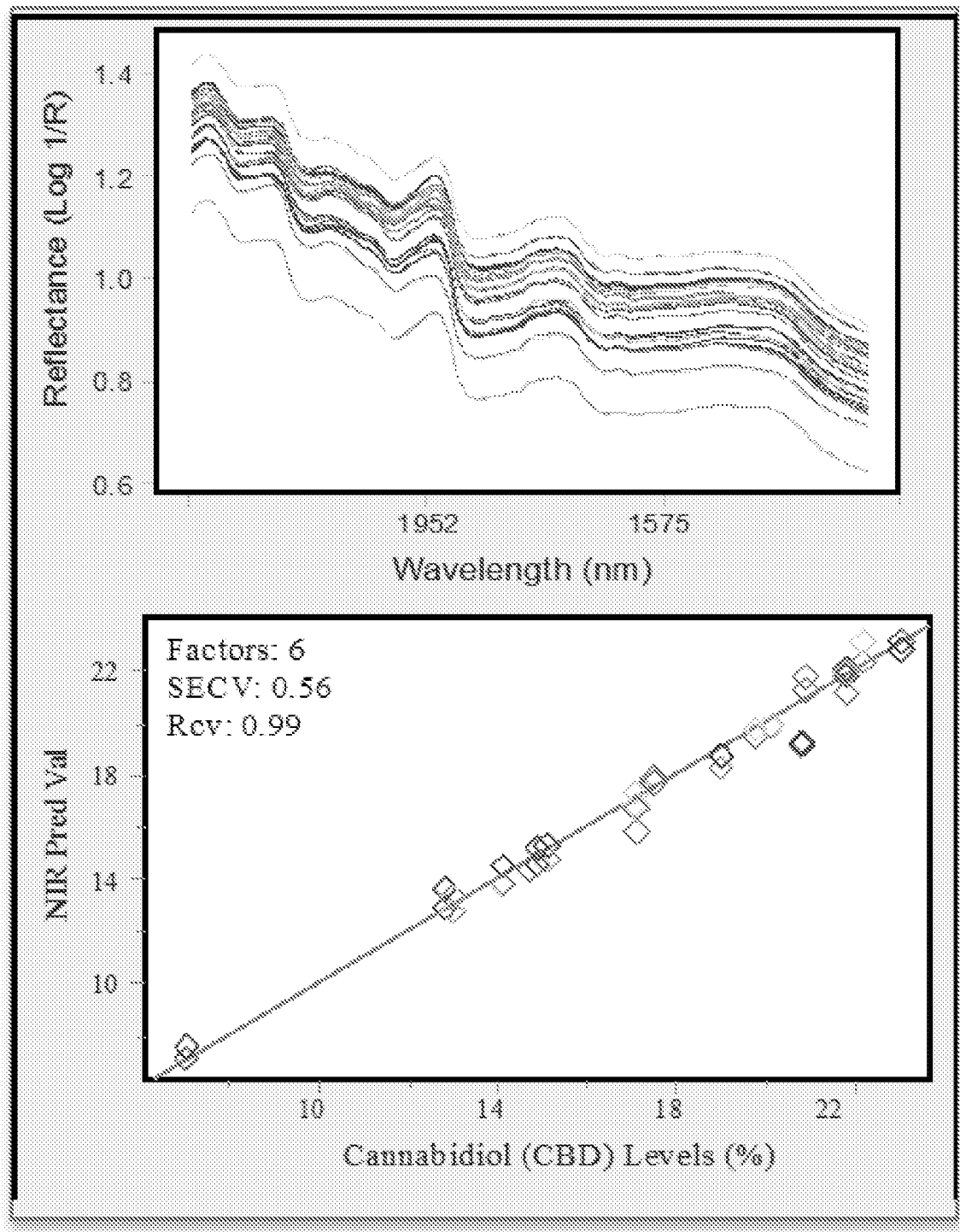
Figure 75:
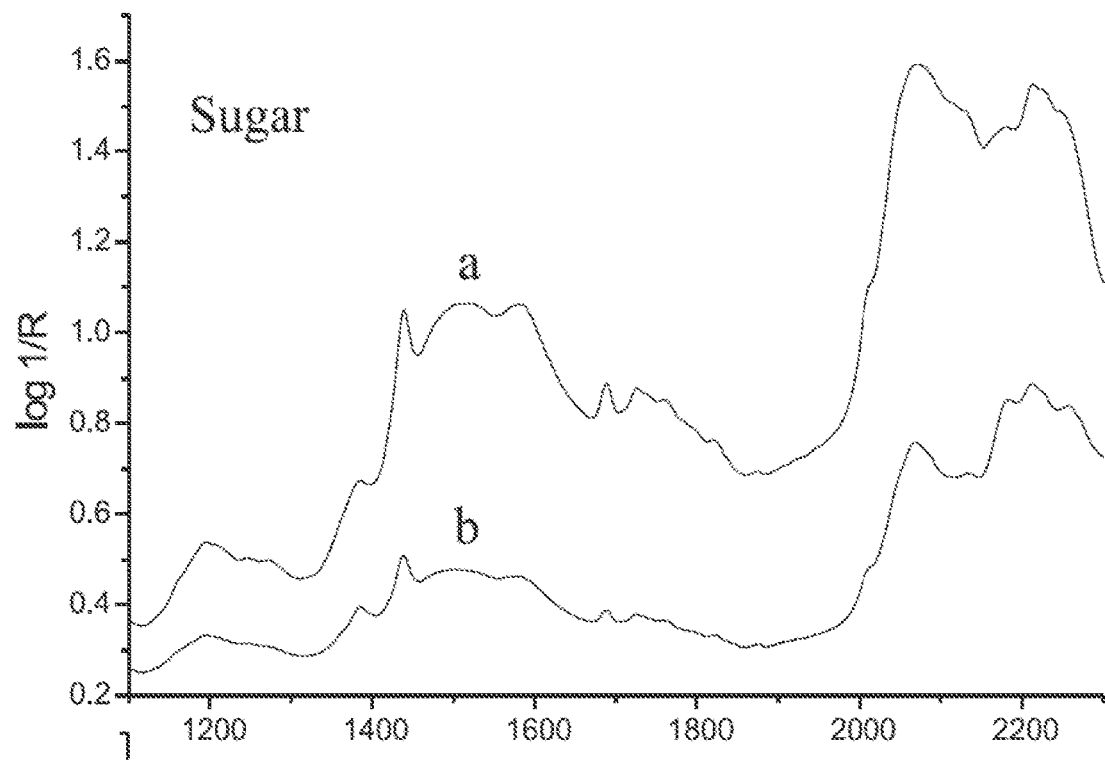
FIG. 75 shows NIR spectra showing difference of sugar.
Figure 76:
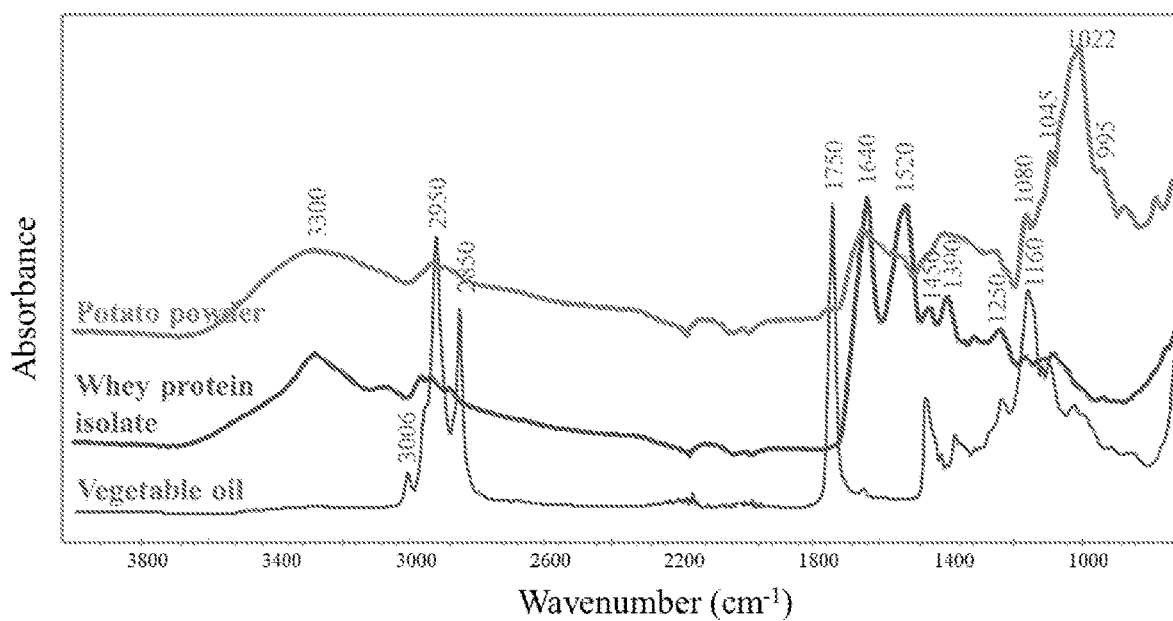
FIG. 76 shows Mid-IR spectra of selected ingredients.

Table 11 shows the performance statistics of the PLSR models. PLS models required few latent variables, determined by cross-validation, to explain the relevant variance in the data matrix and minimize the risk of over-fitting (fitting random noise) or under-fitting (unmodeled important data) the model. The best model performance for estimating the target traits in oats was obtained by using NIR spectral data, with cross-validated models giving standard error of cross-validation (SECV) for estimating levels of B-glucan, starch, and protein in oat powder of 0.11%, 2.2% and 0.6%, respectively. Furthermore, models developed using the newer NeoSpectra Micro NIR device showed slightly better performance in predicting β-glucan, and protein content than the NeoSpectra module NIR. The portable FT-IR and Raman models showed lower performance likely due to the inhomogeneity of the powders. FIG. 31 shows the correlation between the reference content and the predicted value for β-glucan based on the different technologies. Simple linear correlations were performed between different constituent values. β-glucan content was weakly correlated with starch ($R^2$ 0.15) and protein ($R^2$ 0.39) levels.

TABLE 11

Performance of cross-validation and prediction models developed by using NIR, MIR and Raman Instruments for determining important Oat traits

|  | Analyte | Factors | SECV | Rcv |
|---|---|---|---|---|
| Neospectra Module NIR | β-glucan | 3 | 0.12 | 0.89 |
|  | Starch | 5 | 2.09 | 0.88 |
|  | Protein | 4 | 0.70 | 0.91 |
| Neospectra Micro NIR | β-glucan | 3 | 0.10 | 0.91 |
|  | Starch | 6 | 2.28 | 0.84 |
|  | Protein | 6 | 0.55 | 0.95 |
| 4500 FTIR | β-glucan | 6 | 0.14 | 0.84 |
|  | Starch | 6 | 3.01 | 0.68 |
| Progeny Raman 1064 | β-glucan | 5 | 0.18 | 0.69 |
|  | Starch | 6 | 3.47 | 0.57 |

The performance of the PLS models generated in this study matched and/or outperform NIR techniques reported in the literature using benchtop systems. PLS models were generated based on NIR reflectance of grout oats with $R^2$ values of 0.83 (β-glucan) and 0.72 (protein) and SECV of 0.4% (β-glucan) and 0.6% (protein). Similar prediction models were reported for ground oat grouts using a benchtop NIR unit operating in the 250 to 2500 nm range. $R^2$ values of 0.94 and SECV of 0.16% and 0.64% for β-glucan and protein, respectively, were reported.

By using ground oats, NIR models were reported for rapidly (5 sec) predicting important quality traits based on a unique spectral fingerprint. These findings support the use of a palm-size NIR for rapid assessment of β-glucan, protein and starch in breeding selections. Novel miniature NIR systems provides the breeders with a rapid method to screen for unique traits with equivalent levels of reliability and sensitivity as benchtop systems but allow for more flexibility since the unit can be easily be taken to the field.

A sensor system is developed that can be tested in a field environment for screening various nutritional components of oats, as shown by additional data in FIGS. 67-70. This system advances spectroscopic sensing for breeding and quality screening applications (FIG. 18) for a field-deployable sensor using palm-size handheld NIR spectrometers.

Example 8. Handheld and Portable Devices for In-Situ Screening of Food Adulteration and Chemical Contaminants Economic adulteration and counterfeiting of global foods may cost the industry ~$10 to $15 billion per year. Globalization has raised economically motivated adulteration as a key concern. Therefore, appropriate analytical methods/equipment for detection of adulterated products or ingredients are needed. The approaches can be targeted approaches or non-targeted screening. Targeted approaches allow analyzing a known selection of compounds of interest with high sensitivity, reliable identification, and quantification, while non-targeted screening allows profiling complex matrices for unknowns or unidentified compounds using methods such as vibrational spectroscopy, NMR and MS combined with chemometrics.

Vibrational spectroscopy has the advantages of 1) simplicity, sensitivity, and speed; 2) high-throughput; 3) non-destructive analysis; 4) low operational cost. This study shows that vibrational spectroscopy (Raman, NIR and IR) are rapid and cost-effective tools for food quality assurance, deter acts of economic adulteration, detect contaminants in food, including olive oil, whey protein, and honey (FIGS. 55-66). Due to the greater versatility, ruggedness and convenience of potable units, food manufacturers can use the sensor disclosed herein for quickly assessing the quality of their product, allowing for timely correction methods during manufacture. In addition, the sensor has better sensitivity, generating data that can be analyzed using models with large data sets and powerful multivariate classification methods need evaluation.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A portable spectrometer system comprising:
   a spectrometer, wherein the spectrometer is a near infrared (NIR) spectrometer using the wavelength range between about 1350 nm to about 2500 nm;
   a sample stage adjacent the spectrometer;
   a motor coupled to the sample stage;
   an external processor configured to adjust a rotational position of the motor to distribute near infrared (NIR) spectra about a specimen to minimize a spectroscopy scattering effect; and
   a system housing enclosing the motor and the spectrometer;
   wherein rotation of the motor rotates the sample stage, and
   wherein the motor is controllable in response to spectroscopy requirements.

2. The system of claim 1, further comprising an interface device, wherein the interface device and the external processor are each in electronic communication with the spectrometer and the motor.

3. The system of claim 1, wherein the external processor is configured to adjust the rotational position of the motor in response to spectroscopy measurement.

4. The system of claim 1, wherein the external processor is a mobile device.

5. A method of determining a level of a trait in a sample using the system of claim 1, comprising:
   placing the sample on the sample stage of the system;
   measuring a spectrum of the sample within a wavelength range using the spectrometer in the system;
   determining the level of the trait based on the measured spectrum.

6. The method of claim 5, further comprising commanding the system through the external processor to rotate the sample stage for rotating the sample.

7. The method of claim 5, further comprising commanding the system through the external processor to process the data using algorithmic pre-processing.

8. The method of claim 7, wherein the algorithmic pre-processing comprises: the collected spectrum is ratioed against a spectrum collected for a calibration standard.

9. The method of claim 5, further comprising commanding the system through the external processor to apply a chemometric algorithm on the processed data to quantify the trait.

10. The method of claim 9, wherein the chemometric algorithm comprises partial least squares regression, principal component analysis, or artificial neural networks.

11. The method of claim 9, wherein the chemometric algorithm comprises partial least squares regression.

12. The method of claim 5, further comprising translating the quantitative results into a reporting format selected for a system operator.

13. The method of claim 12, wherein the reporting format comprises a table of individual quantities, a graphical representation of the quantities, or an icon indicating the categorization or grade of the sample.

14. The method of claim 5, further comprising displaying the level of the trait on the external processor.

15. A method of determining a level of a trait in a field crop, comprising the following steps:
obtaining a field crop sample;
collecting spectroscopic data on the field crop sample using a portable spectrometer system comprising:
a near infrared (NIR) spectrometer collecting the spectroscopic data at a wavelength range between about 1350 nm to about 2500 nm;
a sample stage adjacent the spectrometer;
a motor coupled to the sample stage;
an external processor configured to adjust a rotational position of the motor to distribute near infrared (NIR) spectra about a specimen to minimize a spectroscopy scattering effect; and
a system housing enclosing the motor and the spectrometer;
wherein rotation of the motor rotates the sample stage, and
wherein the motor is controllable in response to spectroscopy requirements;
processing the data using algorithmic pre-processing;
applying a chemometric algorithm on the processed data to quantify the trait; and
translating the quantitative results into a reporting format selected for a system operator.

16. The method of claim 15, wherein the algorithmic pre-processing comprises: the collected spectrum is ratioed against a spectrum collected for a calibration standard.

17. The method of claim 15, wherein the chemometric algorithm comprises partial least squares regression, principal components analysis, or artificial neural networks.

18. The method of claim 15, wherein the chemometric algorithm comprises partial least squares regression.

* * * * *